(12) United States Patent  (10) Patent No.: US 8,324,395 B2
Hirose et al.  (45) Date of Patent: *Dec. 4, 2012

(54) HETEROCYCLIC COMPOUND AND USE THEREOF

(75) Inventors: Masaaki Hirose, Cambridge, MA (US);
Masanori Okaniwa, Tsukuba (JP);
Takashi Imada, Tsukuba (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 178 days.

This patent is subject to a terminal disclaimer.

(21) Appl. No.: 12/674,801

(22) PCT Filed: Aug. 22, 2008

(86) PCT No.: PCT/JP2008/065011
§ 371 (c)(1),
(2), (4) Date: Feb. 23, 2010

(87) PCT Pub. No.: WO2009/025358
PCT Pub. Date: Feb. 26, 2009

(65) Prior Publication Data
US 2011/0172245 A1   Jul. 14, 2011

(30) Foreign Application Priority Data
Aug. 23, 2007 (JP) ................................ 2007-217633

(51) Int. Cl.
A61K 31/428 (2006.01)
C07D 277/82 (2006.01)
(52) U.S. Cl. ........................................ 548/163; 514/367
(58) Field of Classification Search ................ 548/163
See application file for complete search history.

(56) References Cited

U.S. PATENT DOCUMENTS

| | | | |
|---|---|---|---|
| 2,399,026 A | 4/1946 | Henzi et al. | |
| 4,096,264 A | 6/1978 | Bochis et al. | |
| 6,797,823 B1 | 9/2004 | Kubo et al. | |
| 7,238,813 B2 * | 7/2007 | Cheung et al. | 548/307.4 |
| 2002/0133005 A1 | 9/2002 | Iino et al. | |
| 2004/0058972 A1 | 3/2004 | Davis | |
| 2004/0082583 A1 | 4/2004 | Cheung et al. | |
| 2006/0160832 A1 | 7/2006 | Funahashi et al. | |
| 2006/0241301 A1 | 10/2006 | Hoelzemann et al. | |
| 2007/0021456 A1 | 1/2007 | Mitjans et al. | |
| 2009/0163488 A1 * | 6/2009 | Oguro et al. | 514/233.2 |
| 2010/0216810 A1 * | 8/2010 | Okaniwa et al. | 514/254.02 |
| 2011/0046169 A1 * | 2/2011 | Miyamoto et al. | 514/274 |

FOREIGN PATENT DOCUMENTS

| | | |
|---|---|---|
| JP | 52-73896 | 6/1977 |
| JP | 2008-189659 | 8/2008 |
| WO | 98/35958 | 8/1998 |
| WO | 99/10325 | 3/1999 |
| WO | 99/16438 | 4/1999 |
| WO | 00/41698 | 7/2000 |
| WO | 00/42012 | 7/2000 |
| WO | 01/02359 | 1/2001 |
| WO | 01/32651 | 5/2001 |
| WO | 01/57008 | 8/2001 |
| WO | 01/60814 | 8/2001 |
| WO | 01/66539 | 9/2001 |
| WO | 01/66540 | 9/2001 |
| WO | 02/24680 | 3/2002 |
| WO | 02/44156 | 6/2002 |
| WO | 02/062763 | 8/2002 |
| WO | 02/094808 | 11/2002 |
| WO | 03/022833 | 3/2003 |
| WO | 03/022836 | 3/2003 |

(Continued)

OTHER PUBLICATIONS

Pilyugin et al., CA 146:500952, 2006.*
Folkman, Judah, "Tumor Angiogenesis: Therapeutic Implications", The New England Journal of Medicine, vol. 285, No. 21, Nov. 18, 1971, 1182-1186.
Ferrara, et al., "The Biology of Vascular Endothelial Growth Factor", Endocrine Reviews, vol. 18, No. 1, Feb. 1997, 4-25.
Matter, Alex, "Tumor angiogensis as a therapeutic target", Drug Discovery Today, vol. 6, No. 19, Oct. 2001, 1005-1024.

(Continued)

*Primary Examiner* — Laura L. Stockton
(74) *Attorney, Agent, or Firm* — Hamre, Schumann, Mueller & Larson, P.C.

(57) ABSTRACT

Provided is a heterocyclic compound showing strong Raf inhibitory activity. A compound represented by the formula

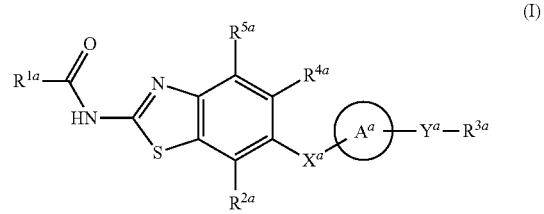

(I)

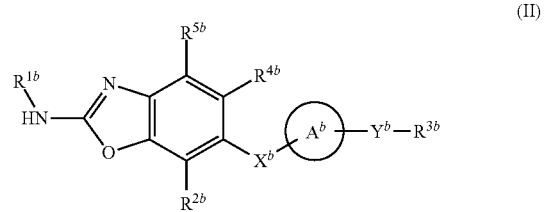

(II)

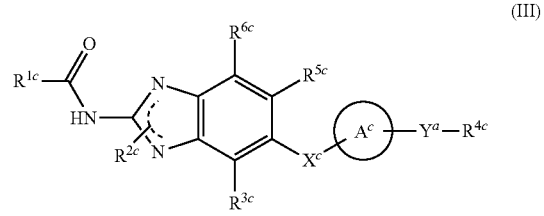

(III)

wherein each symbol is as defined in the specification, or a salt thereof.

4 Claims, No Drawings

FOREIGN PATENT DOCUMENTS

| | | |
|---|---|---|
| WO | 03/022837 | 3/2003 |
| WO | 03/022838 | 3/2003 |
| WO | 03/074515 | 9/2003 |
| WO | 03/082272 | 10/2003 |
| WO | 2004/087153 | 10/2004 |
| WO | 2005/019192 | 3/2005 |
| WO | 2005/019216 | 3/2005 |
| WO | 2005/032548 | 4/2005 |
| WO | 2005/037273 | 4/2005 |
| WO | 2005/112932 | 12/2005 |
| WO | 2006/030031 | 3/2006 |
| WO | 2006/071035 | 7/2006 |
| WO | 2006/076376 | 7/2006 |
| WO | 2007/007886 | 1/2007 |
| WO | 2007/030377 | 3/2007 |
| WO | 2007/041365 | 4/2007 |
| WO | 2007/058482 | 5/2007 |
| WO | 2007/121484 | 10/2007 |
| WO | 2008/016131 | 2/2008 |
| WO | 2008/016192 | 2/2008 |
| WO | 2008/084873 | 7/2008 |
| WO | 2008/150015 | 12/2008 |
| WO | 2009/025358 | 2/2009 |
| WO | 2009/028629 | 3/2009 |
| WO | 2009/028655 | 3/2009 |

OTHER PUBLICATIONS

International Search Report (Form PCT/ISA/210) issued in International Application No. PCT/JP2008/065011, mailed Sep. 16, 2008—4 pages.

Hasegawa, et al., "Discovery of Novel Benzimidazoles as Potent Inhibitors of TIE-2 and VEGFR-2 Tyrosine Kinase Receptors", J. Med. Chem., vol. 50, No. 18, 2007, pp. 4453-4470.

STN Search Result by Applicants—466 pages.

Lowinger, et al., "Design and Discovery of Small Molecules Targeting Raf-1 Kinase", Current Pharmaceutical Design, vol. 8, 2002, pp. 2269-2278.

Aly, et al., "New polymer syntheses IV. Synthesis and characterization of new polyamides containing bis-benzthiazolyl sulphone units in the main chain" High Perform. Polym., vol. 8, No. 2, 1996, pp. 307-314.

Takubo, et al., "Syntheses of Diaryl Sulfone. IV.", Yakugaku Zasshi, vol. 78, 1958, pp. 482-485.

Srivastava, et al., "Studies in antiparasitic agents: Part 20—Synthesis of probenzimidazoles, benzimidazoles and pyrimido[1,2-α]benzimidazoles as possible anthelmintics", Indian Journal of Chemistry, Section B: Organic Chemistry including Medicinal Chemistry, vol. 32B, No. 10, Oct. 1993, pp. 1035-1044.

Singh, et al., "Chemotherapy of Filariasis—On the Search of New Agents Effective on the Reproductive System of Female Adult Worms", Zeitschrift fuer Naturforschung, C: Journal of Biosciences, vol. 45, No. 11-12, 1990, pp. 1210-1214.

Naim, et al., "Studies in antiparasitic agents: Part 11—Synthesis of 5-substituted 2-aklyl/aryl-carbonylaminobenzimidazoles as orally effective anthelmintics", Indian Journal of Chemistry, Section B: Organic Chemistry including Medicinal Chemistry, vol. 29B, No. 5, 1990, pp. 464-470.

Naim, et al., "Studies in antiparasitic agents: Part 17,—Synthesis of 2-acylamino-6-substituted-benzthiazoles as potential anthelmintic agents", Indian Journal of Chemistry, vol. 30B, May 1991, pp. 494-498.

Stella, et al., "Prodrug strategies to overcome poor water solubility", Advanced Drug Delivery Reviews, vol. 59, 2007, pp. 677-694.

Patani, et al., "Bioisosteris: A Rational Approach in Drug Design", Chem. Rev., vol. 96, 1996, pp. 3147-3176.

Cannon, "Analog Design", in Burger's Medicinal Chemistry and Drug Discovery, 6$^{th}$ ed., 2003, Wiley & Sons, pp. 687-714.

* cited by examiner

HETEROCYCLIC COMPOUND AND USE THEREOF

CROSS-REFERENCE TO RELATED APPLICATIONS

This application is a U.S. national stage application of International Patent Application No. PCT/JP2008/065011 filed Aug. 22, 2008 claiming priority from Japanese Patent Application No. JP 2007-217633 filed Aug. 23, 2007.

TECHNICAL FIELD

The present invention relates to a heterocyclic compound and use thereof. More particularly, the present invention relates to a benzothiazole derivative, a benzooxazole derivative and a benzoimidazole derivative having strong Raf inhibitory activity and useful for the prophylaxis or treatment and the like of cancer, and use thereof.

BACKGROUND OF THE INVENTION

Many activities of cancer cells such as growth, metastasis, invasion and the like are caused via intracellular signal transduction from RTK: receptor tyrosine kinases (EGFR, HER2 etc.), which is activated by stimulation by growth factors and mutation, and the activation signal thereof is transmitted downstream via RAS protein. As the intracellular signal transduction pathway via Ras, Ras/Raf/MEK/ERK pathway is best known, which is deeply involved in the control of various cell functions such as cell proliferation, cellular motility, transformation, apoptosis (cell death) resistance and the like.

To block the pathway, inhibitors of growth factor receptors, for example, epithelial growth factor receptor (EGFR) inhibitors gefinitib (trade name: Iressa), and erlotinib (trade name: Tarceva), and human epithelial growth factor receptor type 2 (HER2) inhibitory antibody trastuzumab (trade name: Herceptin) are placed on the market in recent years. They have been reported to be effective for the treatment of some cancer types in clinical practices, such as lung cancer, breast cancer and the like. In addition, it has been shown that inhibitory antibody bevacizumab (trade name: Avastin) against vascular endothelial growth factor (VEGF) inhibits activation of VEGFR in the intratumoral neovascular endothelial cells and shows an antitumor action. These medicaments suppress signal transduction system at the downstream when showing a tumor growth inhibitory action in cancer to be the target cells and vascular endothelial cells, through inhibition of receptor enzyme activity and inhibition of receptor activation.

On the other hand, the Ras/Raf/MEK/ERK pathway is well known to cause highly frequent mutations in cancer. Ras gene is reported to undergo an activation type mutation at codon 12, 13 or 61 of various carcinomass, for example, about 90% of the total of pancreatic cancer, about 35% of non-small cell lung cancer, about 30% of liver cancer and the like, and there are many reports on the correlation between Ras mutation and developing malignant tumor.

With regard to Raf gene, activation mutation in kinase domain of B-Raf in cancer has been reported. It is known that B-Raf mutation, particularly V600E, occurs in various carcinomass, for example, about 60% of the total of malignant melanoma, about 30% of thyroid cancer, about 15% of colon cancer and the like. Particularly, B-Raf (V600E) kinase has about 13-fold MEK phosphorylation activity as compared to wild-type B-Raf kinase, and the activity of B-Raf is deeply involved in the growth of cancer having a mutation in B-Raf.

In these cancers, inhibitions of the upstream growth factor receptor activity and Ras cannot suppress signal transduction system downstream of Raf kinase, which is constantly activated. In this case, since suppression of the downstream signal (Raf/MEK/ERK signal transduction system) cannot be expected, a tumor growth suppressive activity cannot be expected, either. For example, melanoma showing highly frequent B-Raf mutation is highly metastatic and the 5 year survival rate is about 6%, for which no promising therapeutic drug exists at present.

In the Ras/Raf/MEK/ERK pathway, Raf kinase is the most downstream molecule to be activated by mutation. A compound inhibiting Raf activity is considered to be effective as a therapeutic drug for any cancer caused by mutation of growth factor receptor or excessive activation by ligand stimulation, or cancer caused by activation type mutation of Ras.

Raf is a serine/threonine kinase, and is known to include three isoforms of A-Raf, B-Raf and c-Raf (or Raf-1). Raf is activated by Ras and phosphorylates the downstream molecule MEK. The activated MEK further phosphorylates ERK to transmit the signal further downstream. Of three isoforms, B-Raf kinase shows an extreme strong activity of phosphorylating MEK in the basal state, which is about 15- to 20-fold that of A-Raf, c-Raf kinase activity. To undergo process of activation, moreover, c-Raf requires phosphorylation of the 338th serine in the activation loop to obtain the maximum activity (same for A-Raf). However, B-Raf is known to be easily activated as compared to A-Raf and c-Raf, since the corresponding sequence is always phosphorylated.

A compound that inhibits B-Raf kinase activity and mutant B-Raf kinase is considered to suppress cell proliferation particularly in cancer with poor prognosis. Accordingly, the compound becomes an effective therapeutic drug even for cancer for which a growth factor receptor enzyme activity inhibitor is ineffective.

As Raf inhibitors, sorafenib-related derivatives (e.g., patent references 1-3, non-patent reference 1), benzylidene derivatives (e.g., patent reference 4), imidazole derivatives (e.g., patent references 5-8), pyridylfuran derivatives (e.g., patent references 9-12), benzazole derivatives (patent references 13-15) and the like are known.

As compounds structurally similar to the compounds described in present specification, patent document 16 describes a compound usable as a therapeutic drug for cancer, patent document 17 describes a compound usable as a therapeutic drug for cancer, patent document 18 describes a compound usable as a therapeutic drug for cancer, patent document 19 describes a compound usable as a therapeutic drug for cancer, and patent document 20 describes a compound usable as a therapeutic drug for cancer. In addition, patent document 21 and non-patent documents 2-21 also describe structurally similar compounds.

patent reference 1: WO 2000/42012
patent reference 2: WO 2000/41698
patent reference 3: WO 2002/62763
patent reference 4: WO 99/10325
patent reference 5: WO 2002/94808
patent reference 6: WO 2002/24680
patent reference 7: WO 2001/66540
patent reference 8: WO 2001/66539
patent reference 9: WO 2003/22838
patent reference 10: WO 2003/22837
patent reference 11: WO 2003/22836
patent reference 12: WO 2003/22833
patent reference 13: WO 2003/082272
patent reference 14: WO 2005/032548 patent reference 15: WO 2007/030377
patent reference 16: WO 2002/044156
patent reference 17: WO 2006/076376
patent reference 18: WO 2005/112932
patent reference 19: WO 2003/082272
patent reference 20: WO 2005/032548
patent reference 21: U.S. Pat. No. 2,399,026
non-patent reference 1: Current Pharmaceutical Design, 2000, 8, 2269-2278
non-patent document 2: High Performance Polymers (1996), 8(2), 307-314
non-patent document 3: Indian Journal of Chemistry, Section B: Organic Chemistry Including Medicinal Chemistry (1991), 30B(5), 494-8
non-patent document 4: YAKUGAKU ZASSHI 1958, 78, 482-5
non-patent document 5: RN 550299-79-1
non-patent document 6: RN 519016-93-4
non-patent document 7: RN 519016-90-1
non-patent document 8: RN 518992-33-1
non-patent document 9: RN 518992-32-0
non-patent document 10: RN 518992-31-9
non-patent document 11: RN 351520-49-5
non-patent document 12: RN 351520-46-2
non-patent document 13: RN 332022-96-5
non-patent document 14: RN 331424-72-7
non-patent document 15: RN 328111-10-0
non-patent document 16: RN 327032-52-0
non-patent document 17: RN 313238-84-5
non-patent document 18: RN 313238-82-3
non-patent document 19: Indian Journal of Chemistry, Section B: Organic Chemistry Including Medicinal Chemistry (1993), 32B(10), 1035-44
non-patent document 20: Zeitschrift fuer Naturforschung, C: Journal of Biosciences (1990), 45(11-12), 1210-14
non-patent document 20: Indian Journal of Chemistry, Section B: Organic Chemistry Including Medicinal Chemistry (1990), 29B(5), 464-70

DISCLOSURE OF THE INVENTION

Problems to be Solved by the Invention

A Raf inhibitor superior in the efficacy expression, pharmacokinetics, solubility, interaction with other pharmaceutical products, safety and stability is expected to show a therapeutically superior effect. At present, however, such inhibitor sufficiently satisfactory in the efficacy expression, pharmacokinetics, solubility, interaction with other pharmaceutical products, safety and stability has not been found. Thus, there is a demand for the development of a compound sufficiently satisfactory as a pharmaceutical product. Accordingly, an object of the present invention is to provide a compound having low toxicity and sufficiently satisfactory as a pharmaceutical product.

Means of Solving the Problems

The present inventors have conducted intensive studies in an attempt to solve the above-mentioned problems and found that a compound represented by the following formula and a salt thereof have a superior Raf inhibitory activity, which resulted in the completion of the present invention.

Accordingly, the present invention provides the following.
[1] A compound represented by the formula

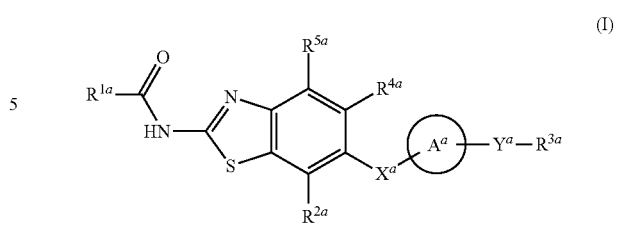

wherein
$R^{1a}$ is a group via a carbon atom;
$R^{2a}$ is a hydrogen atom, a halogen atom, a group via a carbon atom, a group via a nitrogen atom, a group via an oxygen atom, or a group via a sulfur atom;
$R^{3a}$ is an aromatic hydrocarbon group optionally having substituent(s);
$R^{4a}$ is a hydrogen atom, a halogen atom, a group via a carbon atom, a group via a nitrogen atom, a group via an oxygen atom, or a group via a sulfur atom;
$R^{5a}$ is a hydrogen atom, a halogen atom, a group via a carbon atom, a group via a nitrogen atom, a group via an oxygen atom, or a group via a sulfur atom;
$X^a$ is —CO—, —$CR^{6a}R^{7a}$— [wherein $R^{6a}$ and $R^{7a}$ are the same or different and each is a hydrogen atom, a group via a carbon atom, a group via a nitrogen atom, a group via an oxygen atom, or a group via a sulfur atom], —$NR^{8a}$— [wherein $R^{8a}$ is a hydrogen atom, or a group via a carbon atom], —O—, —S—, —S(O)— or —$S(O)_2$—;
$Y^a$ is —NH—, —NHCO—, —CONH— or —NHCONH—; and
ring $A^a$ is a monocycle optionally further having substituent(s) (hereinafter sometimes to be abbreviated as compound (i)) or a salt thereof.
[2] The compound of the above-mentioned [1], wherein $R^{1a}$ is $C_{1-6}$ alkyl optionally having substituent(s),
$C_{3-8}$ cycloalkyl optionally having substituent(s), or
a heterocyclic group optionally having substituent(s) (having a bond on the carbon atom).
[3] The compound of the above-mentioned [1], wherein $R^{2a}$ is a hydrogen atom.
[4] The compound of the above-mentioned [1], wherein $R^{3a}$ is $C_{6-10}$ aryl optionally having substituent(s).
[5] The compound of the above-mentioned [1], wherein $R^{4a}$ is a hydrogen atom or a halogen atom.
[6] The compound of the above-mentioned [1], wherein $R^{5a}$ is a hydrogen atom.
[7] The compound of the above-mentioned [1], wherein $X^a$ is —O—.
[8] The compound of the above-mentioned [1], wherein $Y^a$ is —NHCO— or —CONH—.
[9] The compound of the above-mentioned [1], wherein ring $A^a$ is a benzene ring optionally further having substituent(s).
[10] 3-(1-Cyano-1-methylethyl)-N-[3-({2-[(cyclopropylcarbonyl)amino]-1,3-benzothiazol-6-yl}oxy)phenyl]benzamide (Example A12);
3-(1-cyanocyclopropyl)-N-{3-[(2-{[(4-methylpiperazin-1-yl)acetyl]amino}-1,3-benzothiazol-6-yl)oxy] phenyl}benzamide (Example A16);
N-(3-{[2-(acetylamino)-1,3-benzothiazol-6-yl] oxy}phenyl)-2-chloro-3-(1-cyano-1-methylethyl)benzamide (Example A41); or
N-(3-{[2-(acetylamino)-1,3-benzothiazol-6-yl]oxy}-4-fluorophenyl)-2-chloro-3-(1-cyano-1-methylethyl)benzamide (Example A47);
or a salt thereof,

[11] A compound represented by the formula

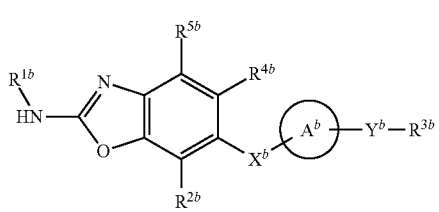

(II)

wherein
$R^{1b}$ is acyl or a cyclic group optionally having substituent(s);
$R^{2b}$ is a hydrogen atom, a halogen atom, a group via a carbon atom, a group via a nitrogen atom, a group via an oxygen atom, or a group via a sulfur atom;
$R^{3b}$ is a hydrocarbon group optionally having substituent(s) or a heterocyclic group optionally having substituent(s);
$R^{4b}$ is a hydrogen atom, a halogen atom, a group via a carbon atom, a group via a nitrogen atom, a group via an oxygen atom, or a group via a sulfur atom;
$R^{5b}$ is a hydrogen atom, a halogen atom, a group via a carbon atom, a group via a nitrogen atom, a group via an oxygen atom, or a group via a sulfur atom;
$X^b$ is —CO—, —$CR^{6b}R^{7b}$— [wherein $R^{6b}$ and $R^{7b}$ are the same or different and each is a hydrogen atom, a group via a carbon atom, a group via a nitrogen atom, a group via an oxygen atom, or a group via a sulfur atom], —$NR^{8b}$— [wherein $R^{8b}$ is a hydrogen atom, or a group via a carbon atom], —O—, —S—, —S(O)— or —$S(O)_2$—;
$Y^b$ is —NH—, —NHCO—, —CONH— or —NHCONH—; and
ring $A^b$ is a ring optionally further having substituent(s), except the following compound

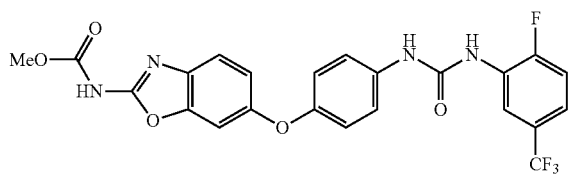

(hereinafter sometimes to be abbreviated as compound (II)), or a salt thereof.

[12] The compound of the above-mentioned [11], wherein $R^{1b}$ is acyl.
[13] The compound of the above-mentioned [11], wherein $R^{2b}$ is a hydrogen atom.
[14] The compound of the above-mentioned [11], wherein $R^{3b}$ is a hydrocarbon group optionally having substituent(s).
[15] The compound of the above-mentioned [11], wherein $R^{4b}$ is a hydrogen atom.
[16] The compound of the above-mentioned [11], wherein $R^{5b}$ is a hydrogen atom.
[17] The compound of the above-mentioned [11], wherein $X^b$ is —O—.
[18] The compound of the above-mentioned [11], wherein $Y^b$ is —NHCO— or —CONH—.
[19] The compound of the above-mentioned [11], wherein ring $A^b$ is a benzene ring optionally further having substituent(s).

[20] A compound represented by the formula

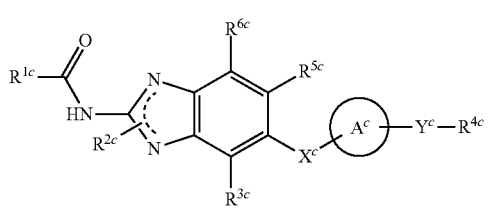

(III)

wherein
$R^{1c}$ is a group via a carbon atom;
$R^{2c}$ is a hydrogen atom or a group via a carbon atom;
$R^{3c}$ is a hydrogen atom, a halogen atom, a group via a carbon atom, a group via a nitrogen atom, a group via an oxygen atom, or a group via a sulfur atom;
$R^{4c}$ is a hydrocarbon group optionally having substituent(s) or a heterocyclic group optionally having substituent(s);
$R^{5c}$ is a hydrogen atom, a halogen atom, a group via a carbon atom, a group via a nitrogen atom, a group via an oxygen atom, or a group via a sulfur atom;
$R^{6c}$ is a hydrogen atom, a halogen atom, a group via a carbon atom, a group via a nitrogen atom, a group via an oxygen atom, or a group via a sulfur atom;
$X^c$ is —CO—, —$CR^{7c}R^{8c}$— [wherein $R^{7c}$ and $R^{8c}$ are the same or different and each is a hydrogen atom, a group via a carbon atom, a group via a nitrogen atom, a group via an oxygen atom, or a group via a sulfur atom], —$NR^{9c}$— [wherein $R^{9c}$ is a hydrogen atom, or a group via a carbon atom], —O—, —S—, —S(O)— or —$S(O)_2$—;
$Y^c$ is —NH—, —NHCO— or —CONH—; and
ring $A^c$ is a ring optionally further having substituent(s), except the following compound

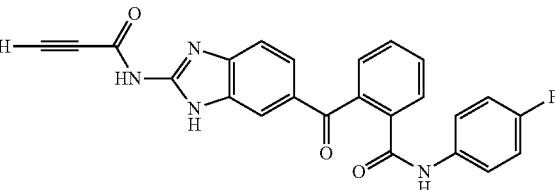

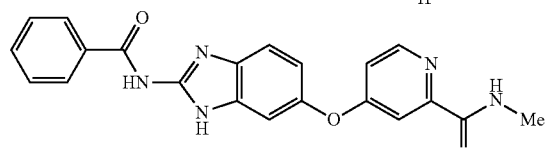

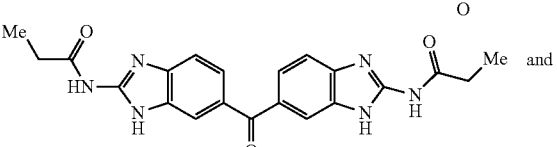

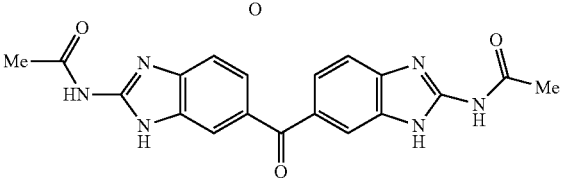

(hereinafter sometimes to be abbreviated as compound (III)), or a salt thereof.

[21] The compound of the above-mentioned [20], which is represented by the formula

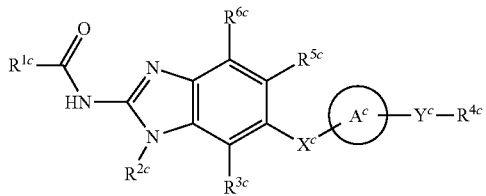

(III')

wherein each symbol is as defined in the above-mentioned [20] (hereinafter sometimes to be abbreviated as compound (III')).
[22] The compound of the above-mentioned [20], wherein $R^{1c}$ is $C_{3-8}$ cycloalkyl optionally having substituent(s).
[23] The compound of the above-mentioned [20], wherein $R^{2c}$ is a hydrogen atom or $C_{1-8}$ alkyl.
[24] The compound of the above-mentioned [20], wherein $R^{3c}$ is a hydrogen atom.
[25] The compound of the above-mentioned [20], wherein $R^{4c}$ is a hydrocarbon group optionally having substituent(s).
[26] The compound of the above-mentioned [20], wherein $R^{5c}$ is a hydrogen atom.
[27] The compound of the above-mentioned [20], wherein $R^{6c}$ is a hydrogen atom.
[28] The compound of the above-mentioned [20], wherein $X^c$ is —O—.
[29] The compound of the above-mentioned [20], wherein $Y^c$ is —NHCO—.
[30] The compound of the above-mentioned [20], wherein ring $A^c$ is a benzene ring optionally further having substituent(s).
[31] A prodrug of the compound of any one of the above-mentioned [1], [11] and [20].
[32] A medicament comprising the compound of any one of the above-mentioned [1], [11] and [20] or a salt thereof or a prodrug thereof.
[33] The medicament of the above-mentioned [32], which is a Raf inhibitor.
[34] The medicament of the above-mentioned [32], which is a prophylactic or therapeutic drug for cancer.
[35] A method of inhibiting Raf, comprising administering an effective amount of the compound of any one of the above-mentioned [1], [11] and [20] or a salt thereof or a prodrug thereof to a mammal.
[36] A method of the prophylaxis or treatment of cancer, comprising administering an effective amount of the compound of any one of the above-mentioned [1], [11] and [20] or a salt thereof or a prodrug thereof to a mammal.
[37] Use of the compound of any one of the above-mentioned [1], [11] and [20] or a salt thereof or a prodrug thereof for the production of a Raf inhibitor.
[38] Use of the compound of any one of the above-mentioned [1], [11] and [20] or a salt thereof or a prodrug thereof for the production of a drug for the prophylaxis or treatment of cancer.

Effect of the Invention

Since the compound of the present invention or a salt thereof or a prodrug thereof has a strong Raf inhibitory action (particularly, B-Raf inhibitory action), it can provide a clinically useful agent for the prophylaxis or treatment of cancer, a cancer growth inhibitor and a cancer metastasis suppressive agent.

DETAILED DESCRIPTION OF THE INVENTION

The present invention is explained in detail in the following.
In the present specification, the "acyl" is
(1) formyl,
(2) alkyl-carbonyl (e.g., $C_{1-6}$ alkyl-carbonyl) optionally having substituent(s),
(3) alkenyl-carbonyl (e.g., $C_{2-6}$ alkenyl-carbonyl) optionally having substituent(s),
(4) alkynyl-carbonyl (e.g., $C_{2-6}$ alkynyl-carbonyl) optionally having substituent(s),
(5) cycloalkyl-carbonyl (e.g., $C_{3-8}$ cycloalkyl-carbonyl) optionally having substituent(s),
(6) cycloalkenyl-carbonyl (e.g., $C_{3-8}$ cycloalkenyl-carbonyl) optionally having substituent(s),
(7) aryl-carbonyl (e.g., $C_{6-10}$ aryl-carbonyl) optionally having substituent(s),
(8) heterocyclyl-carbonyl optionally having substituent(s),
(9) carboxyl,
(10) alkyloxy-carbonyl (e.g., $C_{1-6}$ alkyloxy-carbonyl) optionally having substituent(s),
(11) alkenyloxy-carbonyl (e.g., $C_{2-6}$ alkenyloxy-carbonyl) optionally having substituent(s),
(12) alkynyloxy-carbonyl (e.g., $C_{2-6}$ alkynyloxy-carbonyl) optionally having substituent(s),
(13) cycloalkyloxy-carbonyl (e.g., $C_{3-8}$ cycloalkyloxy-carbonyl) optionally having substituent(s),
(14) cycloalkenyloxy-carbonyl (e.g., $C_{3-8}$ cycloalkenyloxy-carbonyl) optionally having substituent(s),
(15) cycloalkynyloxy-carbonyl (e.g., $C_{3-8}$ cycloalkynyloxy-carbonyl) optionally having substituent(s),
(16) aryloxy-carbonyl (e.g., $C_{6-10}$ aryloxy-carbonyl) optionally having substituent(s),
(17) heterocyclyl-oxy-carbonyl optionally having substituent(s),
(18) carbamoyl optionally having substituent(s)
and the like.

The "$C_{1-6}$ alkyl-carbonyl" of the above-mentioned "$C_{1-6}$ alkyl-carbonyl optionally having substituent(s)" is, for example, acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl and the like.

Examples of the "substituent" of the above-mentioned "$C_{1-6}$ alkyl-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

Substituent group A: a substituent group consisting of
(1) a halogen atom;
(2) cyano;
(3) nitro;
(4) hydroxy;
(5) $C_{3-8}$ cycloalkyl (e.g., cyclopropyl, cyclobutyl, cyclopentyl, cyclohexyl, cycloheptyl, cyclooctyl etc.) optionally having 1 to 3 substituents selected from a halogen atom and cyano;
(6) $C_{6-10}$ aryl (e.g., phenyl, 1-naphthyl, 2-naphthyl etc.) optionally having 1 to 3 substituents selected from a halogen atom and cyano;

(7) C$_{1-6}$ alkyl-oxy (e.g., methoxy, ethoxy, propoxy, isopropoxy, butoxy, isobutoxy, tert-butoxy etc.) optionally having 1 to 3 substituents selected from a halogen atom and cyano;

(8) C$_{2-6}$ alkenyloxy (e.g., ethenyloxy, propenyloxy, butenyloxy, pentenyloxy, hexenyloxy etc.) optionally having 1 to 3 halogen atoms;

(9) C$_{2-6}$ alkynyloxy (e.g., ethynyloxy, propynyloxy, butynyloxy, pentynyloxy, hexynyloxy etc.) optionally having 1 to 3 halogen atoms;

(10) C$_{3-8}$ cycloalkyl-oxy (e.g., cyclopropyloxy, cyclobutyloxy, cyclopentyloxy, cyclohexyloxy etc.) optionally having 1 to 3 halogen atoms;

(11) C$_{3-8}$ cycloalkenyloxy (e.g., cyclopropenyloxy, cyclobutenyloxy, cyclopentenyloxy, cyclohexenyloxy etc.) optionally having 1 to 3 halogen atoms;

(12) C$_{6-10}$ aryloxy (e.g., phenyloxy, 1-naphthyloxy, 2-naphthyloxy etc.) optionally having 1 to 3 halogen atoms;

(13) C$_{3-8}$ cycloalkyl-C$_{1-6}$ alkyl-oxy (e.g., cyclopropylmethyloxy, cyclopropylethyloxy, cyclobutylmethyloxy, cyclopentylmethyloxy, cyclohexylmethyloxy, cyclohexylethyloxy etc.) optionally having 1 to 3 halogen atoms;

(14) C$_{3-8}$ cycloalkenyl-C$_{1-6}$ alkyl-oxy (e.g., cyclopentenylmethyloxy, cyclohexenylmethyloxy, cyclohexenylethyloxy, cyclohexenylpropyloxy etc.) optionally having 1 to 3 halogen atoms;

(15) C$_{6-10}$ aryl-C$_{1-6}$ alkyl-oxy (e.g., phenylmethyloxy, phenylethyloxy etc.) optionally having 1 to 3 halogen atoms;

(16) C$_{1-6}$ alkyl-aminosulfonyl (e.g., methylaminosulfonyl, ethylaminosulfonyl, propylaminosulfonyl etc.);

(17) di-C$_{1-6}$ alkyl-aminosulfonyl (e.g., dimethylaminosulfonyl, diethylaminosulfonyl, dipropylaminosulfonyl etc.);

(18) C$_{1-6}$ alkyl-aminocarbonyl (e.g., methylaminocarbonyl, ethylaminocarbonyl, propylaminocarbonyl etc.);

(19) di-C$_{1-6}$ alkyl-aminocarbonyl (e.g., dimethylaminocarbonyl, diethylaminocarbonyl, dipropylaminocarbonyl etc.);

(20) formyl;

(21) C$_{1-6}$ alkyl-carbonyl (e.g., acetyl, ethylcarbonyl, propylcarbonyl, isopropylcarbonyl etc.);

(22) C$_{2-6}$ alkenyl-carbonyl (e.g., ethenylcarbonyl, propenylcarbonyl, butenylcarbonyl, pentenylcarbonyl, hexenylcarbonyl etc.);

(23) C$_{2-6}$ alkynyl-carbonyl (e.g., ethynylcarbonyl, propynylcarbonyl, butynylcarbonyl, pentynylcarbonyl, hexynylcarbonyl etc.);

(24) C$_{3-8}$ cycloalkyl-carbonyl (e.g., cyclopropylcarbonyl, cyclobutylcarbonyl, cyclopentylcarbonyl, cyclohexylcarbonyl etc.);

(25) C$_{3-8}$ cycloalkenyl-carbonyl (e.g., cyclopropenylcarbonyl, cyclobutenylcarbonyl, cyclopentenylcarbonyl, cyclohexenylcarbonyl etc.);

(26) C$_{6-10}$ aryl-carbonyl (e.g., benzoyl, 1-naphthylcarbonyl, 2-naphthylcarbonyl etc.);

(27) C$_{3-8}$ cycloalkyl-C$_{1-6}$ alkyl-carbonyl (e.g., cyclopropylmethylcarbonyl, cyclopropylethylcarbonyl, cyclobutylmethylcarbonyl, cyclopentylmethylcarbonyl, cyclohexylmethylcarbonyl, cyclohexylethylcarbonyl etc.);

(28) C$_{3-8}$ cycloalkenyl-C$_{1-6}$ alkyl-carbonyl (e.g., cyclopentenylmethylcarbonyl, cyclohexenylmethylcarbonyl, cyclohexenylethylcarbonyl, cyclohexenylpropylcarbonyl etc.);

(29) C$_{6-10}$ aryl-C$_{1-6}$ alkyl-carbonyl (e.g., benzylcarbonyl, phenylethylcarbonyl etc.);

(30) 5- or 6-membered monocyclic aromatic heterocyclyl-carbonyl (e.g., furylcarbonyl, thienylcarbonyl, pyrrolylcarbonyl, oxazolylcarbonyl, isooxazolylcarbonyl, thiazolylcarbonyl, isothiazolylcarbonyl, imidazolylcarbonyl, pyridylcarbonyl, pyrazolylcarbonyl etc.);

(31) 8- to 12-membered condensed aromatic heterocyclyl-carbonyl (e.g., benzofurylcarbonyl, isobenzofurylcarbonyl, benzothienylcarbonyl, isobenzothienylcarbonyl, indolylcarbonyl, isoindolylcarbonyl, 1H-indazolylcarbonyl, benzimidazolylcarbonyl, benzoxazolylcarbonyl etc.);

(32) 3- to 8-membered (preferably 5- or 6-membered) non-aromatic heterocyclyl-carbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidinylcarbonyl etc.);

(33) C$_{1-6}$ alkylsulfonyl (e.g., methylsulfonyl, ethylsulfonyl etc.);

(34) C$_{2-6}$ alkenylsulfonyl (e.g., ethenylsulfonyl, propenylsulfonyl etc.);

(35) C$_{2-6}$ alkynylsulfonyl (e.g., ethynylsulfonyl, propynylsulfonyl, butynylsulfonyl, pentynylsulfonyl, hexynylsulfonyl etc.);

(36) C$_{3-8}$ cycloalkylsulfonyl (e.g., cyclopropylsulfonyl, cyclobutylsulfonyl etc.);

(37) C$_{3-8}$ cycloalkenylsulfonyl (e.g., cyclopropenylsulfonyl, cyclobutenylsulfonyl etc.);

(38) C$_{6-10}$ arylsulfonyl (e.g., phenylsulfonyl etc.);

(39) C$_{3-8}$ cycloalkyl-C$_{1-6}$ alkyl-sulfonyl (e.g., cyclopropylmethylsulfonyl etc.);

(40) C$_{3-8}$ cycloalkenyl-C$_{1-6}$ alkyl-sulfonyl (e.g., cyclopentenylmethylsulfonyl etc.);

(41) C$_{6-10}$ aryl-C$_{1-6}$ alkyl-sulfonyl (e.g., benzylsulfonyl etc.);

(42) 5- or 6-membered monocyclic aromatic heterocyclyl-sulfonyl (e.g., furylsulfonyl, thienylsulfonyl, pyridylsulfonyl etc.);

(43) 8- to 12-membered condensed aromatic heterocyclyl-sulfonyl (e.g., benzofurylsulfonyl, isobenzofurylsulfonyl etc.);

(44) 3- to 8-membered (preferably 5- or 6-membered) non-aromatic heterocyclyl-sulfonyl (e.g., oxiranylsulfonyl, azetidinylsulfonyl etc.);

(45) amino;

(46) mono-C$_{1-6}$ alkylamino (e.g., methylamino, ethylamino, propylamino, isopropylamino, butylamino, isobutylamino, tert-butylamino etc.);

(47) di-C$_{1-6}$ alkylamino (e.g., dimethylamino, diethylamino, dipropylamino, diisopropylamino, dibutylamino, diisobutylamino, di-tert-butylamino etc.);

(48) mono(C$_{1-6}$ alkyl-carbonyl)amino (e.g., acetylamino, ethylcarbonylamino, propylcarbonylamino, tert-butylcarbonylamino etc.) optionally having 1 to 3 halogen atoms;

(49) mono(C$_{3-8}$ cycloalkyl-carbonyl)amino (e.g., cyclopropylcarbonylamino, cyclobutylcarbonylamino, cyclopentylcarbonylamino, cyclohexylcarbonylamino etc.);

(50) mono(C$_{6-10}$ aryl-carbonyl)amino group (e.g., benzoylamino etc.) optionally having 1 to 3 halogen atoms;

(51) mono(5- or 6-membered monocyclic aromatic heterocyclylcarbonyl)amino (e.g., furylcarbonylamino, thienylcarbonylamino, pyrrolylcarbonylamino, oxazolylcarbonylamino, isooxazolylcarbonylamino, thiazolylcarbonylamino, isothiazolylcarbonylamino, imidazolylcarbonylamino, pyridylcarbonylamino, pyrazolylcarbonylamino etc.);

(52) mono(8- to 12-membered condensed aromatic heterocyclylcarbonyl)amino (e.g., benzofurylcarbonylamino, isobenzofurylcarbonylamino, benzothienylcarbonylamino, isobenzothienylcarbonylamino etc.);

(53) mono(3- to 8-membered (preferably 5- or 6-membered) non-aromatic heterocyclyl-carbonyl)amino (e.g., oxiranylcarbonylamino, azetidinylcarbonylamino, oxetanylcarbonylamino etc.);

(54) thiol;

(55) $C_{1-6}$ alkylsulfanyl (e.g., methylsulfanyl, ethylsulfanyl etc.);

(56) $C_{2-6}$ alkenylsulfanyl (e.g., ethenylsulfanyl, propenylsulfanyl etc.);

(57) $C_{2-6}$ alkynylsulfanyl (e.g., ethynylsulfanyl, propynylsulfanyl, butynylsulfanyl, pentynylsulfanyl, hexynylsulfanyl etc.);

(58) $C_{3-8}$ cycloalkylsulfanyl (e.g., cyclopropylsulfanyl, cyclobutylsulfanyl etc.);

(59) $C_{3-8}$ cycloalkenylsulfanyl (e.g., cyclopropenylsulfanyl, cyclobutenylsulfanyl etc.);

(60) $C_{6-10}$ arylsulfanyl (e.g., phenylsulfanyl etc.);

(61) $C_{3-8}$ cycloalkyl-$C_{1-6}$ alkyl-sulfanyl (e.g., cyclopropylmethylsulfanyl etc.);

(62) $C_{3-8}$ cycloalkenyl-$C_{1-6}$ alkyl-sulfanyl (e.g., cyclopentenylmethylsulfanyl etc.);

(63) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl etc.);

(64) a 8- to 12-membered condensed aromatic heterocyclic group (e.g., benzofuryl, isobenzofuryl, benzothienyl, isobenzothienyl, indolyl, isoindolyl, 1H-indazolyl, benzimidazolyl, benzoxazolyl etc.);

(65) a 3- to 8-membered (preferably 5- or 6-membered) non-aromatic heterocyclic group (e.g., oxiranyl, azetidinyl, oxetanyl, thietanyl, pyrrolidinyl, tetrahydrofuryl, thiolanyl, piperidinyl etc.);

(66) 5- or 6-membered monocyclic aromatic heterocyclyl-oxy (e.g., furyloxy, thienyloxy, pyrrolyloxy, oxazolyloxy, isooxazolyloxy, thiazolyloxy, isothiazolyloxy, imidazolyloxy, pyridyloxy, pyrazolyloxy etc.);

(67) 8- to 12-membered condensed aromatic heterocyclyl-oxy (e.g., benzofuryloxy, isobenzofuryloxy, benzothienyloxy, isobenzothienyloxy, indolyloxy, isoindolyloxy, 1H-indazolyloxy, benzimidazolyloxy, benzoxazolyloxy etc.);

(68) 3- to 8-membered (preferably 5- or 6-membered) non-aromatic heterocyclyl-oxy (e.g., oxiranyloxy, azetidinyloxy, oxetanyloxy, thietanyloxy, pyrrolidinyloxy, tetrahydrofuryloxy, thiolanyloxy, piperidinyloxy etc.);

(69) oxo;

(70) $C_{1-6}$ alkylsulfinyl (e.g., methylsulfinyl, ethylsulfinyl etc.);

(71) $C_{2-6}$ alkenylsulfinyl (e.g., ethenylsulfinyl, propenylsulfinyl etc.);

(72) $C_{2-6}$ alkynylsulfinyl (e.g., ethynylsulfinyl, propynylsulfinyl, butynylsulfinyl, pentynylsulfinyl, hexynylsulfinyl etc.);

(73) $C_{3-8}$ cycloalkylsulfinyl (e.g., cyclopropylsulfinyl, cyclobutylsulfinyl etc.);

(74) $C_{3-8}$ cycloalkenylsulfinyl (e.g., cyclopropenylsulfinyl, cyclobutenylsulfinyl etc.);

(75) $C_{6-10}$ arylsulfinyl (e.g., phenylsulfinyl etc.);

(76) $C_{3-8}$ cycloalkyl-$C_{1-6}$ alkyl-sulfinyl (e.g., cyclopropylmethylsulfinyl etc.);

(77) $C_{3-8}$ cycloalkenyl-$C_{1-6}$ alkyl-sulfinyl (e.g., cyclopentenylmethylsulfinyl etc.);

(78) $C_{1-6}$ alkyl-aminothiocarbonyl (e.g., methylaminothiocarbonyl, ethylaminothiocarbonyl, propylaminothiocarbonyl etc.);

(79) di-$C_{1-6}$ alkyl-aminothiocarbonyl (e.g., dimethylaminothiocarbonyl, diethylaminothiocarbonyl, dipropylaminothiocarbonyl etc.);

(80) carboxy;

(81) $C_{1-6}$ alkyl-oxy-carbonyl (e.g., methoxycarbonyl, ethoxycarbonyl, propoxycarbonyl, isopropoxycarbonyl, butoxycarbonyl, isobutoxycarbonyl, tert-butoxycarbonyl etc.);

(82) $C_{2-6}$ alkenyloxy-carbonyl (e.g., ethenyloxycarbonyl, propenyloxycarbonyl, butenyloxycarbonyl, pentenyloxycarbonyl, hexenyloxycarbonyl etc.);

(83) $C_{2-6}$ alkynyloxy-carbonyl (e.g., ethynyloxycarbonyl, propynyloxycarbonyl, butynyloxycarbonyl, pentynyloxycarbonyl, hexynyloxycarbonyl etc.);

(84) $C_{3-8}$ cycloalkyl-oxy-carbonyl (e.g., cyclopropyloxycarbonyl, cyclobutyloxycarbonyl, cyclopentyloxycarbonyl, cyclohexyloxycarbonyl etc.);

(85) $C_{3-8}$ cycloalkenyloxy-carbonyl (e.g., cyclopropenyloxycarbonyl, cyclobutenyloxycarbonyl, cyclopentenyloxycarbonyl, cyclohexenyloxycarbonyl etc.);

(86) $C_{6-10}$ aryloxy-carbonyl (e.g., phenyloxycarbonyl, 1-naphthyloxycarbonyl, 2-naphthyloxycarbonyl etc.);

(87) $C_{3-8}$ cycloalkyl-$C_{1-6}$ alkyl-oxy-carbonyl (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl etc.);

(88) $C_{3-8}$ cycloalkenyl-$C_{1-6}$ alkyl-oxy-carbonyl (e.g., cyclopentenylmethyloxycarbonyl, cyclohexenylmethyloxycarbonyl, cyclohexenylethyloxycarbonyl, cyclohexenylpropyloxycarbonyl etc.); and

(89) $C_{6-10}$ aryl-$C_{1-6}$ alkyl-oxy-carbonyl (e.g., phenylmethyloxycarbonyl, phenylethyloxycarbonyl etc.).

The "$C_{2-6}$ alkenyl-carbonyl" of the above-mentioned "$C_{2-6}$ alkenyl-carbonyl optionally having substituent(s)" is, for example, ethenylcarbonyl, propenylcarbonyl, butenylcarbonyl, pentenylcarbonyl, hexenylcarbonyl and the like.

Examples of the "substituent" of the above-mentioned "$C_{2-6}$ alkenyl-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

The "$C_{2-6}$ alkynyl-carbonyl" of the above-mentioned "$C_{2-6}$ alkynyl-carbonyl optionally having substituent(s)" is, for example, ethynylcarbonyl; propynylcarbonyl, butynylcarbonyl, pentynylcarbonyl, hexynylcarbonyl and the like.

Examples of the "substituent" of the above-mentioned "$C_{2-6}$ alkynyl-carbonyl optionally having substituent(s)" include a substituent selected from substituent group A. While the number of substituents is not particularly limited as long as it is a substitutable number, it is preferably 1 to 5, more preferably 1 to 3. When plural substituents are present, they may be the same or different.

The "$C_{3-8}$ cycloalkyl-carbonyl" of the above-mentioned "$C_{3-8}$ cycloalkyl-carbonyl optionally having substituent(s)" is, for example, cyclopropylcarbonyl, cyclobutylcarbonyl, cyclopentylcarbonyl, cyclohexylcarbonyl, cycloheptylcarbonyl, cyclooctylcarbonyl and the like.

Examples of the "substituent" of the above-mentioned "$C_{3-8}$ cycloalkyl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The "$C_{3-8}$ cycloalkenyl-carbonyl" of the above-mentioned "$C_{3-8}$ cycloalkenyl-carbonyl optionally having substituent(s)" is, for example, cyclopropenylcarbonyl, cyclobutenylcarbonyl, cyclopentenylcarbonyl, cyclohexenylcarbonyl, cycloheptenylcarbonyl, cyclooctenylcarbonyl and the like.

Examples of the "substituent" of the above-mentioned "$C_{3-8}$ cycloalkenyl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The "$C_{6-10}$ aryl-carbonyl" of the above-mentioned "$C_{6-10}$ aryl-carbonyl optionally having substituent(s)" is, for example, benzoyl, 1-naphthoyl, 2-naphthoyl and the like.

Examples of the "substituent" of the above-mentioned "$C_{6-10}$ aryl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The "heterocycle" of the above-mentioned "heterocyclyl-carbonyl optionally having substituent(s)" is, for example, (1) 5- or 6-membered monocyclic aromatic heterocycle (e.g., furan, thiophene, pyrrole, oxazole, isoxazole, thiazole, isothiazole, imidazole, pyridine, pyrazole etc.), (2) 8- to 12-membered condensed aromatic heterocycle (e.g., benzofuran, isobenzofuran, benzothiophene, isobenzothiophene, indole, isoindole, 1H-indazole, benzimidazole, benzoxazole etc.), (3) 3- to 8-membered (preferably 5- or 6-membered) non-aromatic heterocycle (e.g., oxirane, azetidine, oxetane, pyrrolidine, tetrahydrofuran, thiolane, piperidine etc.) and the like.

Examples of the "substituent" of the above-mentioned "heterocyclyl-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{1-6}$ alkyloxy-carbonyl" of the above-mentioned "$C_{1-6}$ alkyloxy-carbonyl optionally having substituent(s)" is, for example, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Examples of the "substituent" of the above-mentioned "$C_{1-6}$ alkyloxy-carbonyl optionally having substituent(s)" include substituents selected from substituent group A. While the number of the substituents is not particularly limited as long as it is a substitutable number, the number is preferably 1 to 5, more preferably 1 to 3. When plural substituents are present, respective substituents may be the same or different.

The "$C_{2-6}$ alkenyloxy-carbonyl" of the above-mentioned "$C_{2-6}$ alkenyloxy-carbonyl optionally having substituent(s)" is, for example, ethenyloxycarbonyl, propenyloxycarbonyl, butenyloxycarbonyl, pentenyloxycarbonyl, hexenyloxycarbonyl and the like.

Examples of the "substituent" of the above-mentioned "$C_{2-6}$ alkenyloxy-carbonyl optionally having substituent(s)" include substituents selected from substituent group A. While the number of the substituents is not particularly limited as long as it is a substitutable number, the number is preferably 1 to 5, more preferably 1 to 3. When plural substituents are present, respective substituents may be the same or different.

The "$C_{2-6}$ alkynyloxy-carbonyl" of the above-mentioned "$C_{2-6}$ alkynyloxy-carbonyl optionally having substituent(s)" is, for example, ethynyloxycarbonyl, propynyloxycarbonyl, butynyloxycarbonyl, pentynyloxycarbonyl, hexynyloxycarbonyl and the like.

Examples of the "substituent" of the above-mentioned "$C_{2-6}$ alkynyloxy-carbonyl optionally having substituent(s)" include substituents selected from substituent group A. While the number of the substituents is not particularly limited as long as it is a substitutable number, the number is preferably 1 to 5, more preferably 1 to 3. When plural substituents are present, respective substituents may be the same or different.

The "$C_{3-8}$ cycloalkyloxy-carbonyl" of the above-mentioned "$C_{3-8}$ cycloalkyloxy-carbonyl optionally having substituent(s)" is, for example, cyclopropyloxycarbonyl, cyclobutyloxycarbonyl, cyclopentyloxycarbonyl, cyclohexyloxycarbonyl, cycloheptyloxycarbonyl, cyclooctyloxycarbonyl and the like.

Examples of the "substituent" of the above-mentioned "$C_{3-8}$ cycloalkyloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The "$C_{3-8}$ cycloalkenyloxy-carbonyl" of the above-mentioned "$C_{3-8}$ cycloalkenyloxy-carbonyl optionally having substituent(s)" is, for example, cyclopropenyloxycarbonyl, cyclobutenyloxycarbonyl, cyclopentenyloxycarbonyl, cyclohexenyloxycarbonyl, cycloheptenyloxycarbonyl, cyclooctenyloxycarbonyl and the like.

Examples of the "substituent" of the above-mentioned "$C_{3-8}$ cycloalkenyloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The "$C_{3-8}$ cycloalkynyloxy-carbonyl" of the above-mentioned "$C_{3-8}$ cycloalkynyloxy-carbonyl optionally having substituent(s)" is, for example, cyclopropynyloxycarbonyl, cyclobutynyloxycarbonyl, cyclopentynyloxycarbonyl, cyclohexynyloxycarbonyl, cycloheptynyloxycarbonyl, cyclooctynyloxycarbonyl and the like.

Examples of the "substituent" of the above-mentioned "$C_{3-8}$ cycloalkynyloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The "$C_{6-10}$ aryloxy-carbonyl" of the above-mentioned "$C_{6-10}$ aryloxy-carbonyl optionally having substituent(s)" is, for example, phenoxycarbonyl, 1-naphthyloxycarbonyl, 2-naphthyloxycarbonyl and the like.

Examples of the "substituent" of the above-mentioned "$C_{6-10}$ aryloxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The "heterocycle" of the above-mentioned "heterocyclyloxy-carbonyl optionally having substituent(s)" is, for example, (1) 5- or 6-membered monocyclic aromatic heterocycle (e.g., furan, thiophene, pyrrole, oxazole, isoxazole, thiazole, isothiazole, imidazole, pyridine, pyrazole etc.), (2) 8- to 12-membered condensed aromatic heterocycle (e.g., benzofuran, isobenzofuran, benzothiophene, isobenzothiophene, indole, isoindole, 1H-indazole, benzimidazole, benzoxazole etc.), (3) 3- to 8-membered (preferably 5- or 6-membered) non-aromatic heterocycle (e.g., oxirane, azetidine, oxetane, pyrrolidine, tetrahydrofuran, thiolane, piperidine etc.) and the like.

Examples of the "substituent" of the above-mentioned "heterocyclyl-oxy-carbonyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

The above-mentioned "carbamoyl optionally having substituent(s)" is carbamoyl optionally having 1 or 2 of the below-mentioned "hydrocarbon group optionally having substituent(s)".

In the present specification, examples of the "cyclic group" of the "cyclic group optionally having substituent(s)" include an aromatic hydrocarbon group, an aromatic heterocyclic group (e.g., monocyclic aromatic heterocyclic group, condensed aromatic heterocyclic group), a nonaromatic cyclic hydrocarbon group, a nonaromatic heterocyclic group, a fused ring group thereof and the like.

Examples of the aromatic hydrocarbon group include $C_{6-10}$ aryl and the like. Specifically, phenyl, 1-naphthyl, 2-naphthyl and the like can be mentioned.

Examples of the monocyclic aromatic heterocyclic group include a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like.

Examples of the monocyclic aromatic heterocyclic group include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,3,5-triazin-2-yl) and the like.

Examples of the "condensed aromatic heterocyclic group" include a group wherein a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like is condensed with $C_{6-10}$ aryl and the like; a group wherein the above-mentioned 5- to 7-membered monocyclic aromatic heterocyclic groups are condensed and the like.

Examples of the condensed aromatic heterocyclic group include quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-1-yl, benzimidazol-2-yl, benzimidazol-5-yl), indolyl (e.g., indol-1-yl, indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl (e.g., 3-benzisoxazolyl), benzotriazolyl (e.g., 1H-1,2,3-benzotriazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the nonaromatic cyclic hydrocarbon group include cycloalkyl, cycloalkenyl, cycloalkadienyl and the like, each of which may be condensed with a benzene ring.

Examples of the nonaromatic cyclic hydrocarbon group include $C_{3-8}$ cycloalkyl (e.g., cyclopropyl, cyclobutyl, cyclopentyl, cyclohexyl, cycloheptyl, cyclooctyl), $C_{3-8}$ cycloalkenyl (e.g., cyclopropenyl, cyclobutenyl, cyclopentenyl, cyclohexenyl, cycloheptenyl, cyclooctenyl), $C_{4-10}$ cycloalkadienyl (e.g., cyclobutadienyl, cyclopentadienyl, cyclohexadienyl, cycloheptadienyl, cyclooctadienyl, cyclononadienyl, cyclodecadienyl), a fused ring group wherein these groups and a benzene ring are condensed (e.g., indanyl (e.g., 1-indanyl), tetrahydronaphthyl (e.g., 1,2,3,4-tetrahydronaphthalen-1-yl), fluorenyl (e.g., 9-fluorenyl) etc.) and the like.

Examples of the nonaromatic heterocyclic group include a 3- to 8-membered (preferably 5- or 6-membered) saturated or unsaturated (preferably saturated) nonaromatic heterocyclic group and the like.

Examples of the nonaromatic heterocyclic group include oxiranyl (e.g., 2-oxiranyl), azetidinyl (e.g., 2-azetidinyl), oxetanyl (e.g., 2-oxetanyl), thietanyl (e.g., 2-thietanyl), pyrrolidinyl (e.g., 1-pyrrolidinyl, 2-pyrrolidinyl, 3-pyrrolidinyl), tetrahydrofuryl (e.g., 2-tetrahydrofuryl, 3-tetrahydrofuryl), thiolanyl (e.g., 2-thiolanyl), piperidinyl (e.g., 1-piperidinyl, 2-piperidinyl, 3-piperidinyl, 4-piperidinyl), tetrahydropyranyl (e.g., 2-tetrahydropyranyl, 3-tetrahydropyranyl, 4-tetrahydropyranyl), thianyl (e.g., 2-thianyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), piperazinyl (e.g., 1-piperazinyl, 2-piperazinyl), azepanyl (e.g., 2-azepanyl), oxepanyl (e.g., 2-oxepanyl), thiepanyl (e.g., 2-thiepanyl), oxazepanyl (e.g., 1,4-oxazepan-5-yl), thiazepanyl (e.g., 1,4-thiazepan-5-yl), azocanyl (e.g., 2-azocanyl), oxocanyl (e.g., 2-oxocanyl), thiocanyl (e.g., 2-thiocanyl), oxazocanyl (e.g., 1,4-oxazocan-5-yl), thiazocanyl (e.g., 1,4-thiazocan-5-yl), dioxinyl (e.g., 2-dioxinyl) and the like.

In the present specification, examples of the "substituent" of the "cyclic group optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

In the present specification, the "halogen atom" is a fluorine atom, a chlorine atom, a bromine atom or an iodine atom.

In the present specification, the "group via a carbon atom" is (1) cyano,
(2) alkyl (e.g., $C_{1-6}$ alkyl) optionally having substituent(s),
(3) alkenyl (e.g., $C_{2-6}$ alkenyl) optionally having substituent(s),
(4) alkynyl (e.g., $C_{2-6}$ alkynyl) optionally having to substituent(s),
(5) cycloalkyl (e.g., $C_{3-8}$ cycloalkyl) optionally having substituent(s),
(6) cycloalkenyl (e.g., $C_{3-8}$ cycloalkenyl) optionally having substituent(s).
(7) aryl (e.g., $C_{6-10}$ aryl) optionally having substituent(s),
(8) acyl,
(9) a heterocyclic group optionally having substituent(s) (having a bond on the carbon atom),
and the like.

The "$C_{1-6}$ alkyl" of the above-mentioned "$C_{1-6}$ alkyl optionally having substituent(s)" is, for example, methyl, ethyl, propyl, isopropyl, butyl, isobutyl, sec-butyl, tert-butyl, pentyl, hexyl and the like.

Examples of the "substituent" of the above-mentioned "$C_{1-6}$ alkyl optionally having substituent(s)" include a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{2-6}$ alkenyl" of the above-mentioned "$C_{2-6}$ alkenyl optionally having substituent(s)" is, for example, ethenyl, propenyl, butenyl, pentenyl, hexenyl and the like.

Examples of the "substituent" of the above-mentioned "$C_{2-6}$ alkenyl optionally having substituent(s)" include a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{2-6}$ alkynyl" of the above-mentioned "$C_{2-6}$ alkynyl optionally having substituent(s)" is, for example, ethynyl, propynyl, butynyl, pentynyl, hexynyl and the like.

Examples of the "substituent" of the above-mentioned "$C_{2-6}$ alkynyl optionally having substituent(s)" include a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{3-8}$ cycloalkyl" of the above-mentioned "$C_{3-8}$ cycloalkyl optionally having substituent(s)" is, for example, cyclopropyl, cyclobutyl, cyclopentyl, cyclohexyl, cycloheptyl, cyclooctyl and the like.

Examples of the "substituent" of the above-mentioned "$C_{3-8}$ cycloalkyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{3-8}$ cycloalkenyl" of the above-mentioned "$C_{3-8}$ cycloalkenyl optionally having substituent(s)" is, for example, cyclopropenyl, cyclobutenyl, cyclopentenyl, cyclohexenyl, cycloheptenyl, cyclooctenyl and the like.

Examples of the "substituent" of the above-mentioned "$C_{3-8}$ cycloalkenyl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

The "$C_{6-10}$ aryl" of the above-mentioned "$C_{6-10}$ aryl optionally having substituent(s)" is, for example, phenyl, 1-naphthyl, 2-naphthyl and the like.

Examples of the "substituent" of the above-mentioned "$C_{6-10}$ aryl optionally having substituent(s)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of substituents is not particularly limited as long as it is a substitutable number, it is preferably 1 to 5, more preferably 1 to 3. When plural substituents are present, they may be the same or different.

Examples of the above-mentioned "heterocyclic group optionally having substituent(s) (having a bond on the carbon atom)" include an aromatic heterocyclic group (e.g., monocyclic aromatic heterocyclic group, condensed aromatic heterocyclic group), a nonaromatic heterocyclic group and the like.

Examples of the monocyclic aromatic heterocyclic group include a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like.

Examples of the monocyclic aromatic heterocyclic group include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl, 6-pyrimidinyl), pyridazinyl (e.g., 3-pyridazinyl, 4-pyridazinyl), pyrazinyl (e.g., 2-pyrazinyl), pyrrolyl (e.g., 2-pyrrolyl, 3-pyrrolyl), imidazolyl (e.g., 2-imidazolyl, 4-imidazolyl, 5-imidazolyl), pyrazolyl (e.g., 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-4-yl), tetrazolyl (e.g., tetrazol-5-yl), triazinyl (e.g., 1,3,5-triazin-2-yl) and the like.

Examples of the condensed aromatic heterocyclic group include a group wherein a 5- to 7-membered monocyclic aromatic heterocyclic group containing, as ring-constituting atom(s) besides carbon atoms, 1 to 4 hetero atoms selected from an oxygen atom, a sulfur atom (optionally oxidized) and a nitrogen atom, and the like is condensed with $C_{6-10}$ aryl and the like; a group wherein the above-mentioned 5- to 7-membered monocyclic aromatic heterocyclic groups are condensed and the like.

Examples of the condensed aromatic heterocyclic group include quinolyl (e.g., 2-quinolyl, 3-quinolyl, 4-quinolyl), isoquinolyl (e.g., 1-isoquinolyl, 3-isoquinolyl, 4-isoquinolyl), quinazolyl (e.g., 2-quinazolyl, 4-quinazolyl), quinoxalyl (e.g., 2-quinoxalyl), benzofuryl (e.g., 2-benzofuryl, 3-benzofuryl), benzothienyl (e.g., 2-benzothienyl, 3-benzothienyl), benzoxazolyl (e.g., 2-benzoxazolyl), benzothiazolyl (e.g., 2-benzothiazolyl, 5-benzothiazolyl, 6-benzothiazolyl), benzimidazolyl (e.g., benzimidazol-2-yl, benzimidazol-5-yl), indolyl (e.g., indol-3-yl, indol-4-yl, indol-5-yl, indol-6-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl), imidazopyrazinyl (e.g., 1H-imidazo[4,5-b]pyrazin-2-yl), benzisoxazolyl (e.g., 3-benzisoxazolyl), benzotriazolyl (e.g., 1H-1,2,3-benzotriazol-5-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

Examples of the nonaromatic heterocyclic group include 3- to 8-membered (preferably 5- or 6-membered) saturated or unsaturated (preferably saturated) nonaromatic heterocyclic group and the like.

Specific examples of the nonaromatic heterocyclic group include oxiranyl (e.g., 2-oxiranyl), azetidinyl (e.g., 2-azetidinyl), oxetanyl (e.g., 2-oxetanyl), thietanyl (e.g., 2-thietanyl), pyrrolidinyl (e.g., 1-pyrrolidinyl, 2-pyrrolidinyl, 3-pyrrolidinyl), tetrahydrofuryl (e.g., 2-tetrahydrofuryl, 3-tetrahydrofuryl), thiolanyl (e.g., 2-thiolanyl), piperidinyl (e.g., 1-piperidinyl, 2-piperidinyl, 3-piperidinyl, 4-piperidinyl), tetrahydropyranyl (e.g., 2-tetrahydropyranyl, 3-tetrahydropyranyl, 4-tetrahydropyranyl), thianyl (e.g., 2-thianyl), morpholinyl (e.g., 2-morpholinyl, 3-morpholinyl, 4-morpholinyl), thiomorpholinyl (e.g., 2-thiomorpholinyl, 3-thiomorpholinyl, 4-thiomorpholinyl), piperazinyl (e.g., 1-piperazinyl, 2-piperazinyl), azepanyl (e.g., 2-azepanyl), oxepanyl (e.g., 2-oxepanyl), thiepanyl (e.g., 2-thiepanyl), oxazepanyl (e.g., 1,4-oxazepan-5-yl), thiazepanyl (e.g., 1,4-thiazepan-5-yl), azocanyl (e.g., 2-azocanyl), oxocanyl (e.g., 2-oxocanyl), thiocanyl (e.g., 2-thiocanyl), oxazocanyl (e.g., 1,4-oxazocan-5-yl), thiazocanyl (e.g., 1,4-thiazocan-5-yl), dioxinyl (e.g., 2-dioxinyl) and the like.

Examples of the "substituent" of the above-mentioned "heterocyclic group optionally having substituent(s) (having a bond on the carbon atom)" include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

In the present specification, the "group via a nitrogen atom" is, for example, (1) nitro, or (2) amino optionally having 1 or 2 of the above-mentioned "group via a carbon atom".

In the present specification, the "group via an oxygen atom" is, for example, hydroxy optionally having one of the above-mentioned "group via a carbon atom".

In the present specification, the "group via a sulfur atom" is, for example, thiol optionally having one of the above-mentioned "group via a carbon atom" or "group via a nitrogen atom", wherein said group may be oxidized.

In the present specification, the "hydrocarbon group optionally having substituent(s)" is $C_{1-6}$ alkyl optionally having substituent(s), $C_{2-6}$ alkenyl optionally having substituent(s), $C_{2-6}$ alkynyl optionally having substituent(s), $C_{3-8}$ cycloalkyl optionally having substituent(s), $C_{3-8}$ cycloalkenyl optionally having substituent(s), $C_{6-10}$ aryl optionally having substituent(s) and acyl, and examples of the "$C_{1-6}$ alkyl optionally having substituent(s), $C_{2-6}$ alkenyl optionally having substituent(s), $C_{2-6}$ alkynyl optionally having substituent(s), $C_{3-8}$ cycloalkyl optionally having substituent(s), $C_{3-8}$ cycloalkenyl optionally having substituent(s), $C_{6-10}$ aryl optionally having substituent(s) and acyl" include those similar to the "$C_{1-6}$ alkyl optionally having substituent(s), $C_{2-6}$ alkenyl optionally having substituent(s), $C_{2-6}$ alkynyl optionally having substituent(s), $C_{3-8}$ cycloalkyl optionally having substituent(s), $C_{3-8}$ cycloalkenyl optionally having substituent(s), $C_{6-10}$ aryl optionally having substituent(s) and acyl", which are explained for the above-mentioned "group via a carbon atom".

In the present specification, the "aromatic hydrocarbon group optionally having substituent(s)" is $C_{6-10}$ aryl optionally having substituent(s) and examples of the "$C_{6-10}$ aryl optionally having substituent(s)" include those similar to the "$C_{6-10}$ aryl optionally having substituent(s)" explained for the above-mentioned "group via a carbon atom".

In the present specification, examples of the "heterocyclic group optionally having substituent(s)" for $R^{3b}$ or $R^{4c}$ include those similar to the "heterocyclic group optionally having substituent(s) (having a bond on the carbon atom)" explained for the above-mentioned "group via a carbon atom", wherein the position of the bond is not limited to a carbon atom.

In the present specification, the "monocycle optionally further having substituent(s)" for ring $A^a$ is a monocycle optionally having substituent(s) other than those shown in the formula.

Examples of the "monocycle" include (1) a benzene ring, (2) a monocyclic aromatic heterocycle, (3) a monocyclic nonaromatic cyclic hydrocarbon ring, and (4) a monocyclic non-aromatic heterocycle.

Examples of the "monocyclic aromatic heterocycle" include a 5- to 7-membered monocyclic aromatic heterocycle containing, as ring-constituting atom(s) besides carbon atoms, 1 to 4 hetero atoms selected from an oxygen atom, a sulfur atom (optionally oxidized) and a nitrogen atom, and the like.

Specifically, furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazole and the like can be mentioned.

Examples of the "monocyclic nonaromatic cyclic hydrocarbon ring" include cycloalkane, cycloalkene, cycloalkadiene and the like. Specifically, $C_{3-8}$ cycloalkane (e.g., cyclopropane, cyclobutane, cyclopentane, cyclohexane, cycloheptane, cyclooctane), $C_{3-8}$ cycloalkene (e.g., cyclopropene, cyclobutene, cyclopentene, cyclohexene, cycloheptene, cyclooctene), $C_{4-10}$ cycloalkadiene (e.g., cyclobutadiene, cyclopentadiene, cyclohexadiene, cycloheptadiene, cyclooctadiene, cyclononadiene, cyclodecadiene) and the like can be mentioned.

Examples of the "monocyclic non-aromatic heterocycle" include 3- to 8-membered (preferably 5- or 6-membered) saturated or unsaturated (preferably saturated) non-aromatic heterocycle and the like.

Specific examples of the "monocyclic non-aromatic heterocycle" include oxirane, azetidine, oxetane, pyrrolidine, tetrahydrofuran, thiolane, piperidine, tetrahydropyran, morpholine, thiomorpholine, piperazine, azepane, oxepane, thiepane, oxazepane, thiazepane and the like.

Examples of the "substituent" of the "monocycle optionally further having substituent(s)" for ring $A^a$ include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

In the present specification, the "ring optionally further having substituent(s)" for ring $A^b$ or ring $A^c$ is a ring optionally having substituent(s) other than those shown in the formulas.

Examples of the "ring" include (1) an aromatic hydrocarbon ring, (2) monocyclic aromatic heterocycle, (3) condensed aromatic heterocycle, (4) a nonaromatic cyclic hydrocarbon ring, (5) non-aromatic heterocycle, (6) a fused ring thereof and the like.

Examples of the "aromatic hydrocarbon ring" include a benzene ring, a naphthalene ring and the like.

Examples of the "monocyclic aromatic heterocycle" include 5- to 7-membered monocyclic aromatic heterocycle containing, as a ring-constituting atom besides carbon atom, 1 to 4 hetero atoms selected from an oxygen atom, a sulfur atom (said sulfur atom is optionally oxidized) and a nitrogen atom, and the like.

Specifically, furan, thiophene, pyridine, pyrimidine, pyridazine, pyrazine, pyrrole, imidazole, pyrazole, thiazole, isothiazole, oxazole, isoxazole, oxadiazole, thiadiazole, triazole, tetrazole, triazole and the like can be mentioned.

Examples of the "fused aromatic heterocycle" include a condensed aromatic heterocycle wherein 5- to 7-membered monocyclic aromatic heterocycle containing, as a ring-constituting atom besides carbon atom, 1 to 4 hetero atoms selected from an oxygen atom, a sulfur atom (said sulfur atom is optionally oxidized) and a nitrogen atom, and the like and an aromatic hydrocarbon ring and the like are fused; condensed aromatic heterocycle wherein the above-mentioned 5- to 7-membered monocyclic aromatic heterocycles are fused and the like.

As the "condensed aromatic heterocycle", quinoline, quinazoline, quinoxaline, benzofuran, benzothiophene, benzoxazole, benzothiazole, benzimidazole, indole, indazole, pyrrolopyrazine, imidazopyridine, imidazopyrazine, benzisoxazole, benzotriazole, pyrazolopyridine, pyrazolothiophene, pyrazolotriazine and the like can be specifically mentioned.

Examples of the "nonaromatic cyclic hydrocarbon ring" include cycloalkane, cycloalkene, cycloalkadiene and the like, each of which may be fused with a benzene ring.

As the "nonaromatic cyclic hydrocarbon ring", $C_{3-8}$ cycloalkane (e.g., cyclopropane, cyclobutane, cyclopentane, cyclohexane, cycloheptane, cyclooctane), $C_{3-8}$ cycloalkene (e.g., cyclopropene, cyclobutene, cyclopentene, cyclohexene, cycloheptene, cyclooctene), $C_{4-10}$ cycloalkadiene (e.g., cyclobutadiene, cyclopentadiene, cyclohexadiene, cycloheptadiene, cyclooctadiene, cyclononadiene, cyclodecadiene), fused ring wherein these rings and a benzene ring are fused (e.g., indane, tetrahydronaphthalene, fluorene etc.) and the like can be specifically mentioned.

Examples of the "non-aromatic heterocycle" include 3- to 8-membered (preferably 5- or 6-membered) saturated or unsaturated (preferably saturated) non-aromatic heterocycle and the like.

As the "non-aromatic heterocycle", oxirane, azetidine, oxetane, pyrrolidine, tetrahydrofuran, thiolane, piperidine, tetrahydropyran, morpholine, thiomorpholine, piperazine, azepane, oxepane, thiepane, oxazepane, thiazepane and the like can be specifically mentioned.

Examples of the "substituent" of the "ring optionally further having substituent(s)" for ring $A^b$ or ring $A^c$ include (1) $C_{1-6}$ alkyl (e.g., methyl, ethyl, propyl, isopropyl, butyl, isobutyl, tert-butyl etc.) optionally having 1 to 3 substituents selected from a halogen atom and cyano, and (2) a substituent selected from substituent group A (excluding oxo). While the number of the substituents is not particularly limited as long as it is a substitutable number, the number is preferably 1 to 5, more preferably 1 to 3. When plural substituents are present, respective substituents may be the same or different.

Compound (I)-compound (III) are described in detail in the following.

1. Compound (I)

$R^{1a}$ is a group via a carbon atom.

$R^{1a}$ is preferably (1) alkyl (e.g., $C_{1-6}$ alkyl) optionally having substituent(s), (2) cycloalkyl (e.g., $C_{3-8}$ cycloalkyl) optionally having substituent(s), (3) a heterocyclic group optionally having substituent(s) (having a bond on carbon atom)

and the like. Among these, (1) $C_{1-6}$ alkyl (particularly, methyl) optionally having one substituent selected from
  (i) hydroxy, and
  (ii) a 5- or 6-membered nonaromatic heterocyclic group (particularly, piperazinyl) optionally having one $C_{1-6}$ alkyl (particularly, methyl), (2) $C_{3-8}$ cycloalkyl (particularly, cyclopropyl), (3) a 5- or 6-membered monocyclic aromatic heterocyclic group (particularly, oxazolyl)

and the like are preferable.

$R^{2a}$ is a hydrogen atom, a halogen atom, a group via a carbon atom, a group via a nitrogen atom, a group via an oxygen atom or a group via a sulfur atom.

$R^{2a}$ is preferably a hydrogen atom.

$R^{3a}$ is an aromatic hydrocarbon group optionally having substituent(s).

$R^{3a}$ is preferably aryl (e.g., $C_{6-10}$ aryl) optionally having substituent(s).

It is particularly preferably $C_{6-10}$ aryl (particularly, phenyl) optionally having 1 or 2 substituents selected from (1) $C_{3-8}$ cycloalkyl (particularly, cyclopropyl) optionally having cyano, (2) $C_{1-6}$ alkyl (e.g., methyl, isopropyl) optionally having 1 to 3 substituents selected from a halogen atom (e.g., fluorine atom) and cyano,
(3) $C_{1-6}$ alkyl-oxy (e.g., isopropoxy) optionally having cyano,
(4) a halogen atom (e.g., chlorine atom), and
(5) cyano.

$R^{4a}$ is a hydrogen atom, a halogen atom, a group via a carbon atom, a group via a nitrogen atom, a group via an oxygen atom or a group via a sulfur atom.

$R^{4a}$ is preferably a hydrogen atom or a halogen atom (e.g., fluorine atom).

$R^{5a}$ is a hydrogen atom, a halogen atom, a group via a carbon atom, a group via a nitrogen atom, a group via an oxygen atom or a group via a sulfur atom.

$R^{5a}$ is preferably a hydrogen atom.

$X^a$ is —CO—, —$CR^{6a}R^{7a}$— ($R^{6a}$ and $R^{7a}$ are the same or different and each is a hydrogen atom, a group via a carbon atom, a group via a nitrogen atom, a group via an oxygen atom or a group via a sulfur atom), —$NR^{8a}$— ($R^{8a}$ is a hydrogen atom or a group via a carbon atom), —O—, —S—, —S(O)— or —S(O)$_2$—.

$X^a$ is preferably —O—.

$Y^a$ is —NH—, —NHCO—, —CONH— or —NHCONH—.

$Y^a$ is preferably —NHCO— or —CONH—.

ring $A^a$ is monocycle optionally further having substituent(s). ring $A^a$ is preferably a benzene ring optionally further having substituent(s).

Particularly, a benzene ring optionally having one substituent selected from
(1) $C_{1-6}$ alkyl (particularly, methyl),
(2) $C_{1-6}$ alkyl-oxy (particularly, methoxy), and
(3) a halogen atom (particularly, fluorine atom)
is preferable.

As compound (1), the compounds described in Examples A1-A31 and the like are preferable.

As compound (1), the compounds described in Examples A32-A49 and the like are also preferable.

Preferable specific examples of compound (1) or a salt thereof include the following.

(Compound I-a)
Compound (1) wherein
$R^{1a}$ is
(1) $C_{1-6}$ alkyl optionally having substituent(s),
(2) $C_{3-6}$ cycloalkyl optionally having substituent(s), or
(3) a heterocyclic group optionally having substituent(s) (having a bond on carbon atom);
$R^{2a}$ is a hydrogen atom;
$R^{3a}$ is $C_{6-10}$ aryl optionally having substituent(s);
$R^{4a}$ is a hydrogen atom or a halogen atom (preferably, fluorine atom);
$R^{5a}$ is a hydrogen atom;
$X^a$ is —O—;
$Y^a$ is —NHCO— or —CONH—; and
ring $A^a$ is a benzene ring optionally further having substituent(s);
or a salt thereof.

(Compound I-b)
Compound (1) wherein
$R^{1a}$ is
(1) $C_{1-6}$ alkyl (preferably, methyl) optionally having one substituent selected from
    (i) hydroxy, and
    (ii) a 5- or 6-membered nonaromatic heterocyclic group (preferably, piperazinyl) optionally having one $C_{1-6}$ alkyl (preferably, methyl),
(2) $C_{3-8}$ cycloalkyl (preferably, cyclopropyl), or
(3) a 5- or 6-membered monocyclic aromatic heterocyclic group (preferably, oxazolyl);
$R^{2a}$ is a hydrogen atom;
$R^{3a}$ is $C_{6-10}$ aryl (preferably, phenyl) optionally having one substituent selected from
(1) $C_{3-8}$ cycloalkyl (preferably, cyclopropyl) optionally having cyano, and
(2) $C_{1-6}$ alkyl (preferably, methyl, isopropyl) optionally having 1 to 3 substituents selected from a halogen atom (preferably, fluorine atom) and cyano;
$R^{4a}$ is a hydrogen atom or a halogen atom (preferably, fluorine atom);
$R^{5a}$ is a hydrogen atom;
$X^a$ is —O—;
$Y^a$ is —NHCO— or —CONH—; and
ring $A^a$ is a benzene ring optionally having one substituent selected from
(1) $C_{1-6}$ alkyl (preferably, methyl), and
(2) $C_{1-6}$ alkyl-oxy (preferably, methoxy);
or a salt thereof.

(Compound I-c)
Compound (1) wherein
$R^{1a}$ is
(1) $C_{1-6}$ alkyl (preferably, methyl) optionally having one substituent selected from
    (i) hydroxy, and
    (ii) 5- or 6-membered nonaromatic heterocyclic group (preferably, piperazinyl) optionally having one $C_{1-6}$ alkyl (preferably, methyl),
(2) $C_{3-8}$ cycloalkyl (preferably, cyclopropyl), or
(3) a 5- or 6-membered monocyclic aromatic heterocyclic group (preferably, oxazolyl);
$R^{2a}$ is a hydrogen atom;
$R^{3a}$ is $C_{6-10}$ aryl (preferably, phenyl) optionally having 1 or 2 substituents selected from
(1) $C_{3-8}$ cycloalkyl (preferably, cyclopropyl) optionally having cyano,
(2) $C_{1-6}$ alkyl (preferably, methyl, isopropyl) optionally having 1 to 3 substituents selected from a halogen atom (preferably, fluorine atom) and cyano,
(3) $C_{1-6}$ alkyl-oxy (preferably, isopropoxy) optionally having cyano,
(4) a halogen atom (preferably, chlorine atom), and
(5) cyano;
$R^{4a}$ is a hydrogen atom or a halogen atom (preferably, fluorine atom);
$R^{5a}$ is a hydrogen atom;
$X^a$ is —O—;
$Y^a$ is —NHCO— or —CONH—; and
ring $A^a$ is a benzene ring optionally having one substituent selected from
(1) $C_{1-6}$ alkyl (preferably, methyl),
(2) $C_{1-6}$ alkyl-oxy (preferably, methoxy), and
(3) a halogen atom (preferably, fluorine atom);
or a salt thereof.

(Compound I-d)
3-(1-cyano-1-methylethyl)-N-[3-({2-[(cyclopropylcarbonyl)amino]-1,3-benzothiazol-6-yl}oxy)phenyl]benzamide (Example A12);
3-(1-cyanocyclopropyl)-N-{3-[(2-{[(4-methylpiperazin-1-yl)acetyl]amino}-1,3-benzothiazol-6-yl)oxy]phenyl}benzamide (Example A16);
N-(3-{[2-(acetylamino)-1,3-benzothiazol-6-yl]oxy}phenyl)-2-chloro-3-(1-cyano-1-methylethyl)benzamide (Example A41); or N-(3-{[2-(acetylamino)-1,3-benzothiazol-6-yl]oxy}-4-fluorophenyl)-2-chloro-3-(1-cyano-1-methylethyl)benzamide (Example A47);
or a salt thereof.

2. Compound (II)

$R^{1b}$ is acyl or a cyclic group optionally having substituent(s).

As $R^{1b}$, acyl is preferable, and cycloalkyl-carbonyl (e.g., $C_{3-8}$ cycloalkyl-carbonyl) optionally having substituent(s) is more preferable. Particularly, $C_{3-8}$ cycloalkyl-carbonyl (particularly, cyclopropylcarbonyl) is preferable.

$R^{2b}$ is a hydrogen atom, a halogen atom, a group via a carbon atom, a group via a nitrogen atom, a group via an oxygen atom or a group via a sulfur atom.

$R^{2b}$ is preferably a hydrogen atom.

$R^{3b}$ is a hydrocarbon group optionally having substituent(s) or a heterocyclic group optionally having substituent(s).

As $R^{3b}$, a hydrocarbon group optionally having substituent(s) is preferable, and aryl (e.g., $C_{6-10}$ aryl) optionally having substituent(s) is more preferable. Particularly, $C_{6-10}$ aryl (particularly, phenyl) optionally having one substituent selected from (1) $C_{3-8}$ cycloalkyl (particularly, cyclopropyl) optionally having cyano and (2) $C_{1-6}$ alkyl (e.g., methyl, isopropyl) optionally having 1 to 3 substituents selected from a halogen atom and cyano is preferable.

$R^{4b}$ is a hydrogen atom, a halogen atom, a group via a carbon atom, a group via a nitrogen atom, a group via an oxygen atom or a group via a sulfur atom.

Preferred as $R^{4b}$ is a hydrogen atom.

$R^{5b}$ is a hydrogen atom, a halogen atom, a group via a carbon atom, a group via a nitrogen atom, a group via an oxygen atom or a group via a sulfur atom.

Preferred as $R^{5b}$ is a hydrogen atom.

$X^b$ is —CO—, —$CR^{6b}R^{7b}$— [wherein $R^{6b}$ and $R^{7b}$ are the same or different and each is a hydrogen atom, a group via a carbon atom, a group via a nitrogen atom, a group via an oxygen atom or a group via a sulfur atom], —$NR^{8b}$— [wherein $R^{8b}$ is a hydrogen atom or a group via a carbon atom], —O—, —S—, —S(O)— or —$S(O)_2$—.

Preferred as $X^b$ is —O—.

$Y^b$ is —NH—, —NHCO—, —CONH— or —NHCONH—.

Preferred as $Y^b$ is —NHCO— or —CONH—.

Ring $A^b$ is a ring optionally further having substituent(s). As ring $A^b$, a benzene ring optionally further having substituent(s) is preferable, and a benzene ring free of further substituent is particularly preferable.

As compound (II), the compounds described in Examples B1-B4 and the like are preferable.

Preferable specific examples of compound (II) or a salt thereof include the following.

(Compound II-a)
Compound (II) wherein
$R^{1b}$ is acyl (preferably, $C_{3-8}$ cycloalkyl-carbonyl optionally having substituent(s));
$R^{2b}$ is a hydrogen atom;
$R^{3b}$ is a hydrocarbon group optionally having substituent(s) (preferably, $C_{6-10}$ aryl optionally having substituent(s));
$R^{4b}$ is a hydrogen atom;
$R^{5b}$ is a hydrogen atom;
$X^b$ is —O—;
$Y^b$ is —NHCO— or —CONH—; and
ring $A^b$ is a benzene ring optionally further having substituent(s);
or a salt thereof.

(Compound II-b)
Compound (II) wherein
$R^{1b}$ is $C_{3-8}$ cycloalkyl-carbonyl (preferably, cyclopropylcarbonyl);
$R^{2b}$ is a hydrogen atom;
$R^{3b}$ is $C_{6-10}$ aryl (preferably, phenyl) optionally having one substituent selected from
(1) $C_{3-8}$ cycloalkyl (particularly, cyclopropyl) optionally having cyano, and
(2) $C_{1-6}$ alkyl (preferably, methyl, isopropyl) optionally having 1 to 3 substituents selected from a halogen atom and cyano;
$R^{4b}$ is a hydrogen atom;
$R^{5b}$ is a hydrogen atom;
$X^b$ is —O—;
$Y^b$ is —NHCO— or —CONH—; and
ring $A^b$ is a benzene ring;
or a salt thereof.

3. Compound (III)

In compound (III), the position of the substituent $R^{2c}$ is not limited as long as it is on a nitrogen atom constituting a benzoimidazole ring. Particularly, a compound having a structure represented by the formula

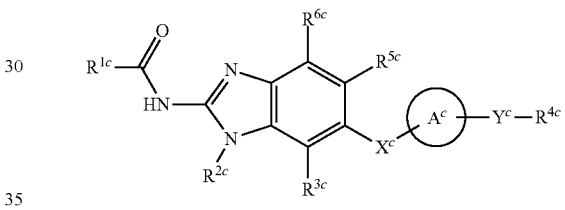

(III')

wherein each substituent is as defined above, is preferable.

$R^{1c}$ is a group via a carbon atom.

As $R^{1c}$, cycloalkyl (e.g., $C_{3-8}$ cycloalkyl) optionally having substituent(s) is preferable. Particularly, $C_{3-8}$ cycloalkyl (particularly, cyclopropyl) is preferable.

$R^{2c}$ is a hydrogen atom, or a group via a carbon atom.

As $R^{2c}$, a hydrogen atom or $C_{1-6}$ alkyl (particularly, methyl) is preferable.

$R^{3c}$ is a hydrogen atom, a halogen atom, a group via a carbon atom, a group via a nitrogen atom, a group via an oxygen atom or a group via a sulfur atom.

Preferred as $R^{3c}$ is a hydrogen atom.

$R^{4c}$ is a hydrocarbon group optionally having substituent(s) or a heterocyclic group optionally having substituent(s).

As $R^{4c}$, a hydrocarbon group optionally having substituent(s) is preferable, and aryl (e.g., $C_{6-10}$ aryl) optionally having substituent(s) is more preferable. Particularly, $C_{6-10}$ aryl (particularly, phenyl) optionally having one substituent selected from (1) $C_{3-8}$ cycloalkyl (particularly, cyclopropyl) optionally having cyano and (2) $C_{1-6}$ alkyl (e.g., methyl, isopropyl) optionally having 1 to 3 substituents selected from halogen atom and cyano is preferable.

$R^{5c}$ is a hydrogen atom, a halogen atom, a group via a carbon atom, a group via a nitrogen atom, a group via an oxygen atom or a group via a sulfur atom.

Preferred as $R^{5c}$ is a hydrogen atom.

$R^{6c}$ is a hydrogen atom, a halogen atom, a group via a carbon atom, a group via a nitrogen atom, a group via an oxygen atom or a group via a sulfur atom.

$R^{6c}$ is preferably a hydrogen atom.

$X^c$ is —CO—, —CR$^{7c}$R$^{8c}$— (R$^{7c}$ and R$^{8c}$ are the same or different and each is a hydrogen atom, a group via a carbon atom, a group via a nitrogen atom, a group via an oxygen atom or a group via a sulfur atom), —NR$^{9c}$— (R$^{9c}$ is a hydrogen atom or a group via a carbon atom), —O—, —S—, —S(O)— or —S(O)$_2$—.

As $X^c$, —O— is preferable.

$Y^c$ is —NH—, —NHCO—, —CONH— or —NHCONH—.

As $Y^c$, —NHCO— is preferable.

Ring $A^c$ is a ring optionally further having substituent(s). As ring $A^c$, a benzene ring optionally further having substituent(s) is preferable, and a benzene ring free of further substituents is particularly preferable.

Preferable specific examples of compound (III) or a salt thereof include the following.

(Compound III-a)

Compound (III) wherein
R$^{1c}$ is C$_{3-8}$ cycloalkyl optionally having substituent(s);
R$^{2c}$ is a hydrogen atom or C$_{1-6}$ alkyl (preferably, methyl);
R$^{3c}$ is a hydrogen atom;
R$^{4c}$ is a hydrocarbon group optionally having substituent(s) (preferably, C$_{6-10}$ aryl optionally having substituent(s));
R$^{5c}$ is a hydrogen atom;
R$^{6c}$ is a hydrogen atom;
$X^c$ is —O—;
$Y^c$ is —NHCO—; and
ring $A^c$ is a benzene ring optionally further having substituent(s);
(preferably, compound (III')) or a salt thereof.

(Compound III-b)

Compound (III) wherein
R$^{1c}$ is C$_{3-8}$ cycloalkyl (preferably, cyclopropyl);
R$^{2c}$ is a hydrogen atom or C$_{1-6}$ alkyl (preferably, methyl);
R$^{3c}$ is a hydrogen atom;
R$^{4c}$ is C$_{6-10}$ aryl (preferably, phenyl) optionally having one substituent selected from
(1) C$_{3-8}$ cycloalkyl (preferably, cyclopropyl) optionally having cyano, and
(2) C$_{1-6}$ alkyl (preferably, methyl, isopropyl) optionally having 1 to 3 substituents selected from halogen atom and cyano;
R$^{5c}$ is a hydrogen atom;
R$^{6c}$ is a hydrogen atom;
$X^c$ is —O—;
$Y^c$ is —NHCO—; and
ring $A^c$ is a benzene ring;
(preferably, compound (III')) or a salt thereof.

As compound (III), the compounds described in Examples C1-C9 and the like are preferable.

Examples of the salt of compound (I), compound (II) and compound (III) (to be sometimes abbreviated as the compound of the present invention in the specification) include metal salt, ammonium salt, a salt with organic base, a salt with inorganic acid, a salt with organic acid, a salt with basic or acidic amino acid and the like. Preferable examples of the metal salt include alkali metal salt such as sodium salt, potassium salt and the like; alkaline earth metal salt such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysine, ornithine and the like, and preferable examples of the salt with acidic amino acid include a salt with aspartic acid, glutamic acid and the like.

Of these, a pharmaceutically acceptable salt is preferable. For example, when a compound has an acidic functional group, an inorganic salt such as alkali metal salt (e.g., sodium salt, potassium salt etc.), alkaline earth metal salt (e.g., calcium salt, magnesium salt etc.) and the like, ammonium salt etc., and when a compound has a basic functional group, for example, a salt with inorganic acid such as hydrochloric acid, hydrobromic acid, nitric acid, sulfuric acid, phosphoric acid and the like, or a salt with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like can be mentioned.

The production methods of the compound of the present invention are explained below.

In the present production methods, halogenated hydrocarbons, aromatic hydrocarbons, alcohols and ethanol as solvents are, for example, the following solvents.

halogenated hydrocarbons:
dichloromethane, chloroform, carbon tetrachloride, 1,2-dichloroethane etc.

aromatic hydrocarbons:
benzene, toluene, xylene etc.

alcohols:
methanol, ethanol, isopropanol, t-butanol etc.

ethers:
diethyl ether, tetrahydrofuran, dioxane etc.

In the present production methods, pyridine hydrochloride, pyridine hydrobromide, pyridine p-toluenesulfonate, quinoline hydrochloride, isoquinoline hydrochloride, pyrimidine hydrochloride, pyrazine hydrochloride, triazine hydrochloride, trimethylamine hydrochloride, triethylamine hydrochloride, N-ethyldiisopropylamine hydrochloride and the like are used as ammonium salts.

In the present production methods, an inorganic base, an organic base and the like are used as a base. Specifically, for example, sodium hydroxide, potassium hydroxide, sodium carbonate, potassium carbonate, cesium carbonate, sodium hydrogen carbonate, potassium hydrogen carbonate, triethylamine, N-ethyldiisopropylamine, pyridine, N,N-dimethylaminopyridine, sodium methoxide, sodium ethoxide, potassium t-butoxide, sodium hydride, sodium amide, diazabicycloundecene (DBU) and the like are used.

In the present production methods, palladium complexes described in, for example, J. Am. Chem. Soc. 1994, 116, 5969-5970, J. Am. Chem. Soc. 1994, 116, 7901-7902, Pure Appl. Chem., 71(8), 1417-1423, 1999 and the like, and the like are used as palladium complexes.

In the present production methods, lithium, sodium, potassium, cesium and the like are used as alkali metals.

In the present production methods, magnesium, calcium and the like are used as alkaline earth metals.

In the present production methods, for example, trityl, 4-methoxybenzyl, acetamidomethyl, tert-butyl and the like can be mentioned as mercapto-protecting groups.

In the present production methods, a starting compound and a production intermediate may be salts. As such salt, those similar to the salts of the aforementioned compound of the present invention can be mentioned.

1. Production Method of Compound (I)

Compound (I) of the present invention can be obtained, for example, according to the following conversion reaction of (I-A) into (I), or a method analogous thereto, and the like. The reaction scheme is shown below. Each symbol in the compounds in the scheme is as defined above, and compound (I-A) encompasses compound (I).

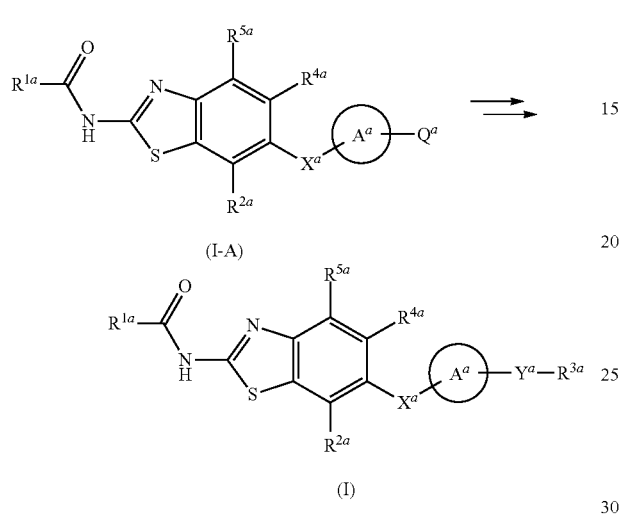

wherein $Q^a$ is any functional group convertable to $Y^a$—$R^{3a}$, or may be $Y^a$—$R^{3a}$ by itself, and other symbols are as defined above.

Compound (I) can be obtained by converting $Q^a$ in compound (I-A) as necessary to a suitable functional group.

For example, compound (I-A) [$Q^a$=COOH] can be converted to (I) [$Y^a$=CONH] by a known general amidation reaction, and can be converted to compound (1) [$Y^a$=NHCO], or compound (I) [$Y^a$=NHCONH] by performing a Curtius rearrangement reaction and then a known general functional group conversion reaction, followed by a known general amidation reaction or ureation reaction.

For example, compound (I-A) [$Q^a$=NO$_2$] can be converted to compound (I-A) [$Q^a$=NH$_2$] by a known general reduction reaction, and then to compound (I) [$Y^a$=NHCO], or compound (I) [$Y^a$=NHCONH] by a known general amidation reaction or ureation reaction. In addition, compound (I-A) [$Q^a$=NH$_2$] can be converted to compound (I) [$Y^a$=NH] by a known general reductive amination reaction or a known general coupling reaction using a palladium catalyst and the like.

In the above formula, (I-A) can be obtained by the following Method A, Method B or Method C, or a method analogous thereto and the like.

Method A:

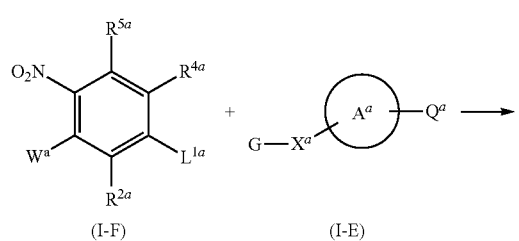

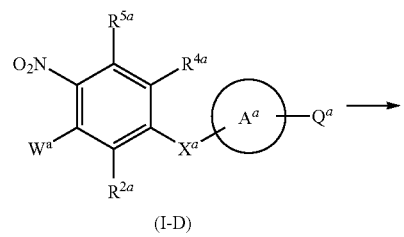

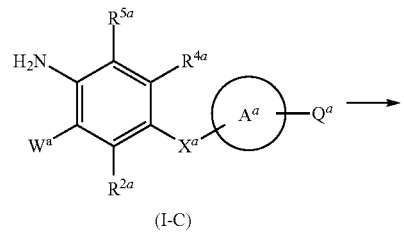

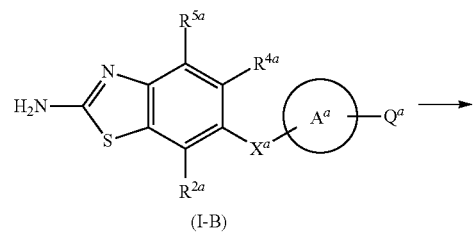

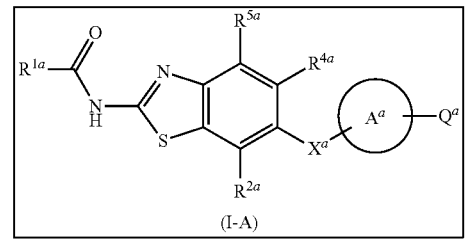

wherein $W^a$ is $SR^{9a}$, SCN or a hydrogen atom, $R^{9a}$ is a hydrogen atom or a protecting group, $L^{1a}$ is a leaving group, G is a hydrogen atom or a metal atom and other symbols are as defined above.

The starting compound (I-A) of this production method can be produced, for example, by subjecting a compound represented by the formula:

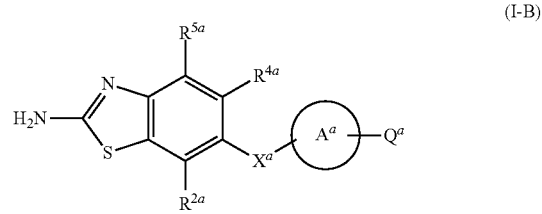

wherein each symbol is as defined above, to a known general acylation reaction using carboxylic acid represented by $R^{1a}$—COOH ($R^{1a}$ is as defined above) or a reactive derivative thereof.

The starting compound (I-B) can be produced, for example, from a compound represented by the formula:

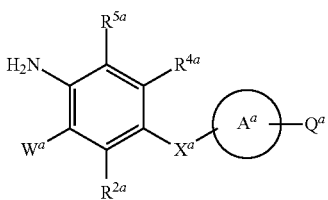

(I-C)

wherein each symbol is as defined above. For example, compound (I-C) [$W^a$=$SR^{9a}$] is converted to compound (I-C) [$W^a$=SH] as necessary by a known general deprotection, which is reacted with cyanogen bromide or 1,1-di-1H-imidazol-1-ylmethanimine to give compound (I-B).

The reaction here is preferably performed in a solvent using 1-10 equivalents, preferably 1-5 equivalents, of cyanogen bromide or 1,1-di-1H-imidazol-1-ylmethanimine relative to compound (I-C) [$W^a$=SH]. In addition, 0 to 10 equivalents, preferably 0 to 2 equivalents, of a base may be used relative to compound (I-C) [$W^a$=SH].

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

For example, compound (I-C) [$W^a$=SCN] can also be converted to compound (I-B) by reacting compound (I-C) [$W^a$=SCN] with 1-10 equivalents, a solvent amount in some cases, preferably 1-5 equivalents of an acid.

As the acid in this reaction, hydrochloric acid, acetic acid, sulfuric acid and the like are used. Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water, acetic acid or a mixed solvent thereof and the like.

The aforementioned reaction can be performed under cooling (about −78° C. 20° C., preferably about −10° C. to 10° C.), at room temperature or under heating (about 40° C.-200° C., preferably about 40° C.-160° C.), and the reaction time is generally about 1-30 hr, preferably about 1-20 hr, more preferably about 1-10 hr.

For example, compound (I-C) [$W^a$=H] can also be converted to compound (I-B) by reacting compound (I-C) [$W^a$=H] with potassium thiocyanate, sodium thiocyanate or ammonium thiocyanate and bromine. In this reaction, compound (I-C) [$W^a$=H] is preferably reacted with 1-10 equivalents, preferably 1-5 equivalents, of potassium thiocyanate, sodium thiocyanate or ammonium thiocyanate and 1-5 equivalents, preferably 1-2 equivalents, of bromine in a solvent.

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water, acetic acid or a mixed solvent thereof and the like can be used.

The aforementioned reaction can be performed under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

The starting compound (I-C) can be produced, for example, by subjecting a compound represented by the formula:

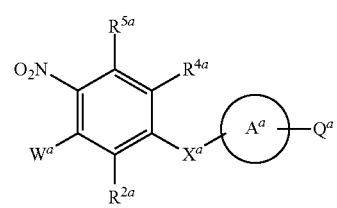

(I-D)

wherein each symbol is as defined above, to a known general reduction reaction to convert nitro to amino.

Compound (I-D) [$W_a$=SCN] can also be directly converted to compound (I-B) by this reduction reaction, without forming compound (I-C) [$W^a$=SCN].

For example, Compound (I-D) [$W^a$=SCN] can also be directly converted to compound (I-B) by reacting compound (I-D) [$W^a$=SCN] with reduced iron in the presence of an acid, without forming compound (I-C) [$W^a$=SCN].

In this reaction, 1-10 equivalents, preferably 1-5 equivalents, of reduced iron and 1-20 equivalents, a solvent amount in some cases, preferably 1-10 equivalents, of an acid are preferably used relative to compound (I-D) [$W^a$=SCN] in a solvent.

As the acid in this reaction, hydrochloric acid, acetic acid, sulfuric acid and the like are used. Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water, acetic acid or a mixed solvent thereof and the like are used.

The aforementioned reaction can be performed under cooling (about −78° C. 20° C., preferably about −10° C. 10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (I-D) can be produced, for example, by reacting a compound represented by the formula:

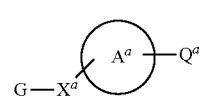

(I-E)

wherein each symbol is as defined above, or a salt thereof with a compound represented by the formula:

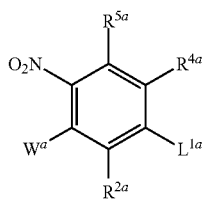

(I-F)

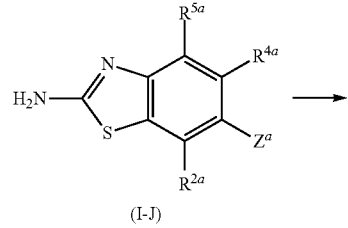

(I-J)

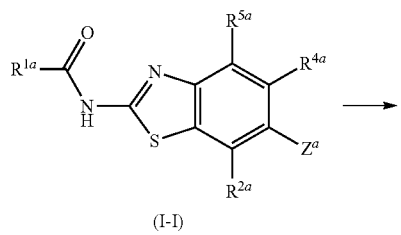

(I-I)

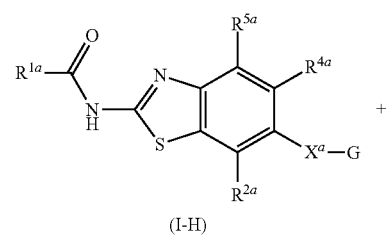

(I-H)

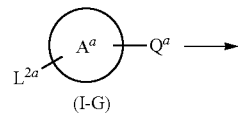

(I-G)

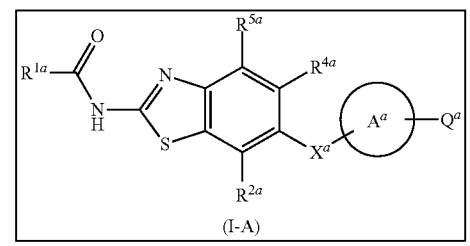

(I-A)

wherein each symbol is as defined above.

In compound (I-E) wherein $X^a$ is —$NR^{8a}$— [$R^{8a}$ is as defined above], —O— or —S—, G is mainly a hydrogen atom but may also be alkali metal or alkaline earth metal.

In compound (I-F), as a leaving group represented by $L^{1a}$, a halogen atom such as fluorine, chlorine, bromine, iodine and the like, a group represented by the formula —$S(O)_k OR^{10a}$ wherein k is 0, 1 or 2 and $R^{10a}$ is $C_{1-4}$ alkyl (e.g., methyl, ethyl, propyl), benzyl, $C_{6-10}$ aryl (e.g., phenyl, tolyl), or a group represented by the formula —$OR^{10a}$ wherein $R^{10a}$ is as defined above is used.

The reaction is preferably performed using 1-5 equivalents, preferably 1-2 equivalents, of compound (I-E) or a salt thereof relative to compound (I-F) in a solvent. In addition, 1 to 10 equivalents, preferably 1 to 2 equivalents, of a base or ammonium salt may be used relative to compound (I-F).

As a catalyst, 0.05-10 equivalents, preferably 0.05-2 equivalents, of a palladium complex may be used relative to compound (I-F).

As the solvent for the aforementioned reaction, for example, halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphoramide, water or a mixed solvent thereof and the like can be used.

The aforementioned reaction can be performed under cooling (about −78 to 20° C., preferably about −10 to 10° C.), at room temperature or under heating (about 40 to 200° C., preferably about 40 to 160° C.), and the reaction time is generally about 1 to 30 hr, preferably about 1 to 20 hr, more preferably about 1 to 10 hr.

In addition, the reaction may be performed under microwave irradiation.

The starting compound (I-E) and compound (I-F) may be commercially available or can be produced from the corresponding starting compound by a means known per se.

Method B:

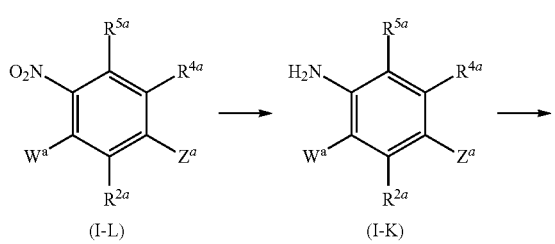

wherein $W^a$ is $SR^{9a}$, SCN is a hydrogen atom, $R^{9a}$ is a hydrogen atom or a protecting group, $Z^a$ is any functional group convertable to $X^a$-G or $X^a$-G by itself, $L^{2a}$ is a leaving group, G is a hydrogen atom or a metal atom and other symbols are as defined above.

The starting compound (I-A) of this production method can also be produced, for example, by reacting a compound represented by the formula:

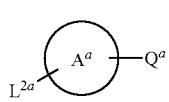

(I-G)

wherein each symbol is as defined above, with a compound represented by the formula:

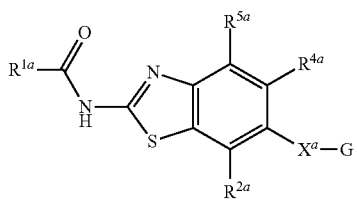

(I-H)

wherein each symbol is as defined above.

In compound (I-G), as a leaving group represented by $L^{2a}$, those similar to the aforementioned leaving group represented by $L^{1a}$ can be mentioned.

In compound (I-H) wherein $X^a$ is —$NR^{8a}$— [$R^{8a}$ is as defined above], —O— or —S—, G is mainly a hydrogen atom but may also be alkali metal or alkaline earth metal.

The reaction is preferably performed using 1-5 equivalents, preferably 1-2 equivalents, of compound (I-H) or a salt thereof relative to compound (I-G) in a solvent. In addition, 1 to 10 equivalents, preferably 1 to 2 equivalents, of a base or ammonium salt may be used relative to compound (I-G). As a catalyst, 0.05-10 equivalents, preferably 0.05-2 equivalents, of a palladium complex may be used relative to compound (I-G).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (I-G) may be commercially available, or can be produced from the corresponding starting compound by a means known per se.

The starting compound (I-H) can be produced, for example, by converting $Z^a$ in a compound represented by the formula:

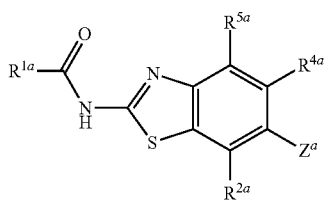

(I-I)

wherein each symbol is as defined above, to a known suitable general functional group as necessary.

For example, compound (I-I) [$Z^a$=$NO_2$] can be converted to compound (I-H) [$X^a$-G=NH—H] by a known general reduction reaction, and then to compound (I-H) [$X^a$-G=$NR^{8a}$—H, $R^{ea}$ is as defined above] by a known general reductive amination reaction or a known general coupling reaction using a palladium catalyst and the like. For example, compound (I-I) [$Z^a$=$SR^{9a}$, $OR^{9a}$; $R^{9a}$ is as defined above] can be converted to compound (I-H) [$X^a$-G=S—H, O—H] as necessary by a known general deprotection.

The starting compound (I-I) can be produced, for example, by subjecting a compound represented by the formula:

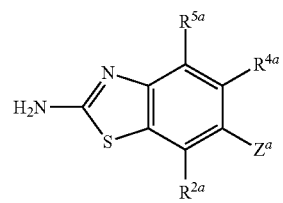

(I-J)

wherein each symbol is as defined above, to a known general acylation reaction using carboxylic acid represented by $R^{1a}$—COOH ($R^{1a}$ is as defined above) or a reactive derivative thereof.

The starting compound (I-J) can be produced, for example, from a compound represented by the formula:

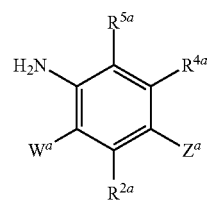

(I-K)

wherein each symbol is as defined above. For example, compound (I-K) [$W^a$=$SR^{9a}$; $R^{9a}$ is as defined above] is converted to compound (I-K) [$W^a$=SH] as necessary by a known general deprotection, which is reacted with cyanogen bromide or 1,1-di-1H-imidazol-1-ylmethanimine to give compound (I-J).

In this reaction, compound (I-K) [$W^a$=SH] is reacted with 1-10 equivalents, preferably 1-5 equivalents, of cyanogen bromide or 1,1-di-1H-imidazol-1-ylmethanimine in a solvent. In addition, 0 to 10 equivalents, preferably 0 to 2 equivalents, of a base may be used relative to compound (I-K) [$W^a$=SH].

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C. 200° C., preferably about 40° C.-160° C.), and the reaction time is generally about 1-30 hr, preferably about 1-20 hr, more preferably about 1-10 hr.

For example, compound (I-K) [$W^a$=SCN] can also be converted to compound (I-J) by reacting compound (I-K) [$W^a$=SCN] with 1-10 equivalents, a solvent amount in some cases, preferably 1-5 equivalents, of an acid.

As the acid in this reaction, hydrochloric acid, acetic acid, sulfuric acid and the like are used. Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water, acetic acid or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr. For example, compound (I-K) [$W^a$=H] can also be converted to compound (I-J) by reacting compound (I-K) [$W^a$=H] with potassium thiocyanate, sodium thiocyanate or ammonium thiocyanate and bromine. In this reaction, compound (I-K) [$W^a$=H] is preferably reacted with 1-10 equivalents, preferably 1-5 equivalents, of potassium thiocyanate, sodium thiocyanate or ammonium thiocyanate, and 1-5 equivalents, preferably 1-2 equivalents, of bromine in a solvent.

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water, acetic acid or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (I-K) may be commercially available, or can be produced by converting nitro to amino by subjecting a compound represented by the formula:

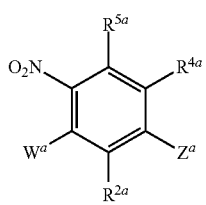

(I-L)

wherein each symbol is as defined above, to a known general reduction reaction.

In addition, compound (I-L) [$W^a$=SCN] can also be converted directly to compound (I-J) by this reduction reaction, without forming compound (I-K) [$W^a$=SCN].

For example, compound (I-L) [$W^a$=SCN] can be directly converted to compound (I-J) by reacting compound (I-L) [$W^a$=SCN] with reduced iron in the presence of an acid, without forming compound (I-K) [$W^a$=SCN].

In this reaction, compound (I-L) [$W^a$=SCN] is preferably reacted with 1-10 equivalents, preferably 1-5 equivalents, of reduced iron, and 1-20 equivalents, a solvent amount in some cases, preferably 1-10 equivalents, of acid in a solvent.

As the acid in this reaction, hydrochloric acid, acetic acid, sulfuric acid and the like are used. Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water, acetic acid or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (I-L) may be commercially available, or can be produced from the corresponding starting compound by a means known per se.

Method C

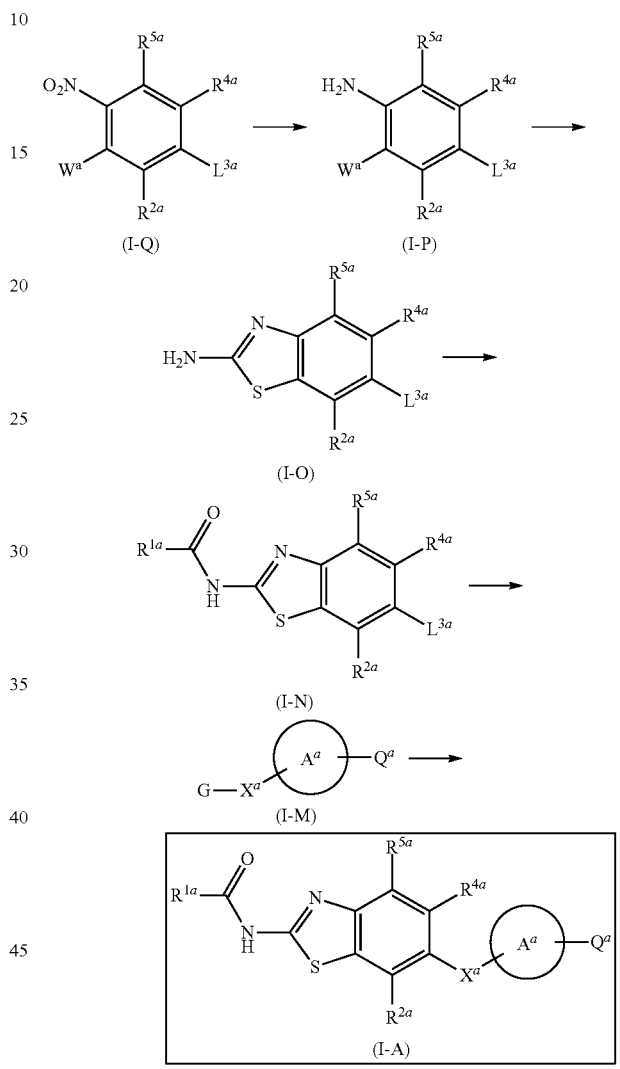

wherein $W^a$ is $SR^{9a}$, SCN or a hydrogen atom, $R^{9a}$ is a hydrogen atom or a protecting group, $L^{3a}$ is a leaving group, G is a hydrogen atom or a metal atom and other symbols are as defined above.

The starting compound (I-A) can also be produced, for example, by reacting a compound represented by the formula:

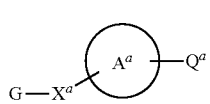

(I-M)

wherein each symbol is as defined above, with a compound represented by the formula:

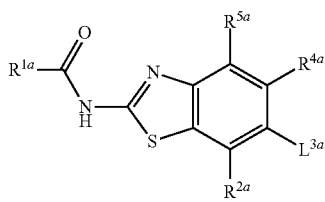

(I-N)

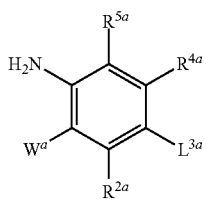

(I-P)

wherein each symbol is as defined above.

In compound (I-M) wherein $X^a$ is —$NR^{8a}$— [$R^{8a}$ is as defined above], —O— or —S—, G is mainly a hydrogen atom but may also be alkali metal or alkaline earth metal.

In compound (I-N), as a leaving group represented by $L^{3a}$, one similar to the aforementioned leaving group represented by $L^{1a}$ is used.

The reaction is preferably performed using 1-5 equivalents, preferably 1-2 equivalents, of compound (I-M) or a salt thereof relative to compound (I-N) in a solvent. In addition, 1 to 10 equivalents, preferably 1 to 2 equivalents, of a base or ammonium salt may be used relative to compound (I-N). As a catalyst, 0.05-10 equivalents, preferably 0.05-2 equivalents, of a palladium complex may be used relative to compound (I-N).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (I-M) may be commercially available, or can be produced from the corresponding starting compound by a means known per se.

The starting compound (I-N) can be produced, for example, by subjecting a compound represented by the formula:

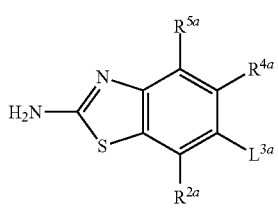

(I-O)

wherein each symbol is as defined above, to a known general acylation reaction using carboxylic acid represented by $R^{1a}$—COOH ($R^{1a}$ is as defined above) or a reactive derivative thereof.

The starting compound (I-O) can be produced, for example, from a compound represented by the formula:

wherein each symbol is as defined above. For example, compound (I-P) [$W^a$=$SR^{9a}$; $R^{9a}$ is as defined above] is converted to compound (I-P) [$W^a$=SH] as necessary by a known general deprotection, which is reacted with cyanogen bromide or 1,1-di-1H-imidazol-1-ylmethanimine to give compound (I-O).

In this reaction, compound (I-P) [$W^a$=SH] is preferably reacted with 1-10 equivalents, preferably 1-5 equivalents, of cyanogen bromide or 1,1-di-1H-imidazol-1-ylmethanimine in a solvent. In addition, 0 to 10 equivalents, preferably 0 to 2 equivalents, of a base may be used relative to compound (I-P) [$W^a$=SH].

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

For example, compound (I-P) [$W^a$=SCN] can also be converted to compound (I-O) by reacting compound (I-P) [$W^a$=SCN] with 1-10 equivalents, a solvent amount in some cases, preferably 1-5 equivalents, of an acid.

As the acid in this reaction, hydrochloric acid, acetic acid, sulfuric acid and the like are used. Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water, acetic acid or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

For example, compound (I-P) [$W^a$=H] can also be converted to compound (I-O) by reacting compound (I-P) [$W^a$=H] with potassium thiocyanate, sodium thiocyanate or ammonium thiocyanate and bromine.

In this reaction, compound (I-P) [$W^a$=H] is preferably reacted with 1-10 equivalents, preferably 1-5 equivalents, of potassium thiocyanate, sodium thiocyanate or ammonium thiocyanate, and 1-5 equivalents, preferably 1-2 equivalents, of bromine in a solvent.

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2- pyrrolidone, dimethyl sulfoxide, hexamethylphosphramide, water, acetic acid or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (I-P) can be produced by converting nitro to amino by subjecting a compound represented by the formula:

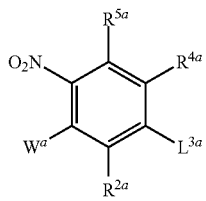

(I-Q)

wherein each symbol is as defined above, to a known general reduction reaction.

In addition, compound (I-Q) [$W^a$=SCN] can also be directly converted to compound (I-O), without forming compound (I-P) [$W^a$=SCN] by this reduction reaction.

For example, compound (I-Q) [$W^a$=SCN] is reacted with reduced iron in the presence of an acid to directly produce compound (I-O), without forming compound (I-P) [$W^a$=SCN].

In this reaction, compound (I-Q) [$W^a$=SCN] is reacted with reduced iron (1-10 equivalents, preferably 1-5 equivalents), and 1-20 equivalents, a solvent amount in some cases, preferably 1-10 equivalents, of an acid in a solvent.

As the acid in this reaction, hydrochloric acid, acetic acid, sulfuric acid and the like are used. Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water, acetic acid or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (I-Q) of Method C may be commercially available, or can be produced from the corresponding starting compound by a means known per se.

2. Production Method of Compound (II)

The production methods of compound (II) of the present invention are described in the following.

Compound (II) of the present invention can be obtained, for example, according to the following conversion reaction of compound (II-A) into compound (II), or a method analogous thereto, and the like. The reaction scheme is shown below. Each symbol in the compounds in the scheme is as defined above, and compound (II-A) encompasses compound (II).

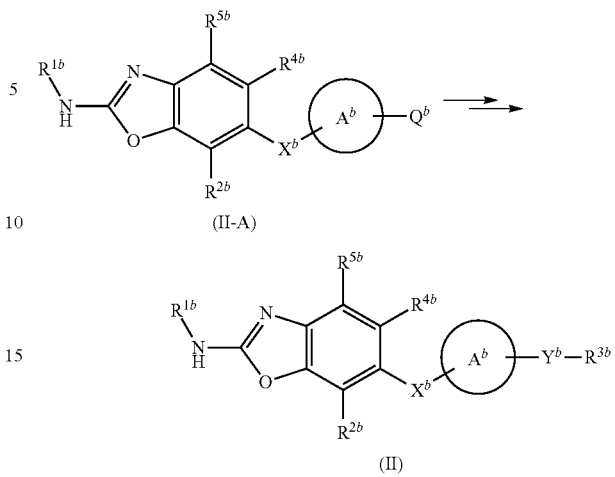

wherein $Q^b$ is any functional group convertable to $Y^b$—$R^{3b}$, or may be $Y^b$—$R^{3b}$ by itself, and other symbols are as defined above.

Compound (II) can be obtained by converting $Q^b$ in compound (II-A) as necessary to a suitable functional group.

For example, compound (II-A) [$Q^b$=COOH] can be converted to compound (II) [$Y^b$=CONH] by a known general amidation reaction, and can be converted to compound (II) [$Y^b$=NHCO], or compound (II) [$Y^b$=NHCONH] by performing a Curtius rearrangement reaction and then a known general functional group conversion reaction, followed by a known general amidation reaction or ureation reaction.

For example, compound (II-A) [$Q^b$=NO_2$] can be converted to compound (II-A) [$Q^b$=NH_2$] by a known general reduction reaction, and then to compound (II) [$Y^b$=NHCO], or compound (II) [$Y^b$=NHCONH] by a known general amidation reaction or ureation reaction. In addition, compound (II-A) [$Q^b$=NH_2$] can be converted to compound (II) [$Y^b$=NH] by a known, general reductive amination reaction or a known general coupling reaction using a palladium catalyst and the like.

Compound (II-A) can be obtained by the following Method A, Method B or Method C, or a method analogous thereto and the like.

Method A:

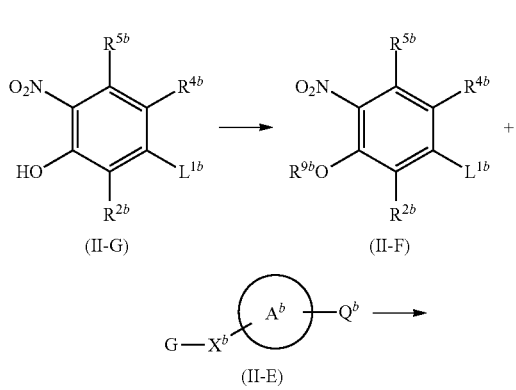

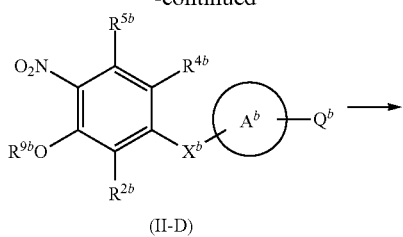

(II-D)

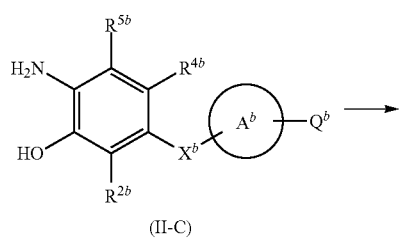

(II-C)

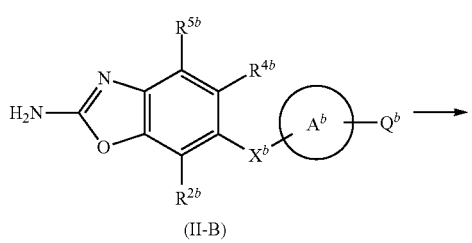

(II-B)

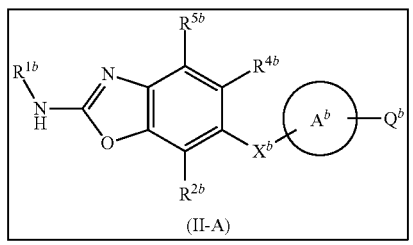

(II-A)

wherein $R^{9b}$ is a hydrogen atom or a protecting group, G is a hydrogen atom or a metal atom, $L^{1b}$ is a leaving group, and other symbols are as defined above.

The starting compound (II-A) ($R^{1b}$ is acyl) of this production method can be produced, for example, by subjecting a compound represented by the formula:

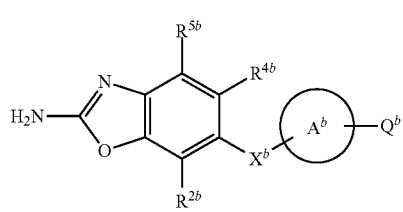

(II-B)

wherein each symbol is as defined above, to a known general acylation reaction using carboxylic acid represented by $R^{1b}$—OH ($R^{1b}$ is acyl) or a reactive derivative thereof.

The starting compound (II-B) can be produced, for example, by reacting a 2-aminophenol derivative represented by the formula:

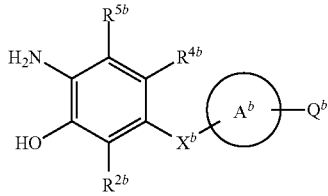

(II-C)

wherein each symbol is as defined above, with cyanogen bromide, cyanamide or 1,1-di-1H-imidazol-1-ylmethanimine.

The reaction is preferably performed using 1-10 equivalents, preferably 1-5 equivalents, of cyanogen bromide, cyanamide or 1,1-di-1H-imidazol-1-ylmethanimine relative to compound (II-C) in a solvent. In addition, 0 to 10 equivalents, preferably 0 to 2 equivalents, of a base may be used relative to compound (II-C).

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like are used.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (II-C) can be produced, for example, by converting a 2-nitrophenol derivative represented by the formula:

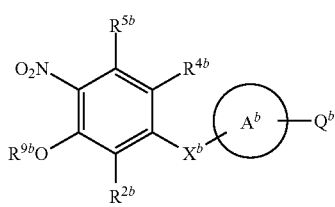

(II-D)

wherein each symbol is as defined above, to compound (II-D) [$R^{9b}$=H] as necessary by a known general deprotection, and converting nitro to amino by a known general reduction reaction. Particularly, compound (II-D) [$R^{9b}$=CH$_2$C$_6$H$_5$] can also be directly converted to compound (II-C) by a known general catalytic hydrogenation reaction.

The starting compound (II-D) can be produced, for example, by reacting a compound represented by the formula:

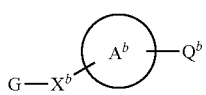

(II-E)

wherein each symbol is as defined above, or a salt thereof with a compound represented by the formula:

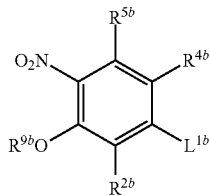

(II-F)

wherein each symbol is as defined above.

In compound (II-E) wherein $X^b$ is —$NR^{8b}$— [$R^{8b}$ is a hydrogen atom or any alkyl or aryl], —O— or —S—, G is mainly a hydrogen atom but may also be alkali metal or alkaline earth metal.

In compound (II-F), as a leaving group represented by $L^{1b}$, a halogen atom such as fluorine, chlorine, bromine, iodine and the like, a group represented by the formula —$S(O)_kR^{10b}$ wherein k is 0, 1 or 2, $R^{10b}$ is $C_{1-4}$ alkyl (e.g., methyl, ethyl, propyl), benzyl, $C_{6-10}$ aryl (e.g., phenyl, tolyl)] or a group represented by the formula —$OR^{10b}$ wherein $R^{10b}$ is as defined above is used.

The reaction is preferably performed using 1-5 equivalents, preferably 1-2 equivalents, of compound (II-E) or a salt thereof relative to compound (II-F) in a solvent. In addition, 1 to 10 equivalents, preferably 1 to 2 equivalents, of a base or ammonium salt may be used relative to compound (II-F). As a catalyst, 0.05-10 equivalents, preferably 0.05-2 equivalents, of a palladium complex may be used relative to compound (II-F).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (II-E) may be commercially available, or can be produced from the corresponding starting compound by a means known per se.

The starting compound (II-F) can be produced, for example, by introducing a protecting group $R^{9b}$ into a compound represented by the formula:

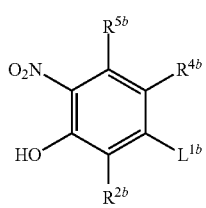

(II-G)

wherein each symbol is as defined above, by a known general reaction.

The starting compound (II-G) may be commercially available, or can be produced from the corresponding starting compound by a means known per se.

Method B:

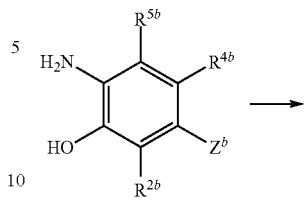

(II-L)

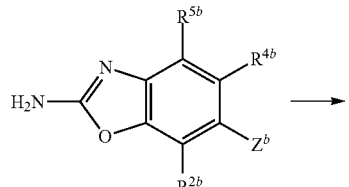

(II-K)

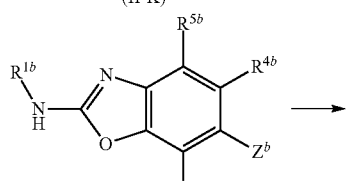

(II-J)

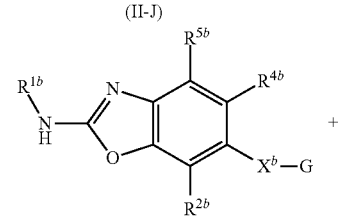

(II-I)

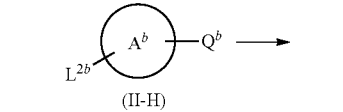

(II-H)

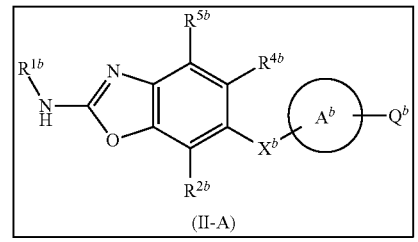

(II-A)

wherein $Z^b$ is any functional group convertable to $X^b$-G or may be $X^b$-G by itself, $L^{2b}$ is a leaving group, and other symbols are as defined above.

The starting compound (II-A) of this production method can also be produced, for example, by reacting a compound represented by the formula:

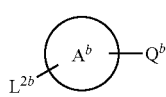

(II-H)

wherein each symbol is as defined above, with a compound represented by the formula:

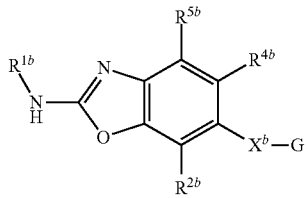

(II-I)

wherein each symbol is as defined above.

In compound (II-H), as a leaving group represented by $L^{2b}$, one similar to the aforementioned leaving group represented by $L^{1b}$ is used.

In compound (II-I) wherein $X^b$ is —$NR^{8b}$— [$R^{8b}$ is a hydrogen atom or any alkyl or aryl], —O— or —S—, G is mainly a hydrogen atom but may also be alkali metal or alkaline earth metal.

The reaction is preferably performed using 1-5 equivalents, preferably 1-2 equivalents, of compound (II-I) or a salt thereof relative to compound (II-H) in a solvent. In addition, 1 to 10 equivalents, preferably 1 to 2 equivalents, of a base or ammonium salt may be used relative to compound (II-H). As a catalyst, 0.05-10 equivalents, preferably 0.05-2 equivalents, of a palladium complex may be used relative to compound (II-H).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (II-H) may be commercially available, or can be produced from the corresponding starting compound by a means known per se.

The starting compound (II-I) can be produced, for example, by converting $Z^b$ in a compound represented by the formula:

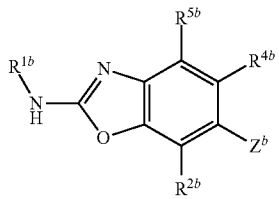

(II-J)

wherein each symbol is as defined above, as necessary to a known general and suitable functional group. For example, compound (II-J) [$Z^b$=$NO_2$] can be converted to compound (II-I) [$X^b$-G=NH—H] by a known general reduction reaction, and thereafter to compound (II-I) [$X^b$-G=$NR^{8b}$—H, $R^{8b}$ is as defined above] by a known general reductive amination reaction or a known general coupling reaction using a palladium catalyst and the like. For example, compound (II-J) [$Z^b$=$SR^{11b}$, $OR^{11b}$; $R^{11b}$ is a protecting group] can be converted to compound (II-I) [$X^b$-G=S—H, O—H] by a known general deprotection.

The starting compound (II-J) ($R^{1b}$ is acyl) can be produced, for example, by subjecting a compound represented by the formula:

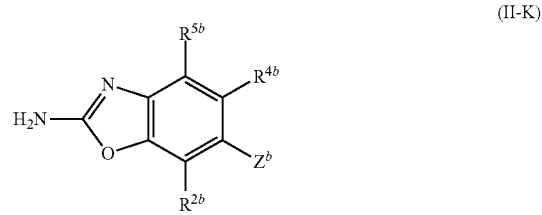

(II-K)

wherein each symbol is as defined above, to a known general acylation reaction using carboxylic acid represented by $R^{1b}$—OH ($R^{1b}$ is acyl) or a reactive derivative thereof.

The starting compound (II-K) can be produced, for example, by reacting a 2-aminophenol derivative represented by the formula:

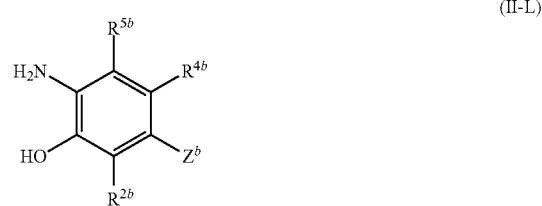

(II-L)

wherein each symbol is as defined above, with cyanogen bromide, cyanamide or 1,1-di-1H-imidazol-1-ylmethanimine.

The reaction is preferably performed using 1-10 equivalents, preferably 1-5 equivalents, of cyanogen bromide, cyanamide or 1,1-di-1H-imidazol-1-ylmethanimine relative to compound (II-L) in a solvent. In addition, 0 to 10 equivalents, preferably 0 to 2 equivalents, of a base may be used relative to compound (II-L).

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like are used.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (II-L) may be commercially available, or can be produced from the corresponding starting compound by a means known per se.

Method C

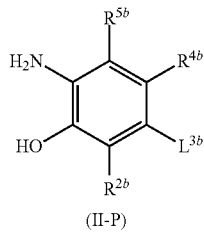

(II-P)

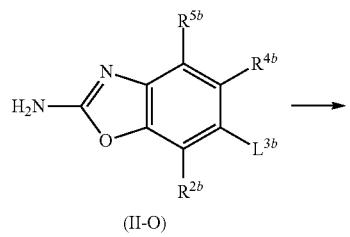

(II-O)

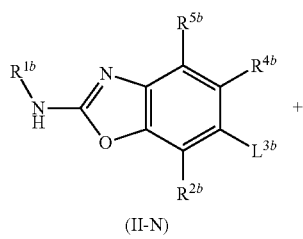

(II-N)

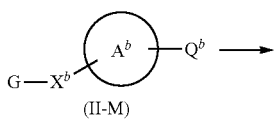

(II-M)

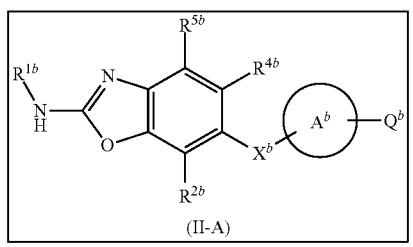

(II-A)

wherein $L^{3b}$ is a leaving group, and other symbols are as defined above.

The starting compound (II-A) can also be produced, for example, by reacting a compound represented by the formula:

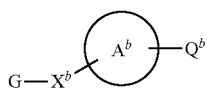

(II-M)

wherein each symbol is as defined above, with a compound represented by the formula:

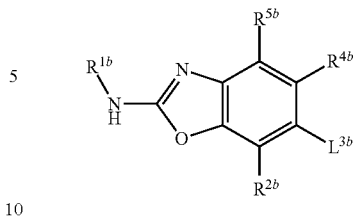

(II-N)

wherein each symbol is as defined above.

In compound (II-M) wherein $X^b$ is $—NR^{8b}—$ [$R^{8b}$ is a hydrogen atom or any alkyl or aryl], —O— or —S—, G is mainly a hydrogen atom but may also be alkali metal or alkaline earth metal.

In compound (II-N), as a leaving group represented by $L^{3b}$, one similar to the aforementioned leaving group represented by $L^{1b}$ is used.

The reaction is preferably performed using 1-5 equivalents, preferably 1-2 equivalents, of compound (II-M) or a salt thereof relative to compound (II-N) in a solvent. In addition, about 1 to 10 equivalents, preferably 1 to 2 equivalents, of a base or ammonium salt may be used relative to compound (II-N). As a catalyst, 0.05-10 equivalents, preferably 0.05-2 equivalents, of a palladium complex may be used relative to compound (II-N).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like are used.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (II-M) may be commercially available, or can be produced from the corresponding starting compound by a means known per se.

The starting compound (II-N) ($R^{1b}$ is acyl) can be produced, for example, by subjecting a compound represented by the formula:

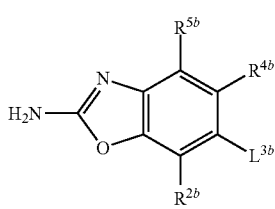

(II-O)

wherein each symbol is as defined above, to a known general acylation reaction using carboxylic acid represented by $R^{1b}$-OH ($R^{1b}$ is acyl) or a reactive derivative thereof.

In compound (II-O), as a leaving group represented by $L^{3b}$, one similar to the aforementioned leaving group represented by $L^{1b}$ is used.

The starting compound (II-O) can be produced, for example, by reacting a 2-aminophenol derivative represented by the formula:

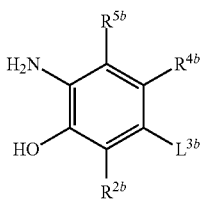

(II-P)

wherein each symbol is as defined above, with cyanogen bromide, cyanamide or 1,1-di-1H-imidazol-1-ylmethanimine.

In compound (II-P), as a leaving group represented by $L^{3b}$, one similar to the aforementioned leaving group represented by $L^{1b}$ is used.

The reaction is preferably performed using 1-10 equivalents, preferably 1-5 equivalents, of cyanogen bromide, cyanamide or 1,1-di-1H-imidazol-1-ylmethanimine relative to compound (II-P) in a solvent. In addition, 0 to 10 equivalents, preferably 0 to 2 equivalents, of a base may be used relative to compound (II-P).

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like are used.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (II-P) may be commercially available, or can be produced from the corresponding starting compound by a means known per se.

3. Production Method of Compound (III)

Compound (III) of the present invention can be obtained, for example, by a conversion reaction of compound (III-A) to compound (III) shown below or a method analogous thereto and the like.

A schematic reaction formulas are shown in the following, wherein each symbol of compound in the schematic showing is as defined above, and compound (III-A) encompasses compound (III).

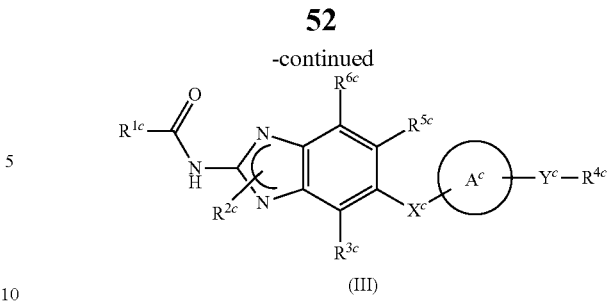

(III)

wherein $Q^c$ is any functional group convertable to $Y^c$-$R^{4c}$, or may be $Y^c$-$R^{4c}$ by itself, and other symbols are as defined above.

Compound (III) can be obtained by converting $Q^c$ in compound (III-A) to a suitable functional group.

For example, compound (III-A) [$Q^c$=COOH] can be converted to compound (III) [$Y^c$=CONH] by a known general amidation reaction, or to compound (III) [$Y^c$=NHCO] by a Curtius rearrangement reaction and thereafter by a known general functional group conversion reaction and a known general amidation reaction.

For example, compound (III-A) [$Q^c$=NO$_2$] can be converted to compound (III-A) [$Q^c$=NR$_2$] by a known general reduction reaction, and then to compound (III) [$Y^c$=NHCO] by a known general amidation reaction. In addition, compound (III-A) [$Q^c$=NH$_2$] can be converted to compound (III) [$Y^c$=NH] by a known general reductive amination reaction or a known general coupling reaction using a palladium catalyst and the like. For example, compound (III-A) [$Q^c$=NHR$^{10c}$; R$^{10c}$ is a proteccting group] can be converted to compound (III-A) [$Q^c$=NH$_2$] by a known general deprotection, and then to compound (III) [$Y^c$=NHCO] by a known general amidation reaction. In addition, compound (III-A) [$Q^c$=NH$_2$] can be converted to compound (III) [$Y^c$=NH] by a known general reductive amination reaction or a known general coupling reaction using a palladium catalyst and the like.

Compound (III-A) of the above formula can be obtained by the following Method A, Method B or Method C, or a method analogous thereto and the like.

Method A:

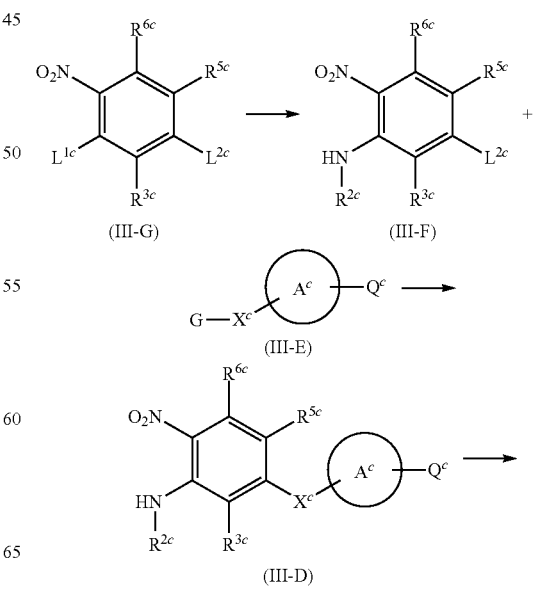

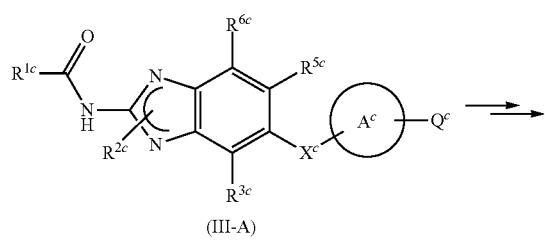

-continued

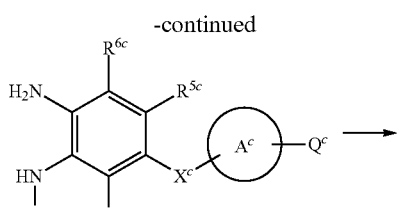
(III-C)

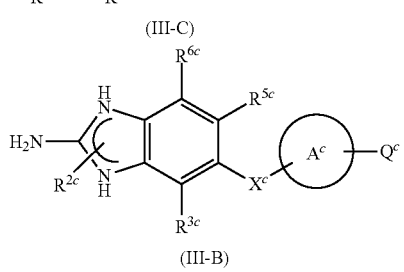
(III-B)

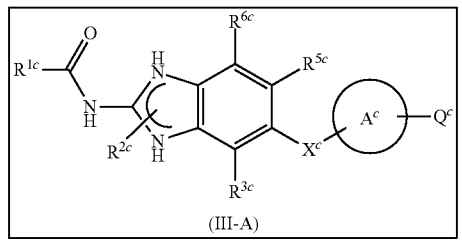
(III-A)

wherein $L^{1c}$ and $L^{2c}$ are leaving groups, G is a hydrogen atom or a metal atom, and other symbols are as defined above.

The starting compound (III-A) of this production method can be produced, for example, by subjecting a compound represented by the formula:

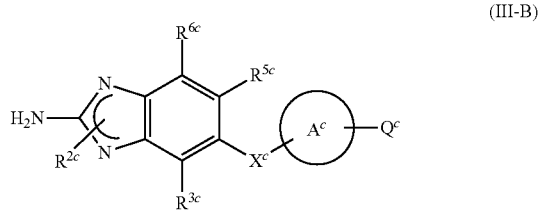
(III-B)

wherein each symbol is as defined above, to a known general acylation reaction using carboxylic acid represented by $R^{1c}$-COOH ($R^{1c}$ is as defined above) or a reactive derivative thereof.

The starting compound (III-B) can be produced, for example, by reacting a o-phenylenediamine derivative represented by the formula:

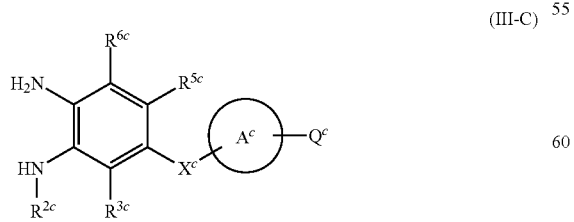
(III-C)

wherein each symbol is as defined above, with cyanogen bromide, cyanamide or 1,1-di-1H-imidazol-1-ylmethanimine.

The reaction is preferably performed using 1-10 equivalents, preferably 1-5 equivalents, of cyanogen bromide, cyanamide or 1,1-di-1H-imidazol-1-ylmethanimine relative to compound (III-C) in a solvent. In addition, 0 to 10 equivalents, preferably 0 to 2 equivalents, of a base may be used relative to compound (III-C).

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (III-C) can be produced, for example, by converting nitro to amino by subjecting a 2-nitroaniline derivative represented by the formula:

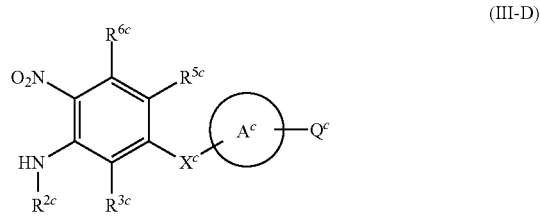
(III-D)

wherein each symbol is as defined above, to a known general reduction reaction.

The starting compound (III-D) can be produced, for example, by reacting a compound represented by the formula:

(III-E)

wherein each symbol is as defined above, or a salt thereof with a o-nitroaniline derivative represented by the formula:

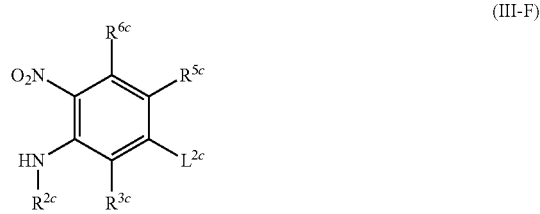
(III-F)

wherein each symbol is as defined above.

In compound (III-E) wherein $X^c$ is —$NR^{9c}$— [$R^{9c}$ is as defined above], —O— or —S—, G is mainly a hydrogen atom but may also be alkali metal or alkaline earth metal.

In compound (III-F), as a leaving group represented by $L^{2c}$, a halogen atom such as fluorine, chlorine, bromine, iodine and the like, a group represented by the formula —$S(O)_kR^{11c}$ wherein k is 0, 1 or 2 and $R^{11c}$ is $C_{1-4}$ alkyl (e.g., methyl, ethyl, propyl), benzyl, $C_{6-10}$ aryl (e.g., phenyl, tolyl), or a group represented by the formula —$OR^{11c}$ wherein $R^{11c}$ is as defined above is used.

The reaction is preferably performed using 1-5 equivalents, preferably 1-2 equivalents, of compound (III-E) or a salt thereof relative to compound (III-F) in a solvent. In addition, about 0 to 10 equivalents, preferably 0 to 2 equivalents, of a base or ammonium salt may be used relative to compound (III-F).

As a catalyst, 0.05-10 equivalents, preferably 0.05-2 equivalents, of a palladium complex may be used relative to compound (III-F).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (III-E) may be commercially available, or can be produced from the corresponding starting compound by a means known per se.

The starting compound (III-F) used may be commercially available or can be produced, for example, by reacting a compound represented by the formula:

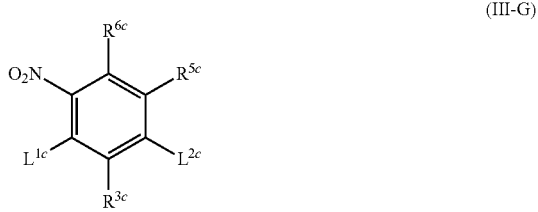

wherein each symbol is as defined above, with an amino compound represented by $R^{2c}NH_2$ ($R^{2c}$ is as defined above) under known general reaction conditions.

In compound (III-G), as a leaving group represented by $L^{1c}$, one similar to the aforementioned leaving group represented by $L^{2c}$ is used.

Starting compound (III-G) may be commercially available or can be produced from the corresponding starting compound according to a method known per se.

Method B:

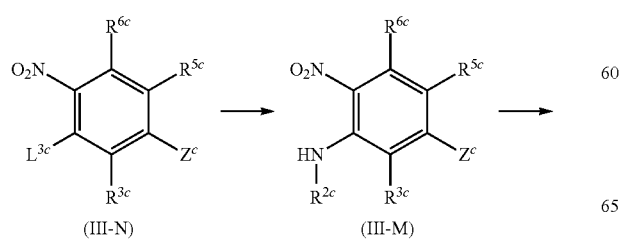

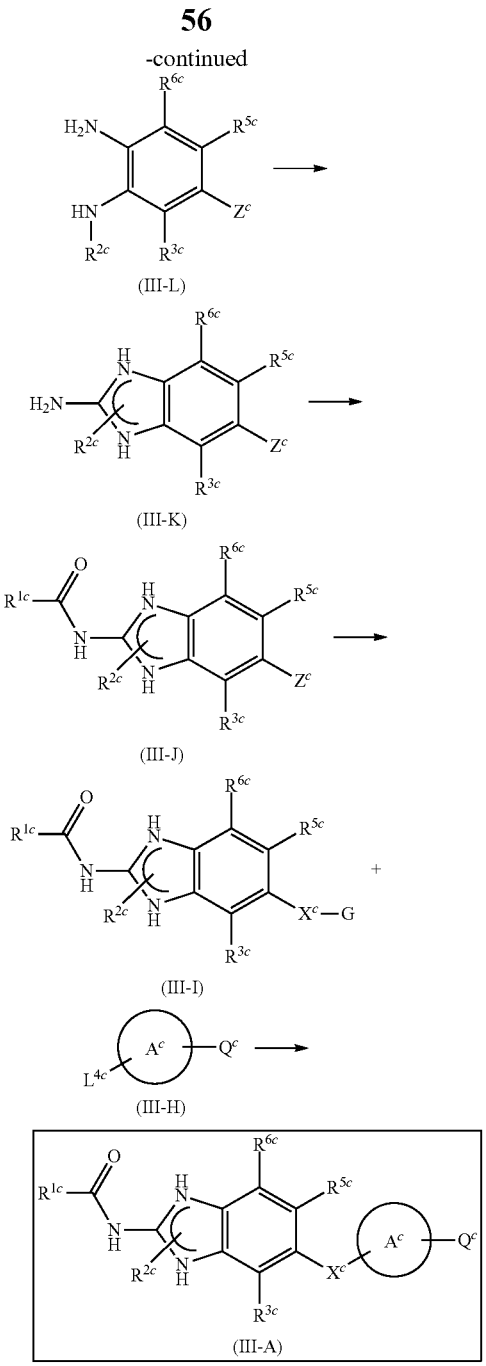

wherein $Z^c$ is any functional group convertible to $X^c$-G, or may be $X^c$-G by itself, $L^{4c}$ is a leaving group, and other symbols are as defined above.

The starting compound (III-A) can also be produced, for example, a compound represented by the formula:

wherein each symbol is as defined above, with a compound represented by the formula:

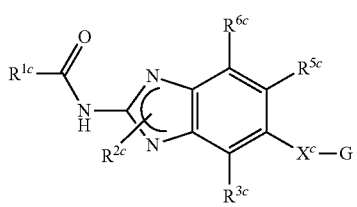

(III-I)

wherein each symbol is as defined above.

In compound (III-H), as a leaving group represented by $L^{4c}$, one similar to the aforementioned leaving group represented by $L^{2c}$ is used.

In compound (III-I) wherein $X^c$ is —$NR^{9c}$— [$R^{9c}$ is as defined above], —O— or —S—, G is mainly a hydrogen atom but may also be alkali metal or alkaline earth metal.

The reaction is preferably performed using 1-5 equivalents, preferably 1-2 equivalents, of compound (III-I) or a salt thereof relative to compound (III-H) in a solvent. In addition, about 1 to 10 equivalents, preferably 1 to 2 equivalents, of a base or ammonium salt may be used relative to compound (III-H). As a catalyst, 0.05-10 equivalents, preferably 0.05-2 equivalents, of a palladium complex may be used relative to compound (III-H).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (III-H) may be commercially available, or can be produced from the corresponding starting compound by a means known per se.

The starting compound (III-I) of Method B can be produced, for example, by converting $Z^c$ in a compound represented by the formula:

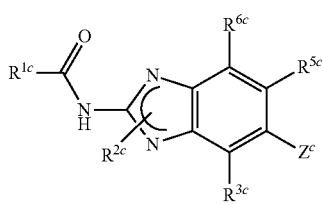

(III-J)

wherein each symbol is as, defined above, as necessary to a known general and suitable functional group. For example, compound (III-J) [$Z^c$=$NO_2$] can be converted to compound (III-I) [$X^c$-G=NH—H] by a known general reduction reaction, and thereafter to compound (III-I) [$X^c$-G=$NR^{9c}$—H, $R^9$ is as defined above] by a known general reductive amination reaction or a known general coupling reaction using a palladium catalyst and the like. For example, compound (III-J)

[$Z^c$=$SR^{12c}$, $OR^{12c}$; $R^{12c}$ is a hydrogen atom or a protecting group] can be converted to compound (III-I) [$X^c$-G=S—H, O—H] as necessary by a known general deprotection.

The starting compound (III-J) can be produced, for example, by subjecting a compound represented by the formula:

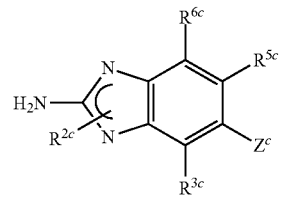

(III-K)

wherein each symbol is as defined above, to a known general acylation reaction using carboxylic acid represented by $R^{1c}$—COOH ($R^{1c}$ is as defined above) or a reactive derivative thereof.

The starting compound (III-K) of Method B can be produced, for example, by reacting a o-phenylenediamine derivative represented by the formula:

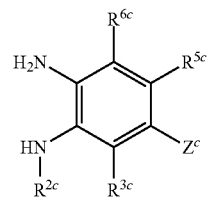

(III-L)

wherein each symbol is as defined above, with cyanogen bromide, cyanamide or 1,1-di-1H-imidazol-1-ylmethanimine.

The reaction is preferably performed using 1-10 equivalents, preferably 1-5 equivalents, of cyanogen bromide, cyanamide or 1,1-di-1H-imidazol-1-ylmethanimine relative to compound (III-L) in a solvent. In addition, 0 to 10 equivalents, preferably 0 to 2 equivalents, of a base may be used relative to compound (III-L).

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (III-L) of Method B may be commercially available, or can be produced by converting nitro to amino by subjecting a o-nitroaniline derivative represented by the formula:

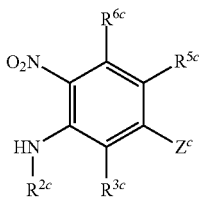

(III-M)

wherein each symbol is as defined above, to a known general reduction reaction.

The starting compound (III-M) may be commercially available, or can be produced by reacting a compound represented by the formula:

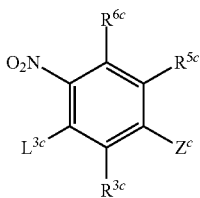

(III-N)

wherein $L^{3c}$ is a leaving group, and other symbols are as defined above, with an amino compound represented by $R^{2c}NH_2$ ($R^{2c}$ is as defined above) under known general reaction conditions.

In compound (III-N), as a leaving group represented by $L^{3c}$, one similar to the aforementioned leaving group represented by $L^{2c}$ is used.

The starting compound (III-N) may be commercially available, or can be produced from the corresponding starting compound by a means known per se.

Method C

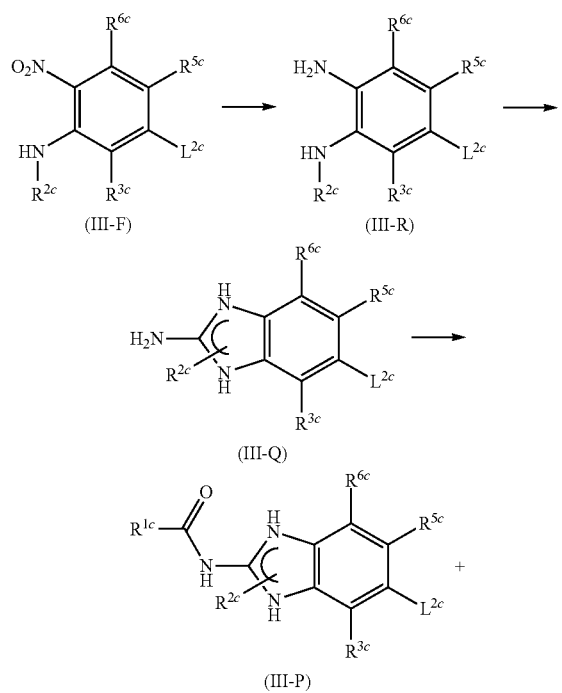

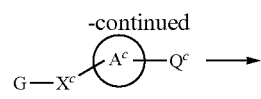

(III-O)

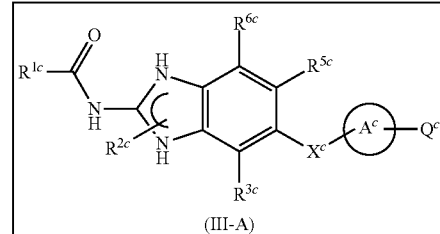

(III-A)

wherein each symbol is as defined above.

The starting compound (III-A) can also be produced, for example, by reacting a compound represented by the formula:

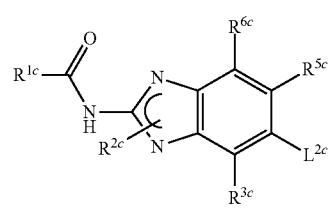

(III-O)

wherein each symbol is as defined above, with a compound represented by the formula:

(III-P)

wherein each symbol is as defined above.

In compound (III-O) wherein $X^c$ is —$NR^{9c}$— [$R^{9c}$ is as defined above], —O— or —S—, G is mainly a hydrogen atom but may also be alkali metal or alkaline earth metal.

The reaction is preferably performed using 1-5 equivalents, preferably 1-2 equivalents, of compound (III-O) or a salt thereof relative to compound (III-P) in a solvent. In addition, about 1 to 10 equivalents, preferably 1 to 2 equivalents, of a base or ammonium salt may be used relative to compound (III-P). As a catalyst, 0.05-10 equivalents, preferably 0.05-2 equivalents, of a palladium complex may be used relative to compound (III-P).

Examples of the solvent for the aforementioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

In addition, the reaction may be performed under microwave irradiation.

The starting compound (III-O) may be commercially available, or can be produced from the corresponding starting compound by a means known per se.

The starting compound (III-P) can be produced, for example, by subjecting a compound represented by the formula:

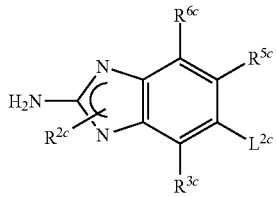

(III-Q)

wherein each symbol is as defined above, to a known general acylation reaction using carboxylic acid represented by $R^{1c}$-COOH ($R^{1c}$ is as defined above) or a reactive derivative thereof.

The starting compound (III-Q) can be produced, for example, by reacting a o-phenylenediamine derivative represented by the formula:

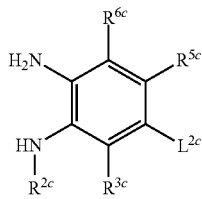

(III-R)

wherein each symbol is as defined above with cyanogen bromide, cyanamide or 1,1-di-1H-imidazol-1-ylmethanimine.

The reaction is preferably performed using 1-10 equivalents, preferably 1-5 equivalents, of cyanogen bromide, cyanamide or 1,1-di-1H-imidazol-1-ylmethanimine relative to compound (III-R) in a solvent. In addition, 0 to 10 equivalents, preferably 0 to 2 equivalents, of a base may be used relative to compound (III-R).

Examples of the solvent for the above-mentioned reaction include halogenated hydrocarbons, aromatic hydrocarbons, alcohols, ethers, acetone, acetonitrile, ethyl acetate, N,N-dimethylformamide, N,N-dimethylacetamide, 1-methyl-2-pyrrolidone, dimethyl sulfoxide, hexamethylphosphramide, water or a mixed solvent thereof and the like.

The aforementioned reaction can be performed under cooling (about −78° C.-20° C., preferably about −10° C.-10° C.), at room temperature or under heating (about 40° C.-200° C., preferably about 40° C.-160° C.), and the reaction time is generally about 1-30 hr, preferably about 1-20 hr, more preferably about 1-10 hr.

The starting compound (III-R) may be commercially available, or can be produced by converting nitro to amino by subjecting o-nitroaniline derivative represented by the aforementioned formula:

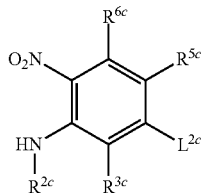

(III-F)

wherein each symbol is as defined above, to a known general reduction reaction.

The compound of the present invention can be isolated and purified by a means known per se, such as phase transfer, concentration, solvent extraction, fractionation, liquid conversion, crystallization, recrystallization, chromatography and the like. When the compound of the present invention is obtained as a free compound, it can be converted to a desired salt by a method known per se or a method analogous thereto. Conversely, when the compound is obtained as a salt, it can be converted to a free form or other desired salt by a method known per se or a method analogous thereto.

The compound of the present invention may be used as a prodrug. A prodrug of the compound of the present invention means a compound converted to the compound of the present invention by a reaction due to an enzyme, a gastric acid, etc. under the physiological condition in the living body, that is, a compound converted to the compound of the present invention by oxidation, reduction, hydrolysis, etc. due to an enzyme, a compound converted to the compound of the present invention by hydrolysis etc. due to gastric acid, and the like.

A prodrug of the compound of the present invention may be a compound obtained by subjecting an amino in the compound of the present invention to an acylation, alkylation or phosphorylation (e.g., a compound obtained by subjecting an amino in the compound of the present invention to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation); a compound obtained by subjecting hydroxyl in the compound of the present invention to acylation, alkylation, phosphorylation or boration (e.g., a compound obtained by subjecting hydroxyl in the compound of the present invention to acetylation, palmitoylation, propanoylation, pivaloylation, succinylation, fumarylation, alanylation or dimethylaminomethylcarbonylation); a compound obtained by subjecting carboxy in the compound of the present invention to esterification or amidation (e.g., a compound obtained by subjecting carboxy in the compound of the present invention to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Any one of these compounds can be produced from the compound of the present invention by a method known per se.

A prodrug of the compound of the present invention may also be a compound converted into the compound of the present invention under physiological conditions, such as those described in IYAKUHIN no KAIHATSU (Development of Pharmaceuticals), Vol. 7, Design of Molecules, p. 163-198, Published by HIROKAWA SHOTEN (1990).

When the compound of the present invention has an isomer such as optical isomer, stereoisomer, positional isomer, rotational isomer and the like, any isomer and a mixture thereof are encompassed in the compound of the present invention. For example, when the compound of the present invention has an optical isomer, an optical isomer separated from a racemate is also encompassed in the compound of the present invention. Such isomers can be obtained as independent products by a synthesis means or a separation means (concentration, solvent extraction, column chromatography, recrystallization and the like) known per se.

The compound of the present invention may be a crystal, and both a single crystal and crystal mixtures are encompassed in the compound of the present invention. Crystals can be produced by crystallization according to crystallization methods known per se.

The compound of the present invention may be a solvate (e.g., hydrate etc.) or a non-solvate, both of which are encompassed in the compound of the present invention.

A compound labeled with an isotope (e.g., $^3$H, $^{14}$C, $^{35}$S, $^{125}$I etc.) is also encompassed in the compound of the present invention.

Furthermore, a deuterium conversion form wherein $^1$H is converted to $^2$H(D) is also encompassed in the compound of the present invention.

The compound of the present invention, or a salt thereof, or a prodrug thereof (in the specification, sometimes to be abbreviated as the compound of the present invention) has an Raf, particularly B-Raf, inhibitory activity, and can provide a clinically useful agent for the prophylaxis or treatment of cancer, and a cancer growth inhibitor, a cancer metastasis suppressive agent. In addition, it can be used for the prophylaxis or treatment of B-Raf dependent diseases in mammals.

The compound of the present invention also has an inhibitory activity on a vascular endothelial growth factor receptor (VEGFR; particularly, VEGFR2).

The compound of the present invention shows a strong inhibitory activity particularly on Raf, especially, selectivity for B-Raf. Since the compound of the present invention is also superior in the efficacy, pharmacokinetics (absorption, distribution, metabolism, excretion etc.), solubility (water-solubility etc.), interaction with other pharmaceutical products, safety (acute toxicity, chronic toxicity, genetic toxicity, reproductive toxicity, cardiotoxicity, carcinogenicity etc.) and stability (chemical stability, stability to enzyme etc.), it is useful as a medicament.

Accordingly, the compound of the present invention is useful as Raf (specifically B-Raf) inhibitor for mammal (e.g., mouse, rat, hamster, rabbit, cat, dog, bovine, sheep, monkey, human, etc.). The compound of the present invention is used as a medicament such as an agent for the prophylaxis or treatment of Raf-related diseases, for example, cancer [e.g., colorectal cancer (e.g., familial colorectal cancer, hereditary nonpolyposis colorectal cancer, gastrointestinal stromal tumor, etc.), lung cancer (e.g., non-small cell lung cancer, small cell lung cancer, malignant mesothelioma, etc.), mesothelioma, pancreatic cancer (e.g., pancreatic duct cancer, etc.), gastric cancer (e.g., papillary adenocarcinoma, mucinous adenocarcinoma, adenosquamous cancer, etc.), breast cancer (e.g., invasive ductal carcinoma, ductal cancer in situ, inflammatory breast cancer, etc.), ovary cancer (e.g., ovarian epithelial cancer, extragonadal germ cell tumor, ovarian germ cell tumor, ovarian low malignant potential tumor, etc.), prostate cancer (e.g., hormone-dependent prostate cancer, non-hormone dependent prostate cancer, etc.), liver cancer (e.g., primary liver cancer, extrahepatic bile duct cancer, etc.), thyroid cancer (e.g., medullary thyroid cancer, etc.), kidney cancer (e.g., renal cell carcinoma, renal pelvis and ureter transitional cell cancer, etc.), uterine cancer, brain tumor (e.g., pineal astrocytoma, pilocytic astrocytoma, diffuse astrocytoma, anaplastic astrocytoma, etc.), melanoma, sarcoma, urinary bladder cancer, blood cancer including multiple myeloma etc.], diabetic retinopathy, rheumatoid arthritis, psoriasis, atherosclerosis, Kaposi's sarcoma, COPD, pain, asthma, endometriosis, nephritis, inflammation such as osteoarthritis and the like and hypertension, a cancer growth inhibitor, a cancer metastasis suppressor, an apoptosis promoter and the like. Of these, it is effective, for example, for colorectal cancer, lung cancer, pancreatic cancer, gastric cancer, breast cancer, ovary cancer, prostate cancer, liver cancer, thyroid cancer, kidney cancer, brain tumor, melanoma, urinary bladder cancer and blood cancer. Particularly, the compound of the present invention is effective for patients with melanoma, thyroid cancer, lung cancer, colorectal cancer, ovary cancer, prostate cancer or kidney cancer.

The compound of the present invention can be administered orally or parenterally as it is or in a mixture with a pharmacologically acceptable carrier.

The dosage form of the compound of the present invention for oral administration is, for example, tablet (including sugar-coated tablet, film-coated tablet, sublingual tablet, buccal tablet, mouth cavity quick-integrating tablet), pill, granule, powder, capsule (including soft capsule, microcapsule), oral preparation such as syrup, emulsion, suspension, films (e.g., mouth cavity mucous membrane adhesion film) and the like, and the dosage form for parenteral administration is, for example, injection, injecting agent, instillation, suppository and the like. In addition, it is effective to make a sustained release preparation by combining the compound with a suitable base (e.g., polymer of butyric acid, polymer of glycolic acid, copolymer of butyric acid-glycolic acid, a mixture of a polymer of butyric acid and a polymer of glycolic acid, polyglycerol fatty acid ester etc.).

As a method for producing the compound of the present invention in the above-mentioned dosage form, a known production method (e.g., the method described in the Japanese Pharmacopoeia) generally used in the pertinent field can be employed. When the above-mentioned dosage form is produced, suitable amounts of additives such as excipient, binder, disintegrant, lubricant, sweetening agent, surfactant, suspending agent, emulsifier and the like, generally used in the pharmaceutical field, are appropriately added as necessary for production.

When the compound of the present invention is prepared into a tablet, for example, it can be produced by adding an excipient, a binder, a disintegrant, a lubricant and the like, and when a pill or a granule is to be prepared, it can be produced by adding an excipient, a binder, a disintegrant and the like. When a powder or a capsule is to be prepared, it can be produced by adding an excipient and the like, when a syrup is to be prepared, it can be produced by adding a sweetener and the like, and when an emulsion or a suspension is to be prepared, it can be produced by adding a suspending agent, a surfactant, an emulsifier and the like.

Examples of the excipient include lactose, sucrose, glucose, starch, sucrose, microcrystalline cellulose, powdered glycyrrhiza, mannitol, sodium hydrogen carbonate, calcium phosphate, calcium sulfate and the like.

Examples of the binder include 5-10 wt % starch liquid paste, 10-20 wt % gum arabic solution or gelatin solution, 1-5 wt % tragacanth solution, carboxymethyl cellulose solution, sodium alginate solution, glycerin and the like.

Examples of the disintegrant include starch, calcium carbonate and the like.

Examples of the lubricant include magnesium stearate, stearic acid, calcium stearate, purified talc and the like.

Examples of the sweetener include glucose, fructose, invert sugar, sorbitol, xylitol, glycerin, simple syrup and the like.

Examples of the surfactant include sodium lauryl sulfate, polysorbate 80, sorbitan monofatty acid ester, polyoxyl 40 stearate and the like.

Examples of the suspending agent include gum arabic, sodium alginate, sodium carboxymethyl cellulose, methyl cellulose, bentonite and the like.

Examples of the emulsifier include gum arabic, tragacanth, gelatin, polysorbate 80 and the like.

Furthermore, when the compound of the present invention is produced in the above-mentioned dosage form, a suitable amount of a colorant, a preservative, an aromatic, a corrigent, a stabilizer, a thickening agent and the like typically used in the field of preparation can be added on demand.

As the injection, intravenous injection as well as subcutaneous injection, intracutaneous injection, intramuscular injection, instillation and the like are mentioned, and as the sustained release preparation, an iontophoresis transdermal agent and the like are mentioned.

Such injections are prepared by methods known per se, or by dissolving, suspending or emulsifying the compound of the present invention in a sterilized aqueous or oily liquid. As an aqueous liquid for injection, physiological saline, isotonic solutions containing glucose or other auxiliary drugs (e.g., D-sorbitol, D-mannitol, sodium chloride and the like) and the like can be mentioned, and they can be used in combination with suitable solubilizing agents, such as alcohols (e.g., ethanol), polyalcohols (e.g., propylene glycol, polyethylene glycol), nonionic surfactants (e.g., polysorbate 80, HCO-50) and the like. As an oily liquid, sesame oil, soybean oil and the like can be mentioned, which may be used in combination with solubilizing agents such as benzyl benzoate, benzyl alcohol and the like. In addition, buffers (e.g., phosphate buffer, sodium acetate buffer), soothing agents (e.g., benzalkonium chloride, procaine hydrochloride and the like), stabilizers (e.g., human serum albumin, polyethylene glycol and the like), preservatives (e.g., benzyl alcohol, phenol and the like) and the like can be blended. A prepared injection is generally filled in an ampoule.

While the content of the compound of the present invention in the medicament of the present invention varies depending on the form of the pharmaceutical preparation, it is generally about 0.01 to 100 wt %, preferably about 2 to 85 wt %, more preferably about 5 to 70 wt %, relative to the entire preparation.

While the content of the additive in the medicament of the present invention varies depending on the form of the pharmaceutical preparation, it is generally about 1 to 99.9 wt %, preferably about 10 to 90 wt %, relative to the entire preparation.

The compound of the present invention is stable and low toxic, and can be used safely. While the daily dose varies depending on the condition and body weight of patients, the kind of compound, administration route and the like, in the case of, for example, oral administration to patients for the treatment of cancer, the daily dose to an adult (body weight about 60 kg) is about 1 to 1000 mg, preferably about 3 to 300 mg, more preferably about 10 to 200 mg, as an active ingredient (the compound of the present invention), which can be given in a single administration or administered in 2 or 3 portions a day.

When the compound of the present invention is administered parenterally, it is generally administered in the form of a liquid (e.g., injection). While the dose varies depending on the subject of administration, target organ, symptom, administration method and the like, it is, for example, about 0.01 mg to about 100 mg, preferably about 0.01 to about 50 mg, more preferably about 0.01 to about 20 mg, in the form of an injection, relative to 1 kg body weight, which is preferably given by intravenous injection.

The compound of the present invention can be used concurrently with other drugs. To be specific, the compound of the present invention can be used together with medicaments such as hormonal therapeutic agents, chemotherapeutic agents, immunotherapeutic agents, medicaments inhibiting the action of cell growth factors or cell growth factor receptors and the like. In the following, the drugs that can be used in combination with the compound of the present invention are abbreviated as concomitant drugs.

Examples of the "hormonal therapeutic agents" include fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, and the like), pill preparations, mepitiostane, testrolactone, aminoglutethimide, LH-RH agonists (e.g., goserelin acetate, buserelin, leuprorelin, and the like), droloxifene, epitiostanol, ethinylestradiol sulfonate, aromatase inhibitors (e.g., fadrozole hydrochloride, anastrozole, retrozole, exemestane, vorozole, formestane, and the like), anti-androgens (e.g., flutamide, bicartamide, nilutamide, and the like), 5α-reductase inhibitors (e.g., finasteride, epristeride, and the like), aderehal cortex hormone drugs (e.g., dexamethasone, prednisolone, betamethasone, triamcinolone, and the like), androgen synthesis inhibitors (e.g., abiraterone, and the like), retinoid and drugs that retard retinoid metabolism (e.g., liarozole, and the like), and the like.

Examples of the "chemotherapeutic agents" include alkylating agents, antimetabolites, anticancer antibiotics, plant-derived anticancer agents, and the like.

Examples of the "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, sodium estramustine phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, DDS preparations thereof, and the like.

Examples of the "antimetabolites" include mercaptopurine, 6-mercaptopurine riboside, thioinosine, methotrexate, pemetrexed, enocitabine, cytarabine, cytarabine ocfosfate, ancitabine hydrochloride, 5-FU drugs (e.g., fluorouracil, tegafur, UFT, doxifluridine, carmofur, gallocitabine, emitefur, capecitabine, and the like), aminopterine, nelzarabine, leucovorin calcium, tabloid, butocine, calcium folinate, levofolinate calcium, cladribine, emitefur, fludarabine, gemcitabine, hydroxycarbamide, pentostatin, piritrexim, idoxuridine, mitoguazone, thiazophrine, ambamustine, bendamustine, DDS preparations thereof, and the like.

Examples of the "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, DDS preparations thereof, and the like.

Examples of the "plant-derived anticancer agents" include etoposide, etoposide phosphate, vinblastine sulfate, vincristine sulfate, vindesine sulfate, teniposide, paclitaxel, docetaxel, vinorelbine, DDS preparations thereof, and the like.

Examples of the "immunotherapeutic agents (BRM)" include picibanil, krestin, sizofuran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, procodazole, anti-CTLA4 antibody, and the like.

Example of the "cell growth factors" in the "medicaments inhibiting the action of cell growth factors or cell growth factor receptors" include any substances that promote cell proliferation, which are normally peptides having not more than 20,000 molecular weight that are capable of exhibiting their activity at low concentrations by binding to a receptor, including (1) EGF (epidermal growth factor) or substances possessing substantially the same activity as EGF [e.g., TGFα, and the like], (2) insulin or substances possessing substantially the same activity as insulin [e.g., insulin, IGF (insulin-like growth factor)-1, IGF-2, and the like], (3) FGF (fibroblast growth factor) or substances possessing substantially the same activity as FGF [e.g., acidic FGF, basic FGF, KGF (keratinocyte growth factor), FGF-10, and the like], and (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin, and the like].

Examples of the "cell growth factor receptors" include any receptors capable of binding to the aforementioned cell growth factors, including EGF receptor, heregulin receptor (HER3, etc.), insulin receptor, IGF receptor-1, IGF receptor-2, FGF receptor-1 or FGF receptor-2, VEGF receptor, angiopoietin receptor (Tie2 etc.), PDGF receptor, and the like.

As the "medicaments inhibiting the action of cell growth factors or cell growth factor receptors", EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor and the like are used. More specifically, anti-VEGF antibody (Bevacizumab etc.), anti-HER2 antibody (Trastuzumab, Pertuzumab etc.), anti-EGFR antibody (Cetuximab, Panitumumab, Matuzumab, Nimotuzumab etc.), anti-VEGFR antibody, Imatinib, Erlotinib, Gefitinib, Sorafenib, Sunitinib, Dasatinib, Lapatinib, Vatalanib, 4-(4-fluoro-2-methyl-1H-indol-5-yloxy)-6-methoxy-7-[3-(1-pyrrolidinyl)propoxy]quinazoline (AZD-2171), Lestaurtinib, Pazopanib, Canertinib, Tandutinib, 3-(4-bromo-2,6-difluorobenzyloxy)-5-[3-[4-(1-pyrrolidinyl)butyl]ureido]isothiazole-4-carboxamide (CP-547632), Axitinib, N-(3,3-dimethyl-2,3-dihydro-1H-indol-6-yl)-2-(pyridin-4-ylmethylamino)pyridine-3-carboxamide (AMG-706), Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, N-[4-[4-(4-methylpiperazin-1-yl)-6-(3-methyl-1H-pyrazol-5-ylamino)pyrimidin-2-ylsulfanyl]phenyl]cyclopropanecarboxamide (VX-680), phosphoric acid 2-[N-[3-[4-[5-[N-(3-fluorophenyl)carbamoylmethyl]-1H-pyrazol-3-ylamino]quinazolin-7-yloxy]propyl]-N-ethylamino]ethyl ester (AZD-1152), 4-[9-chloro-7-(2,6-difluorophenyl)-5H-pyrimido[5,4-d][2]benzazepin-2-ylamino]benzoic acid (MLN-8054), N-[2-methoxy-5-[(E)-2-(2,4,6-trimethoxyphenyl)vinylsulfonylmethyl]phenyl]glycine sodium salt (ON-1910Na), 4-[8-cyclopentyl-7(R)-ethyl-5-methyl-6-oxo-5,6,7,8-tetrahydropteridin-2-ylamino]-3-methoxy-N-(1-methylpiperidin-4-yl)benzamide (BI-2536), 5-(4-bromo-2-chlorophenylamino)-4-fluoro-1-methyl-1H-benzimidazole-6-carbohydroxamic acid 2-hydroxyethyl ester (AZD-6244), N-[2(R),3-dihydroxypropoxy]-3,4-difluoro-2-(2-fluoro-4-iodophenylamino)benzamide (PD-0325901) and the like are used.

In addition to the aforementioned drugs, L-asparaginase, aceglatone, procarbazine hydrochloride, protoporphyrin-cobalt complex salt, mercuric hematoporphyrin-sodium, topoisomerase I inhibitors (e.g., irinotecan, topotecan, and the like), topoisomerase II inhibitors (e.g., sobuzoxane, and the like), differentiation inducers (e.g., retinoid, vitamin D, and the like), other angiogenesis inhibitors (e.g., humagillin, shark extract, COX-2 inhibitor, and the like), α-blockers (e.g., tamsulosin hydrochloride, and the like), bisphosphonic acids (pamidronate, zoledronate, and the like), thalidomide, 5 azacytidine, decitabine, bortezomib, antitumor antibody such as anti-CD20 antibody and the like, toxin labeled antibody and the like can also be used.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer,
(4) a sustained treatment effect can be designed,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

For use of the combination agent of the present invention, the administration time of the compound of the present invention and the concomitant drug is not restricted, and the compound of the present invention and the concomitant drug can be administered to an administration subject simultaneously, or may be administered at different times. The dosage of the concomitant drug may be determined according to the dose clinically set, and can be appropriately selected depending on the administration subject, administration route, disease, combination and the like.

Examples of the administration mode of the combined use of the compound of the present invention and the concomitant drug include the following methods: (1) The compound of the present invention and the concomitant drug are simultaneously produced to give a single preparation, which is then administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route at different times. (4) The compound of the present invention and the concomitant drug are separately produced to give two kinds of preparations which are administered simultaneously by different administration routes. (5) The compound of the present invention and the concomitant drug are separately produced to give two kinds of preparations which are administered by different administration routes at different times (e.g., the compound of the present invention and the concomitant drug are administered in this order, or in the reverse order). The dose of the concomitant drug is appropriately determined in accordance with its clinical dose, and the ratio of the compound of the present invention and the concomitant drug is appropriately determined depending on the administration subject, administration route, target disease, symptom, combination, and the like. For example, when the administration subject is human, the concomitant drug is used in 0.01 to 100 (parts by weight), relative to 1 part by weight of the compound of the present invention.

The combination agent of the present invention has low toxicity and, for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules (including soft capsule), solutions, injections, suppositories, sustained release agents and the like, which can be safely administered orally or parenterally (e.g., local, rectum, venous, and the like). An injection can be administered by intravenous, intramuscular, subcutaneous or intra-tissue administration, or directly to the lesion.

As a pharmacologically acceptable carrier which may be used for preparing the combination agent of the present invention, those similar to the aforementioned pharmacologically acceptable carriers, that can be used for the production of the medicament of the present invention, can be mentioned. Where necessary, the aforementioned additives that can be used for the production of the medicament of the present invention, such as preservatives, antioxidants, colorants, sweetening agents, adsorbents, wetting agents and the like can also be appropriately used in appropriate amounts.

The compounding ratio of the compound of the present invention to the concomitant drug in the combination agent of the present invention can be appropriately set depending on the administration subject, administration route, diseases and the like.

For example, the content of the compound of the present invention in the combination agent of the present invention varies depending on the dosage form, and is usually from about 0.01 to 100% by weight, preferably from about 0.1 to 50% by weight, further preferably from about 0.5 to 20% by weight, based on the entire preparation.

The content of the concomitant drug in the combination agent of the present invention varies depending on the dosage form, and is usually from about 0.01 to 90% by weight, preferably from about 0.1 to 50% by weight, further preferably from about 0.5 to 20% by weight, based on the entire preparation.

The content of additives in the combination agent of the present invention varies depending on the dosage form, and is usually from about 1 to 99.99% by weight, preferably from about 10 to 90% by weight, based on the entire preparation.

When the compound of the present invention and the concomitant drug are separately prepared, the same content may be adopted.

These preparations can be produced by a method known per se, which is generally employed in the preparation process.

For example, the compound of the present invention and the concomitant drug can be made into an aqueous injection together with a dispersing agent (e.g., Tween 80 (manufactured by Atlas Powder, US), HCO 60 (manufactured by Nikko Chemicals), polyethylene glycol, carboxymethylcellulose, sodium alginate, hydroxypropylmethylcellulose, dextrin and the like), a stabilizer (e.g., ascorbic acid, sodium pyrosulfite, and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride, mannitol, sorbitol, glucose and the like), a pH adjuster (e.g., hydrochloric acid, sodium hydroxide and the like), a preservative (e.g., ethyl paraoxybenzoate, benzoic acid, methylparaben, propylparaben, benzyl alcohol and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, or can be dissolved, suspended or emulsified in a vegetable oil such as olive oil, sesame oil, cotton seed oil, corn oil and the like or a solubilizing agent such as propylene glycol and the like and prepared into an oily injection, whereby an injection is afforded.

In addition, an excipient (e.g., lactose, sucrose, starch and the like), a disintegrating agent (e.g., starch, calcium carbonate and the like), a binder (e.g., starch, gum arabic, carboxymethylcellulose, polyvinylpyrrolidone, hydroxypropylcellulose and the like), a lubricant (e.g., talc, magnesium stearate, polyethylene glycol 6000 and the like) and the like may be added to the compound of the present invention or the concomitant drug, and the mixture can be compression-molded, according to a method known per se then if desirable, the molded product can be coated by a method known per se for the purpose of masking of taste, enteric property or durability, to give a preparation for oral administration. As the coating agent, for example, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudoragit (methacrylic acid•acrylic acid copolymer, manufactured by Rohm, DE), pigment (e.g., iron oxide red, titanium dioxide, etc.) and the like can be used. The preparation for oral administration may be any of an immediate-release preparation and a sustained release preparation.

Moreover, the compound of the present invention and the concomitant drug can be made into an oily or aqueous solid, semisolid or liquid suppository according to a method known per se, by mixing them with an oily substrate, aqueous substrate or aqueous gel substrate. As the above-mentioned oily substrate, for example, glycerides of higher fatty acid [e.g., cacao butter, Witepsols (manufactured by Dynamit Nobel, Germany), etc.], glycerides of medium chain fatty acid [e.g., Miglyols (manufactured by Dynamit Nobel, Germany), etc.], or vegetable oils (e.g., sesame oil, soybean oil, cotton seed oil and the like), and the like are mentioned. Furthermore, as the aqueous substrate, for example, polyethylene glycol, propylene glycol and the like are mentioned, and as the aqueous gel substrate, for example, natural gums, cellulose derivatives, vinyl polymers, acrylic acid polymers and the like are mentioned.

As the above-mentioned sustained release preparation, sustained release microcapsules and the like are mentioned. The sustained release microcapsule can be produced by a method known per se, for example, a method shown in the following [2].

The compound of the present invention is preferably molded into a preparation for oral administration such as a solid preparation (e.g., powder, granule, tablet, capsule) and the like, or molded into a preparation for rectal administration such as a suppository and the like. Particularly, a preparation for oral administration is preferable.

The concomitant drug can be made into the above-mentioned drug form depending on the kind of the drug.

[1] An injection of the compound of the present invention or the concomitant drug, and preparation thereof, [2] a sustained release preparation or immediate-release preparation of the compound of the present invention or the concomitant drug, and preparation thereof, [3] a sublingual, buccal or intraoral quick integrating agent of the compound of the present invention or the concomitant drug, and preparation thereof, will be described below specifically.

[1] Injection and Preparation Thereof

An injection prepared by dissolving the compound of the present invention or the concomitant drug into water is preferable. This injection may be allowed to contain a benzoate and/or salicylate.

The injection is obtained by dissolving the compound of the present invention or the concomitant drug, and if desirable, a benzoate and/or salicylate, into water.

As the above-mentioned salts of benzoic acid and salicylic acid, for example, salts of alkali metals such as sodium, potassium and the like, salts of alkaline earth metals such as calcium, magnesium and the like, ammonium salts, meglumine salts, salts with organic bases such as tromethamol and the like, etc. are listed.

The concentration of the compound of the present invention or the concomitant drug in an injection is from 0.5 to 50 w/v %, preferably from about 3 to 20 w/v %. The concentration of a benzoate or/and salicylate is from 0.5 to 50 w/v %, preferably from about 3 to 20 w/v %.

Into the injection of the present invention, additives usually used in an injection, for example, a stabilizer (e.g., ascorbic acid, sodium pyrosulfite and the like), a surfactant (e.g., Polysorbate 80, macrogol and the like), a solubilizer (e.g., glycerin, ethanol and the like), a buffer (e.g., phosphoric acid and alkali metal salt thereof, citric acid and alkali metal salt thereof, and the like), an isotonizing agent (e.g., sodium chloride, potassium chloride and the like), a dispersing agent (e.g., hydroxypropylmethylcellulose, dextrin), a pH regulator (e.g., hydrochloric acid, sodium hydroxide and the like), a preservative (e.g., ethyl paraoxybenzoate, benzoic acid and the like), a dissolving agent (e.g., conc. glycerin, meglumine and the like), a solubilizing agent (e.g., propylene glycol, sucrose and the like), a soothing agent (e.g., glucose, benzyl alcohol and the like), and the like, can be appropriately blended. These additives are generally blended in a proportion usually used in an injection.

It is advantageous that pH of an injection is controlled from pH 2 to 12, preferably from pH 2.5 to 8.0 by addition of a pH regulator.

An injection is obtained by dissolving the compound of the present invention or the concomitant drug and if desirable, a benzoate and/or a salicylate, and if necessary, the above-mentioned additives into water. These may be dissolved in any order, and can be appropriately dissolved in the same manner as in a conventional method of producing an injection.

An aqueous solution for injection may be advantageously heated, alternatively, for example, filter sterilization, high pressure heat sterilization and the like can be conducted in the same manner as for a usual injection, to provide an injection.

It may be advantageous that an aqueous solution for injection is subjected to high pressure heat sterilization at 100 to 121° C. for 5 to 30 min.

Further, a preparation endowed with an antibacterial property of a solution may also be produced so that it can be used as a preparation which is divided and administered multiple-times.

[2] Sustained Release Preparation or Immediate-Release Preparation, and Preparation Thereof A sustained release preparation is preferable which is obtained, if desirable, by coating a nucleus containing the compound of the present invention or the concomitant drug with a film agent such as a water-insoluble substance, swellable polymer and the like. For example, a sustained release preparation for oral administration of once administration per day type is preferable.

As the water-insoluble substance used in a film agent, there are listed, for example, cellulose ethers such as ethylcellulose, butylcellulose and the like, cellulose esters such as cellulose acetate, cellulose propionate and the like, polyvinyl esters such as polyvinyl acetate, polyvinyl butyrate and the like, acrylic acid/methacrylic acid copolymers, methyl methacrylate copolymers, ethoxyethyl methacrylate/cinnamoethyl methacrylate/aminoalkyl methacrylate copolymers, polyacrylic acid, polymethacrylic acid, methacrylic acid alkylamide copolymers, poly(methyl methacrylate), polymethacrylate, polymethacrylamide, aminoalkyl methacrylate copolymers, poly(methacrylic anhydride), glycidyl methacrylate copolymer, particularly, acrylic acid-based polymers such as Eudoragit (Rohm Pharma) such as Eudoragit RS-100, RL-100, RS-30D, RL-30D, RL—PO, RS—PO (ethyl acrylate/methyl methacrylate/trimethylchloride methacrylate/ethyl ammonium copolymer), Eudoragit NE-30D (methyl methacrylate/ethyl acrylate copolymer), and the like, hydrogenated oils such as hydrogenated castor oil (e.g., Lubri wax (Freund Corporation) and the like), waxes such as carnauba wax, fatty acid glycerin ester, paraffin and the like, polyglycerin fatty acid esters, and the like.

As the swellable polymer, polymers having an acidic dissociating group and showing pH dependent swell are preferable, and polymers having an acidic dissociating group, which manifest small swelling in acidic regions such as in stomach and large swelling in neutral regions such as in small intestine and large intestine, are preferable.

As such a polymer having an acidic dissociating group and showing pH dependent swell, cross-linkable polyacrylic acid polymers such as, for example, Carbomer 934P, 940, 941, 974P, 980, 1342 and the like, polycarbophil, calcium polycarbophil (all are manufactured by BF Goodrich), Hiviswako 103, 104, 105, 304 (all are manufactured by Wako Pure Chemical Industries, Ltd.), and the like, are listed.

The film agent used in a sustained release preparation may further contain a hydrophilic substance.

As the hydrophilic substance, for example, polysaccharides which may contain a sulfate group such as pullulan, dextrin, alkali metal alginate and the like, polysaccharides having a hydroxyalkyl or carboxyalkyl such as hydroxypropylcellulose, hydroxypropylmethylcellulose, carboxymethylcellulose sodium and the like, methylcellulose, polyvinylpyrrolidone, polyvinyl alcohol, polyethylene glycol and the like can be mentioned.

The content of a water-insoluble substance in the film agent of a sustained release preparation is from about 30 to about 90% (w/w), preferably from about 35 to about 80% (w/w), further preferably from about 40 to about 75% (w/w), the content of a swellable polymer is from about 3 to about 30% (w/w), preferably from about 3 to about 15% (w/w). The film agent may further contain a hydrophilic substance, and in which case, the content of a hydrophilic substance in the film agent is about 50% (w/w) or less, preferably about 5 to about 40% (w/w), further preferably from about 5 to about 35% (w/w). This % (w/w) indicates % by weight based on a film agent composition which is obtained by removing a solvent (e.g., water, lower alcohols such as methanol, ethanol and the like) from a film agent solution.

The sustained release preparation is produced by preparing a nucleus containing a drugs as exemplified below, then, coating the resulted nucleus with a film agent solution prepared by heat-solving a water-insoluble substance, swellable polymer and the like or by dissolving or dispersing it in a solvent.

I. Preparation of Nucleus Containing Drug

The form of nucleus containing a drug to be coated with a film agent (hereinafter, sometimes simply referred to as nucleus) is not particularly restricted, and preferably, the nucleus is formed into particles such as a granule or fine particle.

When the nucleus is composed of granules or fine particles, the total particle size thereof is preferably from about 150 to about 2000 µm, further preferably, from about 500 to about 1400 µm.

Preparation of the nucleus can be effected by a usual production method. For example, a suitable excipient, binding agent, disintegrating agent, lubricant, stabilizer and the like are mixed with a drug, and the mixture is subjected to a wet extrusion granulating method, fluidized bed granulating method or the like, to prepare a nucleus.

The content of drugs in a nucleus is from about 0.5 to about 95% (w/w), preferably from about 5.0 to about 80% (w/w), further preferably from about 30 to about 70% (w/w).

As the excipient contained in the nucleus, for example, saccharides such as sucrose, lactose, mannitol, glucose and the like, starch, crystalline cellulose, calcium phosphate, corn starch and the like are used. Among them, crystalline cellulose, corn starch are preferable.

As the binding agent, for example, polyvinyl alcohol, hydroxypropylcellulose, polyethylene glycol, polyvinyl pyrrolidone, Pluronic F68, gum Arabic, gelatin, starch and the like are used. As the disintegrating agent, for example, carboxymethylcellulose calcium (ECG505), croscarmelose sodium (Ac-Di-Sol), crosslinked polyvinylpyrrolidone (Crospovidone), low substituted hydroxypropylcellulose (L-HPC) and the like are used. Among them, hydroxypropylcellulose, polyvinylpyrrolidone, lower substituted hydroxypropylcellulose are preferable. As the lubricant and solidification inhibitor, for example, talc, magnesium stearate and inorganic salts thereof are used, and as the lubricant, polyethylene glycol and the like are used. As the stabilizer, acids such as tartaric acid, citric acid, succinic acid, fumaric acid, maleic acid and the like, are used.

A nucleus can also be prepared by, in addition to the above-mentioned productions method, for example, a rolling granulation method in which a drug or a mixture of a drug with an excipient, lubricant and the like is added portionwise onto an inert carrier particle which is the core of the nucleus while spraying a binder dissolved in a suitable solvent such as water, lower alcohol (e.g., methanol, ethanol and the like) and the like, a pan coating method, a fluidized bed coating method or a melt granulating method. As the inert carrier particle, for example, those made of sucrose, lactose, starch, crystalline cellulose or waxes can be used, and the total particle size thereof is preferably from about 100 µm to about 1500 µm.

For separating a drug contained in a nucleus and a film agent, the surface of the nucleus may be coated with a protective agent. As the protective agent, for example, the above-mentioned hydrophilic substances, water-insoluble substances and the like are used. As the protective agent, preferably polyethylene glycol, and polysaccharides having a hydroxyalkyl or carboxyalkyl are used, more preferably, hydroxypropylmethylcellulose and hydroxypropylcellulose are used. The protective agent may contain, as stabilizer, acids such as tartaric acid, citric acid, succinic acid, fumaric acid, maleic acid and the like, and lubricants such as talc and the like. When the protective agent is used, the coating amount is from about 1 to about 15% (w/w), preferably from about 1 to about 10% (w/w), further preferably from about 2 to about 8% (w/w), based on the nucleus.

The protective agent can be coated by a usual coating method, and specifically, the protective agent can be coated by spray-coating the nucleus, for example, by a fluidized bed coating method, pan coating method and the like.

II. Coating of Nucleus with Film Agent

A nucleus obtained in the above-mentioned step I is coated with a film agent solution obtained by heat-solving the above-mentioned water-insoluble substance and pH-dependent swellable polymer, and a hydrophilic substance, or by dissolving or dispersing them in a solvent, to give a sustained release preparation.

As the method for coating a nucleus with a film agent solution, for example, a spray coating method and the like are listed.

The composition ratio of a water-insoluble substance, swellable polymer or hydrophilic substance in a film agent solution is appropriately selected so that the contents of these components in a coated film are the above-mentioned contents, respectively.

The coating amount of a film agent is from about 1 to about 90% (w/w), preferably from about 5 to about 50% (w/w), further preferably from about 5 to about 35% (w/w), based on a nucleus (not including coating amount of protective agent).

As the solvent in a film agent solution, water or an organic solvent can be used alone or in admixture thereof. In the case of use in admixture, the mixing ratio of water to an organic solvent (water/organic solvent: by weight) can be varied in the range from 1 to 100%, and preferably from 1 to about 30%. The organic solvent is not particularly restricted providing it dissolves a water-insoluble substance, and for example, lower alcohols such as methyl alcohol, ethyl alcohol, isopropyl alcohol, n-butyl alcohol and the like, lower alkanone such as acetone and the like, acetonitrile, chloroform, methylene chloride and the like are used. Among them, lower alcohols are preferable, and ethyl alcohol and isopropyl alcohol are particularly preferable. Water, and a mixture of water with an organic solvent are preferably used as a solvent for a film agent. In this case, if necessary, an acid such as tartaric acid, citric acid, succinic acid, fumaric acid, maleic acid and the like may also be added into a film agent solution for stabilizing the film agent solution.

An operation of coating by spray coating can be effected by a usual coating method, and specifically, it can be effected by spray-coating a film agent solution onto a nucleus by a fluidized bed coating method, pan coating method and the like. In this case, if necessary, talc, titanium oxide, magnesium stearate, calcium stearate, light anhydrous silicic acid and the like may also be added as a lubricant, and glycerin fatty acid ester, hydrogenated castor oil, triethyl citrate, cetyl alcohol, stearyl alcohol and the like may also be added as a plasticizer.

After coating with a film agent, if necessary, an antistatic agent such as talc and the like may be mixed.

The immediate-release preparation may be liquid (solution, suspension, emulsion and the like) or solid (particle, pill, tablet and the like). As the immediate-release preparation, oral administration agents and parenteral administration agents such as an injection and the like are used, and oral administration agents are preferable.

The immediate-release preparation, usually, may contain, in addition to an active component drug, also carriers, additives and excipients conventionally used in the pharmaceutical field (hereinafter, sometimes abbreviated as excipient). The excipient used is not particularly restricted providing it is an excipient ordinarily used as a preparation excipient. For example, as the excipient for an oral solid preparation, lactose, starch, corn starch, crystalline cellulose (Avicel PH101, manufactured by Asahi Kasei Corporation, and the like), powder sugar, granulated sugar, mannitol, light anhydrous silicic acid, magnesium carbonate, calcium carbonate, L-cysteine and the like are listed, and preferably, corn starch and mannitol and the like are listed. These excipients can be used alone or in combination of two or more. The content of the excipient is, for example, from about 4.5 to about 99.4 w/w %, preferably from about 20 to about 98.5 w/w %, further preferably from about 30 to about 97 w/w %, based on the total amount of the immediate-release preparation.

The content of a drug in the immediate-release preparation can be appropriately selected in the range from about 0.5 to about 95 w/w %, preferably from about 1 to about 60 w/w % based on the total amount of the immediate-release preparation.

When the immediate-release preparation is an oral solid preparation, it usually contains, in addition to the above-mentioned components, also a disintegrating agent. As this disintegrating agent, for example, carboxymethylcellulose calcium (ECG-505, manufactured by Gotoku Yakuhin), croscarmelose sodium (e.g., Actisol, manufactured by Asahi Kasei Corporation), crospovidone (e.g., Kollidon CL, manufactured by BASF), low substituted hydroxypropylcellulose (Shin-Etsu Chemical Co., Ltd.), carboxymethylstarch (Matsutani Kagaku K. K.), carboxymethylstarch sodium (Exprotab, manufactured by Kimura Sangyo), partially pregelatinized starch (PCS, manufactured by Asahi Kasei Corporation), and the like are used, and for example, those which disintegrate a granule by absorbing water in contact with water, causing swelling, or making a channel between an effective ingredient constituting the nucleus and an excipient, can be used. These disintegrating agents can be used alone or in combination of two or more. The amount of the disintegrating agent used is appropriately selected depending on the kind and blending amount of a drug used, design of releasing property, and the like, and for example, from about 0.05 to about 30 w/w %, preferably from about 0.5 to about 15 w/w %, based on the total amount of the immediate-release preparation.

When the immediate-release preparation is an oral solid preparation, it may further contain, in addition to the above-mentioned composition, if desired, additives conventional in solid preparations. As such an additive, there are used, for example, a binder (e.g., sucrose, gelatin, gum Arabic powder, methylcellulose, hydroxypropylcellulose, hydroxypropylmethylcellulose, carboxymethylcellulose, polyvinylpyrrolidone, pullulan, dextrin and the like), a lubricant (e.g., polyethylene glycol, magnesium stearate, talc, light anhydrous silicic acid (e.g., Aerosil (Nippon Aerosil)), a surfactant (e.g., anionic surfactants such as sodium alkylsulfate and the like, nonionic surfactants such as polyoxyethylene fatty acid ester and polyoxyethylene sorbitan fatty acid ester, polyoxyethylene castor oil derivatives and the like), a colorant (e.g., tar coloring matter, caramel, iron oxide red, titanium oxide, riboflavins), if necessary, an appetizing agent (e.g., sweetening agent, flavoring agent and the like), an adsorbent, preservative, wetting agent, antistatic agent, and the like. Further, as the stabilizer, an organic acid such as tartaric acid, citric acid, succinic acid, fumaric acid and the like may also be added.

As the above-mentioned binder, hydroxypropylcellulose, polyethylene glycol and polyvinylpyrrolidone and the like are preferably used.

The immediate-release preparation can be prepared by, based on a usual technology of producing preparations, mixing the above-mentioned components, and if necessary, further kneading the mixture, and molding it. The above-mentioned mixing is conducted by generally used methods, for example, mixing, kneading and the like. Specifically, when a immediate-release preparation is formed, for example, into a particle, it can be prepared, according to the same means as in the above-mentioned method for preparing a nucleus of a sustained release preparation, by mixing the components using a vertical granulator, universal kneader (manufactured by Hata Tekkosho), fluidized bed granulator FD-5S (manufactured by Powrex Corporation), and the like, and then, granulating the mixture by a wet extrusion granulation method, fluidized bed granulation method and the like.

Thus obtained immediate-release preparation and sustained release preparation may be themselves made into products or made into products appropriately together with preparation excipients and the like, separately, by an ordinary method, then, may be administered simultaneously or may be administered in combination at any administration interval, or they may be themselves made into one preparation for oral administration (e.g., granule, fine particle, tablet, capsule and the like) or made into one preparation for oral administration appropriately together with preparation excipients and the like. It may also be permissible that they are made into granules or fine particles, and filled in the same capsule to be used as a preparation for oral administration.

[3] Sublingual, Buccal or Intraoral Quick Disintegrating Agent and Preparation Thereof Sublingual, buccal or intraoral quick disintegrating agents may be a solid preparation such as tablet and the like, or may be an oral mucosa membrane patch (film).

As the sublingual, buccal or intraoral quick disintegrating agent, a preparation containing the compound of the present invention or the concomitant drug and an excipient is preferable. It may contain also auxiliary agents such as a lubricant, isotonizing agent, hydrophilic carrier, water-dispersible polymer, stabilizer and the like. Further, for easy absorption and increased in vivo use efficiency, $\beta$-cyclodextrin or $\beta$-cyclodextrin derivatives (e.g., hydroxypropyl-$\beta$-cyclodextrin and the like) and the like may also be contained.

As the above-mentioned excipient, lactose, sucrose, D-mannitol, starch, crystalline cellulose, light anhydrous silicic acid and the like are listed. As the lubricant, magnesium stearate, calcium stearate, talc, colloidal silica and the like are listed, and particularly, magnesium stearate and colloidal silica are preferable. As the isotonizing agent, sodium chloride, glucose, fructose, mannitol, sorbitol, lactose, saccharose, glycerin, urea and the like are listed, and particularly, mannitol is preferable. As the hydrophilic carrier, swellable hydrophilic carriers such as crystalline cellulose, ethylcellulose, crosslinkable polyvinylpyrrolidone, light anhydrous silicic acid, silicic acid, dicalcium phosphate, calcium carbonate and the like are listed, and particularly, crystalline cellulose (e.g., microcrystalline cellulose and the like) is preferable. As the water-dispersible polymer, gums (e.g., gum tragacanth, acacia gum, cyamoposis gum), alginates (e.g., sodium alginate), cellulose derivatives (e.g., methylcellulose, carboxymethylcellulose, hydroxymethylcellulose, hydroxypropylcellulose, hydroxypropylmethylcellulose), gelatin, water-soluble starch, polyacrylic acids (e.g., Carbomer), polymethacylic acid, polyvinyl alcohol, polyethylene glycol, polyvinylpyrrolidone, polycarbophil, ascorbic acid, palmitates and the like are listed, and hydroxypropylmethylcellulose, polyacrylic acid, alginate, gelatin, carboxymethylcellulose, polyvinylpyrrolidone, polyethylene glycol and the like are preferable. Particularly, hydroxypropylmethylcellulose is preferable. As the stabilizer, cysteine, thiosorbitol, tartaric acid, citric acid, sodium carbonate, ascorbic acid, glycine, sodium sulfite and the like are listed, and particularly, citric acid and ascorbic acid are preferable.

The sublingual, buccal or intraoral quick disintegrating agent can be produced by mixing the compound of the present invention or the concomitant drug and an excipient by a method known per se. Further, if desired, the above-mentioned auxiliary agents such as a lubricant, isotonizing agent, hydrophilic carrier, water-dispersible polymer, stabilizer, colorant, sweetening agent, preservative and the like may be mixed. The sublingual, buccal or intraoral quick disintegrating agent is obtained by mixing the above-mentioned components simultaneously or at a time interval, then subjecting the mixture to tablet-making molding under pressure. For obtaining suitable hardness, it may also be permissible that the materials are moistened by using a solvent such as water, alcohol and the like if desired before and after the tablet making process, and after the molding, the materials are dried, to obtain a product.

In the case of molding into a mucosa membrane patch (film), the compound of the present invention or the concomitant drug and the above-mentioned water-dispersible polymer (preferably, hydroxypropylcellulose, hydroxypropylmethylcellulose), excipient and the like are dissolved in a solvent such as water and the like, and the resulted solution is cast to give a film. Further, additives such as a plasticizer, stabilizer, antioxidant, preservative, colorant, buffer, sweetening agent and the like may also be added. For imparting suitable elasticity to the film, glycols such as polyethylene glycol, propylene glycol and the like may be contained, or for enhancing adhesion of the film to an intraoral mucosa membrane lining, a bio-adhesive polymer (e.g., polycarbophil, carbopol) may also be contained. In the casting, a solution is poured on the non-adhesive surface, spread to uniform thickness (preferably, about 10 to 1000 micron) by an application tool such as a doctor blade and the like, then, the solution is dried to form a film. It may be advantageous that thus formed film is dried at room temperature or under heat, and cut into a desired area.

A preferable intraorally quick-integrating agent is a solid quick-diffusable administration agent comprised of a network structure consisting of the compound of the present invention or a concomitant drug, and a water-soluble or water-diffusible carrier inactive to the compound of the present invention or the concomitant drug. The network structure can be obtained by evaporating a solvent from a composition comprised of a solution of the compound of the present invention or a concomitant drug in a suitable solvent.

It is preferable that the composition of an intraoral quick disintegrating agent contains a matrix forming agent and a secondary component, in addition to the compound of the present invention or the concomitant drug.

Examples of the matrix forming agent include gelatins, dextrins, animal proteins or vegetable proteins such as soybean, wheat and psyllium seed protein and the like; rubber substances such as gum Arabic, guar gum, agar, xanthan and the like; polysaccharides; alginic acids; carboxymethylcelluloses; carageenans; dextrans; pectines; synthetic polymers such as polyvinylpyrrolidone and the like; substances derived from a gelatin-gum Arabic complex, and the like. Further, saccharides such as mannitol, dextrose, lactose, galactose, trehalose and the like; cyclic saccharides such as cyclodextrin and the like; inorganic salts such as sodium phosphate, sodium chloride and aluminum silicate and the like; amino acids having 2 to 12 carbon atoms such as glycine, L-alanine, L-aspartic acid, L-glutamic acid, L-hydroxyproline, L-isoleucine, L-leucine, L-phenylalanine and the like, are contained.

One or more of the matrix forming agents can be introduced in a solution or suspension before solidification. Such as matrix forming agent may be present in addition to a surfactant, or may be present while a surfactant being excluded. The matrix forming agents aid to maintain the compound of the present invention or the concomitant drug in the solution or suspension in diffused condition, in addition to formation of the matrix.

The composition may contain secondary components such as a preservative, antioxidant, surfactant, thickening agent, colorant, pH controlling agent, flavoring agent, sweetening agent, food taste masking agent and the like. As the suitable colorant, there are listed red, black and yellow iron oxides, and FD & C dyes such as FD & C Blue 2, FD & C Red 40 and the like manufactured by Ellis and Everard. Examples of the suitable flavoring agent include mint, raspberry, licorice, orange, lemon, grapefruit, caramel, vanilla, cherry, grape flavor and combinations thereof. Examples of the suitable pH controlling agent include citric acid, tartaric acid, phosphoric acid, hydrochloric acid and maleic acid. Examples of the suitable sweetening agent include aspartame, acesulfame K and thaumatin and the like. Examples of the suitable food taste masking agent include sodium bicarbonate, ion exchange resin, cyclodextrin-inclusion compounds, adsorbent substances and microcapsulated apomorphine.

The preparation contains the compound of the present invention or the concomitant drug in an amount usually from about 0.1 to about 50% by weight, preferably from about 0.1 to about 30% by weight, and preferable are preparations (such as the above-mentioned sublingual agent, buccal and the like) which can dissolve 90% or more of the compound of the present invention or the concomitant drug (into water) within the time range of about 1 to about 60 min, preferably of about 1 to about 15 min, more preferably of about 2 to about 5 min, and intraoral quick disintegrating preparations which are disintegrated within the range of 1 to 60 sec, preferably of 1 to 30 sec, further preferably of 1 to 10 sec, after placed in an oral cavity.

The content of the above-mentioned excipient in the whole preparation is from about 10 to about 99% by weight, preferably from about 30 to about 90% by weight. The content of β-cyclodextrin or β-cyclodextrin derivative in the whole preparation is from 0 to about 30% by weight. The content of the lubricant in the whole preparation is from about 0.01 to about 10% by weight, preferably from about 1 to about 5% by weight. The content of the isotonizing agent in the whole preparation is from about 0.1 to about 90% by weight, preferably, from about 10 to about 70% by weight. The content of the hydrophilic carrier in the whole preparation is from about 0.1 to about 50% by weight, preferably, from about 10 to about 30% by weight. The content of the water-dispersible polymer in the whole preparation is from about 0.1 to about 30% by weight, preferably, from about 10 to about 25% by weight. The content of the stabilizer in the whole preparation is from about 0.1 to about 10% by weight, preferably, from about 1 to 5% by weight. The above-mentioned preparation may further contain additives such as a colorant, sweetening agent, preservative and the like, if necessary.

The dosage of a combination agent of the present invention differs depending on the kind of a compound of the present invention, age, body weight, condition, drug form, administration method, administration period and the like, and for example, for one cancer patient (adult, body weight: about 60 kg), the combination agent is administered intravenously, at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or several times in division a day. Of course, since the dose as described above varies depending on various conditions, amounts smaller than the above-mentioned dosage may sometimes be sufficient, further, amounts over that range sometimes have to be administered.

The amount of the concomitant drug can be set at any value unless side effects are problematical. The daily dosage in terms of the concomitant drug differs depending on the severity of the symptom, age, sex, body weight, sensitivity difference of the administration subject, administration period, interval, and nature, pharmacy, kind of the pharmaceutical preparation, kind of effective ingredient, and the like, and not particularly restricted, and the amount of a drug is, in the case of oral administration for example, usually from about 0.001 to 2000 mg, preferably from about 0.01 to 500 mg, further preferably from about 0.1 to 100 mg, per 1 kg of a mammal, which is usually administered once to 4-times in division a day.

In administration of a combination agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 min to 3 days, preferably from 10 min to 1 day, more preferably from 15 min to 1 hr after administration of the concomitant drug is exemplified. When the compound of the present invention is administered first, a method in which the concomitant drug is administered within time range of from 1 min to 1 day, preferably from 10 min to 6 hrs, more preferably from 15 min to 1 hr after administration of the compound of the present invention is exemplified.

In a preferable administration method, for example, the concomitant drug which has been molded into an oral administration preparation is administered orally at a daily dose of about 0.001 to 200 mg/kg, and about 15 min later, the compound of the present invention which has been molded into an oral administration preparation is administered orally at a daily dose of about 0.005 to 100 mg/kg.

Furthermore, the compound of the present invention or the combination agent of the present invention can be used concurrently with a non-drug therapy. To be precise, the compound of the present invention or the combination agent of the present invention can be combined with a non-drug therapy such as (1) surgery, (2) hypertensive chemotherapy using angiotensin II etc., (3) gene therapy, (4) thermotherapy, (5) cryotherapy, (6) laser cauterization, (7) radiotherapy, and the like.

For example, by using the compound of the present invention or the combination agent of the present invention before or after an surgery and the like, or before or after a combined treatment of two or three kinds thereof, effects such as prevention of emergence of resistance, prolongation of Disease-Free Survival, suppression of cancer metastasis or recurrence, prolongation of life and the like can be afforded.

In addition, it is possible to combine a treatment with the compound of the present invention or the combination agent of the present invention with a supportive therapy [(i) administration of antibiotic (e.g., β-lactam type such as pansporin and the like, macrolide type such as clarithromycin and the like etc.) for the complication with various infectious diseases, (ii) administration of high-calorie transfusion, amino acid preparation or general vitamin preparation for the improvement of malnutrition, (iii) administration of morphine for pain mitigation, (iv) administration of a medicament for ameliorating side effects such as nausea, vomiting, anorexia, diarrhea, leucopenia, thrombocytopenia, decreased hemoglobin concentration, hair loss; hepatopathy, renopathy, DIC, fever and the like and (v) administration of a medicament for suppressing multiple drug resistance of cancer and the like].

Preferably, the compound of the present invention or the combination agent of the present invention is administered orally (including sustained-release preparations), intravenously (including boluses, infusions and clathrates), subcutaneously and intramuscularly (including boluses, infusions and sustained-release preparations), transdermally, intratumorally or proximally before or after the above-described treatment is conducted.

As a period for administering the compound of the present invention or the combination agent of the present invention before the surgery, etc., for example, it can be administrated 1-time about 30 min to 24 hrs before the surgery, etc., or in 1 to 3 cycles about 3 months to 6 months before the surgery, etc. In this way, the surgery, etc. can be conducted easily because, for example, a cancer tissue would be reduced by administering the compound of the present invention or the combination agent of the present invention before the surgery, and the like.

As a period for administering the compound of the present invention or the combination agent of the present invention after the surgery, etc., for example, it can be administrated repeatedly per a few weeks to 3 months, about 30 min to 24 hrs after the surgery, and the like. In this way, it enhances the effect of the surgery, etc. by administering the compound of the present invention or the combination agent of the present invention after the surgery, and the like.

The present invention is explained in more detail in the following by referring to Examples, Preparation Examples, Experimental Examples and Test Examples, which are not to be construed as limitative.

EXAMPLES

Example A1

Production of 3-(1-cyanocyclopropyl)-N-[3-({2-[(cyclopropylcarbonyl)amino]-1,3-benzothiazol-6-yl}oxy)phenyl]benzamide

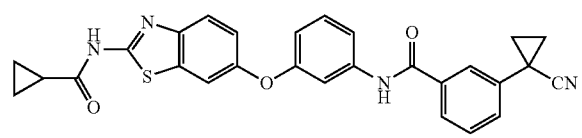

(i) Production of methyl 3-(cyanomethyl)benzoate

To a solution of methyl 3-bromobenzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtered, and the solvent was evaporated under reduced pressure. The residue was purified by silica gel column chromatography (ethyl acetate/hexane=5/95→30/70), and the fraction containing the object product was concentrated under reduced pressure to give the title compound (7.0 g, 91%) as a colorless oil.
$^1$H-NMR (DMSO-$d_6$, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

(ii) Production of methyl 3-(1-cyanocyclopropyl)benzoate

To a solution of methyl 3-(cyanomethyl)benzoate (1.5 g, 8.6 mmol) in dimethyl sulfoxide (30 mL) was added sodium hydride (60% in oil, 1.0 g, 26 mmol) while cooling to not more than 25° C. without causing solidification. The reaction mixture was stirred at room temperature for 30 min, 1,2-dibromoethane (2.4 g, 12.8 mmol) was added, and the mixture was further stirred at room temperature for 10 hr. The reaction mixture was diluted with water (100 mL), and extracted with ethyl acetate (300 mL). The organic layer was washed with saturated brine (100 mL) and dried over anhydrous sodium sulfate, and the insoluble material was filtered off. The solvent was evaporated under reduced pressure, and the residue was purified by silica gel column chromatography (ethyl acetate/hexane=5/95→50/50), and the fraction containing the object product was concentrated under reduced pressure to give the title compound (1.3 g, 76%) as a colorless oil.
$^1$H-NMR (CDCl$_3$, 300 MHz) δ 1.38-1.56 (2H, m), 1.74-1.82 (2H, m), 3.93 (3H, s), 7.40° C.-7.49 (1H, m), 7.55-7.62 (1H, m), 7.88 (1H, t, J=1.5 Hz), 7.96 (1H, dt, J=7.8, 1.5 Hz).

(iii) Production of 3-(1-cyanocyclopropyl)benzoic acid

To a solution of methyl 3-(1-cyanocyclopropyl)benzoate (1.3 g, 6.4 mmol) in tetrahydrofuran (12 mL) were added lithium hydroxide•monohydrate (0.44 g, 11 mmol), methanol (4.0 mL) and water (6.0 mL), and the mixture was stirred at room temperature for 14 hr. The solvent was evaporated under reduced pressure, and the residue was diluted with water (5.0 mL). The mixture was adjusted to pH 5 by slowly adding 1N hydrochloric acid. The resulting white precipitate was collected by filtration, washed with water, and dried to give the title compound (0.73 g, 61%) as a white powder.
$^1$H-NMR (DMSO-$d_6$, 300 MHz) δ 1.50-1.62 (2H, m), 1.76-1.86 (2H, m), 7.41-7.59 (2H, m), 7.82-7.97 (2H, m), 13.19 (1 H, br s).

(iv) Production of 2-amino-1,3-benzothiazol-6-ol

6-Methoxy-1,3-benzothiazole-2-amine (10.4 g, 57.8 mmol) was dissolved in 25% hydrogen bromide acetic acid solution (80 mL), water (40 mL) was added and the mixture was heated under reflux for 16 hr. To the reaction mixture was added sodium iodide (10.4 g, 69.4 mmol) and the mixture was heated under reflux for 12 hr. Sodium iodide (15.2 g, 101 mmol) was added and the mixture was heated under reflux for 16 hr. The reaction mixture was cooled to room temperature, and added to 8N aqueous sodium hydroxide solution (350 mL) stirred vigorously. The reaction mixture was neutralized with 6N hydrochloric acid and stood at 0° C. The resulting dark-gray crystals were collected by filtration and the mother liquid was preserved. The obtained crystals were dissolved in methanol (35 mL) and ethyl acetate (350 mL) and dried over anhydrous magnesium sulfate. The insoluble material was filtered off and the filtrate was concentrated to give the title compound (6.90 g, 72%) as a gray solid.
The mother liquid preserved earlier was extracted with ethyl acetate (250 mL×2), the collected organic layer was dried over anhydrous magnesium sulfate. The insoluble material was filtered off, and the filtrate was concentrated to give the title compound (3.4 g, 35%) as a secondary harvest.
$^1$H-NMR (DMSO-$d_6$, 300 MHz) δ 6.65 (1H, dd, J=2.7, 8.7 Hz), 7.02 (1H, d, J=2.7 Hz), 7.07 (2H, br s), 7.13 (1H, d, J=8.7 Hz), 9.08 (1H, br s).

(v) Production of N-(6-hydroxy-1,3-benzothiazol-2-yl)cyclopropanecarboxamide

To a solution of 2-amino-1,3-benzothiazol-6-ol (3.43 g, 20.6 mmol) in pyridine (50 mL) were added cyclopropanecarbonyl chloride (4 mL, 44.1 mmol) and N,N-dimethylpyridine-4-amine (220 mg, 1.80 mmol), and the mixture was stirred at room temperature for 1.5 hr. To the reaction mixture was added lithium hydroxide monohydrate (2.06 g, 49.1 mmol) in water (50 mL) and the mixture was stirred at the same temperature for 1 hr. 5N Aqueous sodium hydroxide solution (50 mL) was added, and the mixture was stirred at room temperature for 2 days. The reaction mixture was concentrated under reduced pressure, and the residue was dissolved in dilute hydrochloric acid (300 mL, pH 2.0), and extracted with ethyl acetate (250 mL). The organic layer was washed with saturated aqueous sodium hydrogencarbonate solution (150 mL). The earlier aqueous layer was extracted with ethyl acetate (150 mL), and the organic layer was washed with saturated aqueous sodium hydrogencarbonate solution (100 mL). The collected organic layer was dried over anhydrous magnesium sulfate, the insoluble material was filtered off, and the filtrate was concentrated under reduced pressure to give the title compound (3.67 g, 76%) as a pale-gray solid.
$^1$H-NMR (DMSO-$d_6$, 300 MHz) δ 0.91-0.94 (4H, m), 1.91-1.99 (1H, m), 6.87 (1H, dd, J=2.4, 8.7 Hz), 7.25 (1H, d, J=2.4 Hz), 7.52 (1H, d, J=8.7 Hz), 9.49 (1H, br s), 12.39 (1H, br s).

(vi) Production of N-[6-(3-nitrophenoxy)-1,3-benzothiazol-2-yl]cyclopropanecarboxamide To a suspension of N-(6-hydroxy-1,3-benzothiazol-2-yl) cyclopropanecarboxamide (1.53 g, 6.53 mmol) and potassium carbonate (3.72 g, 26.9 mmol) in N,N-dimethylformamide (50 mL) were added 1-fluoro-3-nitrobenzene (1.08 g, 7.65 mmol) and 18-crown-6 (1.07 g, 4.05 mmol), and the mixture was stirred at 150° C. for 14 hr. The reaction mixture was cooled to room temperature, and added to a mixed solvent (1:1, 300 mL) of ethyl acetate and hexane. The mixture was washed with water (200 mL) and saturated brine (200 mL), successively, and dried over anhydrous magnesium sulfate. The insoluble material was collected by filtration, and the residue was subjected to silica gel column chromatography using ethyl acetate and hexane (1:1) as an eluent to give the title compound (840 mg, 36%) as a pale-yellow solid.

$^1$H-NMR (DMSO-$d_6$, 300 MHz) δ 0.95-1.01 (4H, m), 1.97-2.09 (1H, m), 7.02 (1H, dd, J=2.4, 8.4 Hz), 7.50 (1H, ddd, J=0.9, 2.4, 8.4 Hz), 7.65-7.71 (2H, m), 7.79-7.83 (2H, m), 7.98 (1H, ddd, J=0.9, 2.4, 8.4 Hz), 12.65 (1H, br s).

(vii) Production of N-[6-(3-aminophenoxy)-1,3-benzothiazol-2-yl]cyclopropanecarboxamide To a solution of N-[6-(3-nitrophenoxy)-1,3-benzothiazol-2-yl]cyclopropanecarboxamide (840 mg, 2.36 mmol) in ethanol (100 mL) was added iron powder (11.9 g, 212 mmol) with heating under reflux. The obtained suspension was vigorously stirred, and 6N hydrochloric acid (50 mL) was slowly added dropwise. The reaction mixture was refluxed for 2 hr with vigorous stirring, and excess iron powder was filtered off through celite. The filtrate was concentrated to about 50 mL, and the residue was diluted with ethyl acetate (250 mL), washed with 1N aqueous sodium hydroxide solution (100 mL×2) and saturated brine (100 mL), successively, and dried over anhydrous magnesium sulfate. The insoluble material was filtered off, and the filtrate was concentrated to give the title compound (833 mg) as a pale-yellow solid.

$^1$H-NMR (DMSO-$d_6$, 300 MHz) δ 0.93-1.19 (4H, m), 2.00-2.09 (1H, m), 5.18 (2H, br s), 6.12-6.16 (2H, m), 6.30 (1H, ddd, J=0.9, 2.4, 8.1 Hz), 6.98 (1H, t, J=8.1 Hz), 7.09 (1H, dd, J=2.4, 8.1 Hz), 7.60 (1H, d, J=2.4 Hz), 7.70 (1H, d, J=8.1 Hz), 12.55 (1H, br s).

(viii) Production of 3-(1-cyanocyclopropyl)-N-[3-({2-[(cyclopropylcarbonyl)amino]-1,3-benzothiazol-6-yl}oxy)phenyl]benzamide To a suspension of 3-(1-cyanocyclopropyl)benzoic acid (156.5 mg, 0.836 mmol) in toluene (5 mL) was added thionyl chloride (0.2 mL, 2.74 mmol) and the mixture was heated under reflux for 2 hr. The reaction mixture was allowed to cool to room temperature and concentrated under reduced pressure. The obtained residue was used as 3-(1-cyanocyclopropyl)benzoyl chloride. 3-(1-Cyanocyclopropyl)benzoyl chloride prepared above was dissolved in pyridine (5 mL), N-[6-(3-aminophenoxy)-1,3-benzothiazol-2-yl]cyclopropanecarboxamide (114.8 mg, 352.8 gmol) and N,N-dimethylpyridine-4-amine (23.9 mg, 195.6 μmol) were added, and the mixture was stirred at room temperature for 16 hr. The reaction mixture was concentrated under reduced pressure, diluted with dilute hydrochloric acid (50 ml), and extracted with ethyl acetate (100 mL). The organic layer was washed with saturated aqueous sodium hydrogencarbonate solution (50 mL) and dried over anhydrous magnesium sulfate. The insoluble material was filtered off, and the filtrate was concentrated under reduced pressure. The residue was purified by silica gel column chromatography (ethyl acetate/hexane=2/98→80/20) to give the title compound (117 mg, 67%) as a pale-brown amorphous substance.

$^1$H-NMR (DMSO-$d_6$, 300 MHz) δ 0.95-0.97 (4H, m), 1.58-1.62 (2H, m), 1.78-1.82 (2H, m), 1.99-2.03 (1H, m), 6.80 (1H, dd, J=1.8, 8.1 Hz), 7.17 (1H, dd, J=2.4, 8.1 Hz), 7.37 (1H, t, J=8.1 Hz), 7.48-7.58 (4H, m), 7.72-7.86 (4H, m), 10.33 (1H, br s), 12.62 (1H, br s).

Example A2

Production of N-[3-({2-[(cyclopropylcarbonyl)amino]-1,3-benzothiazol-6-yl}oxy)phenyl]-3-(trifluoromethyl)benzamide

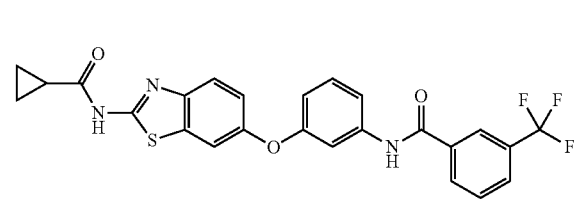

Using 3-(trifluoromethyl)benzoic acid (182 mg, 959 μmol), thionyl chloride (0.4 mL, 5.48 mmol), toluene (5 mL), N-[6-(3-aminophenoxy)-1,3-benzothiazol-2-yl]cyclopropanecarboxamide (129 mg, 395 μmol) produced in Example A1(vii), pyridine (5 mL), and N,N-dimethylpyridine-4-amine (21.3 mg, 176.0 μmol) as starting materials, and in the same manner as in Example A1(viii), the title compound (150 mg, 76%) was obtained as a colorless amorphous substance.

$^1$H-NMR (DMSO-$d_6$, 300 MHz) δ 0.90-1.10 (4H, m), 1.95-2.05 (1H, m), 6.82 (1H, d, J=7.8 Hz), 7.18 (1H, d, J=8.4 Hz), 7.38 (1H, d, J=8.1 Hz), 7.48 (1H, s), 7.59 (1H, d, J=8.1 Hz), 7.73-7.78 (3H, m), 7.95 (1H, d, J=7.2 Hz), 8.21-8.24 (2H, m), 10.49 (1H, br s), 12.62 (1H, br s).

Example A3

Production of 3-(1-cyanocyclopropyl)-N-[5-({2-[(cyclopropylcarbonyl)amino]-1,3-benzothiazol-6-yl}oxy)-2-methylphenyl]benzamide

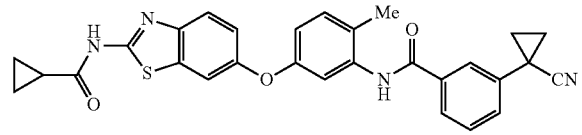

(i) Production of 3-(1-cyanocyclopropyl)-N-(5-hydroxy-2-methylphenyl)benzamide

To a solution of 3-(1-cyanocyclopropyl)benzoic acid (10.0 g, 53.4 mmol) produced in Example A1(iii) in tetrahydrofuran (130 mL) were added oxalyl chloride (5.47 mL, 64.1 mmol) and N,N-dimethylformamide (2 drops), and the mixture was stirred at room temperature for 3 hr. The reaction mixture was concentrated under reduced pressure to give 3-(1-cyanocyclopropyl)benzoyl chloride as a colorless oil.

To a two-layer solution of 3-amino-4-methylphenol (5.92 g, 48.0 mmol) in tetrahydrofuran (40 mL)/1N aqueous sodium hydrogencarbonate solution (54 mL) was added a solution of 3-(1-cyanocyclopropyl)benzoyl chloride synthesized above in tetrahydrofuran (20 mL), and the mixture was stirred at room temperature for 2 hr. Since the reaction mixture showed pH 4-5, sodium hydrogencarbonate (900 mg, 10.7 mmol) was added to adjust the pH to 8-9, and the reaction mixture was further stirred at room temperature for 1 hr.

The aqueous layer was separated, and extracted with ethyl acetate (150 mL). The combined organic layer was washed with saturated brine (150 mL), and dried over anhydrous sodium sulfate. The insoluble material was filtered off, and the filtrate was concentrated under reduced pressure. To the obtained suspension was added ethyl acetate (25 mL)/hexane (50 mL), and the mixture was stirred at room temperature for 20 min. The precipitate was collected by filtration, repeatedly washed with diisopropyl ether/hexane (1:1) and air-dried to give the title compound (12.2 g, 87%) as a pale-yellow powder.

$^1$H-NMR (DMSO-d$_6$, 300 MHz) δ 1.56-1.67 (2H, m), 1.76-1.89 (2H, m), 2.10 (3H, s), 6.59 (1H, dd, J=2.4, 8.1 Hz), 6.80 (1H, d, J=2.4 Hz), 7.04 (1H, d, J=8.1 Hz), 7.45-7.64 (2H, m), 7.80-8.00 (2H, m), 9.26 (1H, s), 9.81 (1H, br s).

(ii) Production of 3-(1-cyanocyclopropyl)-N-[2-methyl-5-(4-nitrophenoxy)phenyl]benzamide To a solution of 1-fluoro-4-nitrobenzene (3.19 g, 22.5 mmol) and 3-(1-cyanocyclopropyl)-N-(5-hydroxy-2-methylphenyl)benzamide (6.00 g, 20.5 mmol) in N,N-dimethylformamide (50 mL) was added potassium carbonate (4.25 g, 30.8 mmol) and the mixture was stirred at 80° C. for 6 hr. The reaction mixture was cooled to room temperature, and concentrated under reduced pressure. The obtained residue was diluted with ethyl acetate (300 mL), washed with water (200 mL) and saturated brine (200 mL), successively, and dried over anhydrous sodium sulfate. The insoluble material was filtered off, and the filtrate was concentrated under reduced pressure. The obtained residue was purified by silica gel column chromatography (hexane/ethyl acetate=80/20→40/60), and the obtained solution was concentrated under reduced pressure to give the title compound (9.08 g, quantitatively) as a yellow oil.

$^1$H-NMR (DMSO-d$_6$, 300 MHz) δ 1.53-1.68 (2H, m), 1.77-1.87 (2H, m), 2.28 (3H, s), 7.04 (1H, dd, J=2.4, 8.4 Hz), 7.10-7.19 (2H, m), 7.27 (1H, d, J=2.4 Hz), 7.40 (1H, d, J=8.4 Hz), 7.50-7.61 (2H, m), 7.81-7.95 (2H, m), 8.23-8.32 (2H, m), 10.02 (1H, s).

(iii) Production of N-[5-(4-aminophenoxy)-2-methylphenyl]-3-(1-cyanocyclopropyl)benzamide A suspension of 3-(1-cyanocyclopropyl)-N-[2-methyl-5-(4-nitrophenoxy)phenyl]benzamide (3.19 g, 22.5 mmol), calcium chloride (5.55 g, 50 mmol) and reduced iron (14.5 g, 260 mmol) in ethanol (540 mL)/water (60 mL) was stirred with heating at 80° C. for 12 hr. The reaction mixture was cooled to room temperature, passed through a pad filled with celite to separate insoluble material, and the insoluble material was washed with ethanol. The filtrate and the washing were combined and concentrated under reduced pressure. The obtained residue was diluted with ethyl acetate (400 mL), washed with 5% aqueous ammonium chloride solution (200 mL), water (200 mL×2), 5% aqueous sodium hydrogencarbonate solution (200 mL) and saturated brine (200 mL), successively, and dried over anhydrous sodium sulfate. The insoluble material was filtered off, and the filtrate was concentrated under reduced pressure to give the title compound (7.0 g, 84%) as a pale-yellow amorphous substance. The obtained compound was used in the next reaction without a further purification.

$^1$H-NMR (DMSO-d$_6$, 300 MHz) δ 1.56-1.65 (2H, m), 1.75-1.86 (2H, m), 2.16 (3H, s), 4.96 (2H, s), 6.49-6.64 (2H, m), 6.68-6.81 (3H, m), 6.86 (1H, d, J=2.4 Hz), 7.19 (1H, d, J=8.4 Hz), 7.44-7.62 (2H, m), 7.77-7.95 (2H, m), 9.90 (1H, s).

(iv) Production of N-{5-[(2-amino-1,3-benzothiazol-6-yl)oxy]-2-methylphenyl}-3-(1-cyanocyclopropyl)benzamide Potassium thiocyanate (7.00 g, 72 mmol) was suspended in acetic acid (120 mL) and the mixture was stirred at room temperature for 10 min. To the obtained solution was added a solution of N-[5-(4-aminophenoxy)-2-methylphenyl]-3-(1-cyanocyclopropyl)benzamide (6.90 g, 18 mmol) in acetic acid (120 mL), and the mixture was further stirred at room temperature for 30 min. To the obtained solution was added dropwise slowly a solution of bromine (3.60 g, 22.5 mmol) in acetic acid (80 mL) and, after the completion of the dropwise addition, the mixture was further stirred at room temperature for 12 hr. The resulting yellow insoluble material was filtered off and washed with acetic acid. The filtrate and the washing were combined and concentrated under reduced pressure. The obtained residue was suspended in ethyl acetate (400 mL), washed with 5% aqueous sodium hydrogencarbonate solution (200 mL×2) and saturated brine (200 mL), successively, and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained solution was concentrated under reduced pressure to give the title compound (6.27 g, 79%) as a pale-yellow amorphous substance.

$^1$H-NMR (DMSO-d$_6$, 300 MHz) δ 1.50-1.72 (2H, m), 1.77-1.91 (2H, m), 2.19 (3H, s), 6.82 (1H, dd, J=2.4, 8.4 Hz), 6.89-7.01 (2H, m), 7.25 (1H, d, J=8.4 Hz), 7.33 (1H, d, J=8.7 Hz), 7.37-7.47 (3H, m), 7.47-7.62 (2H, m), 7.69-7.94 (2H, m), 9.93 (1H, s).

(v) Production of 3-(1-cyanocyclopropyl)-N-[5-({2-[(cyclopropylcarbonyl)amino]-1,3-benzothiazol-6-yl}oxy)-2-methylphenyl]benzamide To a solution of N-{5-[(2-amino-1,3-benzothiazol-6-yl)oxy]-2-methylphenyl}-3-(1-cyanocyclopropyl)benzamide (300 mg, 0.681 mmol) in N,N-dimethylacetamide (3.0 mL) was added cyclopropanecarbonyl chloride (65 μL, 0.715 mmol), and the mixture was stirred at room temperature for 10 hr. To the reaction mixture was added cyclopropanecarbonyl chloride (30 μL, 0.33 mmol), and the mixture was further stirred at room temperature for 3 hr. The reaction mixture was diluted with ethyl acetate (100 mL), washed with 5% aqueous sodium hydrogencarbonate solution (100 mL) and saturated brine (100 mL), successively, and dried over anhydrous sodium sulfate. The insoluble material was filtered off, and the filtrate was concentrated under reduced pressure. The obtained residue was purified by silica gel column chromatography (hexane/ethyl acetate=70/30→0/100), and the obtained solution was concentrated under reduced pressure. The residue was triturated with ethyl acetate/diisopropyl ether to give the title compound (140 mg, 40%) as a colorless solid.

¹H-NMR (DMSO-d₆, 300 MHz) δ 0.89-1.00 (4H, m), 1.54-1.63 (2H, m), 1.76-1.85 (2H, m), 1.92-2.06 (1H, m), 2.21 (3H, s), 6.88 (1H, dd, J=8.4, 2.4 Hz), 7.04 (1H, d, J=2.4 Hz), 7.13 (1H, dd, J=8.7, 2.4 Hz), 7.29 (1H, d, J=8.4 Hz), 7.46-7.61 (2H, m), 7.66 (1H, d, J=2.4 Hz), 7.73 (1H, d, J=8.7 Hz), 7.83 (1H, s), 7.87 (1H, dt, J=6.6, 1.8 Hz), 9.94 (1H, s), 12.61 (1H, s).

7.76-7.85 (2H, m), 7.85-7.92 (1H, m), 8.65 (1H, s), 9.04 (1H, s), 9.95 (1H, s), 12.63 (1H, s).

Example A4

Production of N-[6-(3-{[3-(1-cyanocyclopropyl)benzoyl]amino}-4-methylphenoxy)-1,3-benzothiazol-2-yl]-1,3-oxazole-4-carboxamide

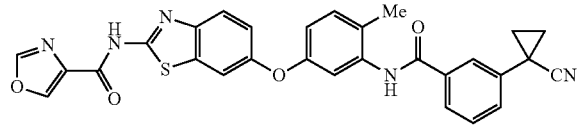

Example A5

Production of 3-(1-cyanocyclopropyl)-N-{2-methyl-5-[(2-{[(4-methylpiperazin-1-yl)acetyl]amino}-1,3-benzothiazol-6-yl)oxy]phenyl}benzamide

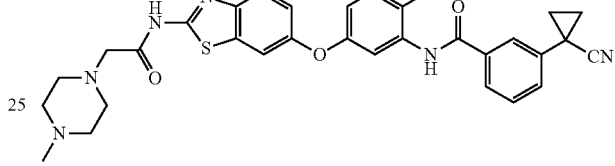

To a solution of 1,3-oxazole-4-carboxylic acid (81 mg, 0.715 mmol) in tetrahydrofuran (1 mL) were added oxalyl chloride (70 μL, 0.817 mmol) and N,N-dimethylformamide (1 drop), and the mixture was stirred at room temperature for 1 hr. The reaction mixture was concentrated under reduced pressure to give 1,3-oxazole-4-carbonyl chloride as a yellow oily substance.

To a solution of 1,3-oxazole-4-carbonyl chloride synthesized above in N,N-dimethylacetamide (3 mL) was added N-{5-[(2-amino-1,3-benzothiazol-6-yl)oxy]-2-methylphenyl}-3-(1-cyanocyclopropyl)benzamide (300 mg, 0.681 mmol) produced in Example A3(iv), and the mixture was stirred at room temperature for 1 hr. To the reaction mixture was added a solution of 1,3-oxazole-4-carbonyl chloride synthesized in the same manner as in the above from 1,3-oxazole-4-carboxylic acid (30 mg, 0.265 mmol), oxalyl chloride (27 μL, 0.316 mmol), N,N-dimethylformamide (1 drop) and tetrahydrofuran (1 mL) in N,N-dimethylacetamide (1 mL), and the mixture was further stirred at room temperature for 3 hr. The reaction mixture was concentrated under reduced pressure, diluted with 5% aqueous sodium hydrogencarbonate solution (200 mL), and extracted with ethyl acetate (300 mL). The organic layer was washed with saturated brine (100 mL), and dried over anhydrous sodium sulfate. The insoluble material was filtered off, and the filtrate was concentrated under reduced pressure. The obtained residue was purified by silica gel column chromatography (hexane/ethyl acetate=50/50→0/100), and triturated with ethyl acetate/hexane to give the title compound (3.84 g, 75%) as a colorless solid.

¹H-NMR (DMSO-d₅, 300 MHz) δ 1.50-1.65 (2H, m), 1.75-1.88 (2H, m), 2.22 (3H, s), 6.90 (1H, dd, J=2.4, 8.4 Hz), 7.06 (1H, d, J=2.4 Hz), 7.18 (1H, dd, J=2.4, 8.7 Hz), 7.30 (1H, d, J=8.4 Hz), 7.48-7.62 (2H, m), 7.74 (1H, d, J=2.4 Hz),

To a solution of N-{5-[(2-amino-1,3-benzothiazol-6-yl)oxy]-2-methylphenyl}-3-(1-cyanocyclopropyl)benzamide (300 mg, 0.681 mmol) produced in Example A3(iv) in N,N-dimethylacetamide (3.0 mL) was added bromoacetic bromide (62 μL, 0.715 mmol), and the mixture was stirred at room temperature for 1 hr. To the reaction mixture was added bromoacetic bromide (20 μL, 0.229 mmol), and the mixture was further stirred at room temperature for 2 hr. The reaction mixture was diluted with ethyl acetate (100 washed with 5% aqueous sodium hydrogencarbonate solution (100 mL) and saturated brine (100 mL), successively, and dried over anhydrous sodium sulfate. The insoluble material was filtered off, and the filtrate was concentrated under reduced pressure to give N-[5-({2-[(chloroacetyl)amino]-1,3-benzothiazol-6-yl}oxy)-2-methylphenyl]-3-(1-cyanocyclopropyl)benzamide as a colorless solid.

N-[5-({2-[(Chloroacetyl)amino]-1,3-benzothiazol-6-yl}oxy)-2-methylphenyl]-3-(1-cyanocyclopropyl)benzamide synthesized above was dissolved in tetrahydrofuran (5.0 mL), triethylamine (188 μL, 1.36 mmol) and 1-methylpiperazine (152 μL, 1.36 mmol) were added, and the mixture was stirred at 60° C. for 8 hr. The reaction mixture was cooled to room temperature, diluted with ethyl acetate (100 mL), washed with water (100 mL) and saturated brine (100 mL), successively, and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained solution was concentrated under reduced pressure. The obtained residue was triturated with ethyl acetate/hexane to give the title compound (141 mg, 36%) as a colorless solid.

¹H-NMR (DMSO-d₆, 300 MHz) δ 1.54-1.65 (2H, m), 1.74-1.84 (2H, m), 2.16 (3H, s), 2.21 (3H, s), 2.34 (4H, br s), 2.45-2.59 (6H, m), 6.88 (1H, dd, J=2.4, 8.4 Hz), 7.04 (1H, d, J=2.4 Hz), 7.13 (1H, dd, J=2.4, 8.7 Hz), 7.28 (1H, 8.4 Hz), 7.48-7.60 (2H, m), 7.68 (1H, d, J=2.4 Hz), 7.73 (1H, d, J=8.7 Hz), 7.82 (1H, s), 7.84-7.91 (1H, m), 9.94 (1H, s), 12.03 (1H, br s).

Example A6

Production of 3-(1-cyanocyclopropyl)-N-(5-{[2-(glycoloylamino)-1,3-benzothiazol-6-yl]oxy}-2-methylphenyl)benzamide

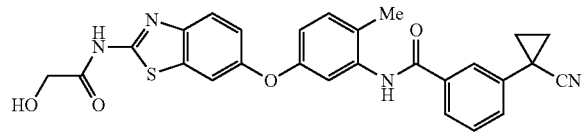

To a solution of N-{5-[(2-amino-1,3-benzothiazol-6-yl)oxy]-2-methylphenyl}-3-(1-cyanocyclopropyl)benzamide (300 mg, 0.681 mmol) produced in Example A3(iv) in tetrahydrofuran (8.0 mL) were added a solution of 2-chloro-2-oxoethyl acetate (77 μL, 0.715 mmol) in tetrahydrofuran (2.0 mL) and triethylamine (141 μL, 1.02 mmol), and the mixture was stirred at room temperature for 30 min. To the reaction mixture were added 2-chloro-2-oxoethyl acetate (154 μL, 1.43 mmol) and triethylamine (290 μL, 2.10 mmol), and the mixture was further stirred at room temperature for 1.5 hr. To the reaction mixture was added 1N aqueous sodium hydroxide solution (10 mL), and the mixture was stirred at room temperature for 30 min and neutralized with 1N hydrochloric acid. The obtained mixture was extracted with ethyl acetate (100 mL×2). The combined organic layer was washed with saturated brine (100 mL), and dried over anhydrous sodium sulfate. The insoluble material was filtered off, and the filtrate was concentrated under reduced pressure. The obtained residue was purified by basic silica gel column chromatography (ethyl acetate/methanol=100/0→90/10), and the obtained solution was concentrated under reduced pressure. The residue was triturated with ethyl acetate/diisopropyl ether to give the title compound (220 mg, 65%) as a colorless solid.

$^1$H-NMR (DMSO-$d_6$, 300 MHz) δ 1.54-1.64 (2H, m), 1.76-1.84 (2H, m), 2.22 (3H, s), 4.19 (2H, s), 5.54 (1H, br s), 6.89 (1H, dd, J=2.4, 8.4 Hz), 7.04 (1H, d, J=2.4 Hz), 7.14 (1H, dd, J=2.4, 8.7 Hz), 7.29 (1H, d, J=8.4 Hz), 7.47-7.61 (2H, m), 7.70 (1H, d, J=2.4 Hz), 7.75 (1H, d, J=8.7 Hz), 7.83 (1H, s), 7.85-7.92 (1H, m), 9.94 (1H, s), 12.02 (1H, br s).

Example A7

Production of 3-(1-cyano-1-methylethyl)-N-[5-({2-[(cyclopropylcarbonyl)amino]-1,3-benzothiazol-6-yl}oxy)-2-methylphenyl]benzamide

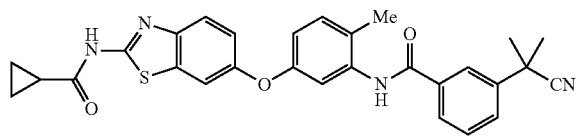

(i) Production of methyl 3-(1-cyano-1-methylethyl)benzoate

To a solution of methyl 3-(cyanomethyl)benzoate (7.0 g, 40 mmol) produced in Example A1(i) in dimethyl sulfoxide (80 mL) was added sodium hydride (60% in oil, 4.8 g, 120 mmol) while cooling to not more than 25° C. without causing solidification. The reaction mixture was stirred at room temperature for 20 min, methyl iodide (7.5 mL, 120 mmol) was added, and the mixture was further stirred at room temperature for 16 hr. The reaction mixture was diluted with water (400 mL) and extracted with ethyl acetate (800 mL). The organic layer was washed with water (400 mL) and saturated brine (400 mL), successively, dried over anhydrous sodium sulfate, and the insoluble material was filtered off. The solvent was evaporated under reduced pressure, and the residue was purified by silica gel column chromatography (ethyl acetate/hexane=5/95→50/50), and the fraction containing the object product was concentrated under reduced pressure to give the title compound (6.4 g, 79%) as a colorless oil.

$^1$H-NMR (DMSO-$d_6$, 300 MHz) δ 1.72 (6H, s), 3.89 (3H, s), 7.61 (1H, t, J=7.8 Hz), 7.82-7.85 (1H, ddd, J=1.2, 2.1, 7.8 Hz), 7.95 (1H, dt, J=7.8, 1.2 Hz), 8.08 (1H, t, J=1.5 Hz).

(ii) Production of 3-(1-cyano-1-methylethyl)benzoic acid

To a solution of methyl 3-(1-cyano-1-methylethyl)benzoate (2.8 g, 14 mmol) in tetrahydrofuran (30 mL) were added lithium hydroxide monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). The mixture was adjusted to pH 3 by slowly adding 1N hydrochloric acid. The resulting white precipitate was collected by filtration, washed with water, and dried to give the title compound (2.5 g, 98%) as a white powder.

$^1$H-NMR (DMSO-$d_6$, 300 MHz) δ 1.72 (6H, s), 7.57 (1H, t, J=7.8 Hz), 7.78 (1H, ddd, J=1.2, 2.1, 7.8 Hz), 7.92 (1H, dt, J=7.8, 1.5 Hz), 8.08 (1H, t, J=1.5 Hz), 13.19 (1H, s).

(iii) Production of 3-(1-cyano-1-methylethyl)-N-(5-hydroxy-2-methylphenyl)benzamide To a solution of 3-(1-cyano-1-methylethyl)benzoic acid (5.00 g, 26.4 mmol) in tetrahydrofuran (50 mL) were added oxalyl chloride (2.70 mL, 31.7 mmol) and N,N-dimethylformamide (2 drops), and the mixture was stirred at room temperature for 1 hr. The reaction mixture was concentrated under reduced pressure to give 3-(1-cyano-1-methylethyl)benzoyl chloride as a pale-yellow oily substance.

To a two-layer solution of 3-amino-4-methylphenol (3.25 g, 26.4 mmol) in tetrahydrofuran (20 mL)/1N aqueous sodium hydrogencarbonate solution (39 mL) was added a solution of 3-(1-cyano-1-methylethyl)benzoyl chloride synthesized above in tetrahydrofuran (20 mL), and the mixture was stirred at room temperature for 3 hr. The aqueous layer was separated, and extracted with ethyl acetate (100 mL). The combined organic layer was washed with 5% aqueous sodium hydrogencarbonate solution (50 mL) and saturated brine (50 mL), successively, and dried over anhydrous sodium sulfate. The insoluble material was filtered off, and the filtrate was concentrated under reduced pressure. The obtained residue was recrystallized from ethyl acetate (45 mL)/hexane (45 mL) to give the title compound (5.95 g, 77%) as a colorless powder.

$^1$H-NMR (DMSO-$d_6$, 300 MHz) δ 1.75 (6H, s), 2.11 (3H, s), 6.59 (1H, dd, J=2.4, 8.1 Hz), 6.81 (1H, d, J=2.4 Hz), 7.04 (1H, d, J=8.1 Hz), 7.59 (1H, t, J=7.8 Hz), 7.65-7.85 (1H, m), 7.94 (1H, d, J=7.8 Hz), 8.07 (1H, s), 9.27 (1H, s), 9.84 (1H, s).

(iv) Production of 3-(1-cyano-1-methylethyl)-N-[2-methyl-5-(4-nitrophenoxy)phenyl]benzamide To a solution of 1-fluoro-4-nitrobenzene (1.26 g, 8.92 mmol) and 3-(1-cyano-1-methylethyl)-N-(5-hydroxy-2-methylphenyl)benzamide (2.50 g, 8.5 mmol) in N,N-dimethylformamide (20 mL) was added potassium carbonate (1.85 g, 13.3 mmol) and the mixture was stirred at 60° C. for 4 hr, and further at 70° C. for 12 hr. The reaction mixture was cooled to room temperature, the insoluble material was filtered off, and the filtrate was concentrated under reduced pressure. The obtained residue was diluted with ethyl acetate (200 ml), washed with 5% aqueous sodium hydrogencarbonate solution (100 mL) and saturated brine (100 mL) successively, and dried over anhydrous sodium sulfate. The insoluble material was filtered off, and the filtrate was concentrated under reduced pressure to give the title compound (3.41 g, 97%) as a yellow amorphous substance. The obtained compound was used in the next reaction without a further purification.

$^1$H-NMR (DMSO-$d_5$, 300 MHz) δ 1.74 (6H, s), 2.29 (3H, s), 7.05 (1H, dd, J=2.4, 8.4 Hz), 7.10-7.19 (2H, m), 7.28 (1H, d, J=2.4 Hz), 7.41 (1H, d, J=8.4 Hz), 7.60 (1H, t, J=7.8 Hz), 7.72-7.80 (1H, m), 7.93-7.99 (1H, m), 8.07 (1H, s), 8.23-8.31 (2H, m), 10.05 (1H, s).

(v) Production of N-[5-(4-aminophenoxy)-2-methylphenyl]-3-(1-cyano-1-methylethyl)benzamide A suspension of 3-(1-cyano-1-methylethyl)-N-[2-methyl-5-(4-nitrophenoxy)phenyl]benzamide (3.50 g, 8.0 mmol), calcium chloride (2.36 g, 21.2 mmol) and reduced iron (4.75 g, 85 mmol) in ethanol (180 mL)/water (20 mL) was stirred with heating at 80° C. for 10 hr. The reaction mixture was cooled to room temperature, passed through a pad filled with celite to separate insoluble material, and the insoluble material was washed with ethanol. The filtrate and the washing were combined and concentrated under reduced pressure. The obtained residue was diluted with ethyl acetate (300 mL), washed with 5% aqueous ammonium chloride solution (200 mL), water (200 mL), 5% aqueous sodium hydrogencarbonate solution (200 mL) and saturated brine (200 mL), successively, and dried over anhydrous sodium sulfate. The insoluble material was filtered off, and the filtrate was concentrated under reduced pressure. The obtained residue was purified by silica gel column chromatography (hexane/ethyl acetate=60/40→0/100), and the obtained solution was concentrated under reduced pressure to give the title compound (2.89 g, 94%) as a colorless amorphous substance.

$^1$H-NMR (DMSO-$d_6$, 300 MHz) δ 1.74 (6H, s), 2.17 (3H, s), 4.97 (2H, s), 6.51-6.64 (2H, m), 6.68-6.83 (3H, m), 6.88 (1H, J=2.4 Hz), 7.20 (1H, d, J=8.4 Hz), 7.58 (1H, t, J=7.8 Hz), 7.69-7.78 (1H, m), 7.93 (1H, d, J=7.8 Hz), 8.05 (1H, s), 9.93 (1H, s).

(vi) Production of N-{5-[(2-amino-1,3-benzothiazol-6-yl)oxy]-2-methylphenyl}-3-(1-cyano-1-methylethyl)benzamide Potassium thiocyanate (4.80 g, 49.2 mmol) was suspended in acetic acid (80 mL) and the mixture was stirred at room temperature for 10 min. To the obtained solution was added a is solution of N-[5-(4-aminophenoxy)-2-methylphenyl]-3-(1-cyano-1-methylethyl)benzamide (5.00 g, 12.3 mmol) in acetic acid (80 mL), and the mixture was further stirred at room temperature for 20 min. To the obtained solution was added dropwise slowly a solution of bromine (2.46 g, 15.4 mmol) in acetic acid (50 mL) and, after the completion of the dropwise addition, the mixture was stirred at room temperature for 6 hr. The resulting yellow insoluble material was filtered off, and washed with acetic acid. The filtrate and the washing were combined and concentrated under reduced pressure. The obtained residue was suspended in ethyl acetate (300 mL), washed with 5% aqueous sodium hydrogencarbonate solution (300 mL) and saturated brine (300 mL), successively, and dried over anhydrous sodium sulfate. Activated carbon was added, and the mixture was stood for a while. The insoluble material was filtered off, and the filtrate was concentrated under reduced pressure to give the title compound (3.57 g, 66%) as a pale-yellow amorphous substance.

$^1$H-NMR (DMSO-$d_6$, 300 MHz) δ 1.73 (6H, s), 2.20 (3H, s), 6.83 (1H, dd, J=2.4, 8.4 Hz), 6.92 (1H, dd, J=2.4, 8.7 Hz), 6.98 (1H, d, J=2.4 Hz), 7.25 (1H, d, J=8.4 Hz), 7.33 (1H, d, J=8.7 Hz), 7.38-7.47 (3H, m), 7.58 (1H, t, J=7.8 Hz), 7.70-7.78 (1H, m), 7.93 (1H, d, J=7.8 Hz), 8.04 (1H, s), 9.95 (1H, s).

(vii) Production of 3-(1-cyano-1-methylethyl)-N-[5-({2-[(cyclopropylcarbonyl)amino]-1,3-benzothiazol-6-yl}oxy)-2-methylphenyl]benzamide To a solution of N-{5-[(2-amino-1,3-benzothiazol-6-yl)oxy]-2-methylphenyl}-3-(1-cyano-1-methylethyl)benzamide (200 mg, 0.452 mmol) in pyridine (4.0 mL) was added cyclopropanecarbonyl chloride (90 μL, 0.994 mmol), and the mixture was stirred at room temperature for 2 hr. The reaction mixture was concentrated under reduced pressure, and the residue was dissolved in methanol (2.0 mL)/tetrahydrofuran (2.0 mL)/water (2.0 mL). 1N Aqueous sodium hydroxide solution (2.0 mL) was added, and the mixture was stirred at room temperature for 1 hr. The reaction mixture was neutralized with 1N hydrochloric acid, diluted with ethyl acetate (100 mL), washed with water (50 mL) and saturated brine (50 mL), successively, and dried over anhydrous sodium sulfate. The insoluble material was filtered off, and the filtrate was concentrated under reduced pressure. The obtained residue was purified by silica gel column chromatography (hexane/ethyl acetate=70/30→0/100), and the obtained solution was concentrated under reduced pressure. The residue was triturated with ethyl acetate/diisopropyl ether to give the title compound (129 mg, 56%) as a colorless amorphous substance.

$^1$H-NMR (DMSO-$d_6$, 300 MHz) δ 0.89-1.00 (4H, m), 1.73 (6H, s), 1.93-2.06 (1H, m), 2.22 (3H, s), 6.89 (1H, dd, J=2.4, 8.4 Hz), 7.05 (1H, d, J=2.4 Hz), 7.14 (1H, dd, J=2.4, 8.7 Hz), 7.29 (1H, d, J=8.4 Hz), 7.58 (1H, t, J=7.8 Hz), 7.67 (1H, d, J=2.4 Hz), 7.71-7.78 (2H, m), 7.92 (1H, d, J=7.8 Hz), 8.04 (1H, s), 9.97 (1H, s), 12.62 (1H, s).

Example A8

Production of N-[6-(3-{[3-(1-cyano-1-methylethyl)benzoyl]amino}-4-methylphenoxy)-1,3-benzothiazol-2-yl]-1,3-oxazole-4-carboxamide

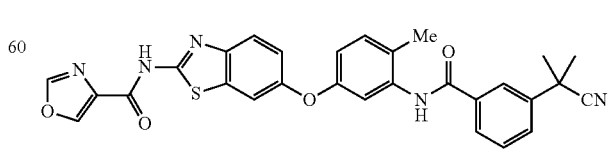

To a solution of 1,3-oxazole-4-carboxylic acid (112 mg, 0.994 mmol) in tetrahydrofuran (4.0 mL) were added oxalyl chloride (127 µL, 1.49 mmol) and N,N-dimethylformamide (1 drop), and the mixture was stirred at room temperature for 1 hr. The reaction mixture was concentrated under reduced pressure to give 1,3-oxazole-4-carbonyl chloride as a yellow oily substance.

1,3-Oxazole-4-carbonyl chloride synthesized above was suspended in pyridine (4.0 mL) at 0° C., N-{5-[(2-amino-1,3-benzothiazol-6-yl)oxy]-2-methylphenyl}-3-(1-cyano-1-methylethyl)benzamide (200 mg, 0.452 mmol) produced in Example A7(vi) was added, and the mixture was stirred at room temperature for 12 hr. The reaction mixture was concentrated under reduced pressure, and the residue was suspended in methanol (4.0 mL). 1N Aqueous sodium hydroxide solution (4.0 mL) was added, and the mixture was stirred at room temperature for 30 min. To the reaction mixture was added 1N hydrochloric acid (10 mL), and the mixture was extracted with ethyl acetate (100 mL). The organic layer was washed with 5% aqueous sodium hydrogencarbonate solution (50 mL) and saturated brine (50 mL), successively, and dried over anhydrous sodium sulfate. The insoluble material was filtered off, and the filtrate was concentrated under reduced pressure. The obtained residue was purified by basic silica gel column chromatography (hexane/ethyl acetate=70/30→0/100), and the obtained solution was concentrated under reduced pressure. The residue was triturated with ethyl acetate/diisopropyl ether to give the title compound (70 mg, 29%) as a colorless solid.

$^1$H-NMR (DMSO-$d_6$, 300 MHz) δ 1.73 (6H, s), 2.23 (3H, s), 6.90 (1H, dd, J=8.4, 2.4 Hz), 7.07 (1H, d, J=2.4 Hz), 7.18 (1H, dd, J=2.4, 8.7 Hz), 7.30 (1H, d, J=8.4 Hz), 7.58 (1H, t, J=7.8 Hz), 7.67-7.85 (3H, m), 7.93 (1H, d, J=7.8 Hz), 8.05 (1H, s), 8.65 (1H, s), 9.04 (1H, s), 9.98 (1H, s), 12.65 (1H, br s).

Example A9

Production of 3-(1-cyano-1-methylethyl)-N-{2-methyl-5-[(2-{[(4-methylpiperazin-1-yl)acetyl]amino}-1,3-benzothiazol-6-yl)oxy]phenyl}benzamide

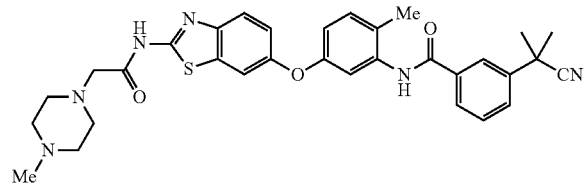

To a solution of N-{5-[(2-amino-1,3-benzothiazol-6-yl)oxy]-2-methylphenyl}-3-(1-cyano-1-methylethyl)benzamide (200 mg, 0.452 mmol) produced in Example A7(vi) in N,N-dimethylformamide (2.0 mL) was added chloroacetic acid chloride (79 µL, 0.995 mmol), and the mixture was stirred at room temperature for 4 hr. The reaction mixture was diluted with ethyl acetate (100 mL), washed with 5% aqueous sodium hydrogencarbonate solution (100 mL), water (100 mL) and saturated brine (100 mL), successively, and dried over anhydrous sodium sulfate. The insoluble material was filtered off, and the filtrate was concentrated under reduced pressure. The obtained residue was purified by silica gel column chromatography (hexane/ethyl acetate=50/50→0/100), and the obtained solution was concentrated under reduced pressure to give N-[5-({2-[(chloroacetyl)amino]-1,3-benzothiazol-6-yl}oxy)-2-methylphenyl]-3-(1-cyano-1-methylethyl)benzamide as a colorless solid.

N-[5-({2-[(Chloroacetyl)amino]-1,3-benzothiazol-6-yl}oxy)-2-methylphenyl]-3-(1-cyano-1-methylethyl)benzamide synthesized above was dissolved in tetrahydrofuran (8.0 mL), triethylamine (155 µL, 1.13 mmol) and 1-methylpiperazine (100 µL, 0.902 mmol) were added, and the mixture was stirred at 60° C. for 8 hr. The reaction mixture was cooled to room temperature, diluted with ethyl acetate (100 mL), washed with water (50 mL×2) and saturated brine (50 mL), successively, and dried over anhydrous sodium sulfate. The insoluble material was filtered off, and the filtrate was concentrated under reduced pressure. The residue was purified by basic silica gel column chromatography (hexane/ethyl acetate=50/50→0/100), and the obtained solution was concentrated under reduced pressure. The residue was triturated with ethyl acetate/hexane to give the title compound (106 mg, 40%) as a colorless solid.

$^1$H-NMR (DMSO-$d_6$, 300 MHz) δ 1.73 (6H, s), 2.16 (3H, s), 2.23 (3H, s), 2.35 (4H, br s), 2.42-2.61 (6H, m), 6.89 (1H, dd, J=2.4, 8.4 Hz), 7.06 (1H, d, J=2.4 Hz), 7.15 (1H, dd, J=2.4, 8.7 Hz), 7.29 (1H, d, J=8.4 Hz), 7.58 (1H, t, J=7.8 Hz), 7.66-7.79 (3H, m), 7.93 (1H, d, J=7.8 Hz), 8.04 (1H, s), 9.97 (1H, s), 12.04 (1H, s).

Example A10

Production of 3-(1-cyano-1-methylethyl)-N-(5-{[2-(glycoloylamino)-1,3-benzothiazol-6-yl]oxy}-2-methylphenyl)benzamide

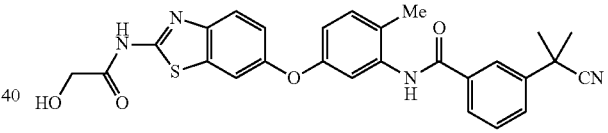

To a solution of N-{5-[(2-amino-1,3-benzothiazol-6-yl)oxy]-2-methylphenyl}-3-(1-cyano-1-methylethyl)benzamide (200 mg, 0.452 mmol) produced in Example A7(vi) in pyridine (4.0 mL) was added 2-chloro-2-oxoethyl acetate (107 µL, 0.994 mmol), and the mixture was stirred at room temperature for 10 hr. The reaction mixture was concentrated under reduced pressure, and the residue was dissolved in methanol (4.0 mL). 1N Aqueous sodium hydroxide solution (4.0 mL) was added, and the mixture was stirred at room temperature for 1 hr. The reaction mixture was neutralized with 1N hydrochloric acid, and extracted with ethyl acetate (100 mL). The organic layer was washed with water (50 mL) and saturated brine (50 mL), successively, and dried over anhydrous sodium sulfate. The insoluble material was filtered off, and the filtrate was concentrated under reduced pressure. The obtained residue was purified by basic silica gel column chromatography (ethyl acetate/methanol=100/0→80/20), and the obtained solution was concentrated under reduced pressure. The residue was triturated with ethyl acetate/diisopropyl ether to give the title compound (120 mg, 53%) as a colorless solid.

$^1$H-NMR (DMSO-$d_6$, 300 MHz) δ 1.73 (6H, s), 2.22 (3H, s), 4.18 (2H, br s), 5.54 (1H, br s), 6.89 (1H, dd, J=2.4, 8.4 Hz), 7.05 (1H, s), 7.14 (1H, dd, J=2.4, 8.7 Hz), 7.29 (1H, d,

J=8.4 Hz), 7.49-7.64 (1H, m), 7.67-7.79 (3H, m), 7.93 (1H, d, J=7.8 Hz), 8.04 (1H, s), 9.97 (1H, s), 12.03 (1H, br s).

Example A11

Production of 3-(1-cyano-1-methylethyl)-N-[3-({2-[(cyclopropylcarbonyl)amino]-5-fluoro-1,3-benzothiazol-6-yl}oxy)phenyl]benzamide

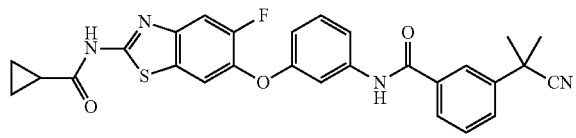

(i) Production of 3-(1-cyano-1-methylethyl)-N-(3-hydroxyphenyl)benzamide

To a solution of 3-(1-cyano-1-methylethyl)benzoic acid (10 g, 52.8 mmol) produced in Example A7(ii) in tetrahydrofuran (100 mL) were added N,N-dimethylformamide (4 drops) and oxalyl chloride (6.28 mL, 72.0 mmol), and the mixture was stirred at room temperature for 1.5 hr. The solvent was evaporated under reduced pressure to give a residue. To a solution of 3-aminophenol (5.24 g, 48.0 mmol) in tetrahydrofuran (40 mL) was added a suspension of sodium hydrogencarbonate (6.05 g, 72.0 mmol) in water (60 mL), and the mixture was stirred vigorously at room temperature. To this mixture was added dropwise a solution of the residue obtained above in tetrahydrofuran (60 mL) under ice-cooling, and the mixture was stirred at room temperature for 5 hr. The aqueous layer of the reaction mixture was separated, and the organic layer was diluted with ethyl acetate and washed with saturated brine. The organic layer was dried over anhydrous magnesium sulfate, and decolorized with activated carbon. The insoluble material was filtered off through a pad filled with two layers of silica gel and celite. The solvent was evaporated under reduced pressure, and the obtained solid was washed with ethyl acetate-hexane mixture to give the title compound (13.03 g, 96%) as a white powder.

$^1$H-NMR (DMSO-d$_6$, 300 MHz) δ 1.75 (6H, s), 6.49-6.55 (1H, m), 7.08-7.18 (2H, m), 7.30-7.34 (1H, m), 7.59 (1H, t, J=7.8 Hz), 7.72-7.77 (1H, m), 7.88-7.93 (1H, m), 8.01 (1H, t, J=1.7 Hz), 9.43 (1H, s), 10.18 (1H, s).

(ii) Production of 3-(1-cyano-1-methylethyl)-N-[3-(2-fluoro-4-nitrophenoxy)phenyl]benzamide To a solution of 1,2-difluoro-4-nitrobenzene (1.19 g, 7.49 mmol) and 3-(1-cyano-1-methylethyl)-N-(5-hydroxy-2-methylphenyl)benzamide (2.0 g, 7.13 mmol) in N,N-dimethylformamide (15 mL) was added potassium carbonate (1.47 g, 10.7 mmol), and the mixture was stirred at 80° C. for 18 hr. The reaction mixture was cooled to room temperature, and concentrated under reduced pressure. The obtained residue was diluted with ethyl acetate (200 mL), washed with water (200 mL) and saturated brine (200 mL), successively, and dried over anhydrous sodium sulfate. The insoluble material was filtered off, and the filtrate was concentrated under reduced pressure. The obtained residue was purified by silica gel column chromatography (hexane/ethyl acetate=95/5→0/30), and the obtained solution was concentrated under reduced pressure to give the title compound (2.09 g, 70%) as a yellow oil.

$^1$H-NMR (DMSO-d$_6$, 300 MHz) δ 1.75 (6H, s), 6.97 (1H, dd, J=2.1, 7.8 Hz), 7.18-7.32 (1H, m), 7.48 (1H, t, J=8.1 Hz), 7.60 (1H, t, J=7.8 Hz), 7.64-7.73 (2H, m), 7.73-7.80 (1H, m), 7.87-7.96 (1H, m), 8.02 (1H, t, J=1.8 Hz), 8.09-8.19 (1H, m), 8.37 (1H, dd, J=2.7, 10.8 Hz), 10.49 (1H, s).

(iii) Production of N-[3-(4-amino-2-fluorophenoxy)phenyl]-3-(1-cyano-1-methylethyl)benzamide A suspension of 3-(1-cyano-1-methylethyl)-N-[3-(2-fluoro-4-nitrophenoxy)phenyl]benzamide (2.03 g, 4.83 mmol), calcium chloride (1.41 g, 12.1 mmol) and reduced iron (2.97 g, 53.1 mmol) in ethanol (300 mL)/water (30 mL) was stirred with heating at 80° C. for 12 hr. The reaction mixture was cooled to room temperature, and passed through a pad filled with celite to separate insoluble material, and the insoluble materials were washed with ethanol. The filtrate and washing were combined and concentrated under reduced pressure. The obtained residue was diluted with ethyl acetate (300 mL), washed with 5% aqueous sodium hydrogencarbonate solution (300 mL), water (200 mL×2) and saturated brine (200 mL), successively, and dried over anhydrous sodium sulfate. The insoluble material was filtered off, and the filtrate was concentrated under reduced pressure. The obtained residue was purified by silica gel column chromatography (hexane/ethyl acetate=70/30→0/100), and the obtained solution was concentrated under reduced pressure to give the title compound (1.94 g, quantitatively) as a yellow amorphous substance.

$^1$H-NMR (DMSO-d$_6$, 300 MHz) δ 1.74 (6H, s), 5.34 (2H, s), 6.35-6.44 (1H, m), 6.49 (1H, dd, J=2.4, 13.2 Hz), 6.61-6.73 (1H, m), 6.80-7.03 (1H, m), 7.28 (1H, t, J=8.1 Hz), 7.36 (1H, t, J=2.1 Hz), 7.41-7.50 (1H, m), 7.57 (1H, t, J=7.8 Hz), 7.67-7.79 (1H, m), 7.83-7.94 (1H, m), 7.99 (1H, t, J=1.8 Hz), 10.31 (1H, s).

(iv) Production of N-{3-[(2-amino-5-fluoro-1,3-benzothiazol-6-yl)oxy]phenyl}-3-(1-cyano-1-methylethyl)benzamide Potassium thiocyanate (500 mg, 5.12 mmol) was suspended in acetic acid (10 mL) and the mixture was stirred at room temperature for 10 min. To the obtained solution was added a solution of N-[3-(4-amino-2-fluorophenoxy)phenyl]-3-(1-cyano-1-methylethyl)benzamide (500 mg, 1.28 mmol) in acetic acid (10 mL), and the mixture was further stirred at room temperature for 15 min. To the obtained solution was added dropwise slowly a solution of bromine (0.225 g, 1.41 mmol) in acetic acid (7.0 mL) and, after the completion of the dropwise addition, the mixture was stirred at room temperature for 14 hr. The resulting yellow insoluble material was filtrated, and washed with acetic acid. The filtrate and washing were combined and concentrated under reduced pressure. The obtained residue was suspended in ethyl acetate (300 mL), washed with 5% aqueous sodium hydrogencarbonate solution (200 mL×2), water (200 mL) and saturated brine (200 ml), successively, and dried over anhydrous sodium sulfate. The insoluble material was filtered off, and the filtrate was concentrated under reduced pressure to give the title compound (0.32 g, 57%) as a yellow amorphous substance. The obtained compound was used in the next reaction without a further purification.

$^1$H-NMR (DMSO-d$_6$, 300 MHz) δ 1.73 (6H, s), 6.74 (1H, dd, J=2.0, 7.8 Hz), 7.25-7.37 (2H, m), 7.40 (1H, t, J=2.0 Hz), 7.49-7.55 (1H, m), 7.57 (1H, t, J=7.8 Hz), 7.61-7.69 (3H, m), 7.70-7.78 (1H, m), 7.85-7.92 (1H, m), 7.98 (1H, t, J=1.6 Hz), 10.32 (1H, s).

(v) Production of 3-(1-cyano-1-methylethyl)-N-[3-({2-[(cyclopropylcarbonyl)amino]-5-fluoro-1,3-benzothiazol-6-yl}oxy)phenyl]benzamide To a solution of N-{3-[(2-amino-5-fluoro-1,3-benzothiazol-6-yl)oxy]phenyl}-3-(1-cyano-1-methylethyl)benzamide (200 mg, 0.448 mmol) in pyridine (4.0 mL) was added cyclopropanecarbonyl chloride (61 μL, 0.672 mmol), and the mixture was stirred at room temperature for 4 hr. The reaction mixture was diluted with ethyl acetate (100 mL), washed with 5% aqueous sodium hydrogencarbonate solution (100 mL) and saturated brine (100 mL), successively, and dried over anhydrous sodium sulfate. The insoluble material was filtered off, and the filtrate was concentrated under reduced pressure. The obtained residue was purified by silica gel column chromatography (hexane/ethyl acetate=60/40→0/100), and the obtained solution was concentrated under reduced pressure. The residue was triturated with ethyl acetate/diisopropyl ether/hexane to give the title compound (118 mg, 51%) as a colorless solid.

$^1$H-NMR (DMSO-$d_6$, 300 MHz) δ 0.87-1.01 (4H, m), 1.73 (6H, s), 1.91-2.06 (1H, m), 6.78 (1H, dd, J=2.1, 7.8 Hz), 7.35 (1H, t, J=7.8 Hz), 7.45 (1H, t, J=2.1 Hz), 7.51-7.62 (2H, m), 7.69-7.76 (1H, m), 7.79 (1H, d, J=11.4 Hz), 7.84-7.91 (1H, m), 7.91-8.04 (2H, m), 10.34 (1H, s), 12.74 (1H, s).

Example A12

Production of 3-(1-cyano-1-methylethyl)-N-[3-({2-[(cyclopropylcarbonyl)amino]-1,3-benzothiazol-6-yl}oxy)phenyl]benzamide

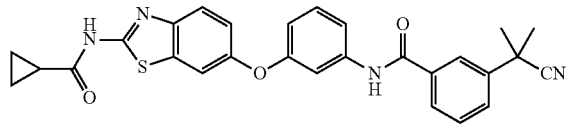

(i) Production of 3-(4-nitrophenoxy)aniline

To a solution of 1-fluoro-4-nitrobenzene (14.1 g, 100 mmol) and 3-aminophenol (11.2 g, 102 mmol) in N,N-dimethylformamide (150 mL) was added potassium carbonate (26.5 g, 191 mmol) and the mixture was stirred at 80° C. for 8 hr. The reaction mixture was cooled to room temperature, diluted with ethyl acetate-hexane (1:1, 250 mL) and washed with water (250 mL×2) and saturated brine (100 mL), successively. The collected aqueous layer was extracted with ethyl acetate-hexane (1:1, 250 mL). The collected organic layer was dried over anhydrous magnesium sulfate, and decolorized with activated carbon. The insoluble material was filtered off through a pad filled with two layers of silica gel and celite, and the filtrate was concentrated. The obtained yellow syrup-like substance was recrystallized from ethyl acetate and hexane to give the title compound (21.8 g, 95%) as yellow crystals.

$^1$H-NMR (DMSO-$d_6$, 300 MHz) δ 5.39 (2H, br s), 6.26 (1H, ddd, J=0.9, 2.4, 7.8 Hz), 6.31 (1H, t, J=2.1 Hz), 6.48 (1H, ddd, J=0.9, 2.1, 8.1 Hz), 7.07-7.14 (3H, m), 8.24 (2H, dt, J=7.2, 3.6 Hz).

(ii) Production of 3-(1-cyano-1-methylethyl)-N-[3-(4-nitrophenoxy)phenyl]benzamide To a solution of 3-(4-nitrophenoxy)aniline (4.69 g, 20.4 mmol) and 3-(1-cyano-1-methylethyl)benzoic acid (3.98 g, 21.0 mmol) produced in Example A7(ii) in pyridine (100 mL) were added 1-ethyl-3-(3-dimethylaminopropyl)carbodiimide hydrochloride (4.69 g, 24.5 mmol) and N,N-dimethylpyridine-4-amine (151 mg, 1.24 mmol), and the mixture was stirred at room temperature for 4 hr. To the reaction mixture was added methanol (50 mL) and the mixture was further stirred at the same temperature for 30 min. The solvent was evaporated under reduced pressure. The residue was diluted with ethyl acetate (200 mL), washed with dilute hydrochloric acid (150 mL×2) and saturated aqueous sodium hydrogencarbonate solution (150 mL), successively, and dried over anhydrous magnesium sulfate. The insoluble material was filtered off, and the filtrate was concentrated under reduced pressure to give the title compound (8.10 g, 99%) as a yellow amorphous substance. The obtained compound was used in the next reaction without a further purification.

$^1$H-NMR (DMSO-$d_6$, 300 MHz) δ 1.75 (6H, s), 6.97 (1H, dd, J=1.8, 8.4 Hz), 7.20 (2H, dt, J=10.5, 3.3 Hz), 7.49 (1H, t, J=7.8 Hz), 7.60 (1H, t, J=7.2 Hz), 7.67-7.71 (2H, m), 7.76 (1H, d, J=8.7 Hz), 7.93 (1H, d, J=7.8 Hz), 8.02 (1H, t, J=1.5 Hz), 8.29 (2H, dt, J=10.5, 3.3 Hz), 10.49 (1H, br s).

(iii) Production of N-[3-(4-aminophenoxy)phenyl]-3-(1-cyano-1-methylethyl)benzamide To a solution of 3-(1-cyano-1-methylethyl)-N-[3-(4-nitrophenoxy)phenyl]benzamide (8.10 g, 20.2 mmol) in tetrahydrofuran (50 mL) and methanol (50 mL) was added 10% palladium-carbon (555 mg), and the mixture was stirred under a hydrogen atmosphere (2.5 atm) at room temperature for 14 hr. The insoluble material was filtered off, and the filtrate was concentrated under reduced pressure to give the title compound (7.34 g, 98%) as a pale-gray amorphous substance. The obtained compound was used in the next reaction without a further purification.

$^1$H-NMR (DMSO-$d_6$, 300 MHz) δ 1.74 (6H, s), 5.00 (2H, br s), 6.58-6.67 (3H, m), 6.77-6.81 (2H, m), 7.27 (1H, t, J=8.1 Hz), 7.37 (1H, t, J=2.1 Hz), 7.43-7.46 (1H, m), 7.58 (1H, t, J=7.8 Hz), 7.74 (1H, ddd, J=0.9, 2.1, 7.8 Hz), 7.90 (1H, dt, J=8.1, 1.2 Hz), 7.99 (1H, t, J=1.5 Hz), 10.30 (1H, br s).

(iv) Production of N-{3-[(2-amino-1,3-benzothiazol-6-yl)oxy]phenyl}-3-(1-cyano-1-methylethyl)benzamide To a solution of potassium thiocyanate (8.09 g, 83.2 mmol) in acetic acid (150 ml) was added a solution of N-[3-(4-aminophenoxy)phenyl]-3-(1-cyano-1-methylethyl)benzamide (7.34 g, 19.8 mmol) in acetic acid (150 ml), and the mixture was stirred at room temperature for 15 min. To the obtained solution was added dropwise a solution of bromine (4.0 g, 25.0 mmol) in acetic acid (100 mL) at room temperature over 30 min or longer and, after the completion of the dropwise addition, the mixture was stirred at room temperature for 4 hr. The resulting yellow solid was filtered off, and the filtrate was concentrated under reduced pressure. The residue was dissolved in tetrahydrofuran (100 mL) and ethyl acetate (200 mL), and basified with 2N aqueous sodium hydroxide solution. The aqueous layer was separated and the organic layer was washed with saturated aqueous ammonium chloride solution (200 mL), and dried over anhydrous magnesium sulfate. The insoluble material was filtered off, and the filtrate was concentrated under reduced pressure to give the title compound (7.4 g, 87%) as a yellow amorphous substance. The obtained compound was used in the next reaction without a further purification.

¹H-NMR (DMSO-d₆, 300 MHz) δ 1.73 (6H, s), 6.73-6.76 (1H, m), 6.96 (1H, dd, J=2.7, 8.7 Hz), 7.31-7.36 (2H, m), 7.42-7.60 (6H, m), 7.72-7.75 (1H, m), 7.89 (1H, d, J=8.1 Hz), 7.98 (1H, t, J=1.8 Hz), 10.33 (1H, br s).

(v) Production of 3-(1-cyano-1-methylethyl)-N-[3-({2-[(cyclopropylcarbonyl)amino]-1,3-benzothiazol-6-yl}oxy)phenyl]benzamide To a solution of N-{3-[(2-amino-1,3-benzothiazol-6-yl)oxy]phenyl}-3-(1-cyano-1-methylethyl)benzamide (5.13 g, 12.0 mmol) in pyridine (50 mL) were added cyclopropanecarbonyl chloride (2.5 mL, 27.6 mmol) and N,N-dimethylpyridine-4-amine (89.3 mg, 731 μmol), and the mixture was stirred at room temperature for 6 hr. The reaction mixture was diluted with methanol (50 mL), 2N aqueous sodium hydroxide solution (10 mL) was added, and the mixture was stirred at room temperature for 3 hr. The reaction mixture was concentrated under reduced pressure, and the residue was suspended in ethyl acetate (300 mL), and washed successively with water (150 mL), dilute hydrochloric acid (100 mL), saturated aqueous sodium hydrogencarbonate solution (100 mL) and saturated brine (100 mL), successively. The organic layer was dried over anhydrous magnesium sulfate, the insoluble material was filtered off, and the filtrate was concentrated under reduced pressure. The residue was purified by silica gel chromatography (hexane/ethyl acetate=95/5→50/50) and recrystallized from ethyl acetate/diisopropyl ether to give the title compound (4.4 g, 88%) as colorless crystals.

¹H-NMR (DMSO-d₆, 300 MHz) δ 0.94-0.97 (4H, m), 1.73 (6H, s), 1.93-2.01 (1H, m), 6.80 (1H, dd, J=1.8, 8.1 Hz), 7.17 (1H, dd, J=2.4, 8.7 Hz), 7.37 (1H, t, J=8.1 Hz), 7.48 (1H, t, J=2.1 Hz), 7.55-7.61 (2H, m), 7.72-7.78 (3H, m), 7.89 (1H, d, J=8.1 Hz), 7.98 (1H, t, J=1.8 Hz), 10.35 (1H, br s), 12.63 (1H, br s).

Example A13

Production of 3-(1-cyano-1-methylethyl)-N-{3-[(2-{[(4-methylpiperazin-1-yl)acetyl]amino}-1,3-benzothiazol-6-yl)oxy]phenyl}benzamide

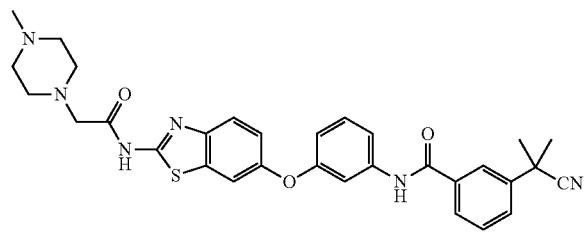

To a solution of N-{3-[(2-amino-1,3-benzothiazol-6-yl)oxy]phenyl}-3-(1-cyano-1-methylethyl)benzamide (452 mg, 1.05 mmol) produced in Example A12(iv) in pyridine (10 mL) were added (4-methylpiperazin-1-yl)acetic acid dihydrochloride (273 mg, 1.18 mmol), N,N-dimethylpyridine-4-amine (89.1 mg, 729 μmol), triethylamine (10 mL) and 1-ethyl-3-(3-dimethylaminopropyl)carbodiimide hydrochloride (492 mg, 2.57 mmol) at room temperature, and the mixture was stirred for 14 hr. To the reaction mixture were added 1-ethyl-3-(3-dimethylaminopropyl)carbodiimide hydrochloride (483 mg, 2.52 mmol) and N,N-dimethylpyridine-4-amine (292 mg, 2.39 mmol) and the mixture was further stirred for 4 hr. To the reaction mixture was added methanol (10 mL), and the mixture was stirred at room temperature for 30 min, and concentrated under reduced pressure. The residue was diluted with ethyl acetate (100 mL), washed with saturated aqueous ammonium chloride solution (50 mL×2) and saturated aqueous sodium hydrogencarbonate solution (50 mL), successively, and dried over anhydrous magnesium sulfate. The insoluble material was filtered off, and the filtrate was concentrated under reduced pressure. The residue was purified by silica gel column chromatography (hexane/ethyl acetate=80/20→20/80) and triturated with ethyl acetate and diisopropyl ether to give the title compound (171 mg, 29%) as a colorless solid.

¹H-NMR (DMSO-d₆, 300 MHz) δ 1.73 (6H, s), 2.16 (3H, s), 2.35 (4H, br s), 2.54 (4H, br s), 3.33 (2H, s), 6.80 (1H, dd, J=1.8, 8.1 Hz), 7.19 (1H, dd, J=2.4, 8.7 Hz), 7.37 (1H, t, J=8.1 Hz), 7.50-7.60 (3H, m), 7.73-7.82 (3H, m), 7.90 (1H, d, J=7.8 Hz), 7.99 (1H, br s), 10.36 (1H, s), 12.04 (1H, br s).

Example A14

Production of 3-(1-cyano-1-methylethyl)-N-(3-{[2-(glycoloylamino)-1,3-benzothiazol-6-yl]oxy}phenyl)benzamide

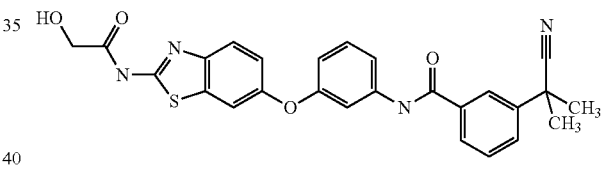

To a solution of N-{3-[(2-amino-1,3-benzothiazol-6-yl)oxy]phenyl}-3-(1-cyano-1-methylethyl)benzamide (347 mg, 810 μmol) produced in Example A12(iv) in pyridine (10 mL) were added 2-chloro-2-oxoethyl acetate (254 mg, 1.86 mmol) and N,N-dimethylpyridine-4-amine (58 mg, 475 μmol), and the mixture was stirred at room temperature for 2 hr. To the reaction mixture was added methanol (10 mL) and the mixture was stirred for 30 min. 10% Aqueous ammonia (2 mL) was added, and the mixture was stirred at room temperature for 2 hr. The reaction mixture was concentrated under reduced pressure, and the residue was diluted with tetrahydrofuran (5 mL) and ethyl acetate (30 mL). The diluted solution was washed with water (50 mL), dilute hydrochloric acid (50 mL), saturated aqueous sodium hydrogencarbonate solution (50 mL) and saturated brine (50 mL), successively, and dried over anhydrous magnesium sulfate. The insoluble material was filtered off, and the filtrate was concentrated under reduced pressure. The residue was purified by basic silica gel column chromatography (ethyl acetate/methanol=100/0→80/20), and triturated with ethyl acetate and diisopropyl ether to give the title compound (264 mg, 67%) as a colorless solid.

¹H-NMR (DMSO-d₆, 300 MHz) δ 1.73 (6H, s), 4.19 (2H, d, J=4.8 Hz), 5.55 (1H, br s), 6.79-6.82 (1H, m), 7.18 (1H, dd, J=2.7, 8.7 Hz), 7.37 (1H, t, J=8.1 Hz), 7.49 (1H, t, J=2.1 Hz), 7.55-7.60 (2H, m), 7.73-7.79 (3H, m), 7.84-7.90 (1H, m), 7.98 (1H, t, J=1.8 Hz), 10.36 (1H, br s), 12.04 (1H, br s).

Example A15

Production of N-[6-(3-{[3-(1-cyanocyclopropyl)benzoyl]amino}phenoxy)-1,3-benzothiazol-2-yl]-1,3-oxazole-4-carboxamide

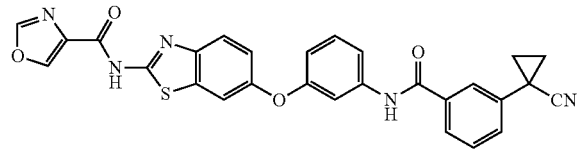

(i) Production of 3-(1-cyanocyclopropyl)-N-[3-(4-nitrophenoxy)phenyl]benzamide

Using 3-(4-nitrophenoxy)aniline (3.21 g, 13.9 mmol) produced in Example A12(i), 3-(1-cyanocyclopropyl)benzoic acid (2.70 g, 14.4 mmol) produced in Example A1(iii), pyridine (100 mL), 1-ethyl-3-(3-dimethylaminopropyl)carbodiimide hydrochloride (3.20 g, 16.7 mmol) and N,N-dimethylpyridine-4-amine (122 mg, 997 μmol) as starting materials, and in the same manner as in Example A12(ii), the title compound (5.1 g, 91%) was obtained as a yellow amorphous substance.

$^1$H-NMR (DMSO-$d_6$, 300 MHz) δ 1.59-1.64 (2H, m), 1.80-1.84 (2H, m), 7.96 (1H, ddd, J=0.9, 2.4, 8.1 Hz), 7.20 (2H, dt, J=7.2, 3.3 Hz), 7.49 (1H, t, J=8.4 Hz), 7.55-7.57 (2H, m), 7.66-7.71 (2H, m), 7.81-7.82 (1H, m), 7.85-7.89 (1H, m), 8.28 (2H, dt, J=6.9, 3.6 Hz), 10.48 (1H, br s).

(ii) Production of N-[3-(4-aminophenoxy)phenyl]-3-(1-cyanocyclopropyl)benzamide

Using 3-(1-cyanocyclopropyl)-N-[3-(4-nitrophenoxy)phenyl]benzamide (5.1 g, 12.7 mmol), tetrahydrofuran (50 mL), methanol (50 mL) and 10% palladium-carbon (455.9 mg) as starting materials, and in the same manner as in Example A12(iii), the title compound (5.25 g) was obtained as a colorless amorphous substance. The obtained compound was used in the next reaction without a further purification.

$^1$H-NMR (DMSO-$d_6$, 300 MHz) δ 1.59-1.63 (2H, m), 1.79-1.83 (2H, m), 5.00 (2H, br s), 6.58-6.66 (3H, m), 6.7.6-6.80 (2H, m), 7.27 (1H, t, J=8.1 Hz), 7.35 (1H, t, J=2.1 Hz), 7.43-7.46 (1H, m), 7.53-7.56 (2H, m), 7.77 (1H, br s), 7.84 (1H, dt, J=6.6, 2.1 Hz), 10.28 (1H, br s).

(iii) Production of N-{3-[(2-amino-1,3-benzothiazol-6-yl)oxy]phenyl}-3-(1-cyanocyclopropyl)benzamide Using potassium thiocyanate (5.52 g, 56.8 mmol), acetic acid (380 mL), N-[3-(4-aminophenoxy)phenyl]-3-(1-cyanocyclopropyl)benzamide (5.25 g), and bromine (3.15 g, 19.7 mmol) as starting materials, and in the same manner as in Example A12(iv), the title compound (4.2 g, total of 2 steps 78%) was obtained as a yellow amorphous substance. The obtained compound was used in the next reaction without a further purification.

$^1$H-NMR (DMSO-$d_6$, 300 MHz) δ 1.60 (2H, dd, J=5.1, 8.1 Hz), 1.80 (2H, dd, J=5.1, 8.1 Hz), 6.74 (1H, ddd, J=0.6, 2.4, 8.1 Hz), 6.95 (1H, dd, J=2.4, 8.4 Hz), 7.30-7.36 (2H, m), 7.41-7.46 (4H, m), 7.51-7.57 (3H, m), 7.77 (1H, br s), 7.84 (1H, dt, J=6.6, 2.1 Hz), 10.30 (1H, br s).

(iv) Production of N-[6-(3-{[3-(1-cyanocyclopropyl)benzoyl]amino}phenoxy)-1,3-benzothiazol-2-yl]-1,3-oxazole-4-carboxamide To a solution of N-{3-[(2-amino-1,3-benzothiazol-6-yl)oxy]phenyl}-3-(1-cyanocyclopropyl)benzamide (330 mg, 774 μmol) in pyridine (10 mL) were added 1,3-oxazole-4-carboxylic acid (120 mg, 1.06 mmol), N,N-dimethylpyridine-4-amine (52.3 mg, 428 μmol) and 1-ethyl-3-(3-dimethylaminopropyl)carbodiimide hydrochloride (220 mg, 1.15 mmol), and the mixture was stirred at room temperature for 12 hr. To the reaction mixture were added 1,3-oxazole-4-carboxylic acid (126 mg, 1.11 mmol) and 1-ethyl-3-(3-dimethylaminopropyl)carbodiimide hydrochloride (652 mg, 3.40 mmol) and the mixture was further stirred at room temperature for 16 hr. To the reaction mixture were added methanol (10 mL) and 2N aqueous sodium hydroxide solution (5 mL) and the mixture was stirred at the same temperature for 3 hr, and the solvent was evaporated under reduced pressure. The residue was diluted with ethyl acetate (50 mL), washed with water (50 mL), 0.1N hydrochloric acid (50 mL), and saturated aqueous sodium hydrogencarbonate solution (50 mL) and dried over anhydrous magnesium sulfate. The insoluble material was filtered off, and the filtrate was concentrated under reduced pressure. The residue was purified by reversed phase silica gel column chromatography (containing 0.1% trifluoroacetic acid, water/acetonitrile=95/5→5/95) and concentrated. The obtained trifluoroacetate was suspended in ethyl acetate (100 mL) and methanol (10 mL), and washed with saturated aqueous sodium hydrogencarbonate solution (50 mL) and saturated brine (50 ml), successively. The organic layer was dried over anhydrous magnesium sulfate, the insoluble material was filtered off and the filtrate was concentrated under reduced pressure. The residue was recrystallized from ethyl acetate and diisopropyl ether to give the title compound (156 mg, 34%) as colorless crystals.

$^1$H-NMR (DMSO-$d_6$, 300 MHz) δ 1.60 (2H, dd, J=5.4, 8.4 Hz), 1.80 (2H, dd, J=5.4, 8.4 Hz), 6.81 (1H, ddd, J=0.9, 2.7, 8.1 Hz), 7.21 (1H, dd, J=2.7, 8.7 Hz), 7.38 (1H, t, J=8.1 Hz), 7.48-7.59 (4H, m), 7.74-7.86 (4H, m), 8.65 (1H, s), 9.03 (1H, s), 10.34 (1H, br s), 12.65 (1H, br s).

Example A16

Production of 3-(1-cyanocyclopropyl)-N-{3-[(2-{[(4-methylpiperazin-1-yl)acetyl]amino}-1,3-benzothiazol-6-yl)oxy]phenyl}benzamide

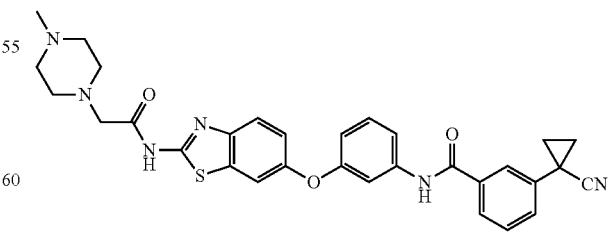

To a solution of N-{3-[(2-amino-1,3-benzothiazol-6-yl)oxy]phenyl}-3-(1-cyanocyclopropyl)benzamide (436 mg, 1.02 mmol) produced in Example A15(iii) in pyridine (10 mL) were added (4-methylpiperazin-1-yl)acetic acid dihydrochloride (278 mg, 1.20 mmol), N,N-dimethylpyridine-4-amine (79.3 mg, 649 μmol) and 1-ethyl-3-(3-dimethylaminopropyl)carbodiimide hydrochloride (470 mg, 2.45 mmol) at room temperature, and the mixture was stirred at room temperature for 14 hr. To the reaction mixture were added 1-ethyl-3-(3-dimethylaminopropyl)carbodiimide hydrochloride (454 mg, 2.37 mmol), (4-methylpiperazin-1-yl)acetic acid dihydrochloride (281 mg, 1.22 mmol), and triethylamine (10 mL) and the mixture was further stirred for 4 hr. To the reaction mixture was added methanol (10 mL) and the mixture was stirred at room temperature for 30 min and concentrated under reduced pressure. The residue was diluted with ethyl acetate (100 mL), washed with saturated aqueous ammonium chloride solution (80 mL×2) and saturated aqueous sodium hydrogencarbonate solution (50 mL), successively, and dried over anhydrous magnesium sulfate. The insoluble material was filtered off, and the filtrate was concentrated under reduced pressure. The residue was purified by silica gel column chromatography (ethyl acetate/methanol=100/0→90/10) and crystallized from ethyl acetate and hexane to give the title compound (136 mg, 24%) as colorless crystals.

$^1$H-NMR (DMSO-d$_6$, 300 MHz) δ 1.60 (2H, dd, J=5.4, 8.4 Hz), 1.80 (2H, dd, J=5.4, 8.4 Hz), 2.15 (3H, s), 2.35 (4H, br s), 2.54 (4H, br s), 3.33 (2H, s), 6.80 (1H, dd, J=1.8, 11.1 Hz), 7.18 (1H, dd, J=2.4, 8.7 Hz), 7.37 (1H, t, J=8.1 Hz), 7.49-7.57 (4H, m), 7.74-7.78 (3H, m), 7.83-7.85 (1H, m), 10.34 (1H, s), 12.05 (1H, br s).

Example A17

Production of 3-(1-cyanocyclopropyl)-N-(3-{[2-(glycoloylamino)-1,3-benzothiazol-6-yl]oxy}phenyl)benzamide

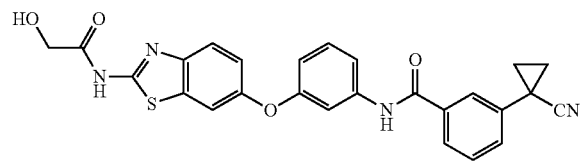

Using N-{3-[(2-amino-1,3-benzothiazol-6-yl)oxy]phenyl}-3-(1-cyanocyclopropyl)benzamide (310 mg, 726 μmol) produced in Example A15(iii), pyridine (10 mL), 2-chloro-2-oxoethyl acetate (269 mg, 1.97 mmol) and N,N-dimethylpyridine-4-amine (62.1 mg, 508 μmol) as starting materials, and in the same manner as in Example A14, the title compound (93 mg, 26%) was obtained as colorless crystals. In this Example, the purification operation was performed using silica gel column chromatography (hexane/ethyl acetate=5/95→20/80).

$^1$H-NMR (DMSO-d$_6$, 300 MHz) δ 1.60 (2H, dd, J=5.4, 8.1 Hz), 1.80 (2H, dd, J=5.4, 8.1 Hz), 4.20 (2H, s), 6.55 (1H, s), 6.80 (1H, dd, J=1.8, 8.1 Hz), 7.18 (1H, dd, J=2.4, 8.7 Hz), 7.37 (1H, t, J=8.1 Hz), 7.48-7.57 (4H, m), 7.75-7.86 (4H, m), 10.35 (1H, br s), 12.05 (1H, br s).

Example A18

Production of 3-(1-cyanocyclopropyl)-N-[3-({2-[(cyclopropylcarbonyl)amino]-1,3-benzothiazol-6-yl}oxy)-4-methoxyphenyl]benzamide

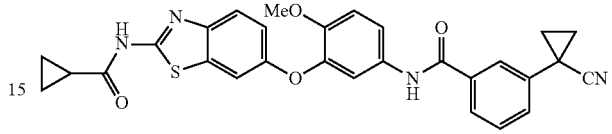

(i) Production of 3-(1-cyanocyclopropyl)-N-(3-hydroxy-4-methoxyphenyl)benzamide

To a suspension of 3-(1-cyanocyclopropyl)benzoic acid (9.40 g, 49.7 mmol) produced in Example A1(iii) in toluene (150 mL) was added thionyl chloride (48.9 g, 411 mmol), and the mixture was heated under reflux for 2 hr. The obtained solution was cooled to room temperature, sodium chloride (1.5 g, 26 mmol) was added and the mixture was further heated under reflux for 1.5 hr. The reaction mixture was cooled to room temperature, the insoluble material was removed and the solvent was evaporated under reduced pressure. The obtained brownish red solid was directly used in the next reaction as 3-(1-cyanocyclopropyl)benzoyl chloride.

To a solution of 5-amino-2-methoxyphenol (7.20 g, 51.7 mmol) in tetrahydrofuran (200 mL) was added water (250 mL) containing sodium hydrogencarbonate (5.00 g, 59.5 mmol) and the mixture was vigorously stirred at room temperature. While vigorously stirring the obtained reaction mixture separated in 2 layers, a solution of 3-(1-cyanocyclopropyl)benzoyl chloride synthesized above in tetrahydrofuran (150 mL) was added slowly at room temperature and the mixture was stirred for 1 hr. Sodium hydrogencarbonate was added to the reaction mixture until the development of carbon dioxide was ceased, and the reaction mixture was further stirred for 12 hr. The aqueous layer was separated, and extracted with ethyl acetate (150 mL×2). The collected organic layer was washed with saturated brine (100 mL), dried over anhydrous magnesium sulfate, and decolorized with activated carbon. The insoluble material was filtered off through a pad filled with two layers of silica gel and celite, and the filtrate was concentrated. The obtained brown solid was recrystallized from ethyl acetate, tetrahydrofuran and diisopropyl ether to give the title compound (14.2 g, 93%) as brownish red crystals.

$^1$H-NMR (DMSO-d$_5$, 300 MHz) δ 1.60-1.64 (2H, m), 1.80-1.84 (2H, m), 3.75 (3H, s), 6.89 (1H, d, J=9.0 Hz), 7.11 (1H, dd, J=2.4, 8.7 Hz), 7.30 (1H; d, J=2.7 Hz), 7.53-7.55 (2H, m), 7.79-7.80 (1H, m), 7.84-7.87 (1H, m), 9.08 (1H, s), 10.06 (1H, br s).

(ii) Production of 3-(1-cyanocyclopropyl)-N-[4-methoxy-3-(4-nitrophenoxy)phenyl]benzamide To a suspension of 3-(1-cyanocyclopropyl)-N-(3-hydroxy-4-methoxyphenyl)-benzamide (1.54 mg, 5.00 mmol) and potassium carbonate (0.69 g, 5.00 mmol) in N,N-dimethylformamide (5 mL) was added 1-fluoro-4-nitrobenzene (0.78 g, 5.50 mmol), and the mixture was stirred at 60° C. for 18 hr. The reaction mixture was poured into water and the mixture was extracted with ethyl acetate. The organic layer was dried over anhydrous magnesium sulfate, and the solvent was evaporated under reduced pressure. The residue was purified by silica gel column chromatography (eluent:hexane/ethyl acetate=1:1), and triturated with diethyl ether to give the title compound (1.90 g, 89%) as a white solid.

$^1$H-NMR (CDCl$_3$, 300 MHz) δ 1.45-1.52 (2H, m), 1.75-1.82 (2H, m), 3.82 (3H, s), 6.97 (2H, d, J=3.6 Hz), 7.03 (1H, d, J=3.6 Hz), 7.44-7.56 (4H, m), 7.72-7.76 (2H, m), 7.88 (1H, br s), 8.28-8.32 (2H, m).

(iii) Production of N-[3-(4-aminophenoxy)-4-methoxyphenyl]-3-(1-cyanocyclopropyl)benzamide A solution of 3-(1-cyanocyclopropyl)-N-[4-methoxy-3-(4-nitrophenoxy)phenyl]benzamide (2.10 g, 4.89 mmol), reduced iron (0.56 g, 10.0 mmol) and calcium chloride (1.11 g, 10.0 mmol) in ethanol (40 mL)/water (10 mL) was stirred at 80° C. for 18 hr. The reaction mixture was poured into 0.5N aqueous sodium hydroxide solution (400 mL), ethyl acetate (300 mL) was added and the mixture was stirred. The insoluble material was filtered off through celite, and the organic layer was separated and dried over anhydrous magnesium sulfate, and the solvent was evaporated under reduced pressure. The residue was purified by silica gel column chromatography (eluent:hexane/ethyl acetate=1:1), and triturated with diethyl ether to give the title compound (1.74 g, 82%) as a pale-yellow solid.

$^1$H-NMR (CDCl$_3$, 300 MHz) δ 1.45-1.52 (2H, m), 1.75-1.80 (2H, m), 3.60 (2H, br s), 3.91 (3H, s), 6.67 (2H, d, J=3.6 Hz), 6.88 (2H, d, J=3.6 Hz), 6.97 (2H, d, J=3.6 Hz), 7.48-7.80 (6H, m).

(iv) Production of N-{3-[(2-amino-1,3-benzothiazol-6-yl)oxy]-4-methoxyphenyl}-3-(1-cyanocyclopropyl)benzamide To a solution (10 mL) of N-[3-(4-aminophenoxy)-4-methoxyphenyl]-3-(1-cyanocyclopropyl)benzamide (1.74 g, 4.36 mmol) in acetic acid was added potassium thiocyanate (1.46 g, 15.0 mmol), and the mixture was stirred at room temperature for 30 min. To the obtained transparent solution was added dropwise bromine (1.20 g, 7.50 mmol) under ice-cooling, and the reaction mixture was stirred at room temperature for 18 hr. The precipitated yellow powder was filtered off through celite, and the filtrate was concentrated under reduced pressure. To the residue was added 0.1N aqueous sodium hydroxide solution, and the mixture was extracted with ethyl acetate. The organic layer was dried over anhydrous magnesium sulfate, and the solvent was evaporated under reduced pressure. The residue was purified by silica gel column chromatography (eluent:hexane/ethyl acetate=1:1), and triturated with diethyl ether to give the title compound (1.08 g, 54%) as a yellow solid.

$^1$H-NMR (CDCl$_3$, 300 MHz) δ 1.40° C.-1.55 (2H, m), 1.70-1.85 (2H, m), 3.95 (3H, s), 5.25 (2H, br s), 6.99 (2H, d, J=3.6 Hz), 7.10-7.30 (2H, m), 7.36-7.52 (4H, m), 7.66-7.78 (2H, m), 7.96 (1H, br s).

(v) Production of 3-(1-cyanocyclopropyl)-N-[3-({2-[(cyclopropylcarbonyl)amino]-1,3-benzothiazol-6-yl}oxy)-4-methoxyphenyl]benzamide A solution of N-{3-[(2-amino-1,3-benzothiazol-6-yl)oxy]-4-methoxyphenyl}-3-(1-cyanocyclopropyl)benzamide (91 mg, 0.20 mmol), cyclopropanecarbonyl chloride (105 mg, 1.00 mmol) and N,N-dimethylpyridine-4-amine (122 mg, 1.00 mmol) in pyridine (2 mL) was stirred at room temperature for 18 hr. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent: hexane/ethyl acetate=1:1), and triturated with diethyl ether to give the title compound (58 mg, 55%) as a pale-yellow solid.

$^1$H-NMR (CDCl$_3$, 300 MHz) δ 0.90-1.02 (2H, m), 1.08-1.18 (2H, m), 1.48-1.58 (2H, m), 1.70-1.82 (2H, m), 1.90-2.00 (1H, m), 3.87 (3H, s), 7.02 (1H, d, J=8.7 Hz), 7.12 (1H, dd, J=2.4, 8.7 Hz), 7.33-7.46 (3H, m), 7.57 (1H, d, J=6.6 Hz), 7.65 (2H, dd, J=6.0, 8.7 Hz), 7.73 (1H, d, J=1.5 Hz), 7.85 (1H, d, J=7.2 Hz), 9.58 (1H, br s), 11.94 (1H, br s).

Example A19

Production of 3-(1-cyanocyclopropyl)-N-(3-{[2-(glycoloylamino)-1,3-benzothiazol-6-yl]oxy}-4-methoxyphenyl)benzamide

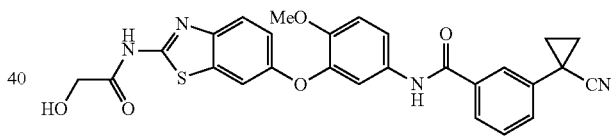

A solution of N-{3-[(2-amino-1,3-benzothiazol-6-yl)oxy]-4-methoxyphenyl}-3-(1-cyanocyclopropyl)benzamide (91 mg, 0.20 mmol) produced in Example A18(iv) and 2-chloro-2-oxoethyl acetate (137 mg, 1.00 mmol) in N,N-dimethylformamide (2 mL) was stirred at room temperature for 18 hr. The reaction mixture was poured into water and the mixture was extracted with ethyl acetate. The organic layer was dried over anhydrous magnesium sulfate, and the solvent was evaporated under reduced pressure. The residue was dissolved in methanol (5 mL)/tetrahydrofuran (5 mL), 8N aqueous sodium hydroxide solution (1 mL) was added under ice-cooling, and the mixture was stirred at room temperature for 30 min. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=1:1), and triturated with acetone to give the title compound (22 mg, 21%) as a pale-yellow solid.

$^1$H-NMR (CDCl$_3$, 300 MHz) δ 1.48-1.55 (2H, m), 1.72-1.80 (2H, m), 3.87 (3H, s), 4.28 (2H, d, 5.7 Hz), 5.52 (1H, t, J=5.7 Hz), 7.02 (1H, d, J=9.0 Hz), 7.15 (1H, dd, J=2.1, 5.7

Hz), 7.35-7.50 (2H, m), 7.55-7.80 (4H, m), 7.88 (1H, br s), 7.85 (1H, d, J=7.8 Hz), 9.57 (1H, br s), 10.54 (1H, br s).

Example A20

Production of 3-(1-cyanocyclopropyl)-N-{4-methoxy-3-[(2-{[(4-methylpiperazin-1-yl)acetyl]amino}-1,3-benzothiazol-6-yl)oxy]phenyl}benzamide

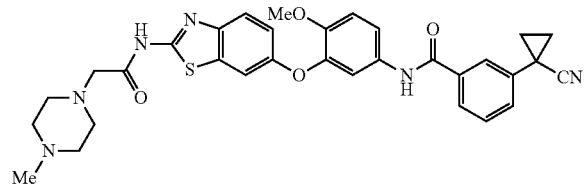

A solution of N-{3-[(2-amino-1,3-benzothiazol-6-yl)oxy]-4-methoxyphenyl}-3-(1-cyanocyclopropyl)benzamide (91 mg, 0.20 mmol)) produced in Example A18(iv) and chloroacetyl chloride (113 mg, 1.00 mmol) in N,N-dimethylformamide (5 mL) was stirred at room temperature for 18 hr. The reaction mixture was poured into water and the mixture was extracted with ethyl acetate. The organic layer was dried over anhydrous magnesium sulfate, the solvent was evaporated under reduced pressure, and the residue was purified by silica gel chromatography (eluent:hexane/ethyl acetate=1:1) to give a colorless oil. This was dissolved in N,N-dimethylformamide (2 mL), 1-methylpiperazine (100 mg, 1.00 mmol) was added, and the mixture was stirred at room temperature for 2 hr. The reaction mixture was poured into water and the mixture was extracted with ethyl acetate. The organic layer was dried over anhydrous magnesium sulfate, and the solvent was evaporated under reduced pressure. The residue was purified by basic silica gel chromatography (eluent:ethyl acetate/methanol=10:1), and triturated with diethyl ether to give the title compound (47 mg, 39%) as a white solid.

$^1$H-NMR (CDCl$_3$, 300 MHz) δ 1.45-1.50 (2H, m), 1.75-1.80 (2H, m), 2.33 (3H, s), 2.40° C.-2.60 (4H, m), 2.60-2.80 (4H, m), 3.27 (2H, s), 3.88 (3H, s), 7.03 (1H, d, 8.7 Hz), 7.16 (1H, dd, J=2.4, 6.0 Hz), 7.35-7.57 (5H, m), 7.65-7.78 (4H, m), 10.36 (1H, br s).

Example A21

Production of 3-(1-cyano-1-methylethyl)-N-[3-({2-[(cyclopropylcarbonyl)amino]-1,3-benzothiazol-6-yl}oxy)-4-methoxyphenyl]benzamide

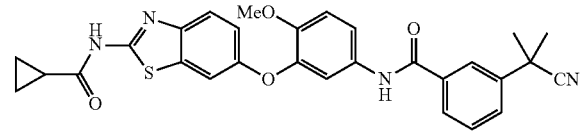

(i) Production of 3-(1-cyano-1-methylethyl)-N-(3-hydroxy-4-methoxyphenyl)benzamide To a solution (20 mL) of 3-(1-cyano-1-methylethyl)benzoic acid (4.92 g, 26.0 mmol) in oxalyl chloride was added N,N-dimethylformamide (0.1 mL), and the mixture was stirred at room temperature for 30 min. Excess reagents were evaporated under reduced pressure, and the obtained residue was dissolved in tetrahydrofuran (20 mL), and 5-amino-2-methoxyphenol (4.17 g, 30.0 mmol) and N-ethyl-N-isopropylpropane-2-amine (6.46 g, 50.0 mmol) were successively added dropwise under ice-cooling. The reaction mixture was stirred at room temperature for 18 hr, poured into water and the mixture was extracted with ethyl acetate. The organic layer was dried over anhydrous magnesium sulfate, and the solvent was evaporated under reduced pressure. The residue was dissolved in methanol (5 mL)/tetrahydrofuran (5 mL), 8N aqueous sodium hydroxide solution (1 mL) was added under ice-cooling, and the mixture was stirred at room temperature for 18 hr. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=5:1), and triturated with diethyl ether to give the title compound (4.70 g, 58%) as a pale-yellow solid.

$^1$H-NMR (CDCl$_3$, 300 MHz) δ 1.77 (6H, s), 3.90 (3H, s), 5.71 (1H, s), 6.85 (1H, d, J=8.7 Hz), 7.15-7.22 (2H, m), 7.52 (1H, t, J=3.6 Hz), 7.68-7.78 (3H, m), 7.96 (1H, br s).

(ii) Production of 3-(1-cyano-1-methylethyl)-N-[4-methoxy-3-(4-nitrophenoxy)phenyl]benzamide Using 3-(1-cyano-1-methylethyl)-N-(3-hydroxy-4-methoxyphenyl)benzamide (1.55 mg, 5.00 mmol), 1-fluoro-4-nitrobenzene (0.78 g, 5.50 mmol) and potassium carbonate (0.69 g, 5.00 mmol), and in the same manner as in Example A18(ii), the title compound (1.80 g, 83%) was obtained as a white powder.

$^1$H-NMR (CDCl$_3$, 300 MHz) δ 1.78 (6H, s), 3.81 (3H, s), 7.00 (2H, d, J=9.3 Hz), 7.06 (1H, d, J=8.7 Hz), 7.44-7.56 (3H, m), 7.65-7.80 (3H, m), 7.96 (1H, d, J=1.8 Hz), 8.20 (2H, d, J=9.3 Hz).

(iii) Production of N-[3-(4-aminophenoxy)-4-methoxyphenyl]-3-(1-cyano-1-methylethyl)benzamide To a solution of 3-(1-cyano-1-methylethyl)-N-[4-methoxy-3-(4-nitrophenoxy)phenyl]benzamide (1.80 g, 4.17 mmol) in methanol (5 mL)/tetrahydrofuran (5 mL) was added 10%-palladium carbon (1 g), and the mixture was vigorously stirred under a hydrogen atmosphere at room temperature for 18 hr. The catalyst was filtered off through celite, and the filtrate was concentrated under reduced pressure to give the title compound (1.10 g, 66%) as a colorless amorphous substance.

$^1$H-NMR (CDCl$_3$, 300 MHz) δ 1.75 (6H, s), 3.57 (2H, br s), 3.91 (3H, s), 6.66 (2H, d, J=8.7 Hz), 6.88 (2H, d, J=8.7 Hz), 6.97 (2H, d, J=8.7 Hz), 7.39 (1H, dd, J=2.4, 8.7 Hz), 7.48 (1H, t, J=7.8 Hz), 7.60-7.75 (3H, m), 7.91 (1H, br s).

(iv) Production of N-{3-[(2-amino-1,3-benzothiazol-6-yl)oxy]-4-methoxyphenyl}-3-(1-cyano-1-methylethyl)benzamide Using N-[3-(4-aminophenoxy)-4-methoxyphenyl]-3-(1-cyano-1-methylethyl)benzamide (1.10 g, 2.74 mmol), potassium thiocyanate (0.97 g, 10.0 mmol) and bromine (0.60 g, 3.75 mmol), and in the same manner as in Example A18(iv), the title compound (1.00 g, 80%) was obtained as a yellow powder.

$^1$H-NMR (CDCl$_3$, 300 MHz) δ 1.74 (6H, s), 3.88 (3H, s), 5.16 (2H, br s), 6.98-7.03 (2H, m), 7.07 (1H, br s), 7.21 (1H, d, J=3.6 Hz), 7.43-7.49 (3H, m), 7.64-7.72 (2H, m), 7.84 (1H, br s), 7.91 (1H, br s).

(v) Production of 3-(1-cyano-1-methylethyl)-N-[3-({2-[(cyclopropylcarbonyl)amino]-1,3-benzothiazol-6-yl}oxy)-4-methoxyphenyl]benzamide Using N-{3-[(2-amino-1,3-benzothiazol-6-yl)oxy]-4-methoxyphenyl}-3-(1-cyano-1-methylethyl)benzamide (115 mg, 0.25 mmol), cyclopropanecarbonyl chloride (105 mg, 1.00 mmol), N,N-dimethylpyridine-4-amine (122 mg, 1.00 mmol) and pyridine (2 mL), and in the same manner as in Example A18(v), the title compound (59 mg, 45%) was obtained as a pale-yellow powder.

$^1$H-NMR (CDCl$_3$, 300 MHz) δ 0.95 (2H, m), 1.14 (2H, m), 1.93 (1H, m), 1.67 (6H, s), 3.87 (3H, s), 7.02 (1H, d, J=9.0 Hz), 7.13 (1H, dd, J=2.4, 9.0 Hz), 7.35 (2H, m), 7.47 (1H, t, J=7.8 Hz), 7.62-7.68 (3H, m), 7.87 (1H, d, J=7.8 Hz), 8.00 (1H, s), 9.43 (1H, br s), 11.84 (1H, br s).

Example A22

Production of 3-(1-cyano-1-methylethyl)-N-(3-{[2-(glycoloylamino)-1,3-benzothiazol-6-yl]oxy}-4-methoxyphenyl)benzamide

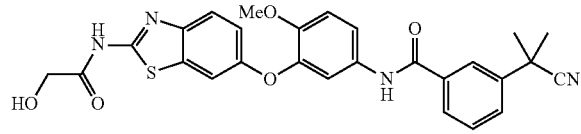

Using N-{3-[(2-amino-1,3-benzothiazol-6-yl)oxy]-4-methoxyphenyl}-3-(1-cyano-1-methylethyl)benzamide (230 mg, 0.50 mmol) produced in Example A21(iv), 2-chloro-2-oxoethyl acetate (273 mg, 2.00 mmol) and N,N-dimethylformamide (5 mL), and in the same manner as in Example A19, the title compound (126 mg, 49%) was obtained as a pale-yellow powder.

$^1$H-NMR (CDCl$_3$, 300 MHz) δ 1.75 (6H, s), 3.24 (1H, br s), 3.88 (3H, s), 4.41 (2H, s), 7.03 (1H, d, J=8.7 Hz), 7.16 (1H, dd, J=2.4, 8.7 Hz), 7.38 (1H, d, J=2.4 Hz), 7.44-7.51 (2H, m), 7.64-7.75 (5H, m), 7.92 (1H, br s), 9.88 (1H, br s).

Example A23

Production of 3-(1-cyano-1-methylethyl)-N-{4-methoxy-3-[(2-{[(4-methylpiperazin-1-yl)acetyl]amino}-1,3-benzothiazol-6-yl)oxy]phenyl}benzamide

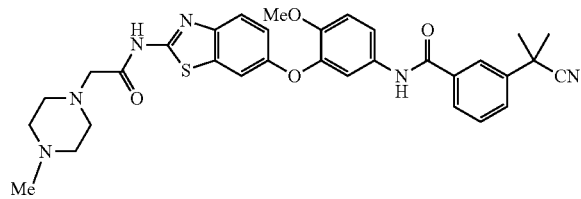

Using N-{3-[(2-amino-1,3-benzothiazol-6-yl)oxy]-4-methoxyphenyl}-3-(1-cyano-1-methylethyl)benzamide (230 mg, 0.50 mmol) produced in Example A21(iv), chloroacetyl chloride (225 mg, 2.00 mmol), 1-methylpiperazine (200 mg, 2.00 mmol) and N,N-dimethylformamide, and in the same manner as in Example A20, the title compound (120 mg, 40%) was obtained as a pale-yellow powder.

$^1$H-NMR (CDCl$_3$, 300 MHz) δ 1.75 (6H, s), 2.33 (3H, s), 2.45-2.60 (4H, m), 2.60-2.75 (4H, m), 3.28 (2H, s), 3.88 (3H, s), 7.04 (1H, d, J=9.0 Hz), 7.17 (1H, dd, J=2.4, 8.7 Hz), 7.27 (1H, s), 7.39 (1H, d, J=2.4 Hz), 7.43-7.52 (2H, m), 7.67-7.75 (4H, m), 7.92 (1H, br s), 10.36 (1H, br s).

Example A24

Production of N-[6-(5-{[3-(1-cyano-1-methylethyl)benzoyl]amino}-2-methoxyphenoxy)-1,3-benzothiazol-2-yl]-1,3-oxazole-4-carboxamide

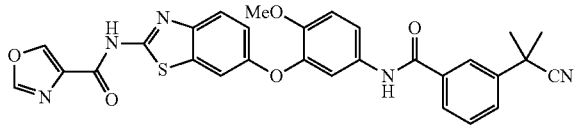

A solution of N-{3-[(2-amino-1,3-benzothiazol-6-yl)oxy]-4-methoxyphenyl}-3-(1-cyano-1-methylethyl)benzamide (230 mg, 0.50 mmol) produced in Example A21(iv), 1,3-oxazole-4-carboxylic acid (113 mg, 1.00 mmol), 1-ethyl-3-(3-dimethylaminopropyl)carbodiimide hydrochloride (192 mg, 1.00 mmol), 1-hydroxybenzotriazole (135 mg, 1.0 mmol) and N-ethyl-N-isopropylpropane-2-amine (260 mg, 2.00 mmol) in N,N-dimethylformamide (5 mL) was stirred at room temperature for 18 hr. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=1:1), and triturated with diethyl ether to give the title compound (183 mg, 66%) as a white solid.

$^1$H-NMR (CDCl$_3$, 300 MHz) δ 1.75 (6H, s), 3.88 (3H, s), 7.05 (1H, d, J=9.0 Hz), 7.19 (1H, dd, J=2.4, 8.7 Hz), 7.27 (1H, s), 7.41 (1H, d, J=2.4 Hz), 7.45-7.52 (2H, m), 7.66-7.78 (4H, m), 7.93 (1H, br s), 7.95 (1H, s), 8.42 (1H, s), 10.07 (1H, br s).

Example A25

Production of 3-({2-[(cyclopropylcarbonyl)amino]-1,3-benzothiazol-6-yl}oxy)-N-[4-(trifluoromethyl)phenyl]benzamide

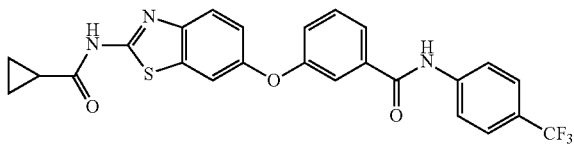

(i) Production of 3-({[4-(trifluoromethyl)phenyl]amino}carbonyl)phenyl acetate

To a solution (20 mL) of 3-(acetyloxy)benzoic acid (18.0 g, 100 mmol) in thionyl chloride was added N,N-dimethylformamide (0.1 mL), and the mixture was stirred at room temperature for 1 hr. Excess reagents were evaporated under reduced pressure, and the obtained residue was dissolved in tetrahydrofuran (50 mL), and 4-(trifluoromethyl)aniline (24.2 g, 150 mmol) and N-ethyl-N-isopropylpropane-2-amine (19.4 g, 150 mmol) were successively added dropwise under ice-cooling. The reaction mixture was stirred at room temperature for 1 hr, poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=5:1), and triturated with diethyl ether to give the title compound (27.7 g, 86%) as a pale-yellow solid.

$^1$H-NMR (CDCl$_3$, 300 MHz) δ 2.34 (3H, s), 7.30 (1H, dd, J=2.4, 8.1 Hz), 7.51 (1H, t, J=8.1 Hz), 7.59-7.64 (3H, m), 7.70-7.78 (3H, m), 7.98 (1H, br s).

(ii) Production of 3-hydroxy-N-[4-(trifluoromethyl)phenyl]benzamide

To a solution of 3-({[4-(trifluoromethyl)phenyl]amino}carbonyl)phenyl acetate (27.7 g, 85.5 mmol) in methanol (100 mL)/tetrahydrofuran (100 mL) was added 8N aqueous sodium hydroxide solution (20 mL) under ice-cooling, and the mixture was stirred at room temperature for 3 hr and dried under reduced pressure to solidness. The residue was poured into dilute hydrochloric acid (pH=2) and the mixture was extracted with ethyl acetate. The organic layer was dried over anhydrous magnesium sulfate, and the solvent was evaporated under reduced pressure. The residue was triturated with diethyl ether to give the title compound (21.7 g, 90%) as a white solid.

$^1$H-NMR (CDCl$_3$, 300 MHz) δ 7.02-7.06 (1H, m), 7.25-7.44 (3H, m), 7.57 (2H, d, J=7.8 Hz), 7.92 (2H, d, J=8.7 Hz), 9.08 (1H, br s) 9.45 (1H, br s).

(iii) Production of 3-(4-nitrophenoxy)-N-[4-(trifluoromethyl)phenyl]benzamide To a suspension of 3-hydroxy-N-[4-(trifluoromethyl)phenyl]benzamide (5.62 g, 20.0 mmol) and potassium carbonate (2.76 g, 20.0 mmol) in N,N-dimethylformamide (20 mL) was added 1-fluoro-4-nitrobenzene (3.10 g, 22.0 mmol), and the mixture was stirred at 60° C. for 18 hr. The reaction mixture was poured into water and the mixture was extracted with ethyl acetate. The organic layer was dried over anhydrous magnesium sulfate, and the solvent was evaporated under reduced pressure. The residue was purified by silica gel column chromatography (eluent:hexane/ethyl acetate=1:1), and triturated with diethyl ether to give the title compound (6.75 g, 84%) as a white solid.

$^1$H-NMR (CDCl$_3$, 300 MHz) δ 7.08 (2H, d, J=7.2 Hz), 7.92 (1H, dd, J=2.4, 8.7 Hz), 7.58-7.65 (4H, m), 7.71-7.79 (3H, m), 7.95 (1H, br s), 8.23 (2H, d, J=8.7 Hz).

(iv) Production of 3-(4-aminophenoxy)-N-[4-(trifluoromethyl)phenyl]benzamide To a solution of 3-(4-nitrophenoxy)-N-[4-(trifluoromethyl)phenyl]benzamide (6.75 g, 16.8 mmol) in methanol (20 mL)/tetrahydrofuran (10 mL) were added 10%-palladium carbon (2 g) and concentrated hydrochloric acid (1 mL), and the mixture was vigorously stirred under a hydrogen atmosphere at room temperature for 3 hr. The catalyst was filtered off through celite, the filtrate was concentrated under reduced pressure, and the obtained residue was triturated with diethyl ether to give the title compound (5.37 g, 86%) as a white solid.

$^1$H-NMR (CDCl$_3$, 300 MHz) δ 3.66 (2H, br s), 6.73 (2H, d, J=5.7 Hz), 6.91 (2H, d, J=6.6 Hz), 7.12-7.17 (1H, m), 7.39-7.52 (3H, m), 7.64 (2H, d, J=8.7 Hz), 7.77 (2H, d, J=8.4 Hz), 7.89 (1H, br s).

(v) Production of 3-[(2-amino-1,3-benzothiazol-6-yl)oxy]-N-[4-(trifluoromethyl)phenyl]benzamide To a solution (50 mL) of 3-(4-aminophenoxy)-N-[4-(trifluoromethyl)phenyl]benzamide (3.72 g, 10.0 mmol) in acetic acid was added potassium thiocyanate (3.89 g, 40.0 mmol), and the mixture was stirred at room temperature for 30 min. To the obtained transparent solution was added dropwise bromine (2.40 g, 15.0 mmol) under ice-cooling, and the reaction mixture was stirred at room temperature for 18 hr. The precipitated yellow powder was filtered off through celite, and the filtrate was concentrated under reduced pressure. To the residue was added 0.1N aqueous sodium hydroxide solution and the mixture was extracted with ethyl acetate. The organic layer was dried over anhydrous magnesium sulfate, and the solvent was evaporated under reduced pressure. The residue was purified by silica gel column chromatography (eluent:hexane/ethyl acetate=1:1), and triturated with diethyl ether to give the title compound (2.93 g, 68%) as a yellow solid.

$^1$H-NMR (CDCl$_3$, 300 MHz) δ 5.68 (2H, br s), 6.99 (1H, dd, J=2.4, 8.7 Hz), 7.12 (1H, dd, J=0.9, 2.4 Hz), 7.25 (1H, s), 7.41 (1H, t, J=8.1 Hz), 7.46 (1H, d, J=4.2 Hz), 7.51-7.65 (4H, m), 7.85 (2H, d, J=8.4 Hz), 9.22 (1H, br s).

(vi) Production of 3-({2-[(cyclopropylcarbonyl)amino]-1,3-benzothiazol-6-yl}oxy)-N-[4-(trifluoromethyl)phenyl]benzamide A solution of 3-[(2-amino-1,3-benzothiazol-6-yl)oxy]-N-[4-(trifluoromethyl)phenyl]benzamide (215 mg, 0.50 mmol) produced in Example A25(v), cyclopropanecarbonyl chloride (210 mg, 2.00 mmol) and N-ethyl-N-isopropylpropane-2-amine (518 mg, 4.00 mmol) in tetrahydrofuran (10 mL) was stirred at room temperature for 18 hr. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=1:1), and triturated with diethyl ether to give the title compound (220 mg, 88%) as a white solid.

$^1$H-NMR (CDCl$_3$, 300 MHz) δ 0.98 (2H, m), 1.18 (2H, m), 1.49 (1H, m), 7.12 (1H, dd, J=2.4, 8.7 Hz), 7.18 (1H, dd,

J=2.7, 8.4 Hz), 7.42-7.48 (2H, m), 7.57-7.73 (5H, m), 7.88 (2H, d, J=8.4 Hz), 9.28 (1H, br s), 11.53 (1H, br s).

Example A26

Production of 3-{[2-(glycoloylamino)-1,3-benzothiazol-6-yl]oxy}-N-[4-(trifluoromethyl)phenyl]benzamide

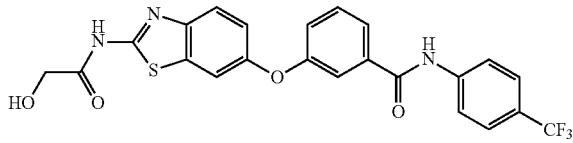

A solution of 3-[(2-amino-1,3-benzothiazol-6-yl)oxy]-N-[4-(trifluoromethyl)phenyl]benzamide (215 mg, 0.50 mmol) produced in Example A25(v), 2-chloro-2-oxoethyl acetate (273 mg, 2.00 mmol) and N-ethyl-N-isopropylpropane-2-amine (518 mg, 4.00 mmol) in tetrahydrofuran (10 mL) was stirred at room temperature for 18 hr. The reaction mixture was poured into water and the mixture was extracted with ethyl acetate. The organic layer was dried over anhydrous magnesium sulfate, and the solvent was evaporated under reduced pressure. The residue was dissolved in methanol (5 mL)/tetrahydrofuran (5 mL), 8N aqueous sodium hydroxide solution (1 mL) was added under ice-cooling, and the mixture was stirred at room temperature for 30 min. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=1:1), and triturated with diethyl ether to give the title compound (140 mg, 57%) as a pale-yellow solid.

$^1$H-NMR (CDCl$_3$, 300 MHz) δ 4.31 (2H, d, J=5.7 Hz), 5.32 (1H, t, J=5.7 Hz), 7.14-7.24 (2H, m), 7.43-7.49 (2H, m), 7.59 (2H, d, J=8.4 Hz), 7.64-7.71 (2H, m), 7.77 (1H, d, J=9.0 Hz), 7.89 (2H, d, J=8.4 Hz), 9.30 (1H, br s), 10.41 (1H, br s).

Example A27

Production of 3-[(2-{[(4-methylpiperazin-1-yl)acetyl]amino}-1,3-benzothiazol-6-yl)oxy]-N-[4-(trifluoromethyl)phenyl]benzamide

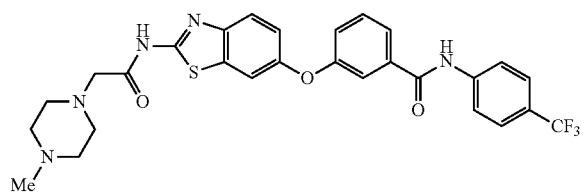

A solution of 3-[(2-amino-1,3-benzothiazol-6-yl)oxy]-N-[4-(trifluoromethyl)phenyl]benzamide (215 mg, 0.50 mmol) produced in Example A25(v), chloroacetyl chloride (225 mg, 2.00 mmol) and N-ethyl-N-isopropylpropane-2-amine (518 mg, 4.00 mmol) in N,N-dimethylformamide (10 mL) was stirred at room temperature for 18 hr. The reaction mixture was poured into water and the mixture was extracted with ethyl acetate. The organic layer was dried over anhydrous magnesium sulfate, the solvent was evaporated under reduced pressure, and the residue was purified by silica gel chromatography (eluent:hexane/ethyl acetate=1:1) to give a colorless oil. This was dissolved in N,N-dimethylformamide (5 mL), 1-methylpiperazine (400 mg, 4.00 mmol) was added, and the mixture was stirred at room temperature for 1 hr. The reaction mixture was poured into water and the mixture was extracted with ethyl acetate. The organic layer was dried over anhydrous magnesium sulfate, and the solvent was evaporated under reduced pressure. The residue was purified by basic silica gel chromatography (eluent:ethyl acetate/methanol=10:1), and triturated with diethyl ether to give the title compound (180 mg, 63%) as a white solid.

$^1$H-NMR (CDCl$_3$, 300 MHz) δ 2.34 (3H, s), 2.40-2.60 (4H, m), 2.60-2.75 (4H, m), 3.30 (2H, s), 7.15-7.25 (2H, m), 7.46-7.52 (3H, m), 7.52-7.64 (3H, m), 7.74-7.81 (3H, m), 7.87 (1H, br s), 10.41 (1H, br s).

Example A28

Production of N-{6-[3-({[4-(trifluoromethyl)phenyl]amino}carbonyl)phenoxy]-1,3-benzothiazol-2-yl}-1,3-oxazole-4-carboxamide

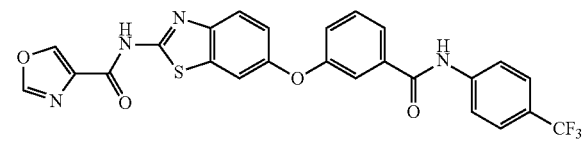

A solution of 3-[(2-amino-1,3-benzothiazol-6-yl)oxy]-N-[4-(trifluoromethyl)phenyl]benzamide (215 mg, 0.50 mmol) produced in Example A25(v), 1,3-oxazole-4-carboxylic acid (113 mg, 1.00 mmol), 1-ethyl-3-(3-dimethylaminopropyl)carbodiimide hydrochloride (192 mg, 1.00 mmol), 1-hydroxybenzotriazole (135 mg, 1.00 mmol) and N-ethyl-N-isopropylpropane-2-amine (260 mg, 2.0 mmol) in N,N-dimethylformamide (5 mL) was stirred at room temperature for 18 hr. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=1:1), and triturated with diethyl ether to give the title compound (90 mg, 34%) as a white solid.

$^1$H-NMR (CDCl$_3$, 300 MHz) δ 7.16-7.22 (2H, m), 7.41-7.50 (2H, m), 7.58 (2H, d, J=8.7 Hz), 7.69-7.76 (2H, m), 7.80

(1H, d, J=8.7 Hz), 7.93 (2H, d, J=8.7 Hz), 8.05 (1H, d, J=0.9 Hz), 8.52 (1H, d, J=0.9 Hz), 9.74 (1H, br s), 10.61 (1H, br s).

Example A29

Production of 3-({2-[(cyclopropylcarbonyl)amino]-1,3-benzothiazol-6-yl}oxy)-N-[3-(trifluoromethyl)phenyl]benzamide

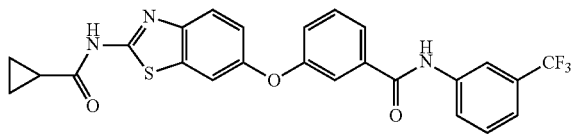

(i) Production of 3-({[3-(trifluoromethyl)phenyl]amino}carbonyl)phenyl acetate

Using 3-(acetyloxy)benzoic acid (9.01 g, 50.0 mmol), thionyl chloride (10 mL), 3-(trifluoromethyl)aniline (12.1 g, 75.0 mmol) and N-ethyl-N-isopropylpropane-2-amine (12.9 g, 100 mmol), and in the same manner as in Example A25(i), the title compound (16.2 g, quantitatively) was obtained as a colorless oil.
$^1$H-NMR (CDCl$_3$, 300 MHz) δ 2.33 (3H, s), 7.26-7.31 (2H, m), 7.41 (1H, d, J=7.8 Hz), 7.45-7.52 (2H, m), 7.69-7.73 (1H, m), 7.85 (1H, d, J=7.8 Hz), 7.91 (1H, s), 8.03 (1H, br s).

(ii) Production of 3-hydroxy-N-[3-(trifluoromethyl)phenyl]benzamide

Using 3-({[3-(trifluoromethyl)phenyl]amino}carbonyl)phenyl acetate (16.2 g, 50 mmol) and 8N aqueous sodium hydroxide solution (10 mL), and in the same manner as in Example A25(ii), the title compound (13.9 g, 99%) was obtained as a white powder.
$^1$H-NMR (CDCl$_3$, 300 MHz) δ 7.00-7.05 (1H, m), 7.25-7.47 (5H, m), 7.99 (1H, d, J=8.4 Hz), 8.14 (1H, s), 9.10 (1H, br s), 9.62 (1H, br s).

(iii) Production of 3-(4-nitrophenoxy)-N-[3-(trifluoromethyl)phenyl]benzamide

Using 3-hydroxy-N-[3-(trifluoromethyl)phenyl]benzamide (2.81 g, 10.0 mmol), 1-fluoro-4-nitrobenzene (1.55 g, 11.0 mmol) and potassium carbonate (1.38 g, 10.0 mmol), and in the same manner as in Example A25(iii), the title compound (3.85 g, 96%) was obtained as a pale-yellow oil.
$^1$H-NMR (CDCl$_3$, 300 MHz) δ 7.03-7.08 (2H, m), 7.28-7.32 (1H, m), 7.42 (1H, d, J=7.8 Hz), 7.50 (1H, t, J=7.8 Hz), 7.57 (1H, t, J=7.8 Hz), 7.63 (1H, s), 7.71-7.75 (1H, m), 7.85 (1H, d, J=8.1 Hz), 7.92 (1H, s), 8.01 (1H, br s), 8.19-8.25 (2H, m).

(iv) Production of 3-(4-aminophenoxy)-N-[3-(trifluoromethyl)phenyl]benzamide

Using 3-(4-nitrophenoxy)-N-[3-(trifluoromethyl)phenyl]benzamide (2.81 g, 10.0 mmol) and 10%-palladium carbon (1 g), and in the same manner as in Example A25(iv), the title compound (2.45 g, 69%) was obtained as a brown oil.
$^1$H-NMR (CDCl$_3$, 300 MHz) δ 3.63 (2H, br s), 6.66-6.72 (2H, m), 6.87-6.91 (2H, m), 7.10-7.16 (1H, m), 7.36-7.50 (5H, m), 7.82 (1H, d, J=8.1 Hz), 7.88-8.00 (2H, m).

(v) Production of 3-[(2-amino-1,3-benzothiazol-6-yl)oxy]-N-[3-(trifluoromethyl)phenyl]benzamide Using 3-(4-aminophenoxy)-N-[3-(trifluoromethyl)phenyl]benzamide (2.45 g, 6.58 mmol), potassium thiocyanate (1.94 g, 20.0 mmol) and bromine (1.20 g, 7.50 mmol), and in the same manner as in Example A25(v), the title compound (2.24 g, 79%) was obtained as a pale-yellow powder.
$^1$H-NMR (CDCl$_3$, 300 MHz) δ 5.15 (2H, br s), 7.05 (1H, dd, J=2.4, 8.7 Hz), 7.16-7.21 (1H, m), 7.30 (1H, d, J=2.4 Hz), 7.39-7.57 (6H, m), 7.83 (1H, d, J=8.1 Hz), 7.88 (1H, br s), 7.92 (1H, br s).

(vi) Production of 3-({2-[(cyclopropylcarbonyl)amino]-1,3-benzothiazol-6-yl}oxy)-N-[3-(trifluoromethyl)phenyl]benzamide A solution of 3-[(2-amino-1,3-benzothiazol-6-yl)oxy]-N-[3-(trifluoromethyl)phenyl]benzamide (429 mg, 1.00 mmol), cyclopropanecarbonyl chloride (525 mg, 5.0 mmol) and N,N-dimethylpyridine-4-amine (610 mg, 5.00 mmol) in pyridine (5 mL) was stirred at room temperature for 2 hr. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=1:1), and triturated with diethyl ether to give the title compound (340 mg, 68%) as a white solid.
$^1$H-NMR (CDCl$_3$, 300 MHz) δ 0.94 (2H, m), 1.15 (2H, m), 1.95 (1H, m), 7.10-7.20 (2H, m), 7.33 (1H, m), 7.43-7.47 (3H, m), 7.69-7.76 (3H, m), 8.03 (1H, d, J=8.1 Hz), 8.12 (1H, s), 9.82 (1H, br s), 11.94 (1H, br s).

Example A30

Production of 3-{[2-(glycoloylamino)-1,3-benzothiazol-6-yl]oxy}-N-[3-(trifluoromethyl)phenyl]benzamide

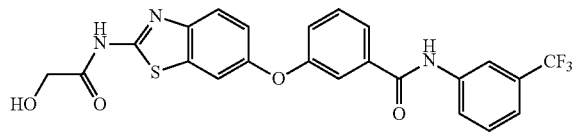

A solution of 3-[(2-amino-1,3-benzothiazol-6-yl)oxy]-N-[3-(trifluoromethyl)phenyl]benzamide (429 mg, 1.0 mmol) produced in Example A29(v) and 2-chloro-2-oxoethyl acetate (546 mg, 4.0 mmol) in N,N-dimethylformamide (5 mL) was stirred at room temperature for 6 hr. The reaction mixture was poured into water and the mixture was extracted with ethyl acetate. The organic layer was dried over anhydrous magnesium sulfate, and the solvent was evaporated under reduced pressure. The residue was dissolved in methanol (5 mL)/tetrahydrofuran (5 mL), 8N aqueous sodium hydroxide solution (1 mL) was added under ice-cooling, and the mixture was stirred at room temperature for 30 min. The reaction mixture was poured into water and the mixture was extracted with ethyl acetate. The organic layer was dried over anhydrous magnesium sulfate, and the solvent was evaporated under reduced pressure. The residue was purified by silica gel chromatography (eluent:hexane/ethyl acetate=1:1), and triturated with diethyl ether to give the title compound (300 mg, 62%) as a pale-yellow solid.

$^1$H-NMR (CDCl$_3$, 300 MHz) δ 4.31 (2H, d, J=5.7 Hz), 5.34 (1H, t, J=5.7 Hz), 7.14-7.21 (2H, m), 7.36 (1H, d, J=7.8 Hz), 7.43-7.49 (3H, m), 7.65-7.78 (3H, m), 8.01 (1H, d, J=8.4 Hz), 8.06 (1H, s), 9.39 (1H, br s), 10.43 (1H, br s).

Example A31

Production of 3-[(2-{[(4-methylpiperazin-1-yl)acetyl]amino}-1,3-benzothiazol-6-yl)oxy]-N-[3-(trifluoromethyl)phenyl]benzamide

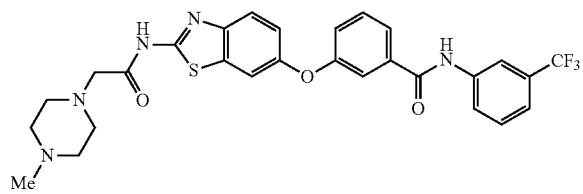

A solution of 3-[(2-amino-1,3-benzothiazol-6-yl)oxy]-N-[3-(trifluoromethyl)phenyl]benzamide (429 mg, 1.0 mmol) produced in Example A29(v) and chloroacetyl chloride (225 mg, 2.0 mmol) in N,N-dimethylformamide (10 mL) was stirred at room temperature for 6 hr. The reaction mixture was poured into water and the mixture was extracted with ethyl acetate. The organic layer was dried over anhydrous magnesium sulfate, the solvent was evaporated under reduced pressure, and the residue was purified by silica gel chromatography (eluent:hexane/ethyl acetate=1:1) to give a colorless oil. This was dissolved in N,N-dimethylformamide (5 mL), 1-methylpiperazine (400 mg, 4.0 mmol) was added, and the mixture was stirred at room temperature for 1 hr. The reaction mixture was poured into water and the mixture was extracted with ethyl acetate. The organic layer was dried over anhydrous magnesium sulfate, and the solvent was evaporated under reduced pressure. The residue was purified by basic silica gel chromatography (eluent:ethyl acetate/methanol=10:1), and triturated with diethyl ether to give the title compound (340 mg, 60%) as a white solid.

$^1$H-NMR (CDCl$_3$, 300 MHz) δ 2.34 (3H, s), 2.42-2.62 (4H, m), 2.62-2.78 (4H, m), 3.30 (2H, s), 7.19-7.26 (2H, m), 7.39-7.61 (6H, m), 7.77-7.88 (3H, m), 7.93 (1H, s), 10.40 (1H, br s).

Example A32

Production of 3-(1-cyano-1-methylethyl)-N-[3-({2-[(cyclopropylcarbonyl)amino]-1,3-benzothiazol-6-yl}oxy)-4-methylphenyl]benzamide

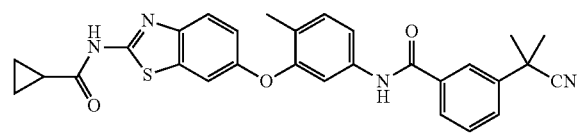

(i) Production of 3-(1-cyano-1-methylethyl)-N-(3-hydroxy-4-methylphenyl)benzamide To a solution of 3-(1-cyano-1-methylethyl)benzoic acid (5.00 g, 26.4 mmol) produced in Example A7(ii) in tetrahydrofuran (50 mL) were added N,N-dimethylformamide (40 μL) and oxalyl chloride (3.20 mL, 36.5 mmol), and the mixture was stirred at room temperature for 1.5 hr. The reaction mixture was concentrated under reduced pressure to give 3-(1-cyano-1-methylethyl)benzoyl chloride.

To a solution of 5-amino-2-methylphenol (3.00 g, 24.3 mmol) in tetrahydrofuran (20 mL) was added a suspension of sodium hydrogencarbonate (3.00 g, 36.5 mmol) in water (30 mL), and the mixture was vigorously stirred at room temperature. To this mixture was added dropwise a solution of 3-(1-cyano-1-methylethyl)benzoyl chloride produced above in tetrahydrofuran (30 mL) under ice-cooling, and the mixture was stirred at room temperature for 5 hr. The aqueous layer was separated from the reaction mixture, and the organic layer was diluted with ethyl acetate and washed with saturated brine. The organic layer was dried over anhydrous magnesium sulfate, and decolorized with activated carbon. The insoluble material was passed through a pad filled with two layers of silica gel and celite for filtration. The solvent was evaporated under reduced pressure, and the obtained solid was washed with ethyl acetate-hexane mixture to give the title compound (6.75 g, 94%) as a white powder.

$^1$H-NMR (DMSO-d$_6$, 300 MHz) δ 1.75 (6H, s), 2.09 (3H, s), 6.97-7.06 (2H, m), 7.37 (1H, s), 7.58 (1H, t, J=7.7 Hz), 7.73 (1H, d, J=7.7 Hz), 7.90 (1H, d, J=7.7 Hz), 8.00 (1H, t, J=1.6 Hz), 9.36 (1H, s), 10.13 (1H, s).

(ii) Production of 3-(1-cyano-1-methylethyl)-N-[4-methyl-3-(4-nitrophenoxy)phenyl]benzamide Using 3-(1-cyano-1-methylethyl)-N-(3-hydroxy-4-methylphenyl)benzamide (1.47 g, 5.0 mmol), 1-fluoro-4-nitrobenzene (0.77 g, 5.5 mmol) and potassium carbonate (0.69 g, 5.0 mmol), and in the same manner as in Example A25(iii), the title compound (2.08 g, quantitatively) was obtained as a yellow oil.

$^1$H-NMR (CDCl$_3$, 300 MHz) δ 1.86 (6H, s), 2.17 (3H, s), 6.97 (2H, dt, J=9.3, 2.7 Hz), 7.31 (1H, t, J=8.4 Hz), 7.36 (1H, dd, J=2.1, 8.4 Hz), 7.53 (1H, t, J=7.8 Hz), 7.55 (1H, s), 7.66-7.70 (1H, m), 7.77 (1H, td, J=1.5, 7.5 Hz), 7.60 (1H, t, J=1.8 Hz), 8.01 (1H, br s), 8.19 (2H, dt, J=9.3, 2.7 Hz).

(iii) Production of N-[3-(4-aminophenoxy)-4-methylphenyl]-3-(1-cyano-1-methylethyl)benzamide Using 3-(1-cyano-1-methylethyl)-N-[4-methyl-3-(4-nitrophenoxy)phenyl]benzamide (2.08 g, 5.0 mmol) and 10%-palladium carbon (0.5 g), and in the same manner as in Example A25(iv), the title compound (1.93 g, quantitative) was obtained as a pink amorphous substance.

$^1$H-NMR (CDCl$_3$, 300 MHz) δ 1.73 (6H, s), 2.29 (3H, s), 3.54 (2H, br s), 6.64 (2H, dt, J=9.0, 2.7 Hz), 6.97 (2H, dt, J=9.0, 2.7 Hz), 6.98 (1H, d, J=1.5 Hz), 7.19 (1H, d, J=8.4 Hz), 7.36 (1H, dd, J=1.5, 8.1 Hz), 7.46 (1H, t, J=7.8 Hz), 7.65-7.71 (2H, m), 7.81 (1H, br s), 7.91 (1H, t, J=1.5 Hz).

(iv) Production of N-{3-[(2-amino-1,3-benzothiazol-6-yl)oxy]-4-methylphenyl}-3-(1-cyano-1-methylethyl)benzamide Using N-[3-(4-aminophenoxy)-4-methylphenyl]-3-(1-cyano-1-methylethyl)benzamide (1.93 g, 5.0 mmol), potassium thiocyanate (1.94 g, 20.0 mmol) and bromine (1.20 g, 7.50 mmol), and in the same manner as in Example A25(v), the title compound (1.00 g, 45%) was obtained as a pale-yellow powder.

¹H-NMR (CDCl₃, 300 MHz) δ 1.74 (6H, s), 2.27 (3H, s), 5.16 (2H, br s), 6.97-7.05 (2H, m), 7.12 (1H, d, J=1.8 Hz), 7.17 (1H, d, J=2.4 Hz), 7.38 (1H, dd, J=2.1, 9.9 Hz), 7.45-7.53 (2H, m), 7.66-7.73 (2H, m), 7.79 (1H, br s), 7.92 (1H, br s).

(v) Production of 3-(1-cyano-1-methylethyl)-N-[3-({2-[(cyclopropylcarbonyl)amino]-1,3-benzothiazol-6-yl}oxy)-4-methylphenyl]benzamide Using N-{3-[(2-amino-1,3-benzothiazol-6-yl)oxy]-4-methylphenyl}-3-(1-cyano-1-methylethyl)benzamide (0.31 g, 0.70 mmol), cyclopropanecarbonyl chloride (0.42 g, 4.0 mmol) and N,N-dimethylpyridine-4-amine (0.49 g, 4.0 mmol), and in the same manner as in Example A29(vi), the title compound (1.00 g, 45%) was obtained as a pale-yellow powder.

¹H-NMR (CDCl₃, 300 MHz) δ 0.90-0.98 (2H, m), 1.10-1.18 (2H, m), 1.75 (6H, s), 1.83-1.94 (1H, m), 2.26 (3H, s), 7.06-7.12 (1H, m), 7.24 (1H, d, J=8.1 Hz), 7.27-7.34 (2H, m), 7.46 (1H, d, J=7.8 Hz), 7.49-7.55 (1H, m), 7.63-7.70 (2H, m), 7.84 (1H, d, J=7.8 Hz), 7.96-8.00 (1H, m), 9.16 (1H, br s), 11.67 (1H, br s).

Example A33

Production of 3-(1-cyano-1-methylethyl)-N-(4-methyl-3-[(2-{[(4-methylpiperazin-1-yl)acetyl]amino}-1,3-benzothiazol-6-yl)oxy]phenyl)benzamide

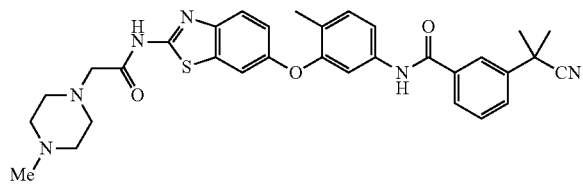

Using N-{3-[(2-amino-1,3-benzothiazol-6-yl)oxy]-4-methylphenyl}-3-(1-cyano-1-methylethyl)benzamide (0.31 g, 0.70 mmol) produced in Example A32(iv), chloroacetyl chloride 0.45 g, 4.0 mmol), and 1-methylpiperazine (0.40 g, 4.0 mmol), and in the same manner as in Example A31, the title compound (0.34 g, 49%) was obtained as a white powder.

¹H-NMR (CDCl₃, 300 MHz) δ 1.75 (6H, s), 2.27 (3H, s), 2.33 (3H, s), 2.47-2.61 (4H, m), 2.61-2.75 (4H, m), 3.28 (2H, s), 7.13 (1H, dd, J=2.4, 8.7 Hz), 7.24-7.29 (2H, m), 7.34 (1H, d, J=2.4 Hz), 7.36 (1H, dd, J=2.1, 8.4 Hz), 7.48 (1H, t, J=7.8 Hz), 7.65-7.78 (4H, m), 7.92 (1H, br s), 10.37 (1H, br s).

Example A34

Production of 3-(1-cyano-1-methylethyl)-N-[3-({2-[(hydroxyacetyl)amino]-1,3-benzothiazol-6-yl}oxy)-4-methylphenyl]benzamide

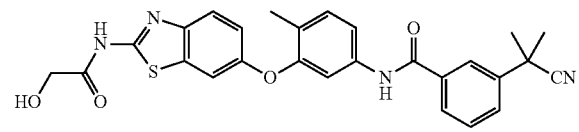

Using N-{3-[(2-amino-1,3-benzothiazol-6-yl)oxy]-4-methylphenyl}-3-(1-cyano-1-methylethyl)benzamide (0.31 g, 0.70 mmol) produced in Example A32(iv), 2-chloro-2-oxoethyl acetate (0.55 g, 4.0 mmol), and 8N aqueous sodium hydroxide solution (1 mL), and in the same manner as in Example A30, the title compound (37 mg, 11%) was obtained as a pale-yellow powder.

¹H-NMR (CDCl₃, 300 MHz) δ 1.74 (6H, s), 2.27 (3H, s), 3.40 (1H, br s), 4.40 (2H, s), 7.13 (1H, dd, J=2.4, 8.7 Hz), 7.24-7.29 (2H, m), 7.34 (1H, d, J=2.7 Hz), 7.36 (1H, dd, J=2.1, 7.8 Hz), 7.48 (1H, t, J=7.8 Hz), 7.65-7.69 (1H, m), 7.70-7.74 (2H, m), 7.83 (1H, br s), 7.91 (1H, br s), 9.98 (1H, br s).

Example A35

Production of 3-(1-cyanocyclopropyl)-N-[3-({2-[(cyclopropylcarbonyl)amino]-1,3-benzothiazol-6-yl}oxy)-4-methylphenyl]benzamide

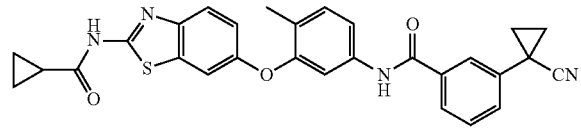

(i) Production of 3-(1-cyanocyclopropyl)-N-(3-hydroxy-4-methylphenyl)benzamide

Using 5-amino-2-methylphenol (6.00 g, 48.5 mmol), 3-(1-cyanocyclopropyl)benzoic acid (6.00 g, 48.5 mmol) produced in Example A1(iii), oxalyl chloride (6.40 mL, 73.0 mmol), N,N-dimethylformamide (40 μL), tetrahydrofuran (250 mL), sodium hydrogencarbonate (6.20 g, 73.0 mmol) and water (60 mL) as starting materials, and in the same manner as in Example A32(i), the title compound (12.4 g, 87%) was obtained as a white powder. The title compound was washed with a mixed solvent of ethyl acetate and hexane.

¹H-NMR (DMSO-d₆, 300 MHz) δ 1.58-1.65 (2H, m), 1.77-1.84 (2H, m), 2.08 (3H, s), 6.96-7.05 (2H, m), 7.35-7.40 (1H, m), 7.49-7.58 (2H, m), 7.77-7.81 (1H, m), 7.82-7.88 (1H, m), 9.34 (1H, s), 10.10 (1H, s).

(ii) Production of 3-(1-cyanocyclopropyl)-N-[4-methyl-3-(4-nitrophenoxy)phenyl]benzamide Using 3-(1-cyanocyclopropyl)-N-(3-hydroxy-4-methylphenyl)benzamide (1.46 g, 5.0 mmol), 1-fluoro-4-nitrobenzene (0.77 g, 5.5 mmol) and potassium carbonate (0.69 g, 5.0 mmol), and in the same manner as in Example A25(iii), the title compound (2.07 g, quantitatively) was obtained as a yellow oil.

¹H-NMR (CDCl₃, 300 MHz) δ 1.47 (2H, dd, J=5.1, 7.8 Hz), 1.78 (2H, dd, J=5.1, 7.8 Hz), 2.17 (3H, s), 6.97 (2H, dt, J=9.3, 2.7 Hz), 7.31 (1H, t, J=8.7 Hz), 7.35 (1H, dd, J=2.1, 8.4 Hz), 7.43-7.55 (3H, m), 7.73 (1H, td, J=1.5, 5.4 Hz), 7.74 (1H, s), 7.98 (1H, br s), 8.20 (2H, dt, J=9.3, 2.7 Hz).

(iii) Production of N-[3-(4-aminophenoxy)-4-methylphenyl]-3-(1-cyanocyclopropyl)benzamide Using 3-(1-cyanocyclopropyl)-N-[4-methyl-3-(4-nitrophenoxy)phenyl]benzamide (2.07 g, 5.0 mmol) and 10%-palladium carbon (0.5 g), and in the same manner as in Example A25(iv), the title compound (1.92 g, quantitatively) was obtained as a pink amorphous substance.

$^1$H-NMR (CDCl$_3$, 300 MHz) δ 1.45 (2H, dd, J=5.1, 7.8 Hz), 1.76 (2H, dd, J=5.1, 7.8 Hz), 2.29 (3H, s), 3.59 (2H, br s), 6.66 (2H, dt, J=8.7, 2.7 Hz), 6.83 (2H, dt, J=8.7, 2.7 Hz), 6.96 (1H, d, J=1.8 Hz), 7.19 (1H, d, J=8.4 Hz), 7.54 (1H, dd, J=2.1, 8.1 Hz), 7.44 (1H, t, J=7.8 Hz), 7.54 (1H, td, J=1.5, 5.1 Hz), 7.65-7.74 (3H, m).

(iv) Production of N-{3-[(2-amino-1,3-benzothiazol-6-yl)oxy]-4-methylphenyl}-3-(1-cyanocyclopropyl) benzamide Using N-[3-(4-aminophenoxy)-4-methylphenyl]-3-(1-cyanocyclopropyl)benzamide (1.92 g, 5.0 mmol), potassium thiocyanate (1.94 g, 20.0 mmol) and bromine (1.20 g, 7.50 mmol), and in the same manner as in Example A25(v), the title compound (0.44 g, 20%) was obtained as a pale-yellow powder. $^1$H-NMR (CDCl$_3$, 300 MHz) δ 1.50 (2H, dd, J=5.1, 7.8 Hz), 1.76 (2H, dd, J=5.1, 7.8 Hz), 2.25 (3H, s), 6.50 (2H, br s), 6.98-7.04 (2H, m), 7.21-7.25 (2H, m), 7.41-7.65 (4H, m), 7.71-7.85 (3H, m).

(v) Production of 3-(1-cyanocyclopropyl)-N-[3-({2-[(cyclopropylcarbonyl)amino]-1,3-benzothiazol-6-yl}oxy)-4-methylphenyl]benzamide Using N-{3-[(2-amino-1,3-benzothiazol-6-yl)oxy]-4-methylphenyl}-3-(1-cyanocyclopropyl)benzamide (0.11 g, 0.25 mmol), cyclopropanecarbonyl chloride (0.21 g, 2.0 mmol), and N,N-dimethylpyridine-4-amine (0.24 g, 2.0 mmol), and in the same manner as in Example A29(vi), the title compound (42 mg, 33%) was obtained as a pale-yellow powder.

$^1$H-NMR (CDCl$_3$, 300 MHz) δ 0.92-1.00 (2H, m), 1.13-1.20 (2H, m), 1.44-1.51 (2H, m), 1.71-1.78 (2H, m), 1.78-1.86 (1H, m), 2.26 (3H, s), 7.06-7.13 (1H, m), 7.22-7.28 (2H, m), 7.30-7.34 (1H, m), 7.40° C.-7.48 (2H, m), 7.53-7.58 (1H, m), 7.62-7.72 (2H, m), 7.73-7.79 (1H, m), 8.56 (1H, br s), 10.95 (1H, br s).

Example A36

Production of 3-(1-cyanocyclopropyl)-N-[3-({2-[(hydroxyacetyl)amino]-1,3-benzothiazol-6-yl}oxy)-4-methylphenyl]benzamide

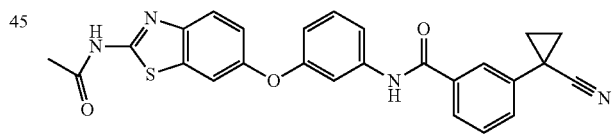

Using N-{3-[(2-amino-1,3-benzothiazol-6-yl)oxy]-4-methylphenyl}-3-(1-cyanocyclopropyl)benzamide (0.11 g, 0.25 mmol) produced in Example A35(iv), 2-chloro-2-oxoethyl acetate (0.27 g, 2.0 mmol), and 8N aqueous sodium hydroxide solution (1 mL), and in the same manner as in Example A30, the title compound (17 mg, 14%) was obtained as a pale-yellow powder.

$^1$H-NMR (CDCl$_3$, 300 MHz) δ 1.50 (2H, dd, J=5.1, 7.8 Hz), 1.75 (2H, dd, J=5.1, 7.8 Hz), 2.26 (3H, s), 4.28 (2H, d, J=5.7 Hz), 5.45 (1H, t, J=5.4 Hz), 7.12 (1H, dd, J=2.4, 9.0 Hz), 7.25 (1H, d, J=8.4 Hz), 7.32-7.36 (2H, m), 7.43 (1H, t, J=7.8 Hz), 7.54 (1H, dd, J=2.4, 8.4 Hz), 7.55-7.60 (1H, m), 7.69-7.74 (2H, m), 7.81-7.88 (1H, m), 9.33 (1H, br s), 10.46 (1H, br s).

Example A37

Production of 3-(1-cyanocyclopropyl)-N-{4-methyl-3-[(2-{[(4-methylpiperazin-1-yl)acetyl]amino}-1,3-benzothiazol-6-yl)oxy]phenyl}benzamide

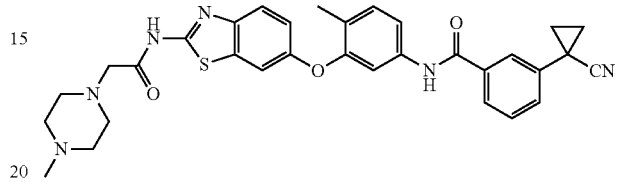

Using N-{3-[(2-amino-1,3-benzothiazol-6-yl)oxy]-4-methylphenyl}-3-(1-cyanocyclopropyl)benzamide (0.11 g, 0.25 mmol) produced in Example A35(iv), chloroacetyl chloride (0.23 g, 2.0 mmol), and 1-methylpiperazine (0.40 g, 4.0 mmol), and in the same manner as in Example A31, the title compound (24 mg, 17%) was obtained as a white powder.

$^1$H-NMR (CDCl$_3$, 300 MHz) δ 1.46 (2H, dd, J=5.4, 7.8 Hz), 1.77 (2H, dd, J=5.4, 7.8 Hz), 2.27 (3H, s), 2.34 (3H, s), 2.48-2.62 (4H, m), 2.62-2.75 (4H, m), 3.28 (2H, s), 7.13 (1H, dd, J=2.4, 8.7 Hz), 7.24-7.29 (2H, m), 7.33-7.38 (2H, m), 7.45 (1H, t, J=7.8 Hz), 7.52-7.57 (1H, m), 7.67-7.72 (3H, m), 7.75 (1H, d, J=8.7 Hz), 10.38 (1H, br s).

Example A38

Production of N-(3-{[2-(acetylamino)-1,3-benzothiazol-6-yl]oxy}phenyl)-3-(1-cyanocyclopropyl)benzamide To a solution of N-{3-[(2-amino-1,3-benzothiazol-6-yl)oxy]phenyl}-3-(1-cyanocyclopropyl)benzamide (200 mg, 0.47 mmol) produced in Example A15(iii) in tetrahydrofuran (20 mL) were added acetyl chloride (0.3 mL, 4.22 mmol) and triethylamine (1.0 mL, 7.18 mmol), and the mixture was stirred at room temperature for 10 min. To the reaction mixture were added water (200 mL) and ethyl acetate (200 mL) and the mixture was stirred for 30 min. The organic layer was separated, and dried over anhydrous magnesium sulfate. The insoluble material was filtered off, and the filtrate was concentrated under reduced pressure. The residue was purified by silica gel chromatography (hexane/ethyl acetate=20/80→0/100), and triturated with ethyl acetate/hexane to give the title compound (151 mg, 69%) as a colorless solid.

$^1$H-NMR (DMSO-d$_6$, 300 MHz) δ 1.52-1.66 (2H, m), 1.73-1.86 (2H, m), 2.19 (3H, s), 6.69-6.86 (1H, m), 7.16 (1H, dd, J=2.5, 8.5 Hz), 7.36 (1H, t, J=8.5 Hz), 7.42-7.61 (4H, m), 7.65-7.91 (4H, m), 10.33 (1H, s), 12.33 (1H, br s).

Example A39

Production of N-(3-{[2-(acetylamino)-1,3-benzothiazol-6-yl]oxy}phenyl)-3-(1-cyano-1-methylethyl)benzamide

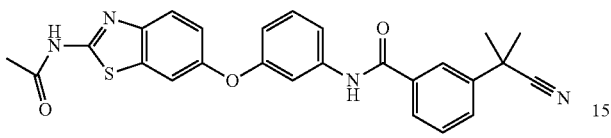

Using N-{3-[(2-amino-1,3-benzothiazol-6-yl)oxy]phenyl}-3-(1-cyano-1-methylethyl)benzamide (100 mg, 0.23 mmol) produced in Example A12(iv), tetrahydrofuran (20 mL), acetyl chloride (0.12 mL, 1.69 mmol) and triethylamine (1.0 mL, 7.18 mmol) as starting materials, and in the same manner as in Example A38, the title compound (50 mg, 46%) was obtained as a colorless solid.

$^1$H-NMR (DMSO-$d_6$, 300 MHz) δ 1.73 (6H, s), 2.19 (3H, s), 6.72-6.85 (1H, m), 7.16 (1H, dd, J=2.5, 8.5 Hz), 7.37 (1H, t, J=8.5 Hz), 7.48 (1H, t, J=2.5 Hz), 7.53-7.63 (2H, m), 7.64-7.82 (3H, m), 7.85-7.93 (1H, br s), 7.98 (1H, t, J=1.5 Hz), 10.35 (1H, s), 12.33 (1H, br s).

Example A40

Production of N-(3-{[2-(acetylamino)-1,3-benzothiazol-6-yl]oxy}phenyl)-2-chloro-3-(1-cyanocyclopropyl)benzamide

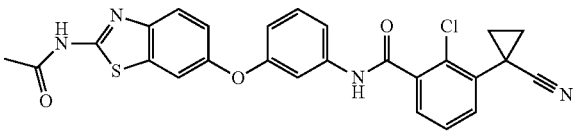

(i) Production of methyl 2-chloro-3-methylbenzoate

A mixture of 2-chloro-3-methylbenzoic acid (25.0 g, 0.146 mol), concentrated sulfuric acid (2 mL) and methanol (160 mL) was stirred at 80° C. for 3 hr. The reaction mixture was concentrated, diluted with ethyl acetate and neutralized with 8N aqueous sodium hydroxide solution. The organic layer was separated, washed with saturated brine, dried over anhydrous magnesium sulfate, and passed through a pad filled with basic silica gel for filtration. The solvent was concentrated under reduced pressure to give the title compound (18.0 g, 66%) as a pale-orange oil. The obtained compound was used in the next reaction without a further purification.

$^1$H-NMR (CDCl$_3$, 300 MHz) δ 2.42 (3H, s), 3.93 (3H, s), 7.19 (1H, t, J=7.6 Hz), 7.32-7.38 (1H, m), 7.56 (1H, dd, J=1.2, 7.6 Hz).

(ii) Production of methyl 3-(bromomethyl)-2-chlorobenzoate

To a solution of methyl 2-chloro-3-methylbenzoate (3.60 g, 19.4 mmol) in acetonitrile (60 mL) were added 1-bromopyrrolidine-2,5-dione (11.46 g, 64.3 mmol) and 2,2'-(E)-diazene-1,2-diylbis(2-methylpropanenitrile) (960 mg, 5.84 mmol), and the mixture was stirred at 90° C. for 26 hr. The reaction mixture was concentrated, insoluble material was filtered off, and the filtrate was concentrated. The obtained residue was purified by silica gel column chromatography (hexane/ethyl acetate=100/0→95/5) to give the title compound (3.42 g, 66%) as a colorless oil.

$^1$H-NMR (CDCl$_3$, 300 MHz) δ 3.94 (3H, s), 4.64 (2H, s), 7.31 (1H, t, J=7.7 Hz), 7.58 (1H, dd, J=1.7, 7.7 Hz), 7.71 (1H, dd, J=1.7, 7.7 Hz).

(iii) Production of methyl 2-chloro-3-(cyanomethyl)benzoate

To a solution of methyl 3-(bromomethyl)-2-chlorobenzoate (748 mg, 2.84 mmol) in N,N-dimethylformamide (7 mL) was added sodium cyanide (412 mg, 8.41 mmol), and the mixture was stirred under a nitrogen stream at 80° C. for 1 hr. The reaction mixture was diluted with a mixed solvent of ethyl acetate and hexane (1:1). The solution was washed with water and saturated brine, dried over anhydrous magnesium sulfate, and filtered. The solvent was evaporated under reduced pressure, and the obtained residue was purified by silica gel column chromatography (hexane/ethyl acetate=98/2→80/20) and crystallized from ethyl acetate/hexane to give the title compound (470 mg, 79%) as white crystals.

$^1$H-NMR (CDCl$_3$, 300 MHz) δ 3.91 (2H, s), 3.95 (3H, s), 7.39 (1H, t, J=7.8 Hz), 7.66-7.72 (1H, m), 7.76-7.81 (1H, m).

(iv) Production of methyl 2-chloro-3-(1-cyanocyclopropyl)benzoate

Using Methyl 2-chloro-3-(cyanomethyl)benzoate (2.00 g, 9.54 mmol), sodium hydride (60% in oil, 1.14 g, 28.6 mmol), 1,2-dibromoethane (1.18 mL, 14.3 mmol) and dimethyl sulfoxide (20 mL) as starting materials, and in the same manner as in Example A1(ii), the title compound (787 mg, 35%) was obtained as a colorless oil.

$^1$H-NMR (CDCl$_3$, 300 MHz) δ 1.33-1.39 (2H, m), 1.76-1.83 (2H, m), 3.95 (3H, s), 7.32 (1H, t, J=7.7 Hz), 7.50 (1H, dd, J=1.7, 7.7 Hz), 7.74 (1H, dd, J=1.7, 7.7 Hz).

(v) Production of 2-chloro-3-(1-cyanocyclopropyl)benzoic acid

Using methyl 2-chloro-3-(1-cyanocyclopropyl)benzoate (684 mg, 2.90 mmol), lithium hydroxide•monohydrate (207 mg, 4.93 mmol), tetrahydrofuran (10 mL), methanol (3 mL) and water (3 mL) as starting materials, and in the same manner as in Example A1(iii), the title compound (457 mg, 71%) was obtained as a white powder.

$^1$H-NMR (CDCl$_3$, 300 MHz) δ 1.32-1.42 (2H, m), 1.79-1.87 (2H, m), 4.47 (1H, br s), 7.37 (1H, t, J=7.7 Hz), 7.56 (1H, dd, J=1.7, 7.7 Hz), 7.95 (1H, dd, J=1.7, 7.7 Hz).

(vi) Production of 2,2,2-trifluoro-N-[3-(4-nitrophenoxy)phenyl]acetamide

To a solution of 3-(4-nitrophenoxy)aniline (11.3 g, 48.9 mmol) produced in Example A12(i) in tetrahydrofuran (120 mL) was added trifluoroacetic acid anhydride (11.3 g, 53.8 mmol), and the mixture was stirred at room temperature for 1 hr. To the reaction mixture were added water (200 mL) and ethyl acetate (200 mL), and the mixture was stirred for 30 min and extracted with ethyl acetate. The organic layer was, dried over anhydrous magnesium sulfate, and the solvent was evaporated under reduced pressure to give the title compound (13.0 g, 81%) as a brown oil.

$^1$H-NMR (DMSO-d$_6$, 300 MHz) δ 7.01-7.11 (1H, m), 7.14-7.25 (2H, m), 7.49-7.57 (2H, m), 7.58-7.66 (1H, m), 8.21-8.33 (2H, m), 11.41 (1H, s).

(vii) Production of N-[3-(4-aminophenoxy)phenyl]-2,2,2-trifluoroacetamide

To a solution of 2,2,2-trifluoro-N-[3-(4-nitrophenoxy)phenyl]acetamide (13.0 g, 39.8 mmol) in ethyl acetate (400 mL) was added 10% palladium-carbon (10 g), and the mixture was stirred at room temperature for 3 hr under a hydrogen atmosphere. The insoluble material was filtered off, and the filtrate was concentrated under reduced pressure to give the title compound (11.7 g, 99%) as a pale-gray amorphous substance. The obtained compound was used in the next reaction without a further purification.

$^1$H-NMR (DMSO-d$_6$, 300 MHz) δ 5.02 (2H, s), 6.55-6.65 (2H, m), 6.70-6.85 (3H, m), 7.18 (1H, t, J=2.1 Hz), 7.25-7.47 (2H, m), 11.21 (1H, br s).

(viii) Production of N-{3-[(2-amino-1,3-benzothiazol-6-yl)oxy]phenyl}-2,2,2-trifluoroacetamide To a solution of potassium thiocyanate (17.5 g, 180.0 mmol) in acetic acid (130 mL) was added a solution of N-[3-(4-aminophenoxy)phenyl]-2,2,2-trifluoroacetamide (13.0 g, 43.9 mmol) in acetic acid (20 mL), and the mixture was stirred at room temperature for 15 min. To the obtained solution was added dropwise a solution of bromine (7.71 g, 48.2 mmol) in acetic acid (30 mL) at room temperature over 30 min or longer and, after the completion of the dropwise addition, the mixture was stirred at room temperature for 13 hr. The resulting yellow solid was filtered off, and the filtrate was concentrated under reduced pressure. The residue was dissolved in ethyl acetate (200 mL), and basified with 8N aqueous sodium hydroxide solution. The aqueous layer was separated, and the organic layer was washed with saturated aqueous sodium hydrogencarbonate solution (200 mL) and saturated brine (50 mL), and dried over anhydrous magnesium sulfate. The insoluble material was filtered off, and the filtrate was concentrated under reduced pressure to give the title compound (10.3 g, 66%) as a yellow amorphous substance. The obtained compound was used in the next reaction without a further purification.

$^1$H-NMR (DMSO-d$_6$, 300 MHz) δ 6.81-6.87 (1H, m), 6.95 (1H, dd, J=2.5, 8.6 Hz), 7.24 (1H, t, J=2.5 Hz), 7.33-7.41 (2H, m), 7.42-7.51 (4H, m), 11.23 (1H, s).

(ix) Production of N-(3-{[2-(acetylamino)-1,3-benzothiazol-6-yl]oxy}phenyl)-2,2,2-trifluoroacetamide To a solution of N-{3-[(2-amino-1,3-benzothiazol-6-yl)oxy]phenyl}-2,2,2-trifluoroacetamide (10.0 g, 28.3 mmol) and pyridine (3.36 g, 42.5 mmol) in tetrahydrofuran (150 mL) was added acetyl chloride (2.44 g, 31.1 mmol), and the mixture was stirred at room temperature for 4 hr. To the reaction mixture were added water (300 mL) and ethyl acetate (500 mL), and the mixture was stirred for 30 min and extracted with ethyl acetate. The organic layer was dried over anhydrous magnesium sulfate, the solvent was evaporated under reduced pressure, and the residue was triturated with ethyl acetate/diisopropyl ether to give the title compound (10.6 g, 95%) as a pale-yellow solid.

$^1$H-NMR (DMSO-d$_6$, 300 MHz) δ 2.20 (3H, s), 6.86-6.91 (1H, m), 7.17 (1H, dd, J=2.5, 8.7 Hz), 7.30 (1H, t, J=2.5 Hz), 7.33-7.52 (2H, m), 7.73-7.79 (2H, m), 11.26 (1H, br s), 12.33 (1H, br s).

(x) Production of N-[6-(3-aminophenoxy)-1,3-benzothiazol-2-yl]acetamide

To a solution of N-(3-{[2-(acetylamino)-1,3-benzothiazol-6-yl]oxy}phenyl)-2,2,2-trifluoroacetamide (10.0 g, 25.3 mmol) in tetrahydrofuran (50 mL) were added methanol (25 mL), water (25 mL) and lithium hydroxide monohydrate (1.50 g, 35.7 mmol), and the mixture was stirred at room temperature for 1 hr. To the reaction mixture were added water (200 mL) and ethyl acetate (250 mL), and the mixture was extracted with ethyl acetate. The organic layer was dried over anhydrous magnesium sulfate, and the filtrate was concentrated under reduced pressure. The residue was purified by silica gel chromatography (hexane/ethyl acetate=20/80→0/100), and triturated with ethyl acetate/hexane to give the title compound (3.10 g, 41%) as a yellow solid.

$^1$H-NMR (DMSO-d$_6$, 300 MHz) δ 2.19 (3H, s), 5.20 (2H, s), 6.07-6.20 (2H, m), 6.25-6.38 (1H, m), 6.98 (1H, t, J=8.0 Hz), 7.09 (1H, dd, J=2.5, 8.8 Hz), 7.63 (1H, d, J=2.5 Hz), 7.71 (1H, d, J=8.8 Hz), 12.29 (1H, br s).

(xi) Production of N-(3-{[2-(acetylamino)-1,3-benzothiazol-6-yl]oxy}phenyl)-2-chloro-3-(1-cyanocyclopropyl)benzamide To a solution of 2-chloro-3-(1-cyanocyclopropyl)benzoic acid (237 mg, 1.07 mmol) in tetrahydrofuran (4 mL) were added oxalyl chloride (170 mg, 1.34 mmol) and N,N-dimethylformamide (10 μL), and the mixture was stirred for 1 hr. The reaction mixture was concentrated under reduced pressure, and the obtained residue was dissolved in N,N-dimethylacetamide (4 mL). N-[6-(3-Aminophenoxy)-1,3-benzothiazol-2-yl]acetamide (160 mg, 0.534 mmol) was added and the mixture was stirred at room temperature for 2 hr. To the reaction mixture were added water (100 mL) and ethyl acetate (100 mL). The organic layer was separated, washed with saturated brine (10 mL), and dried over anhydrous magnesium sulfate. The insoluble material was filtered off, and the filtrate was concentrated under reduced pressure. The residue was purified by silica gel column chromatography (hexane/ethyl acetate=80/20→0/100), and triturated with ethyl acetate/diisopropyl ether to give the title compound (215 mg, 80%) as a yellow solid.

$^1$H-NMR (DMSO-d$_6$, 300 MHz) δ 1.39-1.47 (2H, m), 1.76-1.83 (2H, m), 2.19 (3H, s), 6.74-6.82 (1H, m), 7.16 (1H, dd, J=2.5, 8.8 Hz), 7.29-7.42 (2H, m), 7.42-7.53 (2H, m), 7.54-7.61 (1H, m), 7.64 (1H, dd, J=1.6, 7.6 Hz), 7.70-7.80 (2H, m), 10.61 (1H, s), 12.33 (1H, br s).

Example A41

Production of N-(3-{[2-(acetylamino)-1,3-benzothiazol-6-yl]oxy}phenyl)-2-chloro-3-(1-cyano-1-methylethyl)benzamide

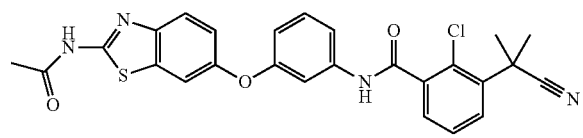

(i) Production of methyl 2-chloro-3-(1-cyano-1-methylethyl)benzoate

A solution of methyl 2-chloro-3-(cyanomethyl)benzoate (30.0 g, 143 mmol) produced in Example A40(iii) in dimethyl sulfoxide (300 ml) was cooled to 15° C., 60% sodium hydride (17.3 g, 432 mmol) was added by small portions, and the mixture was stirred at room temperature for 30 min. To this suspension was added dropwise methyl iodide (27 mL, 434 mmol) at 15° C. over 15 min, and the mixture was stirred at room temperature for 15 hr. To the reaction mixture was added aqueous ammonium chloride solution (300 mL), and the mixture was extracted with diethyl ether/ethyl acetate mixture (1:1, 3×300 mL). The combined organic layer was washed successively with water (200 mL) and saturated brine (100 mL), successively, and dried over anhydrous magnesium sulfate. The insoluble material was filtered off, and the filtrate was concentrated under reduced pressure. The obtained residue was purified by silica gel column chromatography (hexane/ethyl acetate=95/5→50/50), and the fraction containing the object product was concentrated under reduced pressure to give the title compound (27.1 g, 80%) as a pale-yellow oil.
$^1$H-NMR (CDCl$_3$, 300 MHz) δ 1.90 (6H, s), 3.95 (3H, s), 7.36 (1H, dd, J=7.6, 8.1 Hz), 7.56-7.67 (2H, m).

(ii) Production of 2-chloro-3-(1-cyano-1-methylethyl)benzoic acid

To a solution of methyl 2-chloro-3-(1-cyano-1-methylethyl)benzoate (1.67 g, 7.02 mmol) in tetrahydrofuran (24 mL)/methanol (8 mL)/water (8 mL) was added lithium hydroxide•monohydrate (501 mg, 11.9 mmol), and the mixture was stirred at room temperature for 2 hr. The reaction mixture was concentrated under reduced pressure, and 6N hydrochloric acid (2.8 mL) was added dropwise to the residue. The precipitate was collected by filtration, and washed with water to give the title compound (1.43 g, 91%) as a white powder.
$^1$H-NMR (CDCl$_3$, 300 MHz) δ 1.92 (6H, s), 7.41 (1H, t, J=7.8 Hz), 7.67 (1H, dd, J=1.6, 7.8 Hz), 7.85 (1H, dd, J=1.6, 7.8 Hz).

(iii) Production of N-(3-{[2-(acetylamino)-1,3-benzothiazol-6-yl]oxy}phenyl)-2-chloro-3-(1-cyano-1-methylethyl)benzamide To a solution of 2-chloro-3-(1-cyano-1-methylethyl)benzoic acid (240 mg, 1.07 mmol) in tetrahydrofuran (4 mL) were added oxalyl chloride (170 mg, 1.34 mmol) and N,N-dimethylformamide (10 μL), and the mixture was stirred for 1 hr. The reaction mixture was concentrated under reduced pressure, and the obtained residue was dissolved in N,N-dimethylacetamide (4 mL). N-[6-(3-Aminophenoxy)-1,3-benzothiazol-2-yl]acetamide (160 mg, 0.534 mmol) produced in Example A40(x) was added and the mixture was stirred at room temperature for 2 hr. To the reaction mixture were added water (100 mL) and ethyl acetate (100 mL). The organic layer was separated, washed with saturated brine (10 mL), and dried over anhydrous magnesium sulfate. The insoluble material was filtered off, and the filtrate was concentrated under reduced pressure. The residue was purified by silica gel column chromatography (hexane/ethyl acetate=80/20→0/100), and recrystallized from ethyl acetate/diisopropyl ether to give the title compound (201 mg, 75%) as colorless crystals.
$^1$H-NMR (DMSO-d$_6$, 300 MHz) δ 1.82 (6H, s), 2.17 (3H, s), 6.78 (1H, br s), 7.07-7.19 (1H, m), 7.27-7.40 (2H, m), 7.43-7.59 (3H, m), 7.60-7.78 (3H, m), 10.62 (1H, s), 12.34 (1H, s).

Example A42

Production of N-(3-{[2-(acetylamino)-1,3-benzothiazol-6-yl]oxy}phenyl)-3-(1,1-dimethylprop-2-yn-1-yl)benzamide

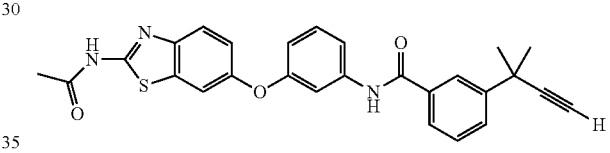

(i) Production of 3-(1,1-dimethyl-2-oxoethyl)benzoic acid

To a solution of 3-(1-cyano-1-methylethyl)benzoic acid (8.60 g, 45.5 mmol) in toluene (60 mL)/tetrahydrofuran (40 mL) was added dropwise 1.0 M hexane solution (100 mL, 100 mmol) of diisobutylaluminum hydride at −78° C. over 1 hr. After the completion of the dropwise addition, the mixture was stirred at −78° C. for 1 hr and at 0° C. for 1 hr. The reaction mixture was poured into a mixture of ethyl acetate (200 mL) and 3N hydrochloric acid (300 mL), and the organic layer was separated from the aqueous layer. The aqueous layer was extracted with ethyl acetate (2×100 mL). The combined organic layer was washed with saturated brine (50 mL), and dried over anhydrous magnesium sulfate. The insoluble material was filtered off, and the filtrate was concentrated under reduced pressure. The obtained residue was crystallized from ethyl acetate/hexane to give the title compound (6.39 g, 73%) as colorless crystals.
$^1$H-NMR (DMSO-d$_6$, 300 MHz) δ 1.43 (6H, s), 7.53 (1H, dt, J=0.6, 7.5 Hz), 7.58 (1H, dt, J=7.5, 1.6 Hz), 7.83-7.85 (1H, m), 7.88 (1H, dt, J=7.5, 1.6 Hz), 9.54 (1H, s), 13.06 (1H, br s)

(ii) Production of methyl 3-(1,1-dimethylprop-2-yn-1-yl)benzoate

To a solution of 3-(1,1-dimethyl-2-oxoethyl)benzoic acid in acetone (60 mL) were added potassium carbonate (3.78 g, 27.3 mmol) and methyl iodide (3.40 mL, 54.6 mmol), and the mixture was stirred at 60° C. for 5 hr. The insoluble material was filtered off, and the filtrate was concentrated under reduced pressure. To the obtained residue was added saturated aqueous sodium hydrogencarbonate solution (50 mL), and the mixture was extracted with ethyl acetate (100 mL, 30 mL). The combined organic layer was washed with saturated brine (20 mL), and dried over anhydrous magnesium sulfate. The insoluble material was filtered off, and the filtrate was concentrated under reduced pressure to give methyl 3-(1,1-dimethyl-2-oxoethyl)benzoate as a yellow oil.

To a suspension of p-acetamidobenzenesulfonyl azide (5.25 g, 21.9 mmol) and potassium carbonate (7.55 g, 54.6 mmol) in acetonitrile (100 mL) was added dimethyl(2-oxopropyl)phosphonate (3.00 mL, 21.9 mmol), and the mixture was stirred at room temperature for 2 hr. Thereafter, to the reaction mixture was added a solution of methyl (1,1-dimethyl-2-oxoethyl)benzoate synthesized above in methanol (20 mL), and the mixture was stirred at room temperature for 16 hr. The insoluble material was filtered off, and the filtrate was concentrated under reduced pressure. To the obtained residue was added saturated aqueous sodium hydrogencarbonate solution (70 mL), and the mixture was extracted with ethyl acetate (100 mL). The combined organic layer was washed with saturated brine (20 mL), and dried over anhydrous magnesium sulfate. The insoluble material was filtered off, and the filtrate was concentrated under reduced pressure. The obtained residue was purified by basic silica gel column chromatography (hexane/ethyl acetate=100/0→90/10), and the fraction containing the object product was concentrated under reduced pressure to give the title compound (2.26 g, 61%) as a colorless oil.

$^1$H-NMR (DMSO-$d_6$, 300 MHz) δ 1.56 (6H, s), 3.34 (1H, s), 3.86 (3H, s), 7.51 (1H, dt, J=0.6, 7.8 Hz), 7.80-7.88 (2H, m), 8.17 (1H, dt, J=0.6, 1.8 Hz).

(iii) Production of 3-(1,1-dimethylprop-2-yn-1-yl)benzoic acid

To a solution of methyl 3-(1,1-dimethylprop-2-yn-1-yl) benzoate (2.26 g, 11.2 mmol) in methanol (15 mL)/tetrahydrofuran (10 mL) was added 2N aqueous sodium hydroxide solution (11.2 mL, 22.4 mmol), and the mixture was stirred at 60° C. for 3 hr. The reaction mixture was neutralized with 6N hydrochloric acid (5 mL), 1N hydrochloric acid (50 mL) was added, and the mixture was extracted with ethyl acetate (100 mL, 20 mL). The combined organic layer was washed with saturated brine (10 and dried over anhydrous magnesium sulfate. The insoluble material was filtered off, and the filtrate was concentrated under reduced pressure. The obtained residue was crystallized from ethyl acetate/hexane to give the title compound (1.94 g, 92%) as colorless crystals.

$^1$H-NMR (DMSO-$d_6$, 300 MHz) δ 1.56 (6H, s), 3.33 (1H, s), 7.48 (1H, t, J=7.6 Hz), 7.72-7.88 (2H, m), 8.16 (1H, t, J=1.6 Hz), 13.01 (1H, br s).

(iv) Production of N-(3-{[2-(acetylamino)-1,3-benzothiazol-6-yl]oxy}phenyl)-3-(1,1-dimethylprop-2-yn-1-yl)benzamide Using N-[6-(3-aminophenoxy)-1,3-benzothiazol-2-yl]acetamide (160 mg, 0.534 mmol) produced in Example A40(x), 3-(1,1-dimethylprop-2-yn-1-yl)benzoic acid (201 mg, 1.07 mmol), tetrahydrofuran (4 mL), N,N-dimethylformamide (10 μL), oxalyl chloride (170 mg, 1.34 mmol) and N,N-dimethylformamide (4 mL), and in the same manner as in Example A40(xi), the title compound (56 mg, 22%) was obtained as a colorless solid.

$^1$H-NMR (DMSO-$d_6$, 300 MHz) δ 1.57 (6H, s), 2.19 (3H, s), 3.35 (1H, s), 6.73-6.83 (1H, m), 7.16 (1H, dd, J=2.5, 8.8 Hz), 7.35 (1H, t, J=8.1 Hz), 7.43-7.59 (3H, m), 7.69-7.84 (4H, m), 8.03 (1H, t, J=1.7 Hz), 10.29 (1H, s), 12.33 (1H, br s).

Example A43

Production of N-(3-{[2-(acetylamino)-1,3-benzothiazol-6-yl]oxy}phenyl)-3-(1-cyano-1-methylethoxy)benzamide

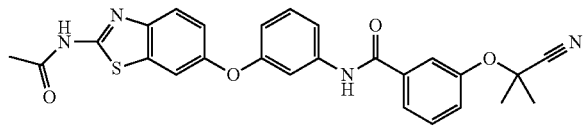

(i) Production of methyl 3-(cyanomethoxy)benzoate

To a solution of methyl 3-hydroxybenzoate (5.00 g, 32.9 mmol) in acetone (60 mL) were added bromoacetonitrile (2.63 mL, 39.4 mmol) and potassium carbonate (6.81 g, 49.3 mmol), and the mixture was stirred at 60° C. for 4 hr. To the reaction mixture was added saturated aqueous sodium hydrogencarbonate solution (100 mL), and the mixture was extracted with ethyl acetate (100 mL, 30 mL). The combined organic layer was washed with saturated brine (10 mL), and dried over anhydrous magnesium sulfate. The insoluble material was filtered off, and the filtrate was concentrated under reduced pressure. The obtained residue was purified by basic silica gel column chromatography (hexane/ethyl acetate=90/10→80/20), and the fraction containing the object product was concentrated under reduced pressure to give the title compound (5.43 g, 86%) as a colorless oil.

$^1$H-NMR (DMSO-$d_6$, 300 MHz) δ 3.87 (3H, s), 5.27 (2H, s), 7.37 (1H, ddd, J=7.8, 2.6, 1.3 Hz), 7.54 (1H, t, J=7.8 Hz), 7.59 (1H, dd, J=2.6, 1.3 Hz), 7.68 (1H, dt, J=7.8, 1.3 Hz).

(ii) Production of methyl 3-(1-cyano-1-methylethoxy)benzoate

To a solution of methyl 3-(cyanomethoxy)benzoate (6.00 g, 31.4 mmol) in tetrahydrofuran (200 mL) was added methyl iodide (15.6 mL, 251 mmol), and 1.1 M tetrahydrofuran solution (62.8 mL, 69.0 mmol) of lithium hexamethyl disilazide was added dropwise at −78° C. over 1.5 hr. After the completion of the dropwise addition, the mixture was stirred at −78° C. for 2 hr. The reaction mixture was poured into a mixture of ethyl acetate (150 mL) and aqueous ammonium chloride solution (150 mL). The organic layer and the aqueous layer were separated, and the aqueous layer was extracted with ethyl acetate (50 ml). The combined organic layer was washed with saturated brine (50 mL), and dried over anhydrous magnesium sulfate. The insoluble material was filtered off, and the filtrate was concentrated under reduced pressure. The obtained residue was purified by silica gel column chromatography (hexane/ethyl acetate=100/0→90/10), and the fraction containing the object product was concentrated under reduced pressure to give the title compound (2.07 g, 30%) as a yellow oil.

$^1$H-NMR (DMSO-$d_6$, 300 MHz) δ 1.71 (6H, s), 3.86 (3H, s), 7.46 (1H, ddd, J=7.8, 2.4, 1.2 Hz), 7.56 (1H, dt, J=7.8, 0.3 Hz), 7.69-7.72 (1H, m), 7.79 (1H, ddd, J=7.8, 1.5, 1.2 Hz).

(iii) Production of 3-(1-cyano-1-methylethoxy)benzoic acid

To a solution of methyl 3-(1-cyano-1-methylethoxy)benzoate (2.07 g, 9.44 mmol) in methanol (12 mL)/tetrahydrofuran (4 mL) was added 2N aqueous sodium hydroxide solution (9.44 mL, 18.9 mmol), and the mixture was stirred at room temperature for 30 min. The reaction mixture was neutralized with 6N hydrochloric acid (5 mL), 1N hydrochloric acid (50 mL) was added, and the mixture was extracted with ethyl acetate (50 mL, 20 mL). The combined organic layer was washed with saturated brine (10 mL), and dried over anhydrous magnesium sulfate. The insoluble material was filtered off, and the filtrate was concentrated under reduced pressure. The obtained residue was purified by silica gel column chromatography (hexane/ethyl acetate=90/10→50/50), and the fraction containing the object product was concentrated under reduced pressure. The obtained residue was crystallized from ethyl acetate/hexane to give the title compound (1.01 g, 51%) as colorless crystals.

$^1$H-NMR (DMSO-$d_6$, 300 MHz) δ 1.72 (6H, s), 7.42 (1H, ddd, J=7.9, 2.5, 1.2 Hz), 7.54 (1H, t, J=7.9 Hz), 7.70-7.73 (1H, m), 7.78 (1H, dt, J=7.9, 1.2 Hz), 13.18 (1H, br s).

(iv) Production of N-(3-{[2-(acetylamino)-1,3-benzothiazol-6-yl]oxy}phenyl)-3-(1-cyano-1-methylethoxy)benzamide To a solution of N-[6-(3-aminophenoxy)-1,3-benzothiazol-2-yl]acetamide (160 mg, 0.534 mmol) produced in Example A40(x) and 3-(1-cyano-1-methylethoxy)benzoic acid (219 mg, 1.07 mmol) in pyridine (5 mL) was added O-(7-azabenzotriazol-1-yl)-N,N,N',N'-tetramethyluronium hexafluorophosphate (407 mg, 1.07 mmol) under ice-cooling, and the mixture was stirred at room temperature for 5 hr. The reaction mixture was poured into water (100 mL), and extracted with ethyl acetate (100 mL×2). The ethyl acetate layers were combined and dried over anhydrous sodium sulfate, and the insoluble material was filtered off, and the filtrate was concentrated under reduced pressure. The obtained residue was purified by silica gel column chromatography (hexane/ethyl acetate=100/0→0/100), and crystallized from ethyl acetate to give the title compound (141 mg, 54%) as colorless crystals.

$^1$H-NMR (DMSO-$d_6$, 300 MHz) δ 1.72 (6H, s), 2.18 (3H, s), 6.71-6.85 (1H, m), 7.15 (1H, dd, J=1.9, 8.9 Hz), 7.28-7.42 (2H, m), 7.47 (1H, s), 7.50-7.60 (2H, m), 7.65 (1H, s), 7.67-7.79 (3H, m), 10.31 (1H, s), 12.30 (1H, br s).

Example A44

Production of N-(3-{[2-(acetylamino)-1,3-benzothiazol-6-yl]oxy}phenyl)-3-[(1,1-dimethylprop-2-yn-1-yl)oxy]benzamide

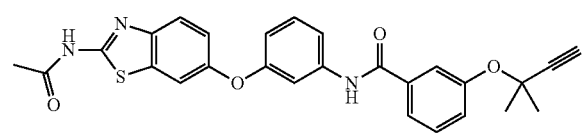

(i) Production of methyl 3-[(1,1-dimethylprop-2-yn-1-yl)oxy]benzoate

To a solution of methyl 3-hydroxybenzoate (10.0 g, 65.7 mmol) in acetonitrile (200 mL) were added 3-chloro-3-methylbut-1-yne (20.0 g, 195 mmol) and copper (II) chloride (88 mg, 0.654 mmol) under ice-cooling, and the mixture was stirred for 15 min under ice-cooling. 1,8-Diazabicyclo[5.4.0]undec-7-ene (10 mL, 70.0 mmol) was added under ice-cooling, and the mixture was stirred at room temperature for 2 hr. The reaction mixture was poured into water (300 mL), and the mixture was extracted with ethyl acetate (400 mL×2). The ethyl acetate layers were combined, and dried over anhydrous sodium sulfate. The insoluble material was filtered off, and the filtrate was concentrated under reduced pressure. The obtained residue was purified by silica gel column chromatography (hexane/ethyl acetate=100/0→0/100) to give the title compound (4.0 g, 28%) as a colorless oil.

$^1$H-NMR (DMSO-$d_6$, 300 MHz) δ 1.66 (6H, s), 2.60 (1H, s), 3.91 (3H, s), 7.34-7.45 (2H, m), 7.73-7.88 (2H, m).

(ii) Production of 3-[(1,1-dimethylprop-2-yn-1-yl)oxy]benzoic acid

To a solution of methyl 3-[(1,1-dimethylprop-2-yn-1-yl)oxy]benzoate (4.0 g, 18.3 mmol) in tetrahydrofuran (10 mL) were added lithium hydroxide•monohydrate (865 mg, 20.6 mmol), methanol (10 mL) and water (5 mL), and the mixture was stirred at room temperature for 12 hr. The reaction mixture was adjusted to pH 3 by slowly adding 1N hydrochloric acid, and extracted with ethyl acetate (100 mL×2). The ethyl acetate layers were combined, and dried over anhydrous sodium sulfate. The insoluble material was filtered off, and the filtrate was concentrated under reduced pressure to give the title compound (3.8 g, 99%) as a colorless oil.

$^1$H-NMR (DMSO-$d_6$, 300 MHz) δ 1.60 (6H, s), 3.71 (1H, s), 7.37-7.46 (2H, m), 7.63-7.65 (1H, m), 7.75-7.76 (1H, m), 12.92 (1H, br s).

(iii) Production of N-(3-{[2-(acetylamino)-1,3-benzothiazol-6-yl]oxy}phenyl)-3-[(1,1-dimethylprop-2-yn-1-yl)oxy]benzamide To a solution of N-[6-(3-aminophenoxy)-1,3-benzothiazol-2-yl]acetamide (160 mg, 0.534 mmol) produced in Example A40(x), 3-[(1,1-dimethylprop-2-yn-1-yl)oxy]benzoic acid (215 mg, 1.07 mmol) in pyridine (5 mL) was added O-(7-azabenzotriazol-1-yl)-N,N,N',N'-tetramethyluronium hexafluorophosphate (407 mg, 1.07 mmol) under ice-cooling, and the mixture was stirred at room temperature for 1 hr. The reaction mixture was poured into water (100 mL), and the mixture was extracted with ethyl acetate (100 mL). The organic layer was dried over anhydrous sodium sulfate, the insoluble material was filtered off, and the filtrate was concentrated under reduced pressure. The obtained residue was purified by silica gel column chromatography (hexane/ethyl acetate=80/20→0/100), and crystallized from ethyl acetate to give the title compound (181 mg, 70%) as colorless crystals.

$^1$H-NMR (DMSO-$d_6$, 300 MHz) δ 1.61 (6H, s), 2.19 (3H, s), 3.70 (1H, s), 6.77 (1H, dd, J=2.5, 8.0 Hz), 7.12-7.19 (1H, m), 7.31-7.47 (3H, m), 7.49 (1H, s), 7.55-7.66 (3H, m), 7.71 (1H, d, J=2.5 Hz), 7.74 (1H, d, J=8.5 Hz), 10.26 (1H, s), 12.32 (1H, br s).

Example A45

Production of N-(3-{[2-(acetylamino)-1,3-benzothiazol-6-yl]oxy}phenyl)-4-chloro-3-(1-cyano-1-methylethyl)benzamide

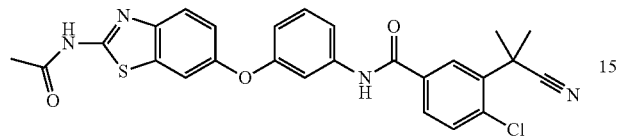

(i) Production of methyl 4-chloro-3-(1-cyano-1-methylethyl)benzoate

To a solution of methyl 4-chloro-3-(cyanomethyl)benzoate (14.0 g, 67 mmol) in dimethyl sulfoxide (300 mL) was added sodium hydride (60% in oil, 9.6 g, 240 mmol). The reaction mixture was stirred at room temperature for 20 min. After stirring, methyl iodide (15 mL, 240 mmol) was added, and the mixture was further stirred at room temperature for 15 hr. The reaction mixture was diluted with water (500 mL), and extracted with ethyl acetate (800 mL). The organic layer was washed with saturated brine (100 mL) and dried over anhydrous sodium sulfate, and the insoluble material was filtered off. The solvent was evaporated under reduced pressure, and the residue was purified by silica gel column chromatography (hexane/ethyl acetate=95/5→50/50), and the fraction containing the object product was concentrated under reduced pressure to give the title compound (8.40 g, 53%) as a colorless oil.

$^1$H-NMR (DMSO-$d_6$, 300 MHz) δ 1.81 (6H, s), 3.91 (3H, s), 7.64-8.01 (2H, m), 8.08 (1H, d, J=1.9 Hz).

(ii) Production of 4-chloro-3-(1-cyano-1-methylethyl)benzoic acid

To a solution of methyl 4-chloro-3-(1-cyano-1-methylethyl)benzoate (8.0 g, 34 mmol) in tetrahydrofuran (30 mL) were added lithium hydroxide•monohydrate (2.13 g, 51 mmol), methanol (100 mL) and water (5 mL), and the mixture was stirred at room temperature for 4 hr. The solvent was evaporated under reduced pressure, and the residue was diluted with water (200 mL). The mixture was adjusted to pH 3 by slowly adding 1N hydrochloric acid. The resulting white precipitate was collected by filtration, washed with water, and dried to give the title compound (7.40 g, 99%) as a white powder.

$^1$H-NMR (DMSO-$d_6$, 300 MHz) δ 1.85 (6H, s), 7.70 (1H, d, J=8.3 Hz), 7.94 (1H, dd, J=2.1, 8.3 Hz), 8.07 (1H, d, J=2.1 Hz), 12.70 (1H, br s).

(iii) Production of N-(3-{[2-(acetylamino)-1,3-benzothiazol-6-yl]oxy}phenyl)-4-chloro-3-(1-cyano-1-methylethyl)benzamide Using N-[6-(3-aminophenoxy)-1,3-benzothiazol-2-yl]acetamide (160 mg, 0.534 mmol) produced in Example A40(x), 4-chloro-3-(1-cyano-1-methylethyl)benzoic acid (240 mg, 1.07 mmol), tetrahydrofuran (4 mL), N,N-dimethylformamide (10 μL), oxalyl chloride (170 mg, 1.34 mmol) and N,N-dimethylformamide (4 mL), and in the same manner as in Example A40(xi), the title compound (112 mg, 42%) was obtained as a colorless solid.

$^1$H-NMR (DMSO-$d_6$, 300 MHz) δ 1.85 (6H, s), 2.20 (3H, s), 6.69-6.86 (1H, m), 7.16 (1H, dd, J=2.5, 8.8 Hz), 7.37 (1H, t, J=8.1 Hz), 7.46 (1H, t, J=2.2 Hz), 7.49-7.56 (1H, m), 7.60-7.82 (3H, m), 7.86-8.05 (2H, m), 10.41 (1H, s), 12.33 (1H, br s).

Example A46

Production of N-(3-{[2-(acetylamino)-1,3-benzothiazol-6-yl]oxy}phenyl)-3-cyanobenzamide

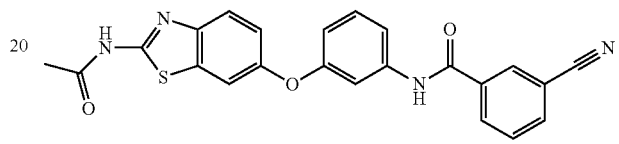

Using N-[6-(3-aminophenoxy)-1,3-benzothiazol-2-yl]acetamide (160 mg, 0.534 mmol) produced in Example A40(x), 3-cyanobenzoic acid (157 mg, 1.07 mmol), tetrahydrofuran (4 mL), N,N-dimethylformamide (10 μL), oxalyl chloride (170 mg, 1.34 mmol) and N,N-dimethylformamide (4 mL), and in the same manner as in Example A40(xi), the title compound (127 mg, 55%) was obtained as a colorless solid.

$^1$H-NMR (DMSO-$d_6$, 300 MHz) δ 2.20 (3H, s), 6.70-6.88 (1H, m), 7.17 (1H, dd, J=2.6, 8.7 Hz), 7.37 (1H, t, J=8.0 Hz), 7.46 (1H, t, J=2.0 Hz), 7.52-7.62 (1H, m), 7.66-7.83 (3H, m), 8.01-8.08 (1H, m), 8.15-8.23 (1H, m), 8.35 (1H, t, J=1.4 Hz), 10.44 (1H, s), 12.34 (1H, s).

Example A47

Production of N-(3-{[2-(acetylamino)-1,3-benzothiazol-6-yl]oxy}-4-fluorophenyl)-2-chloro-3-(1-cyano-1-methylethyl)benzamide

(i) Production of N-[3-(4-aminophenoxy)-4-fluorophenyl]-2-chloro-3-(1-cyano-1-methylethyl)benzamide To a solution of 2-chloro-3-(1-cyano-1-methylethyl)benzoic acid (1.98 g, 8.85 mmol) produced in Example A41(ii) in tetrahydrofuran (40 mL) were added oxalyl chloride (1.41 g, 11.1 mmol) and N,N-dimethylformamide (10 μL), and the mixture was stirred for 1 hr. The reaction mixture was concentrated under reduced pressure, and the obtained residue was dissolved in N,N-dimethylacetamide (40 mL). 4-Fluoro-3-(4-nitrophenoxy)aniline (4.69 g, 20.4 mmol) was added, and the mixture was stirred at room temperature for 14 hr. To the reaction mixture were added water (100 ml), 1N aqueous sodium hydroxide solution (50 mL) and ethyl acetate (200 mL). The organic layer was separated, washed with saturated brine (10 mL), and dried over anhydrous magnesium sulfate. The insoluble material was filtered off, and the filtrate was concentrated under reduced pressure to give 2-chloro-3-(1-cyano-1-methylethyl)-N-[4-fluoro-3-(4-nitrophenoxy)phenyl]benzamide (2.01 g, 99%). The obtained compound was used in the next reaction without a further purification.

To a solution of 2-chloro-3-(1-cyano-1-methylethyl)-N-[4-fluoro-3-(4-nitrophenoxy)phenyl]benzamide (2.00 g, 4.43 mmol) obtained in the above in ethanol (100 mL) were added reduced iron (5.00 g, 89.5 mmol) and 1N hydrochloric acid (5 mL), and the mixture was stirred at 80° C. for 3 hr. To the reaction mixture were added 8N aqueous sodium hydroxide solution (5 mL), ethyl acetate (200 mL) and water (150 mL), and the mixture was stirred. The insoluble material was filtered off through celite. The ethyl acetate layer was separated from the filtrate, dried over anhydrous sodium sulfate, and the insoluble material was filtered off. The solvent was evaporated under reduced pressure, and the residue was purified by silica gel column chromatography (hexane/ethyl acetate=80/20→0/100), and the fraction containing the object product was concentrated under reduced pressure to give the title compound (1.76 g, 94%) as a yellow solid.

$^{1}$H-NMR (DMSO-d$_{6}$, 300 MHz) δ 1.82 (6H, s), 6.97 (1H, dd, J=2.5, 8.7 Hz), 7.31-7.36 (2H, m), 7.36-7.39 (1H, m), 7.43 (2H, s), 7.46-7.54 (4H, m), 7.54-7.59 (1H, m), 7.63 (1H, dd, J=2.0, 7.7 Hz), 10.60 (1H, s).

(ii) Production of N-{3-[(2-amino-1,3-benzothiazol-6-yl)oxy]-4-fluorophenyl}-2-chloro-3-(1-cyano-1-methylethyl)benzamide To a solution of potassium thiocyanate (1.65 g, 17.0 mmol) in acetic acid (15 mL) was added a solution of N-[3-(4-aminophenoxy)-4-fluorophenyl]-2-chloro-3-(1-cyano-1-methylethyl)benzamide (1.75 g, 4.13 mmol) in acetic acid (5 mL), and the mixture was stirred at room temperature for 15 min. To the obtained solution was added dropwise a solution of bromine (726 mg, 4.54 mmol) in acetic acid (15 mL) at room temperature over 30 min or longer. After the completion of the dropwise addition, the mixture was stirred at room temperature for 4 hr. The resulting yellow solid was filtered off, and the filtrate was concentrated under reduced pressure. The residue was dissolved in tetrahydrofuran (100 mL) and ethyl acetate (200 mL), and basified with 2N aqueous sodium hydroxide solution. The aqueous layer was separated, and the organic layer was washed with saturated aqueous ammonium chloride solution (200 mL) and dried over anhydrous magnesium sulfate. The insoluble material was filtered off, and the filtrate was concentrated under reduced pressure to give the title compound (854 mg, 43%) as a yellow amorphous substance. The obtained compound was used in the next reaction without a further purification.

$^{1}$H-NMR (DMSO-d$_{6}$, 300 MHz) δ 1.82 (6H, s), 5.00 (2H, s), 6.59 (2H, d, J=8.1 Hz), 6.80 (2H, d, J=8.1 Hz), 7.21-7.34 (2H, m), 7.39-7.56 (2H, m), 7.57-7.68 (1H, m), 10.56 (1H, s).

(iii) Production of N-(3-{[2-(acetylamino)-1,3-benzothiazol-6-yl]oxy}-4-fluorophenyl)-2-chloro-3-(1-cyano-1-methylethyl)benzamide To a solution of N-{3-[(2-amino-1,3-benzothiazol-6-yl)oxy]-4-fluorophenyl}-2-chloro-3-(1-cyano-1-methylethyl)benzamide (350 mg, 0.73 mmol) in tetrahydrofuran (20 mL) were added acetyl chloride (63 mg, 0.80 mmol) and pyridine (86 mg, 1.09 mmol), and the mixture was stirred at room temperature for 10 min. To the reaction mixture were added water (100 mL) and ethyl acetate (100 mL). After stirring for 30 min, the mixture was extracted with ethyl acetate. The organic layer was dried over anhydrous magnesium sulfate, the insoluble material was filtered off, and the filtrate was concentrated under reduced pressure. The residue was purified by silica gel chromatography (hexane/ethyl acetate=20/80→0/100), and triturated with ethyl acetate/hexane to give the title compound (105 mg, 28%) as a colorless solid.

$^{1}$H-NMR (DMSO-d$_{6}$, 300 MHz) δ 1.82 (6H, s), 2.18 (3H, s), 7.18 (1H, dd, J=2.5, 8.7 Hz), 7.39 (1H, dd, J=8.7, 10.8 Hz), 7.45 (1H, dd, J=2.5, 7.6 Hz), 7.48-7.58 (3H, m), 7.64 (1H, dd, J=2.0, 7.6 Hz), 7.70-7.77 (2H, m), 10.64 (1H, s), 12.33 (1H, br s).

Example A48

Production of 2-chloro-3-(1-cyano-1-methylethyl)-N-[3-({2-[(cyclopropylcarbonyl)amino]-1,3-benzothiazol-6-yl}oxy)-4-fluorophenyl]benzamide

To a solution of N-{3-[(2-amino-1,3-benzothiazol-6-yl)oxy]-4-fluorophenyl}-2-chloro-3-(1-cyano-1-methylethyl)benzamide (350 mg, 0.73 mmol) produced in Example A47 (ii) in tetrahydrofuran (20 mL) were added cyclopropanecarbonyl chloride (114 mg, 1.09 mmol) and pyridine (86 mg, 1.09 mmol), and the mixture was stirred at room temperature for 30 min. Water (100 mL) and ethyl acetate (100 mL) were added to the reaction mixture, and the mixture was stirred for 30 min. The organic layer was separated, and dried over anhydrous magnesium sulfate. The insoluble material was filtered off, and the filtrate was concentrated under reduced pressure. The residue was purified by silica gel chromatography (hexane/ethyl acetate=20/80→0/100), and triturated with ethyl acetate/hexane to give the title compound (162 mg, 40%) as a colorless solid.

$^{1}$H-NMR (DMSO-d$_{6}$, 300 MHz) δ 0.92-0.98 (4H, m), 1.82 (6H, s), 1.91-2.07 (1H, m), 7.18 (1H, dd, J=2.5, 8.5 Hz), 7.39 (1H, dd, J=8.5, 10.5 Hz), 7.45 (1H, dd, J=2.5, 7.5 Hz), 7.50 (1H, d, J=7.5 Hz), 7.53 (1H, d, J=2.5 Hz), 7.54-7.58 (1H, m), 7.64 (1H, dd, J=2.5, 7.5 Hz), 7.72 (1H, d, J=2.5 Hz), 7.74 (1H, d, J=8.5 Hz), 10.64 (1H, s), 12.62 (1H, br s).

Example A49

Production of N-(5-{[2-(acetylamino)-1,3-benzothiazol-6-yl]oxy}-2-methylphenyl)-3-(1-cyano-1-methylethyl)benzamide

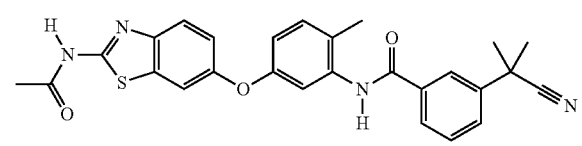

To a solution of N-{5-[(2-amino-1,3-benzothiazol-6-yl)oxy]-2-methylphenyl}-3-(1-cyano-1-methylethyl)benzamide (200 mg, 0.452 mmol) produced in Example A7(vii) in tetrahydrofuran (2.0 mL) were added pyridine (180 μL, 2.25 mmol) and acetyl chloride (51 μL, 0.723 mmol), and the mixture was stirred at room temperature for 2 hr. The reaction mixture was diluted with ethyl acetate (20 mL), washed with 5% aqueous sodium hydrogencarbonate solution (10 mL) and saturated brine (10 mL), successively, and dried over anhydrous sodium sulfate. The insoluble material was filtered off, and the filtrate was concentrated under reduced pressure. The obtained residue was purified by basic silica gel column chromatography (hexane/ethyl acetate=50/50→0/100), and the obtained solution was concentrated under reduced pressure. The residue was recrystallized from 2-butanone/hexane to give the title compound (138 mg, 63%) as colorless crystals.

$^1$H-NMR (DMSO-$d_6$, 300 MHz) δ 1.73 (6H, s), 2.19 (3H, s), 2.22 (3H, s), 6.88 (1H, dd, J=2.5, 8.4 Hz), 7.05 (1H, d, J=2.5 Hz), 7.13 (1H, dd, J=2.5, 8.7 Hz), 7.29 (1H, d, J=8.5 Hz), 7.58 (1H, t, J=7.8 Hz), 7.68 (1H, d, J=2.5 Hz), 7.70-7.80 (2H, m), 7.93 (1H, d, J=7.9 Hz), 8.04 (1H, s), 9.96 (1H, s), 12.32 (1H, s).

Preparation Example A1

A medicament containing the compound of the present invention as an active ingredient can be produced, for example, according to the following formulation.

1. Capsule

| | |
|---|---|
| (1) compound obtained in Example A12 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The rest of (4) is added thereto and the total amount is sealed in a gelatin capsule.

2. Tablet

| | |
|---|---|
| (1) compound obtained in Example A12 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3) and ⅔ of (4), and ½ of (5) are blended and granulated. The rest of (4) and (5) is added to the granules and the mixture is compression formed into a tablet.

Preparation Example A2

The compound (50 mg) obtained in Example A12 is dissolved in the Japanese Pharmacopoeia distilled water for injection (50 mL), and the Japanese Pharmacopoeia distilled water for injection is added to the total amount of 100 mL. This solution is filtered under sterile conditions, and then the solution (1 mL) is filled in a vial for injection under sterile conditions, freeze-dried and sealed.

Example B1

Production of N-[3-({2-[(cyclopropylcarbonyl) amino]-1,3-benzooxazol-6-yl}oxy)phenyl]-3-(trifluoromethyl)benzamide

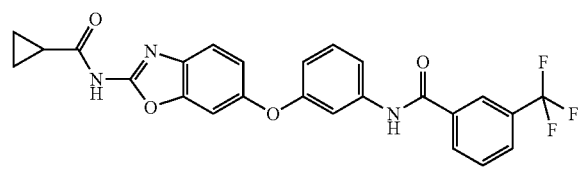

(i) Production of 2-(benzyloxy)-4-fluoro-1-nitrobenzene

To a solution of 5-fluoro-2-nitrophenol (8.05 g, 51.2 mmol) in acetone (100 mL) were added benzyl bromide (8.90 g, 52.0 mmol), potassium carbonate (11.0 g, 79.3 mmol) and sodium iodide (1.51 g, 10.1 mmol) at room temperature, and the mixture was heated under reflux for 2.5 hr. The reaction mixture was cooled to room temperature, the inorganic salt was filtered off, and the filtrate was concentrated. The residue was dissolved in ethyl acetate (150 mL), and the mixture was washed with water (150 mL×2) and saturated brine (100 mL), successively, and dried over anhydrous magnesium sulfate. The insoluble material was filtered off, and the filtrate was concentrated under reduced pressure to give the title compound (13.2 g) as a brown oil.

$^1$H-NMR (CDCl$_3$, 300 MHz) δ 5.22 (2H, s), 6.73 (1H, ddd, J=2.4, 7.2, 9.0 Hz), 6.83 (1H, dd, J=2.4, 10.2 Hz), 7.30-7.50 (5H, m), 7.96 (1H, dd, J=6.0, 9.0 Hz).

(ii) Production of methyl 3-[(3-(benzyloxy)-4-nitrophenoxy]benzoate

To a solution of 2-(benzyloxy)-4-fluoro-1-nitrobenzene (12.0 g, 48.5 mmol) and methyl 3-hydroxybenzoate (7.52 g, 49.4 mmol) in N,N-dimethylformamide (80 mL) was added potassium carbonate (15.4 g, 112 mmol) at room temperature, and the mixture was stirred at 60° C. for 2.5 hr. The reaction mixture was cooled to room temperature, the inorganic salt was collected by filtration, and the inorganic salt was washed with ethyl acetate. The filtrate and the washing were combined, and a mixed solvent (1:1, 200 mL) of ethyl acetate/hexane was added. The mixture was washed with water (200 mL×2) and saturated brine (100 mL), successively, and dried over anhydrous magnesium sulfate. The insoluble material was filtered off, and the filtrate was concentrated under reduced pressure to give the title compound (19.1 g) as a yellow syrup.

$^1$H-NMR (CDCl$_3$, 300 MHz) δ 3.93 (3H, s), 5.16 (2H, s), 6.53 (1H, dd, J=2.7, 9.3 Hz), 6.55 (1H, d, J=2.4 Hz), 7.23 (1H, ddd, J=0.9, 2.4, 9.0 Hz), 7.28-7.42 (5H, m), 7.48 (1H, t, J=7.8 Hz), 7.69 (1H, dd, J=1.5, 2.1 Hz), 7.90-7.98 (2H, m).

(iii) Production of methyl 3-(4-amino-3-hydroxyphenoxy)benzoate

To a solution of methyl 3-[3-(benzyloxy)-4-nitrophenoxy] benzoate (19.1 g, 50.4 mmol) in ethyl acetate (50 mL) were added methanol (80 mL) and 10% palladium-carbon (2.31 g), and the mixture was vigorously stirred at room temperature for 20 hr under a hydrogen atmosphere. 10% Palladium-carbon was filtered off, and the filtrate was concentrated under reduced pressure to give the title compound (13.1 g) as a brown syrup.

$^1$H-NMR (CDCl$_3$, 300 MHz) δ 3.48 (3H, s), 3.88 (2H, br s), 3.89 (1H, br s), 6.42-6.51 (2H, m), 6.73 (1H, d, J=8.1 Hz), 7.13 (1H, ddd, 1.2, 2.7, 8.1 Hz), 7.33 (1H, t, J=8.1 Hz), 7.55 (1H, dd, J=1.5, 2.1 Hz), 7.68 (1H, dt, J=7.8, 0.9 Hz).

(iv) Production of methyl 3-[(2-amino-1,3-benzooxazol-6-yl)oxy]benzoate

To a solution of methyl 3-(4-amino-3-hydroxyphenoxy)benzoate (13.1 g, 50.5 mmol) in tetrahydrofuran (200 mL) was added cyanogen bromide (9.76 g, 92.1 mmol), and the mixture was stirred at room temperature for 16 hr. To the reaction mixture was added cyanogen bromide (1.78 g, 16.8 g), and the mixture was further stirred at room temperature for 3 days. The reaction mixture was diluted with ethyl acetate (300 mL), washed with saturated aqueous sodium hydrogencarbonate solution (150 mL×2) and saturated brine (150 mL), successively, and dried over anhydrous magnesium sulfate. The insoluble material was filtered off, and the filtrate was concentrated under reduced pressure to give the title compound (13.6 g, yield (total of 4 steps) 95%) as brown crystals.

$^1$H-NMR (CDCl$_3$, 300 MHz) δ 3.91 (3H, s), 5.07 (2H, br s), 6.94 (1H, dd, J=2.1, 8.4 Hz), 7.03 (1H, d, J=2.1 Hz), 7.20 (1H, ddd, J=1.2, 2.7, 8.4 Hz), 7.35 (1H, d, J=8.7 Hz), 7.41 (1H, t, J=7.8 Hz), 7.62 (1H, dd, J=1.6, 2.4 Hz), 7.77 (1H, dt, J=7.8, 1.2 Hz).

(v) Production of methyl 3-({2-[(cyclopropylcarbonyl)amino]-1,3-benzooxazol-6-yl}oxy)benzoate To a solution (100 mL) of methyl 3-[(2-amino-1,3-benzooxazol-6-yl)oxy]benzoate (6.84 g, 24.1 mmol) in pyridine were added N,N-dimethylpyridine-4-amine (129 mg, 1.05 mmol) and cyclopropanecarbonyl chloride (2.5 mL, 27.5 mmol), and the mixture was stirred at room temperature for 1.5 hr. To the reaction mixture was added cyclopropanecarbonyl chloride (2.5 mL, 27.5 mmol), and the mixture was further stirred at room temperature for 1.5 hr. Cyclopropanecarbonyl chloride (1.5 mL, 16.5 mmol) was further added to the reaction mixture, and the mixture was continuously stirred at room temperature for 2 hr. The reaction mixture was concentrated under reduced pressure, and the residue was suspended in ethyl acetate (200 mL). This suspension was washed with 0.1N hydrochloric acid (150 mL) and saturated aqueous sodium hydrogencarbonate solution (150 mL), successively. The diluted hydrochloric acid layer was extracted with ethyl acetate (100 mL×2), and the combined organic layers were washed with saturated aqueous sodium hydrogencarbonate solution (150 mL) and saturated brine (150 mL), successively, and dried over anhydrous magnesium sulfate. The insoluble material was filtered off, and the filtrate was concentrated to give a brown amorphous substance (8.2 g).

$^1$H-NMR (DMSO-d$_6$, 300 MHz) δ 0.85-0.95 (4H, m), 2.00-2.15 (1H, m), 3.81 (3H, s), 7.05 (1H, dd, J=2.4, 8.7 Hz), 7.32 (1H, ddd, 0.9, 2.4, 8.1 Hz), 7.43 (1H, t, J=1.5 Hz), 7.47 (1H, d, J=2.4 Hz), 7.52 (1H, t, J=7.8 Hz), 7.60 (1H, d, J=8.4 Hz), 7.70 (1H, dt, J=7.8, 0.9 Hz), 11.94 (1H, br s).

(vi) Production of 3-({2-[(cyclopropylcarbonyl)amino]-1,3-benzooxazol-6-yl}oxy)benzoic acid To a solution of methyl 3-({2-[(cyclopropylcarbonyl)amino]-1,3-benzooxazol-6-yl}oxy)benzoate (8.2 g) in methanol (300 mL) was added 8N aqueous sodium hydroxide solution (50 ml), and the mixture was stirred at room temperature for 2 days. To the reaction mixture was added 6N hydrochloric acid to adjust the pH to about 6.0, and the reaction mixture was concentrated under reduced pressure to about 100 mL. Ethyl acetate (200 mL) was added to the residue, and the mixture was washed with water (150 mL×2). The collected aqueous layer was extracted with ethyl acetate (100 mL×2), and the combined organic layers were dried over anhydrous magnesium sulfate. The insoluble material was filtered off, and the filtrate was concentrated under reduced pressure to give a brown amorphous substance. The obtained crude product was dissolved in toluene (150 mL) and 2-methylpropan-2-ol (100 mL), and the solvent was evaporated under reduced pressure. An azeotropic operation with toluene and 2-methylpropan-2-ol was further repeated twice to remove water from the crude product. The obtained brown amorphous substance (8.6 g) was used as the title compound in the next operation without a further purification.

$^1$H-NMR (DMSO-d$_6$, 300 MHz) δ 0.87-0.97 (4H, m), 2.05-2.08 (1H, m), 7.06 (1H, dd, J=2.4, 8.7 Hz), 7.23-7.42 (2H, m), 7.48-7.54 (2H, m), 7.60 (1H, d, J=8.7 Hz), 7.69 (1H, dt, J=7.8, 1.2 Hz), 9.73 (1H, br s), 11.93 (1H, br s). M+H=339.05

(vii) Production of N-[6-(3-aminophenoxy)-1,3-benzooxazol-2-yl]cyclopropanecarboxamide To a solution of 3-({2-[(cyclopropylcarbonyl)amino]-1,3-benzooxazol-6-yl}oxy)benzoic acid (8.6 g) in tetrahydrofuran (100 mL) and 2-methylpropan-2-ol (50 mL) were added N-ethyl-N-isopropylpropan-2-amine (20 L, 115 mmol) and diphenylphosphoryl azide (22 mL, 102 mmol), and the mixture was heated under reflux for 6 hr. The reaction mixture was cooled to room temperature, and concentrated under reduced pressure. The residue was dissolved in ethyl acetate (250 mL), and the mixture was washed with saturated aqueous sodium hydrogencarbonate solution (100 mL×2) and saturated brine (100 mL), successively, and dried over anhydrous magnesium sulfate. The insoluble material was filtered off, and the filtrate was concentrated under reduced pressure. The residue was purified by silica gel column chromatography (ethyl acetate/hexane=2/98→80/20) to give the objective tert-butyl [3-({2-[(cyclopropylcarbonyl)amino]-1,3-benzooxazol-6-yl}oxy)phenyl]carbamate as a brown amorphous substance (3.25 g). The obtained compound was used in the next operation without further purification.

tert-Butyl [3-({2-[(cyclopropylcarbonyl)amino]-1,3-benzooxazol-6-yl}oxy)phenyl]carbamate (3.25 g) produced above was dissolved in trifluoroacetic acid (50 mL) at room temperature, and the mixture was heated under reflux for 1.5 hr. The reaction mixture was cooled to room temperature, and trifluoroacetic acid was evaporated under reduced pressure. The residue was diluted with ethyl acetate (150 mL), washed with saturated aqueous sodium hydrogencarbonate solution (100 mL×2) and brine (100 mL), successively, and dried over anhydrous magnesium sulfate. The insoluble material was filtered off, and the filtrate was concentrated under reduced pressure. The residue was purified by silica gel column chromatography (ethyl acetate/hexane=2/98→80/20) to give the title compound (1.1 g, total of 4 steps 14%) as a brown solid.

$^1$H-NMR (CDCl$_3$, 300 MHz) δ 1.01-1.08 (2H, m), 1.22-1.27 (2H, m), 2.10-2.40 (1H, m), 3.73 (2H, br s), 6.34 (1H, t, J=2.1 Hz), 6.40 (1H, ddd, J=0.9, 2.4, 8.1 Hz), 6.45 (1H, ddd, J=0.9, 2.1, 8.1 Hz), 7.03 (1H, dd, J=2.4, 8.7 Hz), 7.12 (1H, t, J=8.1 Hz), 7.17 (1H, d, J=2.1 Hz), 7.49 (1H, br d, J=9.4 Hz), 9.60 (1H, br s).

(viii) Production of N-[3-({2-[(cyclopropylcarbonyl) amino]-1,3-benzooxazol-6-yl}oxy)phenyl]-3-(trifluoromethyl)benzamide To a suspension of 3-(trifluoromethyl)benzoic acid (329 mg, 1.73 mmol) in toluene (5 mL) was added thionyl chloride (1 mL, 13.7 mmol), and the mixture was heated under reflux for 2.5 hr. The obtained colorless solution was cooled to room temperature, and the solvent was evaporated under reduced pressure. The obtained brown oil was used as 3-(trifluoromethyl)benzoyl chloride for the next reaction.

To a solution of N-[6-(3-aminophenoxy)-1,3-benzooxazol-2-yl]cyclopropanecarboxamide (128 mg, 415 µmol) in pyridine (3 mL) were added a solution of 3-(trifluoromethyl) benzoyl chloride prepared above in pyridine (2 mL) and N,N-dimethylpyridine-4-amine (58.9 mg, 482 µmol), and the mixture was stirred at room temperature for 2 hr. The reaction mixture was concentrated under reduced pressure, and the residue was dissolved in methanol (10 mL) and ethyl acetate (100 mL). This solution was washed with 0.1N hydrochloric acid (50 mL) and saturated aqueous sodium hydrogencarbonate solution (50 mL), successively, and dried over anhydrous magnesium sulfate. The insoluble material was filtered off, and the filtrate was concentrated under reduced pressure. The residue was purified by silica gel column chromatography (ethyl acetate/hexane=2/98→80/20) to give the title compound (101 mg, 50%) as a colorless solid.

$^1$H-NMR (DMSO-d$_6$, 300 MHz) δ 0.90-0.95 (4H, m), 2.00-2.15 (1H, m), 6.80-6.83 (1H, m), 7.05 (1H, dd, J=2.4, 8.7 Hz), 7.38 (1H, t, J=8.1 Hz), 7.43-7.49 (2H, m), 7.56-7.60 (2H, m), 7.77 (1H, t, J=7.8 Hz), 7.96 (1H, d, J=7.8 Hz), 8.21-8.24 (2H, m), 10.49 (1H, br s), 11.92 (1H, br s).

Example B2

Production of 3-(1-cyanocyclopropyl)-N-[3-({2-[(cyclopropylcarbonyl)amino]-1,3-benzooxazol-6-yl}oxy)phenyl]benzamide

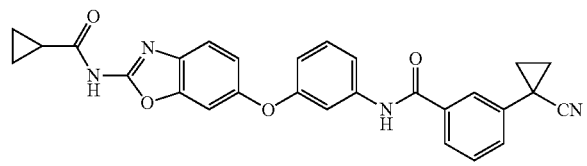

(i) Production of methyl 3-(cyanomethyl)benzoate

To a solution of methyl 3-bromobenzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtered, and the solvent was evaporated under reduced pressure. The residue was purified by silica gel column chromatography (ethyl acetate/hexane=5/95→30/70), and the fraction containing the object product was concentrated under reduced pressure to give the title compound (7.0 g, 91%) as a colorless oil.

$^1$H-NMR (DMSO-d$_6$, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

(ii) Production of methyl 3-(1-cyanocyclopropyl)benzoate

To a solution of methyl 3-(cyanomethyl)benzoate (1.5 g, 8.6 mmol) in dimethyl sulfoxide (30 mL) was added sodium hydride (60% in oil, 1.0 g, 26 mmol) under cooling to not more than 25° C. without causing solidification. The reaction mixture was stirred at room temperature for 30 min. After stirring, 1,2-dibromoethane (2.4 g, 12.8 mmol) was added, and the mixture was further stirred at room temperature for 10 hr. The reaction mixture was diluted with water (100 mL), and extracted with ethyl acetate (300 mL). The organic layer was washed with saturated brine (100 mL) and dried over anhydrous sodium sulfate, and the insoluble material was filtered off. The solvent was evaporated under reduced pressure, the residue was purified by silica gel column chromatography (ethyl acetate/hexane=5/95→50/50), and the fraction containing the object product was concentrated under reduced pressure to give the title compound (1.3 g, 76%) as a colorless oil.

$^1$H-NMR (CDCl$_3$, 300 MHz) δ 1.38-1.56 (2H, m), 1.74-1.82 (2H, m), 3.93 (3H, s), 7.40° C.-7.49 (1H, m), 7.55-7.62 (1H, m), 7.88 (1H, t, J=1.5 Hz), 7.96 (1H, dt, J=7.8, 1.5 Hz).

(iii) Production of 3-(1-cyanocyclopropyl)benzoic acid

To a solution of methyl 3-(1-cyanocyclopropyl)benzoate (1.3 g, 6.4 mmol) in tetrahydrofuran (12 mL) were added lithium hydroxide•monohydrate (0.44 g, 11 mmol), methanol (4.0 mL) and water (6.0 mL), and the mixture was stirred at room temperature for 14 hr. The solvent was evaporated under reduced pressure, and the residue was diluted with water (5.0 mL). The mixture was adjusted to pH 5 by slowly adding 1N hydrochloric acid. The resulting white precipitate was collected by filtration, washed with water, and dried to give the title compound (0.73 g, 61%) as a white powder.

$^1$H-NMR (DMSO-d$_6$, 300 MHz) δ 1.50-1.62 (2H, m), 1.76-1.86 (2H, m), 7.41-7.59 (2H, m), 7.82-7.97 (2H, m), 13.19 (1H, br s).

(iv)

Using 3-(1-cyanocyclopropyl)benzoic acid (224 mg, 1.19 mmol), thionyl chloride (1 mL, 13.7 mmol), toluene (5 mL), N-[6-(3-aminophenoxy)-1,3-benzooxazol-2-yl]cyclopropanecarboxamide (131 mg, 424 µmol) produced in Example B1(vii), pyridine (5 mL), and N,N-dimethylpyridine-4-amine (28.1 mg, 230 µmol) as starting materials, and in the same manner as in Example B1(viii), the title compound (135 mg, 66%) was obtained as a colorless solid.

$^1$H-NMR (DMSO-d$_6$, 300 MHz) δ 0.90-0.95 (4H, m), 1.58-1.62 (2H, m), 1.79-1.83 (2H, m), 2.00-2.10 (1H, m), 6.77-6.81 (1H, m), 7.05 (1H, dd, J=2.4, 8.4 Hz), 7.36 (1H, t, J=8.1 Hz), 7.43 (1H, d, J=2.1 Hz), 7.48 (1H, t, J=2.1 Hz), 7.53-7.61 (4H, m), 7.78-7.79 (1H, m), 7.84 (1H, dt, J=6.6, 2.4 Hz), 10.33 (1H, br s), 11.91 (1H, br s).

Example B3

Production of 3-(1-cyano-1-methylethyl)-N-[3-({2-[(cyclopropylcarbonyl)amino]-1,3-benzooxazol-6-yl}oxy)phenyl]benzamide

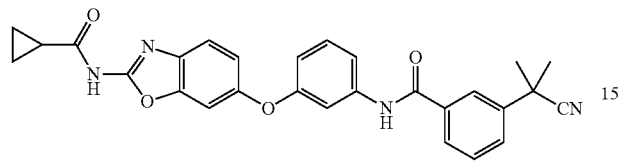

(i) Production of methyl 3-(1-cyano-1-methylethyl)benzoate

To a solution of methyl 3-(cyanomethyl)benzoate (7.0 g, 40 mmol) produced in Example B2(i) in dimethyl sulfoxide (80 mL) was added sodium hydride (60% in oil, 4.8 g, 120 mmol) under cooling to not more than 25° C. without causing solidification. The reaction mixture was stirred at room temperature for 20 min. After stirring, methyl iodide (7.5 mL, 120 mmol) was added, and the mixture was further stirred at room temperature for 16 hr. The reaction mixture was diluted with water (400 mL), and extracted with ethyl acetate (800 mL). The organic layer was washed with water (400 mL) and saturated brine (400 mL), successively, and dried over anhydrous sodium sulfate, and the insoluble material was filtered off. The solvent was evaporated under reduced pressure, the residue was purified by silica gel column chromatography (ethyl acetate/hexane=5/95→50/50), and the fraction containing the object product was concentrated under reduced pressure to give the title compound (6.4 g, 79%) as a colorless oil.

$^1$H-NMR (DMSO-$d_6$, 300 MHz) δ 1.72 (6H, s), 3.89 (3H, s), 7.61 (1H, t, J=7.8 Hz), 7.82-7.85 (1H, ddd, J=1.2, 2.1, 7.8 Hz), 7.95 (1H, dt, J=7.8, 1.2 Hz), 8.08 (1H, t, J=1.5 Hz).

(ii) Production of 3-(1-cyano-1-methylethyl)benzoic acid

To a solution of methyl 3-(1-cyano-1-methylethyl)benzoate (2.8 g, 14 mmol) in tetrahydrofuran (30 mL) were added lithium hydroxide·monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). The mixture was adjusted to pH 3 by slowly adding 1N hydrochloric acid. The resulting white precipitate was collected by filtration, washed with water, and dried to give the title compound (2.5 g, 98%) as a white powder.

$^1$H-NMR (DMSO-$d_6$, 300 MHz) δ 1.72 (6H, s), 7.57 (1H, t, J=7.8 Hz), 7.78 (1H, ddd, J=1.2, 2.1, 7.8 Hz), 7.92 (1H, dt, J=7.8, 1.5 Hz), 8.08 (1H, t, J=1.5 Hz), 13.19 (1H, s).

(iii) Using 3-(1-cyano-1-methylethyl)benzoic acid (222 mg, 1.72 mmol), thionyl chloride (1 mL, 13.7 mmol), toluene (5 mL), N-[6-(3-aminophenoxy)-1,3-benzooxazol-2-yl]cyclopropanecarboxamide (126 mg, 407 μmol) produced in Example B1(vii), pyridine (5 mL), and N,N-dimethylpyridine-4-amine (68.5 mg, 561 μmol) as starting materials, and in the same manner as in Example B1(viii), the title compound (145 mg, 74%) was obtained as a colorless amorphous substance.

$^1$H-NMR (DMSO-$d_6$, 300 MHz) δ 0.90-0.94 (4H, m), 1.74 (6H, s), 2.00-2.10 (1H, m), 6.78-6.81 (1H, m), 7.05 (1H, dd, J=2.4, 8.4 Hz), 7.37 (1H, t, J=8.4 Hz), 7.44 (1H, d, J=2.4 Hz), 7.50 (1H, t, J=2.1 Hz), 7.55-7.61 (3H, m), 7.73-7.76 (1H, m), 7.90 (1H, d, J=7.8 Hz), 7.99-8.00 (1H, m), 10.35 (1H, br s), 11.92 (1H, br s).

Example B4

Production of 3-({2-[(cyclopropylcarbonyl)amino]-1,3-benzooxazol-6-yl}oxy)-N-[3-(trifluoromethyl)phenyl]benzamide

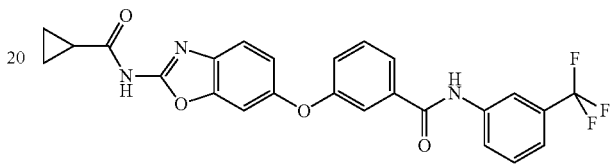

To a solution of 3-({2-[(cyclopropylcarbonyl)amino]-1,3-benzooxazol-6-yl}oxy)benzoic acid (221 mg, 653 μmol) produced in Example B1(vi) in pyridine (5 mL) were added 3-(trifluoromethyl)aniline (298 mg, 1.85 mmol), 1-ethyl-3-(3-dimethylaminopropyl)carbodiimide hydrochloride (328 mg, 1.71 mmol) and N,N-dimethylpyridine-4-amine (21.6 mmol, 177 μmol), and the mixture was stirred at room temperature for 14 hr. The mixture was concentrated under reduced pressure, and the obtained residue was dissolved in methanol (1 mL) and ethyl acetate (50 mL). This solution was washed with 0.1N hydrochloric acid (50 mL), saturated aqueous sodium hydrogencarbonate solution (50 mL) and saturated brine (50 mL), successively, and dried over anhydrous magnesium sulfate. The insoluble material was filtered off, and the filtrate was concentrated. The residue was purified by silica gel column chromatography (ethyl acetate/hexane=2/98→80/20), and triturated with diisopropyl ether to give the title compound (57.3 mg, 18%) as a pale-brown solid.

$^1$H-NMR (DMSO-$d_6$, 300 MHz) δ 0.90-0.93 (4H, m), 2.00-2.15 (1H, m), 7.07 (1H, dd, J=2.4, 8.4 Hz), 7.24-7.27 (1H, m), 7.45-7.47 (2H, m), 7.52-7.65 (4H, m), 7.76 (1H, d, J=8.4 Hz), 8.03 (1H, d, J=8.7 Hz), 8.23 (1H, s), 10.56 (1H, br s), 11.93 (1H, br s).

Preparation Example B1

A medicament containing the compound of the present invention as an active ingredient can be produced, for example, according to the following formulation.

1. Capsule

| | |
|---|---|
| (1) compound obtained in Example B1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The rest of (4) is added and the total amount is sealed in a gelatin capsule.

2. Tablet

| | | |
|---|---|---|
| (1) compound obtained in Example B1 | 40 mg | |
| (2) lactose | 58 mg | |
| (3) cornstarch | 18 mg | |
| (4) microcrystalline cellulose | 3.5 mg | |
| (5) magnesium stearate | 0.5 mg | |
| 1 tablet | 120 mg | |

(1), (2), (3), ⅔ of (4) and ½ of (5) are blended and granulated. The rest of (4) and (5) is added to the granules and the mixture is compression formed into a tablet.

Formulation Example B2

The compound (50 mg) obtained in Example B1 is dissolved in the Japanese Pharmacopoeia distilled water for injection (50 mL), and the Japanese Pharmacopoeia distilled water for injection is added to the total amount of 100 mL. This solution is filtered under sterile conditions, and then the solution (1 mL) is filled in a vial for injection under sterile conditions, freeze-dried and sealed.

Example C1

Production of N-[3-({2-[(cyclopropylcarbonyl)amino]-1H-benzimidazol-6-yl}oxy)phenyl]-3-(trifluoromethyl)benzamide

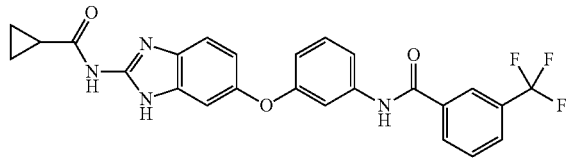

(i) Production of tert-butyl (3-hydroxyphenyl)carbamate

To a solution of 3-aminophenol (25.6 g, 234 mmol) in tetrahydrofuran (300 mL) was added di-tert-butyl dicarbonate (59.8 g, 274 mmol), and the mixture was stirred with heating at 60° C. for 14 hr. The reaction mixture was concentrated under reduced pressure, and the residue was recrystallized from diisopropyl ether (75 mL) and hexane (150 mL) to give the title compound (36 g, 73%) as colorless crystals.

$^1$H-NMR (CDCl$_3$, 300 MHz) δ 1.53 (9H, s), 5.79 (1H, br s), 6.53-6.57 (2H, m), 6.75 (1H, ddd, J=0.6, 1.8, 8.1 Hz), 7.10-7.16 (2H, m).

(ii) Production of tert-butyl [3-(3-amino-4-nitrophenoxy)phenyl]carbamate

To a solution of tert-butyl (3-hydroxyphenyl)carbamate (6.89 g, 32.9 mmol) and 5-fluoro-2-nitroaniline (5.09 g, 32.6 mmol) in N,N-dimethylformamide (100 mL) was added potassium carbonate (11.2 g, 80.9 mmol), and the mixture was vigorously stirred at 100° C. for 14 hr. The reaction mixture was cooled to room temperature, diluted with ethyl acetate (125 ml) and hexane (125 mL), washed with water (150 mL×2) and saturated brine (100 mL), successively, and dried over anhydrous magnesium sulfate. The insoluble material was filtered off, and the filtrate was concentrated under reduced pressure. The obtained residue was subjected to silica gel column chromatography (ethyl acetate/hexane=2/98→30/70) to give the title compound (7.7 g, 69%) as a yellow solid.

$^1$H-NMR (CDCl$_3$, 300 MHz) δ 1.54 (9H, s), 6.13 (2H, br s), 6.19 (1H, d, J=2.7 Hz), 6.35 (1H, dd, J=2.4, 6.3 Hz), 6.57 (1H, br s), 6.74-6.78 (1H, m), 7.11-7.16 (1H, m), 7.28-7.35 (2H, m), 8.12 (1H, d, J=9.6 Hz).

(iii) Production of tert-butyl [3-(3,4-diaminophenoxy)phenyl]carbamate tert-Butyl [3-(3-amino-4-nitrophenoxy)phenyl]carbamate (5.51 g, 15.6 mmol) and 10% palladium-carbon (875 mg) were dissolved in tetrahydrofuran (20 mL) and methanol (100 mL), and the mixture was stirred at room temperature for 18 hr under a hydrogen atmosphere (3 atm). Palladium-carbon was filtered off, and the filtrate was concentrated under reduced pressure to give the title compound (5.17 g) as a purple amorphous substance.

$^1$H-NMR (CDCl$_3$, 300 MHz) δ 1.49 (9H, s), 3.24 (2H, br s), 3.49 (2H, br s), 6.37-6.43 (3H, m), 6.61 (1H, ddd, J=0.9, 2.4, 8.1 Hz), 6.66 (1H, d, J=8.1 Hz), 6.90 (1H, t, J=2.1 Hz), 7.07-7.11 (1H, m), 7.17 (1H, t, J=8.1 Hz).

(iv) Production of tert-butyl {3-[(2-amino-1H-benzimidazol-6-yl)oxy]phenyl}carbamate To a solution of tert-butyl [3-(3,4-diaminophenoxy)phenyl]carbamate (3.00 g, 9.51 mmol) in tetrahydrofuran (150 mL) was added cyanogen bromide (2.93 g, 27.7 mmol), and the mixture was stirred at room temperature for 3 days. The reaction mixture was diluted with ethyl acetate (300 mL), washed with saturated aqueous sodium hydrogencarbonate solution (100 mL×2) and saturated brine (100 mL), successively, and dried over anhydrous magnesium sulfate. The insoluble material was filtered off, and the filtrate was concentrated to give the title compound (4.37 g) as a brown solid.

$^1$H-NMR (CDCl$_3$, 300 MHz) δ 1.44 (9H, s), 4.16 (2H, br s), 6.59-6.69 (2H, m), 6.77-6.90 (2H, m), 6.96-6.98 (2H, m), 7.05 (1H, d, J=8.4 Hz), 7.14 (1H, t, J=8.1 Hz).

(v) Production of tert-butyl [3-({2-[(cyclopropylcarbonyl)amino]-1H-benzimidazol-6-yl}oxy)phenyl]carbamate To a solution of tert-butyl {3-[(2-amino-1H-benzimidazol-6-yl)oxy]phenyl}carbamate (1.30 g, 3.82 mmol) in pyridine (50 mL) were added cyclopropanecarbonyl chloride (1 mL, 11.0 mmol) and N,N-dimethylpyridine-4-amine (21.3 mg, 174 μmol), and the mixture was stirred at room temperature for 16 hr. To the reaction mixture were added methanol (30 mL) and 8N aqueous sodium hydroxide solution (3 mL), and the mixture was stirred at the same temperature for 2.5 hr. The reaction mixture was concentrated under reduced pressure, and the residue was dissolved in methanol (5 mL) and ethyl acetate (50 mL). This solution was washed with 0.1N hydrochloric acid (50 mL) and saturated aqueous sodium hydrogencarbonate solution (50 mL), successively, and dried over anhydrous magnesium sulfate. The insoluble material was filtered off, and the filtrate was concentrated under reduced pressure. The residue was recrystallized from ethyl acetate and diisopropyl ether to give the title compound (1.53 g, 98%) as colorless crystals.

$^1$H-NMR (DMSO-d$_6$, 300 MHz) δ 0.90-0.92 (4H, m), 1.42 (9H, s), 1.92-1.99 (1H, m), 6.51-6.55 (1H, m), 6.80 (1H, dd,

J=2.1, 8.4 Hz), 7.02-7.21 (3H, m), 7.36-7.41 (2H, m), 9.36 (1H, br s), 11.83 (1H, br s), 12.01 (1H, br s).

(vi) Production of N-[6-(3-aminophenoxy)-1H-benzimidazol-2-yl]cyclopropanecarboxamide tert-Butyl [3-({2-[(cyclopropylcarbonyl)amino]-1H-benzimidazol-6-yl}oxy)phenyl]carbamate (1.58 g, 3.88 mmol) was suspended in trifluoroacetic acid (50 mL), and the reaction mixture was heated under reflux for 1 hr. The reaction mixture was cooled to room temperature, and concentrated under reduced pressure. The residue was diluted with ethyl acetate (200 mL), and washed with 0.1N hydrochloric acid (100 mL) and saturated aqueous sodium hydrogencarbonate solution (100 mL), successively. The collected aqueous layer was extracted with ethyl acetate (100 mL×2). The collected organic layer was dried over anhydrous magnesium sulfate, the insoluble material was filtered off, and the filtrate was concentrated under reduced pressure. The residue was recrystallized from methanol to give the title compound (1.06 g, 88%) as pale-brown crystals.

$^1$H-NMR (DMSO-$d_6$, 300 MHz) δ 0.90-0.92 (4H, m), 1.91-2.01 (1H, m), 5.13 (2H, br s), 6.07-6.10 (2H, m), 6.22-6.26 (1H, m), 6.79 (1H, dd, J=2.4, 8.7 Hz), 6.91-7.12 (2H, m), 7.40 (1H, br d, J=8.4 Hz), 11.81 (1H, br s), 11.99 (1H, br s).

(vii) Production of N-[3-({2-[(cyclopropylcarbonyl)amino]-1H-benzimidazol-6-yl}oxy)phenyl]-3-(trifluoromethyl)benzamide To a solution of N-[6-(3-aminophenoxy)-1H-benzimidazol-2-yl]cyclopropanecarboxamide (159 mg, 516 μmol) and 3-(trifluoromethyl)benzoic acid (191 mg, 1.01 mmol) in pyridine (5 mL) were added 1-ethyl-3-(3-dimethylaminopropyl)carbodiimide hydrochloride (375 mg, 1.96 mmol) and N,N-dimethylpyridine-4-amine (18.5 mg, 151 μmol), and the mixture was stirred at room temperature for 12 hr. Methanol (5 mL) was added to the reaction mixture, and the mixture was further stirred at room temperature for 2 hr and concentrated under reduced pressure. The residue was diluted with methanol (1 mL) and ethyl acetate (30 mL), washed with 0.1N hydrochloric acid (50 mL) and saturated aqueous sodium hydrogencarbonate solution (50 mL), successively, and dried over anhydrous magnesium sulfate. The insoluble material was filtered off, and the filtrate was concentrated. The residue was subjected to silica gel column chromatography (ethyl acetate/hexane=2/98→80/20), and the obtained crude crystals were recrystallized from acetone and diisopropyl ether to give the title compound (135 mg, 54%) as colorless crystals.

$^1$H-NMR (DMSO-$d_6$, 300 MHz) δ 0.91-0.93 (4H, m), 1.96-2.00 (1H, m), 6.74-6.77 (1H, m), 6.86 (1H, dd, J=2.1, 8.7 Hz), 7.10-7.15 (1H, m), 7.34 (1H, t, J=8.1 Hz), 7.40-7.45 (2H, m), 7.52-7.55 (1H, m), 7.76 (1H, t, J=7.8 Hz), 7.95 (1H, d, J=7.8 Hz), 8.19-8.23 (2H, m), 10.45 (1H, br s), 11.84 (1H, br s), 12.03 (1H, br s).

Example C2

Production of 3-(1-cyano-1-methylethyl)-N-[3-({2-[(cyclopropylcarbonyl)amino]-1H-benzimidazol-6-yl}oxy)phenyl]benzamide

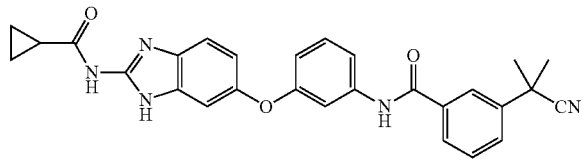

(i) Production of methyl 3-(cyanomethyl)benzoate

To a solution of methyl 3-bromobenzoate (10.0 g, 44 mmol) in acetonitrile (100 mL) were added potassium cyanide (5.7 g, 87 mmol) and 18-crown-6 (1.0 g), and the mixture was stirred at room temperature for 3 days. The reaction mixture was filtered, and the solvent was evaporated under reduced pressure. The residue was purified by silica gel column chromatography (ethyl acetate/hexane=5/95→30/70), and the fraction containing the object product was concentrated under reduced pressure to give the title compound (7.0 g, 91%) as a colorless oil.

$^1$H-NMR (DMSO-$d_6$, 300 MHz) δ 3.88 (3H, s), 4.17 (2H, s), 7.57 (1H, t, J=7.6 Hz), 7.61-7.69 (1H, m), 7.88-7.95 (1H, m), 7.97 (1H, br s).

(ii) Production of methyl 3-(1-cyano-1-methylethyl)benzoate

To a solution of methyl 3-(cyanomethyl)benzoate (7.0 g, 40 mmol) in dimethyl sulfoxide (80 mL) was added sodium hydride (60% in oil, 4.8 g, 120 mmol) under cooling to not more than 25° C. without causing solidification. The reaction mixture was stirred at room temperature for 20 min. After stirring, methyl iodide (7.5 mL, 120 mmol) was added, and the mixture was further stirred at room temperature for 16 hr. The reaction mixture was diluted with water (400 mL) and the mixture was extracted with ethyl acetate (800 mL). The organic layer was washed with water (400 mL) and saturated brine (400 mL), successively, and dried over anhydrous sodium sulfate, and the insoluble material was filtered off. The solvent was evaporated under reduced pressure, the residue was purified by silica gel column chromatography (ethyl acetate/hexane=5/95→50/50), and the fraction containing the object product was concentrated under reduced pressure to give the title compound (6.4 g, 79%) as a colorless oil.

$^1$H-NMR (DMSO-$d_6$, 300 MHz) δ 1.72 (6H, s), 3.89 (3H, s), 7.61 (1H, t, J=7.8 Hz), 7.84 (1H, ddd, J=1.2, 2.1, 7.8 Hz), 7.95 (1H, dt, J=7.8, 1.2 Hz), 8.08 (1H, t, J=1.5 Hz).

(iii) Production of 3-(1-cyano-1-methylethyl)benzoic acid

To a solution of methyl 3-(1-cyano-1-methylethyl)benzoate (2.8 g, 14 mmol) in tetrahydrofuran (30 mL) were, added lithium hydroxide·monohydrate (0.98 g, 24 mmol), methanol (10 mL) and water (10 mL), and the mixture was stirred at room temperature for 18 hr. The solvent was evaporated under reduced pressure, and the residue was diluted with water (15 mL). The mixture was adjusted to pH 3 by slowly adding 1N hydrochloric acid. The resulting white precipitate was collected by filtration, washed with water, and dried to give the title compound (2.5 g, 98%) as a white powder.

$^1$H-NMR (DMSO-$d_6$, 300 MHz) δ 1.72 (6H, s), 7.57 (1H, t, J=7.8 Hz), 7.78 (1H, ddd, J=1.2, 2.1, 7.8 Hz), 7.92 (1H, dt, J=7.8, 1.5 Hz), 8.08 (1H, t, J=1.5 Hz), 13.19 (1H, s).

(iv) Production of 3-(1-cyano-1-methylethyl)-N-[3-({2-[(cyclopropylcarbonyl)amino]-1H-benzimidazol-6-yl}oxy)phenyl]benzamide Using N-[6-(3-aminophenoxy)-1H-benzimidazol-2-yl]cyclopropanecarboxamide (156 mg, 506 mmol) produced in Example C1(vi), 3-(1-cyano-1-methylethyl)benzoic acid (195 mg, 1.03 mmol), pyridine (5 mL), 1-ethyl-3-(3-dimethylaminopropyl)carbodiimide hydrochloride (407 mg, 2.12 mmol) and N,N-dimethylpyridine-4-amine (58.2 mg, 476 μmol) as starting materials, and in the same manner as in Example C1(vii), the title compound (168 mg, 69%) was obtained as colorless crystals.

$^1$H-NMR (DMSO-$d_6$, 300 MHz) δ 0.91-0.93 (4H, m), 1.73 (6H, s), 1.94-2.00 (1H, m), 6.74 (1H, dd, J=1.8, 7.8 Hz), 8.85 (1H, dd, J=2.4, 8.4 Hz), 7.05-7.18 (1H, m), 7.32 (1H, t, J=8.1 Hz), 7.41-7.59 (4H, m), 7.72-7.75 (1H, m), 7.88 (1H, d, J=7.8 Hz), 7.97-7.98 (1H, m), 10.31 (1H, br s), 11.84 (1H, br s), 12.03 (1H, br s).

Example C3

Production of 3-(1-cyanocyclopropyl)-N-[3-({2-[(cyclopropylcarbonyl)amino]-1H-benzimidazol-6-yl}oxy)phenyl]benzamide

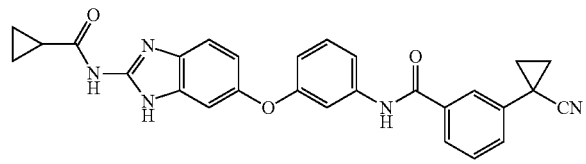

(i) Production of methyl 3-(1-cyanocyclopropyl)benzoate

To a solution of methyl 3-(cyanomethyl)benzoate (1.5 g, 8.6 mmol) produced in Example C2(i) in dimethyl sulfoxide (30 mL) was added sodium hydride (60% in oil, 1.0 g, 26 mmol) under cooling to not more than 25° C. without causing solidification. The reaction mixture was stirred at room temperature for 30 min. After stirring, 1,2-dibromoethane (2.4 g, 12.8 mmol) was added, and the mixture was further stirred at room temperature for 10 hr. The reaction mixture was diluted with water (100 mL), and extracted with ethyl acetate (300 mL). The organic layer was washed with saturated brine (100 mL) and dried over anhydrous sodium sulfate, and the insoluble material was filtered off. The solvent was evaporated under reduced pressure, the residue was purified by silica gel column chromatography (ethyl acetate/hexane=5/95→50/50), and the fraction containing the object product was concentrated under reduced pressure to give the title compound (1.3 g, 76%) as a colorless oil.

$^1$H-NMR (CDCl$_3$, 300 MHz) δ 1.38-1.56 (2H, m), 1.74-1.82 (2H, m), 3.93 (3H, s), 7.40° C.-7.49 (1H, m), 7.55-7.62 (1H, m), 7.88 (1H, t, J=1.5 Hz), 7.96 (1H, dt, J=7.8, 1.5 Hz).

(ii) Production of 3-(1-cyanocyclopropyl)benzoic acid

To a solution of methyl 3-(1-cyanocyclopropyl)benzoate (1.3 g, 6.4 mmol) in tetrahydrofuran (12 mL) were added lithium hydroxide•monohydrate (0.44 g, 11 mmol), methanol (4.0 mL) and water (6.0 mL), and the mixture was stirred at room temperature for 14 hr. The solvent was evaporated under reduced pressure, and the residue was diluted with water (5.0 mL). The mixture was adjusted to pH 5 by slowly adding 1N hydrochloric acid. The resulting, white precipitate was collected by filtration, washed with water, and dried to give the title compound (0.73 g, 61%) as a white powder.

$^1$H-NMR (DMSO-$d_6$, 300 MHz) δ 1.50-1.62 (2H, m), 1.76-1.86 (2H, m), 7.41-7.59 (2H, m), 7.82-7.97 (2H, m), 13.19 (1H, br s).

(iii) Production of 3-(1-cyanocyclopropyl)-N-[3-({2-[(cyclopropylcarbonyl)amino]-1H-benzimidazol-6-yl}oxy)phenyl]benzamide Using N-[6-(3-aminophenoxy)-1H-benzimidazol-2-yl]cyclopropanecarboxamide (159 mg, 515 μmol) produced in Example C1(vi), 3-(1-cyanocyclopropyl)benzoic acid (210 mg, 1.12 mmol), pyridine (5 mL), 1-ethyl-3-(3-dimethylaminopropyl)carbodiimide hydrochloride (307 mg, 1.60 mmol) and N,N-dimethylpyridine-4-amine (58.1 mg, 47.6 μmol) as starting materials, and in the same manner as in Example C1(vii), the title compound (107 mg, 43%) was obtained as colorless crystals.

$^1$H-NMR (DMSO-$d_6$, 300 MHz) δ 0.91-0.93 (4H, m), 1.57-1.62 (2H, m), 1.78-1.82 (2H, m), 1.95-1.99 (1H, m), 6.73 (1H, dd, J=2.1, 8.1 Hz), 6.85 (1H, d, J=8.1 Hz), 7.08-7.57 (7H, m), 7.76 (1H, s), 7.83 (1H, dt, J=1.8, 6.6 Hz), 10.29 (1H, br s), 11.84 (1H, br d, J=9.9 Hz), 12.05 (1H, br d, J=11.7 Hz).

Example C4

Production of N-[3-({2-[(cyclopropylcarbonyl)amino]-1-methyl-1H-benzimidazol-6-yl}oxy)phenyl]-3-(trifluoromethyl)benzamide

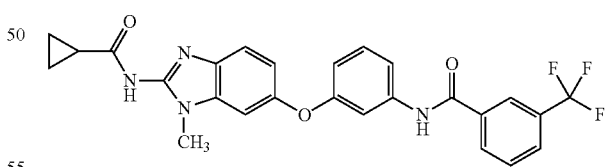

(i) Production of 5-fluoro-N-methyl-2-nitroaniline 2,4-Difluoro-1-nitrobenzene (25.0 g, 157 mmol) was stirred and thereto was added dropwise 40% aqueous methylamine solution (38.4 g) at 0° C. over not less than 15 min. After the completion of the dropwise addition, the mixture was continuously stirred at the same temperature for 1.5 hr. Water (500 mL) was added to the reaction mixture, and the resulting solid was collected by filtration to give the title compound (26.4 g, 99%) as yellow crystals.

¹H-NMR (DMSO-d₆, 300 MHz) δ 2.94 (3H, d, J=4.8 Hz), 6.53 (1H, ddd, J=2.7, 7.8, 10.2 Hz), 6.78 (1H, dd, J=2.7, 12.3 Hz), 8.17 (1H, dd, J=6.3, 9.6 Hz), 8.32 (1H, br s).

(ii) Production of tert-butyl {3-[3-(methylamino)-4-nitrophenoxy]phenyl}carbamate Using tert-butyl (3-hydroxyphenyl)carbamate (11.0 g, 52.3 mmol) produced in Example C1(i), 5-fluoro-N-methyl-2-nitroaniline (8.58 g, 50.4 mmol), N,N-dimethylformamide (200 ml) and potassium carbonate (28.6 g, 207 mmol) as starting materials, and in the same manner as in Example C1(ii) except that the reaction temperature was set to 80° C., the title compound (21.8 g) was obtained as an orange syrup.

¹H-NMR (CDCl₃, 300 MHz) δ 1.51 (9H, s), 2.92 (3H, d, J=5.1 Hz), 6.22 (1H, dd, J=2.7, 9.6 Hz), 6.29 (1H, d, J=2.4 Hz), 6.64 (1H, br s), 6.75 (1H, ddd, J=0.9, 2.4, 8.1 Hz), 7.12 (1H, d, J=8.4 Hz), 7.27-7.33 (2H, m), 8.14 (1H, d, J=9.6 Hz), 8.19 (1H, br d, J=4.8 Hz).

(iii) Production of tert-butyl {3-[4-amino-3-(methylamino)phenoxy]phenyl}carbamate Using tert-butyl {3-[3-(methylamino)-4-nitrophenoxy]phenyl}carbamate (10.9 g, 30.4 mmol), 10% palladium-carbon (1.8 g), tetrahydrofuran (150 mL), ethanol (100 mL) and hydrogen (3 atm) as starting materials, and in the same manner as in Example C1(iii), the title compound (10.1 g) was obtained as a black tar-like substance.

¹H-NMR (CDCl₃, 300 MHz) δ 1.49 (9H, s), 2.81 (4H, s), 2.88 (1H, s), 2.95 (1H, s), 6.31 (1H, dd, J=2.7, 8.1 Hz), 6.37 (1H, d, J=2.4 Hz), 6.47 (1H, br s), 6.60-6.67 (2H, m), 6.89 (1H, t, J=2.1 Hz), 7.11-7.20 (2H, m).

(iv) Production of tert-butyl {3-[(2-amino-1-methyl-1H-benzimidazol-6-yl)oxy]phenyl}carbamate Using tert-butyl {3-[4-amino-3-(methylamino)phenoxy]phenyl}carbamate (10.1 g, 30.4 mmol) produced in Example C4(iii), tetrahydrofuran (200 mL) and cyanogen bromide (4.33 g, 40.9 mmol) as starting materials, and in the same manner as in Example C1(iv), the title compound (7.46 g, yield (total of 2 steps) 69%) was obtained as a black amorphous substance.

¹H-NMR (DMSO-d₆, 300 MHz) δ 1.43 (9H, s), 3.33 (2H, br s), 3.46 (3H, s), 6.47-6.50 (2H, m), 6.65 (1H, dd, J=2.4, 8.4 Hz), 6.92 (1H, d, J=2.4 Hz), 7.10-7.19 (3H, m), 9.34 (1H, br s).

(v) Production of tert-butyl [3-({2-[(cyclopropylcarbonyl)amino]-1-methyl-1H-benzimidazol-6-yl}oxy)phenyl]carbamate Using tert-butyl {3-[(2-amino-1-methyl-1H-benzimidazol-6-yl)oxy]phenyl}carbamate (2.45 g, 6.91 mmol), pyridine (100 mL), cyclopropanecarbonyl chloride (3.0 mL, 33.1 mmol) and N,N-dimethylpyridine-4-amine (258 mg, 2.11 mmol) as starting materials, and in the same manner as in Example C1(v), the title compound (1.89 g, 65%) was obtained as a pale-brown amorphous substance.

¹H-NMR (CDCl₃, 300 MHz) δ 0.85-0.90 (2H, m), 1.06-1.11 (2H, m), 1.50 (9H, s), 1.80-1.90 (1H, m), 3.60 (3H, m), 6.56 (1H, br s), 6.64-6.68 (1H, m), 6.90-6.94 (2H, m), 7.08-7.11 (2H, m), 7.20-7.33 (2H, m), 8.63-8.65 (1H, m).

(vi) Production of N-[6-(3-aminophenoxy)-1-methyl-1H-benzimidazol-2-yl]cyclopropanecarboxamide Using tert-butyl [3-({2-[(cyclopropylcarbonyl)amino]-1-methyl-1H-benzimidazol-6-yl}oxy)phenyl]carbamate (1.52 g, 3.60 mmol) and trifluoroacetic acid (50 mL) as starting materials, and in the same manner as in Example C1(vi), the title compound (1.02 g, 88%) was obtained as a pink amorphous substance.

¹H-NMR (CDCl₃, 300 MHz) δ 0.93-0.98 (2H, m), 1.11-1.13 (2H, m), 1.94-1.99 (1H, m), 3.68 (3H, s), 6.34 (1H, t, J=2.1 Hz), 6.38-6.41 (1H, m), 6.46-6.49 (1H, m), 6.96 (1H, d, J=2.1 Hz), 7.03 (1H, dd, J=2.1, 8.4 Hz), 7.14 (1H, t, J=8.1 Hz), 7.28-7.37 (1H, m).

(vii) Production of N-[3-({2-[(cyclopropylcarbonyl)amino]-1-methyl-1H-benzimidazol-6-yl}oxy)phenyl]-3-(trifluoromethyl)benzamide To a solution of N-[6-(3-aminophenoxy)-1-methyl-1H-benzimidazol-2-yl]cyclopropanecarboxamide (200 mg, 620 μmol) in pyridine (5 mL) were added 3-(trifluoromethyl) benzoic acid (241 mg, 1.27 mmol), 1-ethyl-3-(3-dimethylaminopropyl)carbodiimide hydrochloride (479 mg, 2.50 mmol) and N,N-dimethylpyridine-4-amine (28.3 mg, 232 μmol), and the mixture was stirred at room temperature for 2 hr. To the reaction mixture were added methanol (2 mL) and 8N aqueous sodium hydroxide solution (2 mL), and the mixture was further stirred at room temperature for 30 min. The reaction mixture was concentrated under reduced pressure, and the residue was dissolved in ethyl acetate (50 mL) and methanol (1 mL). This solution was washed with water (50 ml), 0.1N hydrochloric acid (50 mL) and saturated aqueous sodium hydrogencarbonate solution (50 mL), successively, and dried over anhydrous magnesium sulfate, and the insoluble material was filtered off. The filtrate was concentrated under reduced pressure, and the residue was subjected to silica gel column chromatography (ethyl acetate/hexane=2/98→80/20), and further purified by reversed phase silica gel column chromatography (containing 0.1% trifluoroacetic acid, water/acetonitrile=95/5→0/100). The fraction containing the object product was concentrated, and the residue was dissolved in ethyl acetate (50 mL) and methanol (10 mL). The mixture was washed with saturated aqueous sodium hydrogencarbonate solution (50 mL), and dried over anhydrous magnesium sulfate. The insoluble material was filtered off, and the filtrate was concentrated. The obtained residue was recrystallized from acetone and diisopropyl ether to give the title compound (139 mg, 45%) as colorless crystals.

¹H-NMR (DMSO-d₆, 300 MHz) δ 0.87-0.90 (4H, m), 1.91-1.96 (1H, m), 3.33 (3H, s), 6.78 (1H, d, J=8.1 Hz), 6.94 (1H, d, J=8.1 Hz), 7.26-7.43 (3H, m), 7.56-7.59 (2H, m), 7.76

(1H, t, J=7.8 Hz), 7.95 (1H, J=7.8 Hz), 8.20-8.23 (2H, m), 10.45 (1H, br s), 10.87 (1H, br s).

Example C5

Production of 3-(1-cyano-1-methylethyl)-N-[3-({2-[(cyclopropylcarbonyl)amino]-1-methyl-1H-benzimidazol-6-yl}oxy)phenyl]benzamide

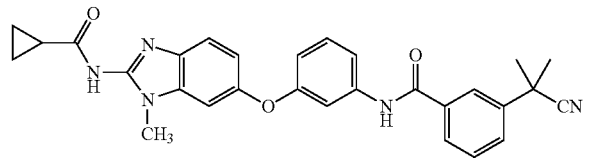

Using N-[6-(3-aminophenoxy)-1-methyl-1H-benzimidazol-2-yl]cyclopropanecarboxamide (166 mg, 514.3 μmol) produced in Example C4(vi), 3-(1-cyano-1-methylethyl)benzoic acid (316 mg, 1.67 mmol), pyridine (5 mL), 1-ethyl-3-(3-dimethylaminopropyl)carbodiimide hydrochloride (456 mg, 2.38 mmol) and N,N-dimethylpyridine-4-amine (38.9 mg, 318 μmol) as starting materials, and in the same manner as in Example C4(vii), the title compound (97.3 mg, 38%) was obtained as colorless crystals.

$^1$H-NMR (DMSO-d$_6$, 300 MHz) δ 0.82-0.92 (4H, m), 1.73 (6H, s), 1.90-2.05 (1H, m), 3.54 (3H, s), 6.76 (1H, dd, J=1.8, 7.8 Hz), 6.94 (1H, d, J=8.1 Hz), 7.31-7.37 (2H, m), 7.41-7.60 (4H, m), 7.72-7.75 (1H, m), 7.90 (1H, d, J=7.8 Hz), 7.98-8.00 (1H, m), 10.35 (1H, br s), 10.89 (1H, br s).

Example C6

Production of 3-(1-cyanocyclopropyl)-N-[3-({2-[(cyclopropylcarbonyl)amino]-1-methyl-1H-benzimidazol-6-yl}oxy)phenyl]benzamide

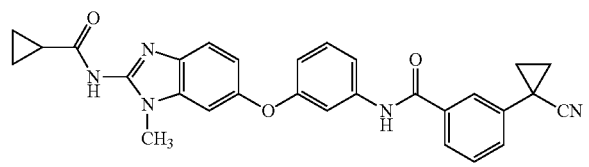

Using N-[6-(3-aminophenoxy)-1-methyl-1H-benzimidazol-2-yl]cyclopropanecarboxamide (168 mg, 522 μmol) produced in Example C4(vi), 3-(1-cyanocyclopropyl)benzoic acid (303 mg, 1.62 mmol), pyridine (5 mL), 1-ethyl-3-(3-dimethylaminopropyl)carbodiimide hydrochloride (382 mg, 1.99 mmol) and N,N-dimethylpyridine-4-amine (39.1 mg, 320 μmol) as starting materials, and in the same manner as in Example C4(vii), the title compound (67.4 mg, 26%) was obtained as colorless crystals.

$^1$H-NMR (DMSO-d$_6$, 300 MHz) δ 0.86-0.90 (4H, m), 1.57-1.62 (2H, m), 1.78-1.82 (2H, m), 1.90-2.02 (1H, m), 3.53 (3H, s), 6.76 (1H, d, J=7.8 Hz), 6.94 (1H, d, J=8.1 Hz), 7.26-7.59 (7H, m), 7.77 (1H, s), 7.82-7.85 (1H, m), 10.29 (1H, br s), 10.87 (1H, br s).

Preparation Example C1

A medicament containing the compound of the present invention as an active ingredient can be produced, for example, according to the following formulation.

1. Capsule

| | |
|---|---|
| (1) compound of Example C1 | 40 mg |
| (2) lactose | 70 mg |
| (3) microcrystalline cellulose | 9 mg |
| (4) magnesium stearate | 1 mg |
| 1 capsule | 120 mg |

(1), (2), (3) and ½ of (4) are blended and granulated. The rest of (4) is added and the total amount is sealed in a gelatin capsule.

2. Tablet

| | |
|---|---|
| (1) compound of Example C1 | 40 mg |
| (2) lactose | 58 mg |
| (3) cornstarch | 18 mg |
| (4) microcrystalline cellulose | 3.5 mg |
| (5) magnesium stearate | 0.5 mg |
| 1 tablet | 120 mg |

(1), (2), (3), ⅔ of (4) and ½ of (5) are blended and granulated. The rest of (4) and (5) is added to the granules and the mixture is compression formed into a tablet.

Preparation Example C2

The compound (50 mg) obtained in Example C1 is dissolved in the Japanese Pharmacopoeia distilled water for injection (50 mL), and the Japanese Pharmacopoeia distilled water for injection is added to the total amount of 100 mL. This solution is filtered under sterile conditions. The solution (1 mL) is filled under sterile conditions in a vial for injection, freeze-dried and sealed.

Experimental Example 1

Cloning of Human BRAF Gene and Preparation of Recombinant Baculovirus

Human BRAF gene was cloned by PCR using human Testis cDNA library (Clontech) as a template. The primer used for PCR was prepared from base sequence (Genbank Accession No.: NM_004333) information of BRAF gene by adding a base sequence encoding flag peptide and a recognition sequence of the restriction enzyme to area encoding the BRAF kinase domain region, so that the protein contains an N-terminal. Flag. The primer base sequence is shown below.

```
BRAF-U:                             (SEQ ID NO:1)
5'-AAAGAATTCACCATGGACTACAAGGACGACGATGACAAGACCC
CCCCTGCCTCATTACCTGGCT-3'
and BRAF-L:                             (SEQ ID NO:2)
5'-AAAAGTCGACTCAGTGGACAGGAAACGCACCATAT-3'
```

The PCR reaction was conducted using Pyrobest (Takara Shuzo Co., Ltd). The obtained PCR product was electrophoresed on agarose gel (1%), the DNA fragment amplified by PCR was recovered from the gel, and then digested with restriction enzymes EcoRI and SalI. The DNA treated with the restriction enzymes was electrophoresed on agarose gel (1%), and the obtained DNA fragment was recovered. The recovered DNA fragment was ligated to plasmid pFAST- BAC1 (Invitrogen) digested with restriction enzymes EcoRI and SalI to give expression plasmid pFB-BRAF, and the base sequence of the insert fragment was confirmed. In addition, mutation was introduced into V600E using a Quick change Site Directed Mutagenesis kit (Stratagene). The base sequences of the primers used are shown in the following.

```
V600E-U:                              (SEQ ID NO:3)
5'-GGTCTAGCTACAGAGAAATCTCGATGGAG-3'
and V600E-L:                              (SEQ ID NO:4)
5'-CTCCATCGAGATTTCTCTGTAGCTAGACC-3'
```

The obtained plasmid was sequenced to confirm the introduction of mutation into V600E. The DNA was digested with restriction enzymes EcoRI and SalI, DNA treated with the restriction enzymes was electrophoresed on agarose gel (1%), and the obtained DNA fragment was recovered. The recovered DNA fragment was ligated to plasmid pFASTBAC1 (Invitrogen) digested with restriction enzymes EcoRI and SalI to give expression plasmid pFB-V600E.

Using BAC-TO-BAC Baculovirus Expression System (Invitrogen), virus stock BAC-V600E of recombinant baculovirus was prepared.

Experimental Example 2

Preparation of BRAF (V600E) Protein

SF-21 cells were sown at 1×10$^6$ cells/mL to Sf-900II SFM medium (1 L, Invitrogen) containing 10% fetal bovine serum (Trace), 50 mg/L Gentamicin (Invitrogen) and 0.1% Pluronic F-68 (Invitrogen), and shaking culture was performed using a 2 L volume Erlenmeyer flask at 27° C., 100 rpm. After culturing for 24 hr, recombinant baculovirus BAC-V600E (13.4 mL) was added to the mixture, and the mixture was further cultured for 3 days. The culture medium was centrifuged at 2,000 rpm for 5 min to give virus-infected cells. The infected cells were washed with a phosphate buffered saline (Invitrogen), centrifuged under the same conditions, and the cells were preserved at −80° C. The cryopreserved cells were thawed in ice, suspended in buffer A (50 mM Tris buffer (30 mL, pH 7.4) containing 20% glycerol, 0.15 M NaCl) supplemented with Complete Protease Inhibitor (Boehringer), and ruptured 3 times with a Polytron homogenizer (Kinematica) at 20,000 rpm for 30 sec. The ruptured medium was clarified by centrifugation at 40,000 rpm for 30 min and filtered with a 0.45 μm filter. The filtrate was passed through a column packed with Anti-FLAG M2 Affinity Gel (4 mL, Sigma) at a flow rate of about 0.5 mL/min. The column was washed with buffer A, and eluted with buffer A containing 100 μg/mL of FLAG peptide. The buffer of this eluate was exchanged using NAP25 column (Amersham Bioscience) equilibrated with buffer A and the fractions were cryopreserved at −80° C.

Test Example 1

Determination of BRAF (V600E) Kinase Inhibitory Activity

A test compound (2.5 μL) dissolved in dimethyl sulfoxide (DMSO) was added to 37.5 μL of a reaction mixture (25 mM HEPES (pH 7.5), 10 mM magnesium acetate, 1 mM dithiothreitol) containing BRAF (V600E) enzyme (30 ng) and recombinant type protein GST-MEK1 (K96R) 250 ng, and the mixture was incubated at room temperature for 10 min. ATP solution (10 μL, 2.5 μM ATP, 0.1 μCi [γ-$^{32}$P]ATP) was added to the obtained mixture, and the mixture was reacted at room temperature for 20 min. The reaction was quenched by adding 50 μL of ice-cooled. 20% trichloroacetic acid (Wako Pure Chemical Industries, Ltd.) to the reaction mixture. The reaction mixture was allowed to stand at 4° C. for 30 min, and the acid-precipitable fraction was transferred to GF/C filter plate (Millipore Corporation) using cell harvester (PerkinElmer). The plate was dried at 45° C. for 60 min, and 40 μL of MicroScinti 0 (PerkinElmer) was added thereto. The radioactivity was measured using TopCount (PerkinElmer). The kinase inhibitory rate (%) of the test compound was calculated by the following formula:

Inhibitory rate (%)=(1−(count of test compound−blank)÷(control−blank))×100

The count of the solution reacted without addition of the compound was used as a "control", and the count of the solution without the compound and enzyme was used as a "blank".

The obtained results are shown in Table 1. The results show that the compound of the present invention strongly inhibits an activity of BRAF (V600E) kinase.

TABLE 1

| Example No. (compound No.) | Inhibitory rate (%) at 1.0 μM |
| --- | --- |
| A1 | 98 |
| A6 | 99 |
| A12 | 100 |
| A15 | 100 |
| A21 | 98 |
| A25 | 100 |
| A29 | 100 |
| B1 | 100 |
| C1 | 99 |

Test Example 2

Colon Cancer Cell HT-29 Intracellular MEK Phosphorylation Inhibitory Action In Vitro A cell suspension (500 μL) of human colon cancer cell HT-29 was plated in a 48-well plate (100,000 cells/well), and the cells were cultured overnight at 37° C. in the presence of 5% CO$_2$, treated with a test compound (250 μL/well) diluted in 3-fold dilution series and cultured for two more hours. After 2 hr, the culture medium containing the test compound was removed, and the cells were lysed with SDS sample buffer (100 μL/well) and heated at 95° C. for 5 min. Thereafter, the cells were applied to SDS-PAGE, and the protein was transferred onto Sequi-Blot™ PVDF Membrane (Bio-Rad) by the Western blot method. The cells were blocked with a block-Ace solution (Snow Brand Milk Products Co., Ltd) dissolved in phosphate buffer to 5% W/V, and reacted overnight with anti-phosphorylated MEK1/2 (Ser217/221) (Cell signaling #9121) diluted 1000-fold with phosphate buffer containing 0.4% block-Ace. The membrane was washed with phosphate buffer containing 0.1% Tween 20 (Wako Pure Chemical Industries, Ltd.), and reacted at room temperature for 1 hr with HRP labeled rabbit IgG polyclonal antibody (Cell signaling #7074) diluted 1000-fold with phosphate buffer containing 0.4% block-Ace. The membrane was washed in the same manner as above, chemical luminescence of a phosphorylated MEK1/2 protein labeled with the antibody, which was caused by ECL-plus Detection Reagent (Amersham bioscience), was detected by Luminescent Image Analyzer LAS-1000 (FUJIFILM Corporation). Taking the luminescence of the control group free of the test compound as 100%, the concentration ($IC_{50}$ value) of the compound necessary for inhibiting the residual luminescence to 50% of the control group was calculated. The results are shown in Table 2.

TABLE 2

| Example No. (compound No.) | $IC_{50}$ (nM) |
| --- | --- |
| A7 | <500 |
| A10 | <500 |
| A14 | <500 |
| A16 | <500 |
| A21 | <500 |
| A26 | <500 |
| B3 | <500 |

Test Example 3

Colon Cancer Cell HT-29 Growth Suppressive Action In Vitro

A cell suspension (100 μL, 3,000 cells/well) of human colon cancer cell HT-29 (purchased from ATCC) was plated in a 96-well plate, and the cells were cultured at 37° C. in a 5% carbon dioxide gas incubator. The next day, 2-fold serial dilution of each test compound solution (diluted from maximum concentration 20 μM) (100 μL) was added, and the cells were cultured for 3 days. The culture medium containing the test compound was removed, and the cells were washed with phosphate buffer (PBS). A 50% trichloroacetic acid solution was added to the final concentration of 10% (v/v), and the mixture was stood overnight at 4° C., whereby the cells were fixed to the plate. Then, a dye SRB 0.4% (w/v) solution (dissolved in 1% acetic acid) was added at 50 μl/well, whereby the cell protein was fixed and stained (Skehan et al., Journal Of National Cancer Institute, vol. 82, pp. 1107-1112, 1990). The cells were washed 3 times with 1% acetic acid solution (200 μL/well), and 100 μL of an extract (10 mM Tris buffer) was added to extract the dye. The absorbance at an absorption wavelength 550 nM was measured, and cell amount was measured as a protein amount. Taking the protein amount of the control group free of the test compound solution as 100%, the proportion of the residual protein amount of each treatment group was determined and the concentration of the compound necessary for suppressing the residual cell amount to 50% of the control ($IC_{50}$ value) was calculated. The results are shown in Table 3.

TABLE 3

| Example No. (compound No.) | $IC_{50}$ (nM) |
| --- | --- |
| A2 | <500 |
| A12 | <500 |
| A13 | <500 |
| A23 | <500 |
| A41 | <500 |
| A47 | <500 |
| A49 | <500 |

INDUSTRIAL APPLICABILITY

The compounds, a salt thereof and a prodrug thereof of the present invention show superior inhibitory activity on Raf. Therefore, a clinically useful agent for the prophylaxis or treatment of diseases related to Raf (e.g., cancer etc.) can be provided. Moreover, since compounds, a salt thereof and a prodrug thereof of the present invention are also superior in efficacy expression, pharmacokinetics, solubility, interaction with other pharmaceutical products, safety and stability, they are useful as medicaments.

This application is based on Japanese patent application No. 2007-217633, the contents of which are incorporated in full herein by this reference.

The invention claimed is:

1. A compound represented by the formula

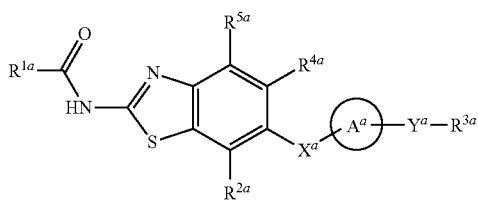

(I)

wherein $R^{1a}$ is (1) $C_{1-6}$ alkyl optionally substituted with one substituent selected from the group consisting of
  (i) hydroxy, and
  (ii) a 5- or 6-membered nonaromatic heterocyclic group optionally substituted with one $C_{1-6}$ alkyl substituent,
(2) $C_{3-8}$ cycloalkyl, or
(3) oxazolyl;

$R^{2a}$ is a hydrogen atom;

$R^{3a}$ is $C_{6-10}$ aryl optionally substituted with 1 or 2 substituents selected from the group consisting of
(1) $C_{3-8}$ cycloalkyl optionally substituted with cyano,
(2) $C_{1-6}$ alkyl optionally substituted with 1 to 3 substituents selected from the group consisting of a halogen atom and cyano,
(3) $C_{1-6}$ alkyl-oxy optionally substituted with cyano,
(4) a halogen atom, and
(5) cyano;

$R^{4a}$ is a hydrogen atom or a halogen atom;

$R^{5a}$ is a hydrogen atom;

$X^a$ is —O—;

$Y^a$ is —NH—, —NHCO—, or —CONH—; and ring $A^a$ is a benzene ring optionally substituted with one substituent selected from the group consisting of
(1) $C_{1-6}$ alkyl,
(2) $C_{1-6}$ alkyl-oxy, and
(3) a halogen atom, or a salt thereof.

2. The compound according to claim 1, wherein the $Y^a$ is —NHCO— or —CONH—.

3. 3-(1-Cyano-1-methylethyl)-N-[3-({2-[(cyclopropylcarbonyl)amino]-1,3-benzothiazol-6-yl}oxy)phenyl]benzamide;

3-(1-cyanocyclopropyl)-N-{3-[(2-{[(4-methylpiperazin-1-yl)acetyl]amino}-1,3-benzothiazol-6-yl)oxy]phenyl}benzamide;

N-(3-{[2-(acetylamino)-1,3-benzothiazol-6-yl]oxy}phenyl)-2-chloro-3-(1-cyano-1-methylethyl)benzamide; or N-(3-{[2-(acetylamino)-1,3-benzothiazol-6-yl]oxy}-4-fluorophenyl)-2-chloro-3-(1-cyano-1-methylethyl)benzamide;

or a salt thereof.

4. A medicament comprising the compound or the salt thereof according to claim 1 and a pharmacologically acceptable carrier.

* * * * *

SEQUENCE LISTING

```
<160> NUMBER OF SEQ ID NOS: 4

<210> SEQ ID NO 1
<211> LENGTH: 64
<212> TYPE: DNA
<213> ORGANISM: Artificial
<220> FEATURE:
<223> OTHER INFORMATION: primer for cloning human BRAF gene

<400> SEQUENCE: 1
aaagaattca ccatggacta caaggacgac gatgacaaga ccccccctgc ctcattacct      60
ggct                                                                   64

<210> SEQ ID NO 2
<211> LENGTH: 35
<212> TYPE: DNA
<213> ORGANISM: Artificial
<220> FEATURE:
<223> OTHER INFORMATION: primer for cloning human BRAF gene

<400> SEQUENCE: 2
aaaagtcgac tcagtggaca ggaaacgcac catat                                 35
```

```
<210> SEQ ID NO 3
<211> LENGTH: 29
<212> TYPE: DNA
<213> ORGANISM: Artificial
<220> FEATURE:
<223> OTHER INFORMATION: primer for cloning human BRAF gene

<400> SEQUENCE: 3
ggtctagcta cagagaaatc tcgatggag                                 29

<210> SEQ ID NO 4
<211> LENGTH: 29
<212> TYPE: DNA
<213> ORGANISM: Artificial
<220> FEATURE:
<223> OTHER INFORMATION: primer for cloning human BRAF gene

<400> SEQUENCE: 4
ctccatcgag atttctctgt agctagacc                                 29
```